US009279002B2

(12) United States Patent
Ibrahim et al.

(10) Patent No.: US 9,279,002 B2
(45) Date of Patent: Mar. 8, 2016

(54) IMMUNOTHERAPY AND DIAGNOSIS OF MUCORMYCOSIS USING COTH

(75) Inventors: Ashraf S. Ibrahim, Irvine, CA (US); Mingfu Liu, Carson, CA (US); Teklegiorgis Ghebremariam, Los Angeles, CA (US); Yue Fu, Torrance, CA (US); John E. Edwards, Palos Verdes Estates, CA (US); Scott Filler, Rancho Palos Verdes, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 54 days.

(21) Appl. No.: 13/620,563

(22) Filed: Sep. 14, 2012

(65) Prior Publication Data
US 2013/0108642 A1 May 2, 2013

Related U.S. Application Data

(60) Provisional application No. 61/535,257, filed on Sep. 15, 2011.

(51) Int. Cl.
*C07K 14/37* (2006.01)
*C07K 16/14* (2006.01)
*A61K 39/00* (2006.01)

(52) U.S. Cl.
CPC .......... *C07K 14/37* (2013.01); *C07K 16/14* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,405,712 A | 9/1983 | Woude et al. |
| 4,493,795 A | 1/1985 | Nestor et al. |
| 4,650,764 A | 3/1987 | Temin et al. |
| 4,889,953 A | 12/1989 | Inoue et al. |
| 4,897,355 A | 1/1990 | Eppstein et al. |
| 5,252,479 A | 10/1993 | Srivastava et al. |
| 5,283,173 A | 2/1994 | Fields et al. |
| 5,334,761 A | 8/1994 | Gebeyehu et al. |
| 5,399,346 A | 3/1995 | Anderson et al. |
| 5,468,614 A | 11/1995 | Fields et al. |
| 5,667,973 A | 9/1997 | Fields et al. |
| 5,693,762 A | 12/1997 | Queen et al. |
| 5,877,397 A | 3/1999 | Lonberg et al. |
| 2005/0232947 A1 | 10/2005 | Cutting et al. |

(Continued)

FOREIGN PATENT DOCUMENTS

| | | |
|---|---|---|
| WO | 89/05345 | 6/1989 |
| WO | 90/06997 | 6/1990 |

(Continued)

OTHER PUBLICATIONS

Jensen et al. (Veterinary Pathology, vol. 33, pp. 176-183).*

(Continued)

*Primary Examiner* — Robert A Zeman
(74) *Attorney, Agent, or Firm* — Pillsbury Winthrop Shaw Pittman LLP

(57) ABSTRACT

The invention provided Mucorales CotH polypeptides and encoding nucleic acid molecules. The Mucorales CotH polypeptides and encoding nucleic acids can be advantageously used to diagnose, treat or prevent fungal conditions, in particular mucormycosis.

10 Claims, 64 Drawing Sheets

(56) References Cited

U.S. PATENT DOCUMENTS

| | | | |
|---|---|---|---|
| 2010/0055244 | A1 | 3/2010 | Henriques et al. |
| 2011/0059111 | A1 | 3/2011 | Ibrahim et al. |
| 2011/0171267 | A1 | 7/2011 | Bourinbaiar et al. |
| 2012/0093828 | A1 | 4/2012 | Ibrahim et al. |

FOREIGN PATENT DOCUMENTS

| | | |
|---|---|---|
| WO | 92/05266 | 4/1992 |
| WO | 92/07573 | 5/1992 |
| WO | 92/14829 | 9/1992 |

OTHER PUBLICATIONS

Fukuzawa et al. (Virchows Arch. vol. 427, pp. 407-414).*
Campbell, A.M. (Monoclonal Antibody Technology, Elsevier, N.Y. 1984; chapter 1, pp. 1-32).*
Ma et al. PLoS Genetics vol. 5, Issue 7).*
Skolnick et al. (Trends in Biotechnology 18: 34-39, 2000).*
Greenspan et al. (Nature Biotechnology 7: 936-937, 1999).*
Marr et al., "Epidemiology and Outcome of Mould Infections in Hematopoietic Stem Cell Transplant Recipients," Clin. Infect. Dis. 34(7):909-917 (2002).
Mertens et al., "Plasmids for expression of heterologous proteins in Rhizopus oryzae," Archives of microbiology 186:41-50 (2006).
Michielse et al., "Development of a system for integrative and stable transformation of the zygomycete Rhizopus oryzae by Agrobacterium-mediated DNA transfer," Mol. Genet. Genomics, 271:499-510 (2004).
Mocarski et al., "Recombinant Cytomegalovirus-based Expression Vectors," Viral Vectors, Y. Gluzman and S.H. Hughes, Eds., Cold Spring Harbor Laboratory, Cold Spring Harbor, N.Y., 1988, pp. 78-84.
Morris et al., "Immunoglobulin Binding Protein (BiP) Function is Required to Protect Cells from Endoplasmic Reticulum Stress but is Not Required for the Secretion of Selective Proteins," J. Biol. Chem., 272:4327-4334 (1997).
Naclerio et al., "Bacillus subtilis Spore Coat Assembly Requires cotH Gene Expression," J. Bacteriol., 178:6407 (1996).
Nakayashiki et al., "RNA silencing as a tool for exploring gene function in ascomycete fungi," Fungal Genet. Biol., 42:275-283 (2005).
No et al., "Ecdysone-inducible gene expression in mammalian cells and transgenic mice," Proc. Natl. Acad. Sci. USA, 93:3346-3351 (1996).
Onodera et al., "Development of Improved Adenosine Deaminase Retroviral Vectors," J. Virol., 72:1769-1774 (1998).
Piccini et al., "Vaccinia Virus as an Expression Vector," Meth. Enzymology, 153:545-563 (1987).
Pitarch et al., "Two-Dimensional gel electrophoresis as analytical tool for identifying Candida albicans immunogenic proteins," Electrophoresis, 20:1001-1010 (1999).
Pitarch et al., "Decoding Serological Response to Candida Cell Wall Immunome into Novel Diagnostic, Prognostic, and Therapeutic Candidates for Systemic Candidiasis by Proteomic and Bioinformatic Analyses," Mol. Cell. Proteomics, 5:79-96 (2006).
Reddy et al., "Endoplasmic Reticulum Chaperone Protein GRP78 Protects Cells from Apoptosis Induced by Topoisomerase Inhibitors," J. Biol. Chem., 278:20915-20924 (2003).
Ribes et al. Zygomycetes in Human Disease, Clin Microbiol Rev 13:236-301 (2000).
Rodwell et al., "Linker Technology: Antibody-Mediated Delivery Systems," Biotech., 3:889-894 (1984).
Shackleford et al., "Construction of a clonable, infectious, and tumorigenic mouse mammary tumor virus provirus and a derivative genetic vector," Proc. Natl. Acad. Sci. USA, 85:9655-9659 (1988).
Shevchenko et al., "Linking genome and proteome by mass spectrometry: Large-scale identification of yeast proteins from two dimensional gels," Proc Natl Acad Sci U S A, 93: 14440-14445(1996).
Shevchenko et al., "Mass Spectometric Sequencing of Proteins from Silver-Stained Polyacrylamide Gels," Anal. Chem., 68(5):850-8 (1996).
Skory and Ibrahim, "Native and modiWed lactate dehydrogenase expression in a fumaric acid producing isolate Rhizopus oryzae 99-880," Curr. Genet. 52:23-33 (2007).
Skory, Curr. "Induction of Rhizopus oryzae Pyruvate Decarboxylase Genes," Microbiol., 47: 59-64 (2003).
Skory, "Homologous recombination and double-strand break repair in the transformation of Rhizopus oryzae," Mol. Genet. Genomics 268: 397-406 (2002).
Snyder et al., "Correction of hemophilia B in canine and murine models using recombinant adeno-associated viral vectors," Nature Med., 5:64-70 (1999).
Spellberg et al., "The Deferaxirox-AmBisome Therapy for Mucormycosis (DEFEAT Mucor) study: a randomized, double-blinded, placebo-controlled trial," J Antimicorbiol Chemother 67(3):715-722 (2012).
Spellberg et al., "Novel Perspectives on Mucormycosis: Pathophysiology, Presentation, and Management," Clin. Microbiol. Rev. 18:556-69 (2005).
Ventura et al., "Pneumonia With Cunninghamella Species in Patients With Hematologic Malignancies," Cancer 58:1534-36 (1986).
Wang et al., "Sustained correction of bleeding disorder in hemophilia B mice by gene therapy," Proc. Natl. Acad. Sci. USA, 96:3906-3910 (1999).
Weintraub, "Pulmonary Mucormycosis Caused by Cunnunghamella elegans in a Patient with Chronic Myelogenous Leukemia," Sci. American, Jan. 1990, pp. 40).
Wesley et al., "Construct design for efficient, effective and highthroughput gene silencing in plants," Plant J., 27:581-590 (2001).
Winter and Harris, "Humanized Antibodies," Immunol. Today 14:243-246 (1993).
Wu et al., "Detectin protein-protein interactions by far western blotting," Nat. Protoc., 2:3278-3284 (2007).
Yao et al., Functional ecdysone receptor is the product of EcR and UlNature, 366:476-479 (1993).
Ye et al., "Regulated Delivery of Therapeutic Proteins After in Vivo Somatic Cell Gene Transfer," Science, 283:88-91 (1999).
Zabner et al., "Safety and efficacy of repetitive adenovirus-mediated transfer of CFTR cDNA to airway epithelia of primates and cotton rats," Nature Genetics, 6:75-83 (1994).
UNIPROT Direct Submission I1BVT3_RHIo9 (Jun. 13, 2012) [Retreived from the internet Dec. 21, 2012: http://www.uniprot.org/uniprot/I1BVT3.txt?version=1], 100% identify with SEQ ID No. 1.
UNIPROT Direct Submission I1C4E4_RHIO9 (Jun. 13, 2012) [Retreived from the internet Mar. 20, 2013: <http://www.uniprot.org/uniprot/I1c4E4txt?cersion=1>], 100% identity with SEQ ID No. 3.
UNIPROT Direct Submission I1CFE1_RHIO9, Jun. 13, 2012 [Retreived from the Internet Mar. 20, 2013: <http://www.uniprot.org/uniprot/I1CFE1.txt?version=1>], 100% Identity with SEQ ID No. 5, 11, 30, 39, 40.
GenBank Direct Submission EE003752.ROE00007341 Rhizopus oryzae Company Rhizopus oryzae cDNA, mRNA sequence. 2006. [Retreived from the internet Mar. 20, 2013: <http://www.ncbi.nih.gov/nucest/EE003752>], nucletides 2-571 100% Identical to SEQ ID No. 2, Nucleotides 27-596.
GenBank Direct Submission EE006028.1ROE00001908 Rhizopus oryzae Company Rhizopus oryzae cDNA, mRNA sequence. 2006. [Retreived from the Internet Mar. 20, 2013: <http://www.ncbi.nlm.nih.gov.nucest/EE006028>] nucleotides 16-616, 80.4% identical to SEQ ID No. 4, nucleotides 574-1174.
GenBank Direct Submission EE006055.1 ROE00006050 Rhizopus oryzae Company Rhizopus oryzae cDNA, mRNA sequence. 2006. [Retreived from the Internet Mar. 20, 2013: <http://http:www.ncbi.nlm.nih.gov/nucest/EE006055>].
GenBank Direct Submission EE007119.ROE00012671 Rhizopus oryzae Company Rhizopus oryzae cDNA, mRNA, 2006. [Retreived from the internet Mar. 20, 2013: <http://www.ncbi.nlm.nih.gov/nucest/EE007119>] nucleotides 12-593 97.8% identical to SEQ ID No. 17, Nucleotides 18-598.

(56) References Cited

OTHER PUBLICATIONS

Isticato et al., "CotC-CotU heterodimerization during assembly of the Cacillus subtillis spore coat," J. Bacteriol., 190(4):1267-1275 (2008).
Isticato et al., "CotE Binds to CotC and CotU and Mediates Their Interaction during Spore Coat formation in Cacillus subtilis," J. Bacteriol., 192(4):949-954 (2010).
Gomes et al., "Mucormycosis caused by unusual mucormycetes, non-Rhizopus, Mucor, and *lichtheimia* species," Clin. Microbiol. Rev., 24(2):411-445 (2011).
Ibrahim, "Host cell invasion in mucormycosis: Role of Iron," Curr. Opin. Microbiol., 14(4):406-411 (2011).
Ibrahim et al., "Mucormycosis and Entomophthoramycosis (Zygomycosis)," Essentials of Clinical Mycology, 265-280 (2011).
Ibrahim et al., "Pathogenesis of mucormycosis," Clin. Infect. Dis., 54 Suppl, 1:S16-22 (2012).
Giglio et al., "Organization and evolution of the cotG and cotH genes of Bacillus subtilis," J. Bactiol., 193(23):6664-6673 (2011).
Kimura et al., "Chlamydospores of *Rhizopus microsporus* var. rhizopodiformis in tissue of pulmonary mucormycosis," Mycopathologia, 174((5-6):441-450 (2012).
Ibrahim et al., "Host-pathogen interactions during mucormycosis," Mycoses, 55(Suppl. 4): 1-56:34-35 (2012).
Aurameas et al., "Coupling of Enzymes to Antibodies and Antigens," Scand. J. Immunol., vol. 8, Suppl. 7:7-23 (1978).
Bearer et al., "Cutaneous Zygomycosis Caused by Saksenaea vasiformis in a Diabetic Patient," Journal of Clinical Microbiology 32:1823-1824 (1994).
Berkner, "Development of Adenovirus Vectors for the Expression of Heterologuous Genes," Biotechniques, 6:616-626 (1988).
Blaese et al., "T Lymphocyte-Directed Gene Therapy for ADA-SCID: Initial Trial Results After 4 Years," Science, 270:475-479 (1995).
Burcin et al., "Andenovirus-mediated regulable target gene expression in vivo," Proc. Natl. Acad. Sci. USA, 96:355-360 (1999).
Cohen et al., "Designing antisense oligonucleotides as pharmaceutical agents," TIPS, 10:435-437 (1989).
Cohen-Abbo et al., "Cunninghamella Infections: Review and Report of Two Cases of Cunninghamella Pneumonia in Immunocompromised Children," Clinical Infectious Diseases 17:173-177 (1993).
Cotten et al., "High-efficiency receptor-mediated delivery of small and large (48 kilobase gene constructs using the endosome-disruption activity of defective or chemically inactivated adenovirus particles," Proc. Natl. Acad. Sci. USA, 89:6094-6098 (1992).
Danos et al., "Safe and efficient generation of recombinant retroviruses with amphotropic and ecotropic host ranges," Proc. Natl. Acad. Sci. USA, 85:6460-6464 (1988).
DeLuca, "Immunofluorescence Analysis", in Antibody As a Tool, pp. 189-231 (1982).
Donahue et al., "Reduction in SIV replication in rhesus macaques infused with autologous lymphocytes engineered with antiviral genes," Nature Med., 4:181-186 (1998).
EMBL-EBI Direct Submission CH476740.1. Rhizopus oryzae RA 99-880 Supercontig 3.9 genomic scaffold, whole genome shot gun sequence (2005).
Galfre et al., "Production of Antibodies," Meth. Enzymol., 73(3):46 (1981).
Geller et al., "A Defective HSV-1 Vector Expresses *Escherichia coli* β-Galactosidase in Cultured Peripheral Neurons," Science, 241:1667-1669 (1988).
GenBank Direct Submission EIE87171.1 (Apr. 18, 2012) (Retrieved from the internet Dec. 21, 2012) <http://www.ncbi.nlm.nih.gov/protein/EIE87171.1>.
GenBank Direct Submission E69605. Spore coat protein (inner) cotH-Bacilus subtitils (Retrieved from the internet Mar. 20, 2013) <http://www.ncbi.nlm.nig.gov/protein/E69605?report=genpept>.
Gerbremariam et al., "Abstract WG15-3. Downregulationof CotH impairs the ability of Rhizops oryzae to invade and damage human umbilical vein endothelial cells," Mycoses, 55(4):57-94 (2012).

Geysen et al. "Use of peptide synthesis to probe viral antigens for epitopes to a resolution of a single amino acid," Proc. Natl. Acad. Sci. USA 81: 3998 (1984).
Giorno et al., "Morphogenesis of the Bacillus anthracis Spore," J. Bacteriol., 189:691-705 (2007).
Gleissner et al., "Improved Outcome of Zygomycosis in Patients with Hematological Diseases?," Leuk. Lymphoma 45(7):1351-1360 (2004).
Goldman et al., "Lentiviral Vectors for Gene Therapy of Cystic Fibrosis," Human Gene Therapy, 10:2261-2268 (1997).
Gossen & Bizard, "Tight control of gene expression in mammalian cells by tetracycline-responsive promoters," Proc. Natl. Acad. Sci. USA, 89:5547-5551 (1992).
Gossen et al., "Transcriptional Activation by Tetracyclines in Mammalian Cells," Science, 268:1766-1769 (1995).
Graham et al., "Manipulation of Adenovirus Vectors," Meth. Mol. Biol., 7:109-127 (1991).
Greelish et al., "Stable restoration of the sarcoglycan complex in dystrophic muscle perfused with histamine and a recombinant adeno-associated viral vector," Nature Med., 5:439-443 (1999).
Herzog et al., "Long-term correction of canine hemophilia B by gene transfer of blood coagulation factor IX mediated by adeno-associated viral vector," Nature Med., 5:56-63 (1999).
Huse et al., "Generation of a Large Combinational Library of the Immunoglobulin Repertoire in Phage Lambda," Science 246:1275-1281 (1989).
Ibrahim et al. Zygomycosis, p. 241-251, in W. E. Dismukes, P. G. Pappas, and J. D. Sobel (ed.), Clinical Mycology, Oxford University Press, New York (2003).
Ibrahim et al., "Liposomal Amphotericin B, and Not Amphotericin B Deoxycholate, Improves Survival of Diabetic Mice Infected with Rhizopus oryzae," Antimicrob. Agents Chemother., 47:3343-3344 (2003).
Ibrahim et al., "Caspofungin Inhibits Rhizopus oryzae 1,3-β-D-Glucan Synthase, Lowers Burden in Brain Measured by Quantitative PCR, and Improves Survival at a Low but Not a High Dose during Murine Disseminated Zygomycosis," Antimicrob. Agents Chemother., 49:721-727 (2005).
Ibrahim et al., "Rhizopus oryzae Adheres to, Is Phagocytosed by, and Damages Endothelial Cells In Vitro," Infect. Immun. 73:778-783 (2005).
Ibrahim et al., "Adherence to and Damage of Endothelial Cells by Cryptococcus neoformans In Vitro: Role of the Capsule," Infect. Immun., 63:4368-4374 (1995).
Ibrahim et al., "The iron chelator deferasirox protects mice from mucormycosis through iron starvation," J. Clin. Invest., 117:2649-2657 (2007).
Ibrahim et al., "Bacterial Endosymbiosis is Widely Present among Zygomycetes but Does Not Contribute to the Pathogenesis of Mucormycosis," J. Infect. Dis., 198:1083-1090 (2008).
Ibrahim et al., "The high affinity iron permease is a key virulence factor required for Rhizopus oryzae pathogenesismmi_7234 587.. 604," Mol. Microbiol., 77:587-604 (2010).
Isberg and Leong, "Multiple PI Chain Integrins Are Receptors for Invasin, a Protein That Promotes Bacterial Penetration into Mammalian Cells," Cell 60:861-871 (1990).
Jaffe et al., "Culture of Human Endothelial Cells Derived from Umbilical Veins," J. Clin. Invest. 52:2745-2756 (1973).
Kafri et al., "Sustained expression of genes delivered directly into liver and muscle by lentiviral vectors," Nature Genetics, 17:314-317 (1997).
Kamalam and Thambiah, "Cutaneous Infection by Syncephalastrum," Sabouraudia 18:19-20 (1980).
Kemna et al., "Cokeromyces recurvatus, a Mucoraceous Zygomycete Rarely Isolated in Clinical Laboratories," Journal of Clinical Microbiology 32:843-45 (1994).
Kohler and Milstein, "Continuous cultures of fused cells secreting antibody of predefined specificity," Nature 256:495-499 (1975).
Kontoyianis et al., "Infections Due to Cunninghamella bertholletiae in Patients with Cancer: Report of Three Cases and Review," Clinical Infectious Diseases 18:925-928 (1994).
Kontoyiannis et al, "Zygomycosis in the 1990s in a Tertiary-Care Cancer Center," Clin. Infect. Dis. 30(6):851-856 (2000).

(56) References Cited

OTHER PUBLICATIONS

Kwon-Chung et al., "Pulmonary Mucormycosis Caused by Cunninghamella elegans in a Patient with Chronic Myelogenous Leukemia," American Journal of Clinical Pathology 64:544-548 (1975).

Kwon-Chung, K. J., and J. E. Bennett, Mucormycosis, p. 524-559, Medical Mycology, Lea & Febiger, Philadelphia (1992).

Lee et al., "Glucocorticoids regulate expression of dihydrofolate reductase cDNA in mouse mammary tumour virus chimaeric plasmids," Nature, 294:228-232 (1981).

Li et al., "Assessment of Recombinant Adenoviral Vectors for Hepatic Gene Therapy," Human Gene Therapy, 4:403-409 (1993).

Liu et al., "The endothelial cell receptor GRP78 is required for mucormycosis pathogenesis in diabetic mice," J. Clin. Invest. 120:1914-24 (2010).

Luban et al., "The yeast two-hybrid system for studying protein-protein interactions," Curr. Opin. Biotechnol. 6:59-64 (1995).

Lye et al., "Subcutaneous Zygomycosis Due to Saksenaea Vasiformis: Rapid Isolate Idenification Using a Modified Sporulation Technique," Pathology 28:364-365 (1996).

\* cited by examiner 18 putative glycosylation sites with 10-N-linked and 8-O-linked sites.

|  | CotH1 | CotH2 | CotH3 | RO3G_16295 |
|---|---|---|---|---|
| CotH1 |  | 46% | 46% | 10% |
| CotH2 |  |  | 78% | 10% |
| CotH3 |  |  |  | 9% |
| RO3G_16295 |  |  |  |  |

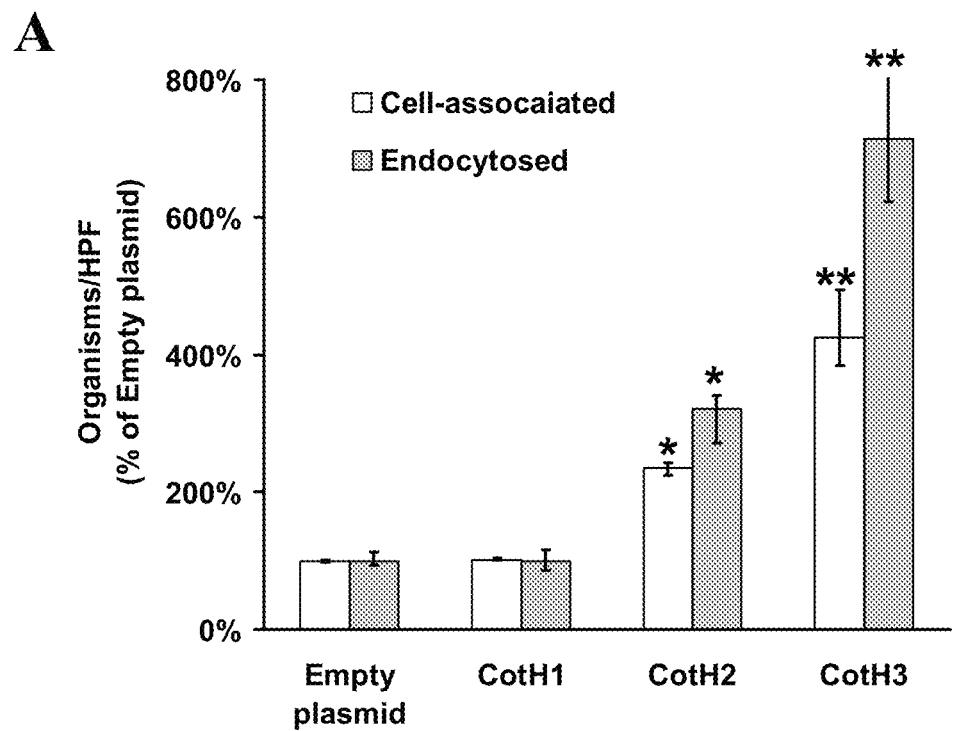
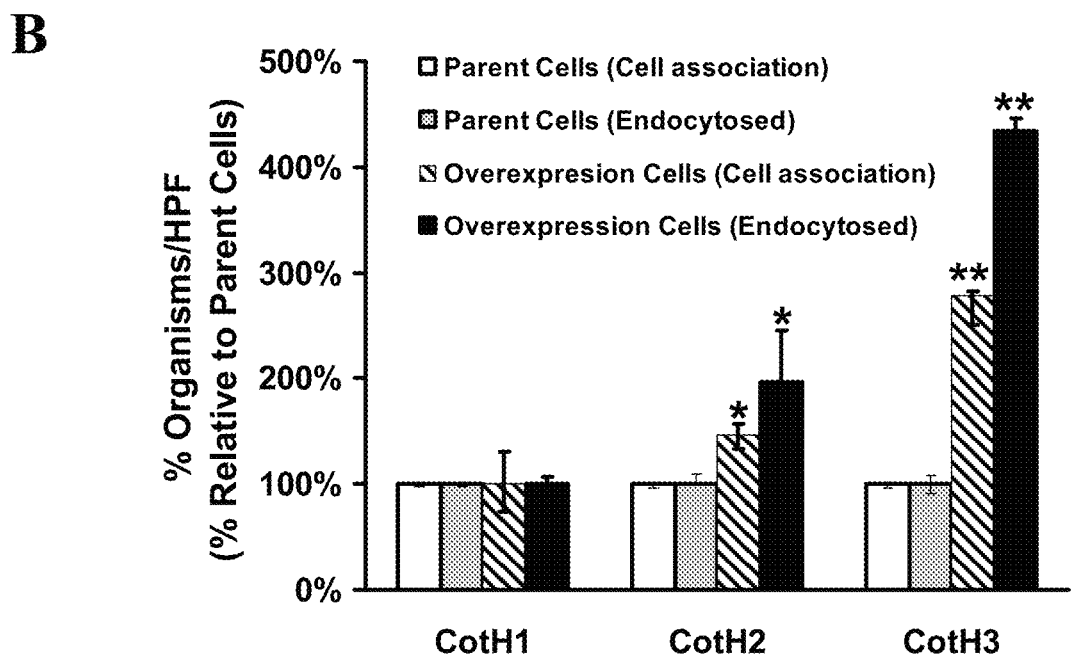
FIGURE 8

>CotH1 (RO3G_05018) (mw=68.77)
MKSLLFVVFIFLTTTYAAKVSFKVIAPDAKNRVHVNINGVLVELKASDPDVPYYTGFAELKHGQSY
NYVVDGNAEPFKRLLNGSSTKNEFFNRPVTYATNIPELPSILTEGSWTRGDTSNPIWDSNYVPSIF
VTGNPREMNELIENVKKNTYKTKITFIGPETINTFEGCTLGLHKPGRKHNDAKQSWIWALPEGQFM
ANRNWFKIRHMEEDPTQLREKLYADILRKMGTYANEANMVRFFINKEGMGIFNMLDDVIMYSYINA
MFYHGDTPEQLGGLYDGASGASFNFPGDFDSFIPNVESPLDQDAIEPFSKAFTSIDFLEDEQVKTI
GKYFDYDQFLRFMVMEFLTGDWDGYWQEQTNDGAYIDINDHNKIYYLGQDFDATFGVNLEQKREFV
NVSYTEYPKLFPGGVLINRLLQNPGVKKTFENYLKITVQEIFNNATLGPYVTARHEFLAPDLQWDR
SIKQRSPGNIFGWTFEQTYENLFEGVTAPGKNSGGADWGLLEWVAAKEKAVKSYLSSSEAADAATV
TQVPEAPGTDGTPSESTAWPHANTRFRQAEASNTHKIGTSSPSNFIVKIKQGTVSSSSSIKRTPCI
LPLVILASTLFASFF*

Coding sequence (exons only):1830nt

ATGAAATCCCTACTTTTTGTTGTATTCATCTTTTTAACAACAACATATGCCGCTAAAGTATCATTT
AAAGTTATCGCTCCTGATGCTAAAAACAGAGTTCATGTCAATATCAATGGAGTACTTGTCGAATTA
AAGGCCAGTGATCCAGATGTTCCTTACTACACCGGTTTTGCTGAACTAAAGCATGGACAAAGTTAT
AATTACGTTGTCGATGGAAATGCAGAGCCATTCAAACGTCTATTGAATGGCTCTTCTACTAAAAAC
GAGTTCTTCAATCGACCTGTAACCTACGCTACCAACATTCCCGAGCTACCCAGCATTCTTACTGAA
GGTAGCTGGACTCGTGGAGATACGAGTAATCCTATTTGGGATAGTAACTATGTCCCTTCTATCTTT
GTCACTGGAAATCCAAGGGAAATGAATGAATTAATTGAGAATGTGAAAAAGAACACATATAAAACA
AAAATCACTTTTATTGGACCTGAGACTATCAACACATTTGAGGGTTGTACCCTTGGACTTCATAAA
CCTGGGCGTAAACATAATGATGCTAAACAATCTTGGATATGGGCTCTCCCTGAAGGTCAATTTATG
GCGAATCGAAATTGGTTTAAGATTCGACATATGGAAGAAGATCCTACACAACTTCGTGAAAGCTT
TATGCAGATATCCTTCGAAAGATGGGAACCTATGCGAATGAGGCCAATATGGTTCGATTCTTTATA
AACAAGGAAGGCATGGGTATCTTTAATATGTTGGACGATGTTATTATGTATTCTTATATTAATGCC
ATGTTTTACCACGGTGATACTCCTGAACAGCTCGGTGGTCTTTACGACGGTGCCTCTGGTGCCTCA
TTCAATTTTCCTGGTGACTTTGATAGCTTCATCCCGAATGTCGAATCCCCGCTTGACCAAGATGCT
ATCGAGCCTTTTTCTAAAGCCTTTACTAGTATTGACTTTTTGGAAGACGAACAGGTCAAGACGATC
GGAAAGTATTTTGATTATGACCAATTCCTTCGTTTCATGGTCATGGAGTTCCTTACCGGTGACTGG
GATGGCTACTGGCAAGAGCAAACAAATGATGGGGCCTATATTGATATCAACGACCACAACAAAATT
TATTACTTGGGGCAGGATTTTGACGCCACCTTTGGTGTAAATCTTGAACAAAAACGAGAGTTTGTC
AATGTGTCTTATACTGAATACCCCAAACTGTTTCCTGGAGGTGTCTTGATCAACAGACTTCTTCAA
AACCCAGGTGTCAAGAAACGTTTGAAAACTATCTGAAAATCACAGTACAAGAGATCTTCAACAAC
GCCACGCTCGGCCCCTATGTCACTGCTCGCCACGAATTCCTTGCTCCAGATCTTCAGTGGGATCGT
TCGATAAAACAACGGTCTCCTGGAAATATCTTTGGTTGGACGTTCGAGCAGACATATGAAAATCTA
TTTGAAGGTGTCACTGCTCCTGGAAAAAACTCGGGTGGTGCTGATTGGGGTCTTCTTGAATGGGTG
GCTGCAAAGGAAAAGCAGTCAAAAGTTACCTCAGTTCGTCTGAAGCCGCTGATGCTGCCACTGTT
ACGCAAGTACCAGAAGCTCCTGGTACAGATGGCACTCCTTCCGAATCAACTGCCTGGCCTCATGCC
AATACAAGGTTCAGACAAGCCGAAGCTTCTAATACTCATAAAATAGGCACCTCATCGCCTTCTAAT
TTTATTGTTAAAATCAAGCAAGGTACTGTGTCATCGTCTTCATCTATCAAAAGAACCCCATGTATT
CTACCTCTTGTTATCTTG GCTAGCACTTTATTTGCCTCTTTCTTCTAG

FIGURE 9

>CotH2 (RO3G_08029) (mw=65.26)
MKLSLTIVSSSFLVAIAHAASVQFNLIAPSATDVKVSVNGQQVALTASDPNVPYFTGSAEVGGTEE
SFERSLAGITNSTFNDFYNRPVTYANLPQLPWPIENDPQWTRKGKKAEIFDDNYIPSVFFHGDDSQ
VQDLVKNVPKDKVTGTLTFIGSNYVHSFANVSFGIHGAGKKHNNAKQSWKWTLSGTDTMGNRNHFK
LRHMEEDPTQIRERLYADILHAMGTYANETTMVRLFINGQGFGTFNMLDDITEFSYINAMFYGGNP
PATLGPLFDGASGADFIYHPGNLDGYSSWKPNKDNANGEGYEAFDPLCKAWNETDYTDNTAIANFE
KMFDTEHFLRFMVIEYLTAHWDGYWMGQTNDGAYRDPSDNNKWYFLDQDFDATFGVNLDVPENKDF
ISVSYKDFPSRYPAGVMANGLLQNADKKAKFEQYLTETVRVLFNNVTLTNRVLAIHNFLSPDLEWD
RSIVQQSPGTNFGWTFEQTSQNLWQGVSAPNNNGGGAEWGLVEYIAAKSQAMAKEFNITIVSEPVG
PPAANGTATSTNDGGNTHTAAGESKPASSSESSGSKIASQSVSGASRSAVSTVLLGVTALVATAIF
*

Coding sequence (exons only):1785nt

ATGAAATTATCACTCACTATAGTATCCTCTTCATTTTTAGTAGCCATTGCACATGCTGCTTCAGTA
CAATTCAATTTAATTGCTCCAAGTGCAACTGATGTCAAAGTATCTGTAAATGGACAGCAGGTTGCC
CTTACAGCTTCAGACCCTAATGTGCCTTATTTCACCGGATCTGCTGAAGTTGGTGGAACTGAAGAA
AGCTTTGAGCGTTCTCTCGCTGGTATTACAAACTCCACATTAATGATTTTTATAACCGTCCTGTT
ACTTACGCTAACCTTCCTCAATTACCATGGCCAATTGAAAATGATCCACAATGGACTCGCAAAGGA
AAGAAAGCTGAAATATTTGACGACAACTACATCCCCTCCGTATTCTTTCACGGTGATGATAGCCAA
GTCCAAGATTTGGTTAAAAATGTGCCCAAAGACAAGTTACTGGCACCTTGACTTTCATTGGGTCC
AATTACGTTCATTCTTTCGCAAATGTCTCCTTTGGAATTCATGGTGCAGGAAAGAAGCACAACAAT
GCAAAGCAATCCTGGAAGTGGACCTTGTCTGGTACTGATACTATGGGCAACCGTAACCATTTTAAG
CTTCGTCATATGGAAGAAGATCCTACACAGATCCGTGAACGTCTTTATGCTGATATATTGCATGCT
ATGGGAACCTATGCCAATGAGACCACTATGGTCCGATTGTTTATTAACGGTCAAGGTTTTGGTACC
TTCAACATGCTAGACGATATTACTGAATTTTCTTACATCAATGCCATGTTCTATGGTGGTAATCCT
CCTGCTACTTTAGGACCTCTATTTGATGGTGCAAGCGGTGCAGACTTTATTTACCATCCTGGTAAT
CTCGATGGTTATTCCTCTTGGAAACCTAATAAGGACAACGCAAACGGTGAAGGCTATGAGGCCTTT
GATCCTCTATGTAAGGCTTGGAACGAAACCGACTATACCGATAACACAGCCATTGCCAACTTTGAA
AAAATGTTTGATACCGAGCACTTTTTACGATTCATGGTGATTGAATATCTAACTGCTCACTGGGAT
GGTTATTGGATGGGACAGACCAACGATGGTGCTTATCGTGACCCAAGTGACAATAACAAGTGGTAC
TTTTTGGATCAAGATTTTGATGCCACATTTGGTGTCAATTTGGACGTTCCTGAGAATAAAGACTTT
ATCAGTGTCTCCTACAAGGATTTCCCATCTCGTTACCCTGCTGGTGTCATGGCCAATGGTCTCTTA
CAGAATGCTGATAAAAAGCCAAGTTTGAACAGTACTTGACTGAAACTGTTCGCGTCTTGTTCAAT
AATGTCACTTTGACTAATCGTGTCTTGGCTATCCACAACTTCCTCTCTCCTGATCTTGAATGGGAT
CGATCCATCGTTCAACAGTCGCCTGGTACTAATTTTGGATGGACCTTTGAGCAAACTTCTCAAAAC
TTATGGCAAGGTGTCTCAGCCCCAAATAACAACGGAGGTGGTGCTGAGTGGGGCTTGGTTGAATAT
ATCGCAGCAAAATCCCAAGCCATGGCTAAGGAATTTAATATCACTATTGTCTCTGAACCTGTAGGT
CCTCCTGCTGCTAATGGAACTGCAACTTCTACTAATGATGGTGGTAACACTCATACCGCTGCCGGA
GAAAGTAAGCCTGCCTCAAGTTCTGAATCTTCCGGTTCGAAAATTGCTTCTCAAAGCGTATCAGGT
GCTTCCCGTTCTGCTGTATCTACCGTCTTATTAGGTGTTACAGCTTTAGTTGCCACTGCTATCTTT
TAA

FIGURE 10

>CotH3 (RO3G_11882) (mw=65.77)

MKLSIISAAFLVAITHAASIKFNVIAPNATDVKVSVNGQQVTLTASDANVPYFTGSAEVGASKTYK
YVAGGTEESFDRSLDGITNSTLNDFYNRPVTYANLPQLPWPIEKDPQWTRSGSKADIFDDNYIPSV
FFHGDDSQVQNVVKNVPADRISGTLTFIGSNYVYSFQNVSFGIHGAGKKHNNAKQSWNWILSGSDT
MGNRNFFKLRHMEEDPTQIRERLYSDILHAMGTYANDATMVRLFINNQGFGTFNMLDDITQFSYIN
AKFYNGKPPATLGPLYDGASGADFLYHPGNLDGYSSWVANTANPNGEAYEALDPLCKAWNETTYTD
NTAIANFEKMFDLDRFMRFMVIEYLTADWDGYWMGQTNDGAYRDPTDNNKWYFLDQDFDGTFGVNL
AAPEGNAFLDVSYKDFPSRYPGAVMINNLLQNADKKATFEKYLTETVRVLFNNVTLTNRVLALHNF
LLPDLEWDRSIVQQSPGINFGWTFDQVTQNLWQGVTAPNNNGGGAAFGLVEYIAAKAQAVAKEFNI
SIVSQPVGPPSANGTTAAAPAPAAGNSTGKGGNQSISSSASSNKTSAQSTSGASRSKTAPIVLAIS
ALALLVF*

Coding sequence (exons only):1806nt

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
TATGTTGCAGGTGGAACAGAAGAAAGTTTTGATCGTTCTCTTGATGGAATCACAAACTCAACACTT
AATGATTTTTATAACCGCCCCGTCACTTATGCTAACCTTCCTCAATTACCTTGGCCAATTGAAAAA
GACCCTCAGTGGACTCGTTCTGGAAGCAAAGCCGACATTTTCGATGACAATTATATTCCCAGCGTT
TTTTTCCACGGAGATGACAGTCAAGTCCAAAATGTGGTTAAAAACGTACCTGCTGACCGAATCAGT
GGTACACTGACCTTTATTGGATCTAATTACGTCTACTCTTTCCAGAATGTCTCATTTGGTATTCAC
GGTGCTGGCAAGAAACACAACAATGCAAAACAATCTTGGAACTGGATATTGTCTGGAAGTGATACG
ATGGGTAACCGCAATTTCTTTAAGCTTCGACATATGGAAGAAGATCCTACACAGATTCGTGAACGT
CTTTATTCTGACATTTTACATGCCATGGGTACTTATGCCAATGATGCTACCATGGTTCGATTGTTT
ATTAACAACCAAGGCTTCGGTACCTTCAACATGTTGGATGATATCACTCAATTCTCCTATATCAAT
GCTAAATTTTATAATGGCAAACCACCTGCTACCTTGGGTCCTCTCTATGATGGTGCCTCTGGTGCA
GACTTCTTATATCATCCTGGTAACCTCGATGGATACTCTTCTTGGGTTGCCAACACAGCCAATCCT
AATGGTGAAGCTTATGAAGCTCTTGATCCTCTCTGTAAGGCCTGGAACGAGACGACCTATACCGAT
AATACAGCCATTGCAAACTTTGAAAAAATGTTTGATCTCGACCGTTTCATGCGTTTCATGGTTATT
GAATACTTGACTGCCGATTGGGATGGTTACTGGATGGGACAGACCAATGATGGTGCCTATCGTGAT
CCAACTGATAATAACAAGTGGTACTTTTTAGATCAAGACTTTGATGGTACTTTTGGTGTCAACTTG
GCTGCACCCGAAGGCAATGCTTTTCTTGATGTTTCTTACAAGGATTTCCCTTCTCGTTACCCTGGC
GCTGTCATGATCAACAACCTCTTACAGAATGCTGATAAAAAGGCCACCTTTGAAAAATATTTGACT
GAGACTGTGCGTGTGCTGTTCAATAATGTCACCTTGACTAACCGTGTCTTGGCCCTTCACAACTTC
CTCTTGCCTGATCTTGAATGGGATCGTTCGATCGTTCAACAATCTCCTGGTATTAACTTTGGTTGG
ACATTTGATCAAGTCACTCAAAACTTGTGGCAAGGTGTCACTGCACCCAATAACAATGGAGGTGGT
GCTGCTTTTGGTTTAGTTGAATATATTGCTGCAAAGGCACAAGCTGTAGCTAAGGAATTTAATATT
TCTATCGTTTCCCAACCTGTTGGCCCTCCTTCTGCTAATGGTACTACTGCTGCTGCTCCTGCTCCT
GCTGCTGGCAATTCTACTGGAAAAGGAGGAAATCAATCTATTTCTAGCAGTGCTTCATCCAACAAA
ACCTCGGCTCAAAGCACATCAGGTGCTTCTCGTTCCAAGACTGCGCCCATCGTTTTAGCCATTTCC
GCTTTAGCTCTCCTTGTATTCTAA

MIATPFEMFQCQMYILCLVLIAFSFTCVNTQQLCNGYAEYCNKPYNSLTYLLTHNSYGYVSNPAAN
QLCPITTQLADGVRGIKLSAVKATNATTDGTITADSIYLCHTSCIILNAGPAVNTLRTIKEWVEQN
PNEVVTIMWNNVDAFDGNAFEAAYNASGIIEYSYQQPKKNYTWPTLGELIASGKRVINFGDTYYQQ
DLPWLLTEYDYVFETPYENHNESSFSCTIDRPQDPASPTEFLYVMNHFLYGSLQLGSLPIEIPQKG
IANTTNSDNSLMKQAKTCTEKFGRQPNFLEIDFYNLGDALKITAELNNVTYKGSGSLQCDTYAAQQ
ASSSSTDSSEAIQTISISSVSLLLTLIAATFFIFF*

Coding sequence (exons only):1098nt

ATGATTGCTACCCCTTTTGAAATGTTTCAATGTCAAATGTATATTTTATGTTTAGTACTCATTGCA
TTTTCATTTACTTGTGTCAATACTCAACAGCTCTGTAATGGGTATGCAGAGTATTGTAATAAGCCT
TACAACTCGCTCACCTACCTCTTGACACATAATTCATATGGTTATGTATCTAACCCTGCTGCTAAT
CAACTCTGTCCTATCACTACTCAACTTGCAGATGGTGTTCGAGGCATCAAGCTGTCAGCCGTTAAA
GCAACAAATGCAACTACAGATGGTACCATTACAGCGGACAGCATTTATCTTTGTCACACATCGTGT
ATTATATTAAATGCTGGTCCAGCAGTCAATACCCTTCGTACGATTAAAGAATGGGTCGAGCAAAAC
CCTAATGAAGTAGTGACAATCATGTGGAATAATGTGGATGCCTTTGATGGGAATGCATTTGAGGCT
GCTTATAATGCAAGTGGTATCATTGAATATAGTTATCAGCAACCTAAAAAAAACTATACTTGGCCA
ACGTTAGGTGAATTAATTGCTAGTGGAAAAAGAGTAATTAATTTTGGTGATACTTATTATCAACAG
GATCTTCCCTGGTTATTAACAGAATATGATTATGTGTTCGAGACACCTTATGAAAATCATAACGAA
AGTTCATTTAGTTGCACTATTGATCGACCTCAAGATCCTGCCAGCCCAACCGAATTCTTATACGTC
ATGAACCATTTTTTGTATGGTTCACTTCAATTGGGTTCACTACCTATCGAGATACCTCAAAAAGGC
ATAGCCAACACAACCAACTCTGATAATTCGCTCATGAAACAAGCTAAAACATGTACCGAGAAATTT
GGTCGTCAACCCAACTTTTTAGAAATAGATTTTATAACCTGGGTGATGCACTCAAGATTACTGCA
GAATTAAACAATGTCACCTACAAAGGTTCAGGAAGTTTGCAGTGTGATACATATGCTGCTCAACAA
GCAAGTAGTTCAAGTACAGACTCATCCGAAGCAATTCAAACAATTAGTATTAGTTCAGTTAGTTTA
CTATTAACTTTAATTGCTGCAACATTCTTTATTTTCTTTTAA

FIGURE 12

```
RO3G_11882    SKLSIISAAFLVAITRAASINFTVIAPNATIYKVSVKQQVTLEASDANVPYFTGSAEVGASNTIKYVAGGTERSPDRSL
Stigmatella   MPEKFLETPEDTEEASVCLETLRGPNSTYRPLVIA   SLLLSPCLLPTADGDGEKGGEPPPD   AGNPEEAGVEDA
                                **           *              *    *    *    *           **

RO3G_11882    DGITNSTLNDFINRPVTYANLPQLFWPIEKEPQSTRSGENADIFDSNYIPSYFEEGDSQVQNYVKNVPADHISGTLFFI
Stigmatella   GGPSEGDAGDGGESPDAGGRGEPDAGEDGGETDGEETREPAEPLFEGRHISRFEINLSQEALASLQAEPDEYVEGALKLQ
                *                    *             *            **           *  *   *

RO3G_11882    GSNIVYSPQNVSPGIEGACENHEPAKQSWEEILEEBDTESNPEF   FELASMEEDPTQIPERLYSDILKAMSTYANDA
Stigmatella   VGEAQSIDLPKVGVELEGQLGSERFLEQKAAFVLNFGRFVEQNLPELKKLTLEMMVQDPEEIEERLGTRLFEAMEVEAPRA
                *       *       *                  *      *   **  * ***       **   *  *

RO3G_11882    TGVRLFINPQGFGTFEPQLGDTTQFEYIERAKFYNGEPPRTIGPLYGASGARDFLEPGELGGISSNPANTANPEGEAFEAL
Stigmatella   AERPIPHINGALYGLYFALESFIDNSVFLKEEFGERN           GNLYEGQEGSDLY     LEEEATYEQDKGEDYG    FEEL
                **     *         *             *         * **  *   *         *            *           *

RO3G_11882    DPLCKAEWETTVTDENTAIAENPEKMFDLDEEMRFNVIEYLTAEWDGYEEEQFTNDGAYREPTDEEKWYFLDQDFDGTFGVEL
Stigmatella   TELAKALEQSTEPE  TFLEDVEQVIDLDEYLRFAATELFIEEWDGYVEYREENFYLYRAPSDG   EWVFIEWGIDQTFGEIV
                * **   *    *          ***     **   *      ****         *    ** * *      *     * ***

RO3G_11882    AAPEGESFLD  VSTKDFPSRYPGAVEIEELLQEADERASFEKYLIETVRYLFNNVTLTERVLAIKEPLLFELEEERSIVQ
Stigmatella   GYESSAHGRLQPMCIESLPCRYPIAQAYEQVLIPVEELSNVEQAEEELGI  FLETDVQEDPRKEVDVGTVTEEMTERIDFLK
                         *       ***   *      *              *              *   *   *

RO3G_11882    QEPGEEPGWEEDQGVTQEELMQGVTAPEEEGGGEAAF   GLVEYIAAEAQEVAEEDFN  ISIVEQPVEEPEENGTTAAEEAP
Stigmatella   NRPTDVPLRLGCVDFNGCEECERGELAPAPGGGRIAFCPGTVENAAAEADCVAQEGRLVSIELQPEQTAVEAGAPALSTGPEE
                       *                        **  **   **   *  *     **   **      **   *    *

RO3G_11882    AESNETEKGGNQSISSEASESNFTSEQSTEEGAEPEEKTEEFIVLAEEAEALEVE
Stigmatella   IGLSEEAEEGYPAESDQTPINPTLEATEEFFNQERSDGVQLIEEAEFTWEEVTEEPTASYVTELEPP
                  *    *     * *                              *    *
```

Total alignment length :626
Overall identity :     18.05 % (113/626)

FIGURE 17

```
RO3G_16295      MRSLMIVATLLTGALASTTTASTTTSSATDTAAIVTLSGTVDPLSLEGATGSVTYPSVT
Talaromyces RO3G_16295                                                 MIATPFEMPQCQMYILCLVLIA
Talaromyces     TTITLSTPKDSKTSTGTGTRSGNVTDAYTTTSGTVEMLVGSQGTSTLAPNATALRNSTAT
                                                                              *
RO3G_16295      FSFTCVNTQ QLCNGYAEYCNKPYNSLTYLLTHNS YGYVSNPAANQLCPITTQLADGVR
Talaromyces     TSTTPLPTNTQPCNGYVEPCARNYSNITYVAAHNSPFDRKGNIASNQQYSVTTQLNDGIR
                *  *    *  * **** * *   *   **   ***      * * **    **** ** *
RO3G_16295      GIKLSAVKATNATTDGTITADSIYLCHTSCIILNAGPAVNTLRTIKEWVEQNPNEVVTIM
Talaromyces     MLQFQA    ELQNGTIR    LCHTSCDLLNVGPLSEYLTTVIRWLNNNPYEVITIL
                           ***        ******  ** **     * *     * ** ** **
RO3G_16295      WNNVDAYDGNAFEAAYNASGIIEYSYQQPKENYT  WPTLGELIASGKRVINFSD TYY
Talaromyces     MGNYDLVGVGNFTAPIIRSGLSRYVYTPPKIPMSLNDWPVLSELILTQKRVIIFMDYNAN
                * *     * *    ** *  *  ** *       *  ** * ***  **** * *
RO3G_16295      QQDLPWLLTEYDYVPETPYENRNESSFSCTIDRPQD  PASPTEFLYVMNHPLYGSLQLG
Talaromyces     QTEVPYILDEFTQMWETPF SPTEFAFPCTVQRPPNLSPESAKQILYMANHNLNVEISFS
                *        *     ***    *  *     ** *  *         **   **  *
RO3G_16295      SLPIEIPQKGIANTTNSDN   SLMKQAKTCTEKFGRQPNFLEIDFYNLGEA   LKIT
Talaromyces     GLDLLIPNTAVLNETNGVSGYRSLGLMANSCTTTWGRPPNFLLVDYYNEGSSPGSVPEVA
                 *  **   *  **  **     *  *   *  *   ** **** *  **  *
RO3G_16295      ASLNNVTYKGSGSLQCDTVAAQQASSSSTDSSEAIQTISISSVSLLLTLIAATPFIFF
Talaromyces     ASNNNVTYNGH    CCGSNTSGALRLQTPDAVWMFVVAALSVLLCMN
                ** *****  *                  *           *   * **

Total alignment length: 478
Overall identity :25.94 % (124/478)
Inner consensus gaps : 39
Sequence lengths:
RO3G_16295 365
Talaromyces 453
```

FIGURE 18

```
RO3G_16295.3
Penicillium    MPSLWMAVRLLTSRLVQSTTAASSSSSTLSSASDTDSAGIVTLSGTVDPLSIDGATGSVT RO3G_16295.3                                               MIATPPEMFQCQMYILCLVLIA
Penicillium    YPSVTTTITLSTDSSTISGTVTNTTDVTTTTVLVGSQAATILAPNATASINSTTATGTA
                                                                                *
RO3G_16295.3   FSFTCVNTQQLCNGYAEFCNKPYNSLTYLLTHNS  YSYVSNPAANQLCPITTQLADGVRG
Penicillium    TTAPLPTNTQPCNGYVEFCARNYSNITYVAAHNSPFNRQGNIASNQQYPVTTQLNDGIRM
                    * ****   * *       *   **    ***      *  * **  * **** ** *
RO3G_16295.3   IKLSAVKATNATTDSTITADSIYLCHTSCIILNAGPAVNTLRTIKEWVEQNPNEVVTIMW
Penicillium    LQFQV          RLQNGSLYLCHTSCDLLNVGTLQDYLTTVTRWLNNNPYEVITILM
                              * *******  **  *          * *     ** ** **
RO3G_16295.3   RNVDAFDGNAFEAAYNASGIIEYSYQQPKKNY   TWPTLGELIASGKRVINFGD  TYYQ
Penicillium    GNYDLIGVGNFTDPIVNSGLSKYAYQPPKIFMGLDDWPMLSELILTQKRAIIFMDYNANQ
                 *  *       *      **   * **  **        **  ***   **  *    *
RO3G_16295.3   QDLPWLLTEYDYVPETPYENHNESSFSCTIDRPQDPASPT  EPLYVMNHPLYGSLQLSS
Penicillium    TEVPYILDEFTQSWETPF SFTDPNFPCTVQRPPNLSTERAKSIMYMANHNLNVEISFSG
                 * *       ***     **   * *   ***                 ** **
RO3G_16295.3   LPIEIPQKGIANTTNSD  NSLMKQAKTCTEKFGRQPNFLEIDFYNLGD    ALKITA
Penicillium    LDILIPNTAVLNSTNSVPGYRSLGLMANNCTATWGRFPNFLIVDIYNNGNFPSSVFQVAA
                * * **     * **       **  *  **    ** **** *  **  *        *
RO3G_16295.3   EINNVTYKGSGSLQCDTYAAQQASSSSTDSSEAIQTISISSVSLLLTLIAATFFIFF
Penicillium    ENNNVTYSGNCCRSMASGALRLBIPGKWNFAMAVSAFLFI
               * ***** *        *              *
```

Total alignment length: 477
Overall identity  :24.11 % (115/477)
Inner consensus gaps : 41
Sequence lengths:
RO3G_16295.3 365
Penicillium 449

FIGURE 19

```
RO3G_16295.3
Aspergillus        MRLIAHLLPLLAVGVWFSLAKDDSTTTTTTTGNNGGLTLRGTVTSSISEATLPTGKYLSY RO3G_16295.3                                                    NIATPPEMFQCQMY
Aspergillus        TTTMTLDDGHTVTSTGAKSATTTSNSTTTSGNFTTTVTSSSQSLTLLVGRQTGGVNGTNA RO3G_16295.3       ILCLVLIAFSFTCVNTQQLCNGYAEYCNKFYNSLTYLLTHNS  YGYVSNPAANQLCFITT
Aspergillus        TTTATSTASSTFVVNTQF CNGRAEFCAREYSNITNVAAHNSPFVKPGNAAANQALKVTA
                           *  *   ****  *** **  *   *    ***    *  ****    *

RO3G_16295.3       QLADGVRGIKLSAVKAENATTDGTITADSIYLCHTSCIILNAGPAVNTLRTIKEWVEQNP
Aspergillus        QLDDGIRMLQFQTHLVNN          TLYLCHTSCELLNSGPLEDYLTTVTKWVKTHP
                   ** ** *                     *******  ** **   *  **   *  *

RO3G_16295.3       NEVVTIMWNNVDAFDSMAFEAAYNASGIIEYSYQQPKKNYT  WPTLGELIASGKRVIN
Aspergillus        YDVVTILIGNYDYVDPSNPTGPMQNSGLMDYVFTPSKIPMALEDWPTMSSKILSGKRAVV
                    ****       *  *       **  *       ***   *** * ****

RO3G_16295.3       FGDTYYQQDL PWLLTEYDYVFETPYEMHKESGFSCTIDRPQDPASFT  EFLYVMNHFL
Aspergillus        FMDYQANQTAYPWLMDEFSQWETPF SPTDAAFPCTEQRPPDLSAQDAKDRMYMANHNL
                   * *         *** ** *  ***   *  *** **  **     *     * ** *

RO3G_16295.3       IGSLQLGSLPIRIPQEGIANTTNSDN   SLMKQAKTCTEKFGRQPNFLEIDFYNLGD
Aspergillus        NLDINIASISLLIPNTASLNQTNAVSGYGSLQKMARNCTAKWDRPPNFLLVDYYNYGNIN
                       * **     * **    *  *      ** *  * **  * ****  * **  *

RO3G_16295.3        ALEITAELNNVTYEGSGSLQCDTYAAQQASSSSTDSSEAIQTISISSVSLLLTLIAAT
Aspergillus        GSVFEVAAEMNNVTWDG    KC CGAASAASSVMFGVSVMSTLLLIAGVQYMASIF
                       ** ****  *       *   **  ***   *      **         *   *

RO3G_16295.3       PFIFF
Aspergillus

Total alignment length: 485
Overall identity  :25.15 % (122/485)
Inner consensus gaps : 38
Sequence lengths:
RO3G_16295.3 365
Aspergillus 460
```

FIGURE 20

```
RO3G_16295.3      MRLTWLLTLLAASPVLSQNTDSDSDSDSDSSTTTDSNEEAISQSLAEIASAITTTVDDAT
Aspergillus RO3G_16295.3                                                                  NIAT
Aspergillus       VPSGDYITYSTTVYLTSTHGTVIGSTAVQVTGTPNANATTSANATITSTSDTVTVLIGGQ RO3G_16295.3      PFEMFQCQMYILCLVLIAFSFTCVNTQQLCNGYAEYCNKFYNSLTYLLTHNS YGYVSNP
Aspergillus       TTISGNSTGNSTHSATFSPSQTFVVNTQPCNGWFEFCIRKYSNITQVAAHNSPFVAQGNV
                   *  *     *  ***  *  *     *     ***       *

RO3G_16295.3      AANQLCPITTQLADGVRGIKLSAVKAENATTDGTITADSIYLCHTSCIILNAGPAVNTLR
Aspergillus       AANQALDVHYQLDDGVRMLQFQT         HISNGTRYLCHTSCDLLNVGPLEDYLS
                  ****    ** ****                        *******  **  **     *

RO3G_16295.3      TIKEWVEQNPNEVVTIMWNNVDAFDGNAFEAAYNASGIIEYSYQQPKENY  TWPTLGE
Aspergillus       NITEWLEQHPYDVVTILIGNYDYVDPGNFTTPMENSGLMDPVFTPPMIPMGLEDWPTLGS
                    *** * *  ****   *  *  *     *      **         *      *****

RO3G_16295.3      LIASGKRVINFGDTYYQQEL  PWLLTEYDYVFETPYENHNESGFSCTIDRPQDPASFT
Aspergillus       IILSGKRAIVFMDYQANQTAYPWLMDEFSQMWETPF SPTDRDFPCTVQRPPDLAAEDAE
                   * ***** * *  *   *  *** *    *  * ***      * ** * **    *

RO3G_16295.3      EFLYVENHFLEGSLQLGSLFIEIPQEGIANTTNSDN   SLMKQAKTCTEKFGRQPNFLE
Aspergillus       EKMYMANHNLNIDFSIASLNLLIPNTALLNETNADRGYGSVGRMAENCTTLWNRPPNFLL
                  *  **  **     * ***  ** **   *    *      *    *** *  * ****

RO3G_16295.3      IDFYNLGD   ALFITAELNEVTYFGSGELQCDTYRAQQASSSSTDSSEAIQTISISSV
Aspergillus       VDYYNEGNFNGSVFQVAADMNGVSYDRDSC CCTLSAASSLGPCAMMSAVLFFVGLQVL
                   * ***        *  *   *  * *       *  *   *          *

RO3G_16295.3      SLLLTLIAATFFIFF
Aspergillus       AWL
                    *

Total alignment length: 495
Overall identity :23.43 % (116/495)
Inner consensus gaps : 38
Sequence lengths:
RO3G_16295.3 365
Aspergillus 470
```

FIGURE 21

```
RO3G_16295.3              MIATPFEMFQCQMYILCLVLIAFSFTCVNTQQLCNGYASYCNKPYNSLTYL
Ustilago      MPQFIQLLSLVSALVIVSSLVGAVPHPVLDAAVETLVERASVCNGDASLCSKLYSNVTYI
                                  ** *     * *          *** **     *    **
RO3G_16295.3  LTHNSYGYVSNPAA     NQLCFITTQLADGVRGIKLSAVKATNATTDGTITADSIYLCH
Ustilago      GAHNSYAVGTLAGASVGKNQEQSVTQQLTDGIRLLQVQARKSSNSTS        GSGINLCH
                ****           *    **     * ** **  *     *    *    *  * ***
RO3G_16295.3  TSCIILNAGPAVNTLRTIKEWVEQNPNEVVTIMWNNVDAFDGNAFBAAYNASGIIEYSYQ
Ustilago      SSCQIENGGTLENYLSKVKTWVDSNPNDVITILIVNSDRQPVSSFGTAPQSTGLASKAYS
               ** *   *        * **  * ** ***  **    *       *    *   *
RO3G_16295.3  QPERNY    TWPTLGELIASGKRVINFGDTTTQ QDLPWLLTEYDYVFETPYENMNESSF
Ustilago      FGTAALAKDSWPTLGSLIDSGKNLVVFIDNSADVSSVPYILPHPQNTVENPY NQISVPF
                 *****  ** ***   * *       *   *        * **  *          *
RO3G_16295.3  SCTIDRPQDPASPTRFLYVKNHFLYGSLQLGSLPIEIPQKGIANTTNSDNSLMKQARTCT
Ustilago      NCSVDRINSGSEPSNLMYLINHYLDSSFNLFGTTVFVPNTAQLNTTNSLSSIMTDAGNCA
               * **     *    * *  **  *   *                *****  *   *   *
RO3G_16295.3  EKFGR QPNPLEIDFYNLGDA  LKITAELNRVTYKGSGSLQCDTYAAGQASSSSTDSSE
Ustilago      SLEGTGYPTYVLTDFYDVGDGSVFQAAAQMNGVQYTAKPIGMATKSGSEGSSGSSSSGAA
                 *      *** **    *        *   *    *         * **
RO3G_16295.3  AIQTISISSVSLLLTLIAATFFIFF
Ustilago      STKVNAIAAVATFMTMFALASTLA
                  *    *   *    *
Total alignment length: 385
Overall identity :29.35 % (113/385)
Inner consensus gaps : 17
Sequence lengths:
RO3G_16295.3 365
Ustilago 378
```

FIGURE 22

| | |
|---|---|
| RO3G_16295.3 | |
| Coccidioides | MLLSFRLLAVASLLRSIYADDIITLTGTNIPPSLSVGDPIPSDTSQLYKSYSSVYTVSAT |
| RO3G_16295.3 | MIATPFEMFQCQMYILCLVLIAFSPTCV NT |
| Coccidioides | DKQLESARTGTETATGSEKTATSDGGTLLIGSKRVSTTNGTTLSGNATATSTESAAVPTN |
| | * * * |
| RO3G_16295.3 | QQLCNGYAEYCNKPYNSLTYLLTHNS YGYVSNPAANQLCPITTQLADGVRGIKLSAVKA |
| Coccidioides | TRPCNGYFEFCERKYSNITHIAAHNSPFVRPGNIAGNQELDVTIQLNDGIRMLQFQT |
| | **** * * * * *** * * ** * ** ** * |
| RO3G_16295.3 | TNATTDGTITADSIYLCHTSCIILNAGPAVNTLRTIKEWVEQNPNEVVTIMPNNVDAPDG |
| Coccidioides | NYIRGTIR LCHSSCDLLDVGPLEDILREVADWLRANPYDVVSILMGNSNFILP |
| | *** *** ** * ** ** * ** ** * |
| RO3G_16295.3 | NAFEAAYNASGIIEYSYQQPKKNYT WPTLGELIASGKRVINFGDTYYQQ DLPWLLT |
| Coccidioides | TNYTKPIENSGLIDYVYTPPKIPMALDDWPLLSHFILTGQRAIVYLDYKANQTEVPYLLE |
| | ** * * ** ** ** * *** * * ** |
| RO3G_16295.3 | EYDYVFETPYENSNESSFSCTIDRPQDFASPT EFLYVRNHFLYGSLQLGSLFIEIPQK |
| Coccidioides | EFSQMWETPFSPTNRD FPCVVHRPPGLSAEDAKERLYMANHNLNTEVSLAGASLLVPNT |
| | * *** * * * ** ** ** * * * |
| RO3G_16295.3 | GIANTTNSDN SLMEQAKTCTEKFGRQPNFLEIDFYNLGE ALEITAELNNVTYK |
| Coccidioides | VLLNETNAVSGYGSAGAMAGNCTEQWTRPPNFILVDFYNIGHFNGSVFSVAASCNNVTYN |
| | * ** * * *** *** * * * ***** |
| RO3G_16295.3 | GSGSLQCDTYAAQQASSSSTDESEAIQTISISSVSLLLTLIAATPFIFF |
| Coccidioides | RKCCGR QTSAASKGLSSGAKQSFFVGLLATITTSLLFTLP |
| | * ** ** * *** ** |

Total alignment length: 469
Overall identity :23.88 % (112/469)
Inner consensus gaps : 36
Sequence lengths:
RO3G_16295.3 365
Coccidioides 449

FIGURE 23

```
RO3G_16295.3                                              MIATPFEMPQCQMYILCLVLIAFSPT
Neurospora     MPSLISSLATALLLVSGICAIPQGPSGAESGIVSAVSAASVSTAGVAVSQATTASPSTSN RO3G_16295.3   CVNTQQLCNGYAEYCNKPYNSLTYLLTHNSYGPVSNPAANQLCPITTQLADGVRGIKLSA
Neurospora     AASGISACNNSPLLCDPAYNNVTHMSAHDSSFLRDASTSDSLAGNQYFNATVALDAGIRL
                      **     *   **   *    *  *            *            *

RO3G_16295.3   VKAINATTDGTITADSIYLCHTSCIILRAGPAVNTLETIKEWVEQNPNEVVTIMWNNVDA
Neurospora     LQAGVHDVNGTLQ        LCHTSCELLDAGPLQDWLAKIKFWMDNNPNEVVTILLVNSDN
                  *  **            ******  * ***   *  ** *  *******   * *

RO3G_16295.3   PDGNAPEAAYNASGIIEYSYQQPK   KNYTWPTLGELIASGKRVINF GDTYYQQDLPW
Neurospora     KLVEDYAAVFEGSGISTYGYQLSNGSSASNTWPTLGDMITSNKRLVTFIASIDYSPTYPT
                      *   ***   *  **      ******  *  **     *     *     *

RO3G_16295.3   LLTEYDYVFETPYENHNESSFSCTIDRPQDPASPTE       FLYVMNHFLYGSLQLGSLF
Neurospora     LLSEFDHVFETAYNVLSLSGFNCTLDRPKGQSAGDAISAGLKPLMNHFADSLLQGVQI
               **  *  ****  *      *  ** ***  *                  ****    *  *

RO3G_16295.3   IEIPQKGIANT  TNSDNSLMKQAKTCTEKFGRQPNFLEIDFYNLGDAIKITAELNNVTY
Neurospora     PDETDIDITNSPDTSTTGNLGLRADTCVKQWGVKPTFILVDFFDHGPAIDTADRLNGITA
                 *  *   *      *   *   *  **  **   *  ** *  **   * **   *

RO3G_16295.3   KGSGSLQEDTYAAQQASESSTESSBAIQTISIESVSLLLTLIAATPFIFF
Neurospora     TGRKSVSGES KGNTSQAGENESPMGKNVALIAFVVFALAMV
                * *           *              *   *  *
```

Total alignment length: 410  
Overall identity : 25.12 % (103/410)  
Inner consensus gaps : 24  
Sequence lengths:  
RO3G_16295.3 365  
Neurospora 396

FIGURE 24

```
RO3G_16295.3    MIATPFEMPQCQMYILCLVLIAFSPTCVNTQQLCNGYAEYCNKPYNSLTYLLTHNSYGYV
Cryptococcus                    MLPHLILSLASIFALPAVPAATTCNGHSELCSRLYSNVTFIGAHDSYAVG
                                 *   * ***  *  *   *    *  *

RO3G_16295.3    SNPAANQLCPITTQLADGVRGIKLSAVKATNAFTDGTITADSIYLCHTSCIILNAGPAVN
Cryptococcus    SSVADEQDKDVTSQLNDGIRTLQIQAHNAS            DGIRLCHSSCSLLDSGLMSD
                * *  *   * ** **  *     *  *              * * *** **   *

RO3G_16295.3    YLRTIKSWVSQNPNEVVTIMWNNVDAFDGNAFEAAYNASGIISYSY    QQPKKNYTWPF
Cryptococcus    YLSTVASWVNENPNDVITIVIVNSDMLFFTSFSFVPSSAGLSSKVYTPASQPTQLSDWPS
                ** *  *** **** * *   * *   *    *   *  *  *  *     *    **

RO3G_16295.3    LGELIASGKKVINFGDFYYQ QDLPWLLTEYDYVPETPYENHNESSFSCTIDRPQDFASP
Cryptococcus    LSDMIDAGTTVVAFMDYKADTSSVPTLLDEPAAMWEDAY GVTTQBFGCAVNRSSGDTSS
                *  * *  * * *  *  *       * * *        *  *  *    *     *

RO3G_16295.3    TEFLYVMNHFLYGSLQLGSLFISIPQKGIANTTNSDN    SLMKQAKTCTEKFGRQPNFL
Cryptococcus    QFFL    INHFLDSTTSFSSIQVFVPNKEFLNETNAETGTSSIGYEVNNCRQLWGRNPNHI
                 **      ****        *        *     *     ** **

RO3G_16295.3    EIDFY    NLSDALKITAELNNVTYKSSGSLQCDTYAAQQASSSSTDSSEAIQTISISSVS
Cryptococcus    LLDPYDSNGNSPFNVAASLNGVSAP TNTVTAGTASATSSGTAAVVSTQSLSG SVTSIE
                  * *           *** *  * *     *   * *   *

RO3G_16295.3    LLLTLIAATFFIFF
Cryptococcus    GIRKGITLGFGVMLGVGMGVGRVFL
                   *       *

Total alignment length: 385
Overall identity :25.97 % (100/385)
Inner consensus gaps : 34
Sequence lengths:
RO3G_16295.3 365
Cryptococcus 360
```

FIGURE 25

```
RO3G_16295
S.lividans   MSLTVLAAASVVESTVLDFGFTGQVLEDEEAYQRFYEEVLVDPRSTFFTSDLLERLPYKQSTITENLKVYVPPKTLRPNG RO3G_16295
S.lividans   QGQIAESVRYLEGDRERLRITVDLEPVVANVERLSQAYPGDAVAALQKRSEPDFQAFVQHLSELVARVVAGEAPLDSLPT RO3G_16295
S.lividans   LPLSRSQSDAATDALSRLVPDGASRDGVRSTVLTSLDRGDVASAKLASIAPVALTDQVSDAAKSMLSEAKQSTWVVSVGVR RO3G_16295
S.lividans   PGTEALAPLDFARKVTRLFQEVVEPAAAVLCAAALTLLWFLSPSFARRRLIPLGWVPAARASLMALTYLVLRLTLSDTLF RO3G_16295                                                         MIATPFEMFQCQMYILCLV
S.lividans   GTPPGNFPASTGLLADVQAAALDRLLPTSVVVSVILLSAGSLLITVGKVWQTPPSVPVLTDFRHVPALTFTVTAVSLVGT
                                                                      *    *     *

RO3G_16295   LIAFSFTCVNTQQLCSGYAEYCNFPYRSLTYLLTHNSYGYVSREAARNQLKP   ITTQLADGVRGIKLSAVE    AT
S.lividans   KLAFVAISGSSESICQGSAELCDARYDETAQLASHNASATTADEFIGPLQDPDIVGQLGAGSRVLLLUTHRWERSEEVAE
                  *   *  ** **  *    *  *    *  **         *      *   *  ** ** **           *

RO3G_16295   NATTDGTITAG          SIYLCHTSCIILNAGPAVRTLRTINEWVEQHPNEVVTISWNNVDAFDGNAPBA
S.lividans   RLSTSDFSPAKPRRLTAILQRVNFPSPGLWLCHSVCGA GAIELEPTLRQIGEWLRDNPTKIVTLILQ  DGVDAVTYQD
                  *    *                 ***  *    *     *** * **     ** * **      *   *

RO3G_16295   AEBASGI IKSSYQQEKK   PYTWPTLGELIASGKRVINFGDTIYQQDLPWLATEYDYVFETPYENPEKSFSCTIDRPQDP
S.lividans   AFKPAGLSDLLYSFGPDFGRFWPKLGGSIDSGRRLVVFAERA  DGFAPWYPNLYFYGKETPFAFKSPDKKSCLPNR
                 *     *    *    ** **   * ***   *    *     *** * **    ** * **        * *

RO3G_16295   ASPFKPLYVSNHFLYGGLQLGSLFIDIFQESIANFTNSDNGLMKQANTCTRKFSRQPNFLEIDFINLGDALKITAELNNV
S.lividans   GGSDKRLFLLNKFVTAG  GGLRLD       AGVVNSRQRVLERAENCERQERGRPVNFIAVDYRTIGDALGAVNELNAE
                  ***         *  *          **         *  *    **  **   *    ****      ***

RO3G_16295   TYKGSGSLQCD  TYRAQQRSSSSTDSSEAIQKTSISSVSLLLTLIAATFFIFF
S.lividans   SVSDGPRVFVERTPSRIPGAAEARSRGGAPRHEAVSS
                   *         *             *      *
```

Total alignment length: 773
Overall identity : 11.51 % (89/773)
Inner consensus gaps : 59
Sequence lengths:
RO3G_16295 365
S.lividans 740 V

FIGURE 26

>CotH3 from Rhizopus oryzae 99-880 (including introns from Data base)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
GTAATCATAAATTTAGTTTGAATTCAATGAGATTAATCATCTTATTCTATAGTATGTTGCAGGTGG
AACAGAAGAAAGTTTTGATCGTTCTCTTGATGGAATCACAAACTCAACACTTAATGATTTTTATAA
CCGCCCCGTCACTTATGCTAACCTTCCTCAATTACCTTGGCCAATTGAAAAGACGTAAGTTATTT
TATTTTTATCTTTTCTCAGCTAAAATAAACATTGTCTTTCTCAGCCTCAGTGGACTCGTTCTGGAA
GCAAAGCCGACATTTTCGATGACAATTATATTCCCAGCGTTTTTTTCCACGGAGATGACAGTCAAG
TCCAAAATGTGGTTAAAAACGTACCTGCTGACCGAATCAGTGGTACACTGACCTTTATTGGATCTA
ATTACGTCTACTCTTTCCAGAATGTCTCATTTGGTATTCACGGTGCTGGCAAGAAACACAACAATG
CAAAACAATCTTGGAACTGGATATTGTCTGGAAGTGATACGATGGGTAACCGCAATTTCTTTAAGC
TTCGACATATGGAAGAAGATCCTACACAGATTCGTGAACGTCTTTATTCTGACATTTTACATGCCA
TGGGTACTTATGCCAATGATGCTACCATGGTTCGATTGTTTATTAACAACCAAGGCTTCGGTACCT
TCAACATGTTGGATGATATCACTCAATTCTCCTATATCAATGCTAAATTTTATAATGGCAAACCAC
CTGCTACCTTGGGTCCTCTCTATGATGGTGCCTCTGGTGCAGACTTCTTATATCATCCTGGTAACC
TCGATGGATACTCTTCTTGGGTTGCCAACACAGCCAATCCTAATGGTGAAGCTTATGAAGCTCTTG
ATCCTCTCTGTAAGGCCTGGAACGAGACGACCTATACCGATAATACAGCCATTGCAAACTTTGAAA
AAATGTTTGATCTCGACCGTTTCATGCGTTTCATGGTTATTGAATACTTGACTGCCGATTGGGATG
GTTACTGGATGGGACAGACCAATGATGGTGCCTATCGTGATCCAACTGATAATAACAAGTGGTACT
TTTTAGATCAAGACTTTGATGGTACTTTTGGTGTCAACTTGGCTGCACCCGAAGGCAATGCTTTTC
TTGATGTTTCTTACAAGGATTTCCCTTCTCGTTACCCTGGCGCTGTCATGATCAACAACCTCTTAC
AGAATGCTGATAAAAAGGCCACCTTTGAAAAATATTTGACTGAGACTGTGCGTGTGCTGTTCAATA
ATGTCACCTTGACTAACCGTGTCTTGGCCCTTCACAACTTCCTCTTGCCTGATCTTGAATGGGATC
GTTCGATCGTTCAACAATCTCCTGGTATTAACTTTGGTTGGACATTTGATCAAGTCACTCAAAACT
TGTGGCAAGGTGTCACTGCACCCAATAACAATGGAGGTGGTGCTGCTTTTGGTTTAGTTGAATATA
TTGCTGCAAAGGCACAAGCTGTAGCTAAGGAATTTAATATTTCTATCGTTTCCCAACCTGTTGGCC
CTCCTTCTGCTAATGGTACTACTGCTGCTGCTCCTGCTCCTGCTGCTGGCAATTCTACTGGAAAAG
GAGGAAATCAATCTATTTCTAGCAGTGCTTCATCCAACAAAACCTCGGCTCAAAGCACATCAGGTG
CTTCTCGTTCCAAGACTGCGCCCATCGTTTTAGCCATTTCCGCTTTAGCTCTCCTTGTATTCTAA

FIGURE 27

CotH3 from Rhizopus oryzae 99-880 (exon only from Data base)

```
ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
TATGTTGCAGGTGGAACAGAAGAAAGTTTTGATCGTTCTCTTGATGGAATCACAAACTCAACACTT
AATGATTTTTATAACCGCCCCGTCACTTATGCTAACCTTCCTCAATTACCTTGGCCAATTGAAAAA
GACCCTCAGTGGACTCGTTCTGGAAGCAAAGCCGACATTTTCGATGACAATTATATTCCCAGCGTT
TTTTTCCACGGAGATGACAGTCAAGTCCAAAATGTGGTTAAAAACGTACCTGCTGACCGAATCAGT
GGTACACTGACCTTTATTGGATCTAATTACGTCTACTCTTTCCAGAATGTCTCATTTGGTATTCAC
GGTGCTGGCAAGAAACACAACAATGCAAACAATCTTGGAACTGGATATTGTCTGGAAGTGATACG
ATGGGTAACCGCAATTTCTTTAAGCTTCGACATATGGAAGAAGATCCTACACAGATTCGTGAACGT
CTTTATTCTGACATTTTACATGCCATGGGTACTTATGCCAATGATGCTACCATGGTTCGATTGTTT
ATTAACAACCAAGGCTTCGGTACCTTCAACATGTTGGATGATATCACTCAATTCTCCTATATCAAT
GCTAAATTTTATAATGGCAAACCACCTGCTACCTTGGGTCCTCTCTATGATGGTGCCTCTGGTGCA
GACTTCTTATATCATCCTGGTAACCTCGATGGATACTCTTCTTGGGTTGCCAACACAGCCAATCCT
AATGGTGAAGCTTATGAAGCTCTTGATCCTCTCTGTAAGGCCTGGAACGAGACGACCTATACCGAT
AATACAGCCATTGCAAACTTTGAAAAATGTTTGATCTCGACCGTTTCATGCGTTTCATGGTTATT
GAATACTTGACTGCCGATTGGGATGGTTACTGGATGGGACAGACCAATGATGGTGCCTATCGTGAT
CCAACTGATAATAACAAGTGGTACTTTTTAGATCAAGACTTTGATGGTACTTTTGGTGTCAACTTG
GCTGCACCCGAAGGCAATGCTTTTCTTGATGTTTCTTACAAGGATTTCCCTTCTCGTTACCCTGGC
GCTGTCATGATCAACAACCTCTTACAGAATGCTGATAAAAAGGCCACCTTTGAAAAATATTTGACT
GAGACTGTGCGTGTGCTGTTCAATAATGTCACCTTGACTAACCGTGTCTTGGCCCTTCACAACTTC
CTCTTGCCTGATCTTGAATGGGATCGTTCGATCGTTCAACAATCTCCTGGTATTAACTTTGGTTGG
ACATTTGATCAAGTCACTCAAAACTTGTGGCAAGGTGTCACTGCACCCAATAACAATGGAGGTGGT
GCTGCTTTTGGTTTAGTTGAATATATTGCTGCAAAGGCACAAGCTGTAGCTAAGGAATTTAATATT
TCTATCGTTTCCCAACCTGTTGGCCCTCCTTCTGCTAATGGTACTACTGCTGCTGCTCCTGCTCCT
GCTGCTGGCAATTCTACTGGAAAAGGAGGAAATCAATCTATTTCTAGCAGTGCTTCATCCAACAAA
ACCTCGGCTCAAAGCACATCAGGTGCTTCTCGTTCCAAGACTGCGCCCATCGTTTTAGCCATTTCC
GCTTTAGCTCTCCTTGTATTCTAA
```

FIGURE 28

>CotH3 from Rhizopus oryzae 99-880 (predicted amino acids)

MKLSIISAAFLVAITHAASIKFNVIAPNATDVKVSVNGQQVTLTASDANVPYFTGSAEVGASKTYK
YVAGGTEESFDRSLDGITNSTLNDFYNRPVTYANLPQLPWPIEKDPQWTRSGSKADIFDDNYIPSV
FFHGDDSQVQNVVKNVPADRISGTLTFIGSNYVYSFQNVSFGIHGAGKKHNNAKQSWNWILSGSDT
MGNRNFFKLRHMEEDPTQIRERLYSDILHAMGTYANDATMVRLFINNQGFGTFNMLDDITQFSYIN
AKFYNGKPPATLGPLYDGASGADFLYHPGNLDGYSSWVANTANPNGEAYEALDPLCKAWNETTYTD
NTAIANFEKMFDLDRFMRFMVIEYLTADWDGYWMGQTNDGAYRDPTDNNKWYFLDQDFDGTFGVNL
AAPEGNAFLDVSYKDFPSRYPGAVMINNLLQNADKKATFEKYLTETVRVLFNNVTLTNRVLALHNF
LLPDLEWDRSIVQQSPGINFGWTFDQVTQNLWQGVTAPNNNGGGAAFGLVEYIAAKAQAVAKEFNI
SIVSQPVGPPSANGTTAAAPAPAAGNSTGKGGNQSISSSASSNKTSAQSTSGASRSKTAPIVLAIS
ALALLVF*

FIGURE 29

>CotH3 from Rhizopus oryzae 99-880(including introns from
sequenced data)

```
ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
GTAATCATAAATTTAGTTTGAATTCAATGAGATTAATCATCTTATTCTATAGTATGTTGCAGGTGG
AACAGAAGAAAGTTTTGATCGTTCTCTTGATGGAATCACAAACTCAACACTTAATGATTTTTATAA
CCGCCCCGTCACTTATGCTAACCTTCCTCAATTACCTTGGCCAATTGAAAAGACGTAAGTTATTT
TATTTTTATCTTTTCTCAGCTAAAATAAACATTGTCTTTCTCAGCCTCAGTGGACTCGTTCTGGAA
GCAAAGCCGACATTTTCGATGACAATTATATTCCCAGCGTTTTTTTCCACGGAGATGACAGTCAAG
TCCAAAATGTGGTTAAAAACGTACCTGCTGACCGAATCAGTGGTACACTGACCTTTATTGGATCTA
ATTACGTCTACTCTTTCCAGAATGTCTCATTTGGTATTCACGGTGCTGGCAAGAAACACAACAATG
CAAAACAATCTTGGAACTGGATATTGTCTGGAAGTGATACGATGGGTAACCGCAATTTCTTTAAGC
TTCGACATATGGAAGAAGATCCTACACAGATTCGTGAACGTCTTTATTCTGACATTTTACATGCCA
TGGGTACTTATGCCAATGATGCTACCATGGTTCGATTGTTTATTAACAACCAAGGCTTCGGTACCT
TCAACATGTTGGATGATATCACTCAATTCTCCTATATCAATGCTAAATTTTATAATGGCAAACCAC
CTGCTACCTTGGGTCCTCTCTATGATGGTGCCTCTGGTGCAGACTTCTTATATCATCCTGGTAACC
TCGATGGATACTCTTCTTGGGTTGCCAACACAGCCAATCCTAATGGTGAAGCTTATGAAGCTCTTG
ATCCTCTCTGTAAGGCCTGGAACGAGACGACCTATACCGATAATACAGCCATTGCAAACTTTGAAA
AAATGTTTGATCTCGACCGTTTCATGCGTTTCATGGTTATTGAATACTTGACTGCCGATTGGGATG
GTTACTGGATGGGACAGACCAATGATGGTGCCTATCGTGATCCAACTGATAATAACAAGTGGTACT
TTTTAGATCAAGACTTTGATGGTACTTTTGGTGTCAACTTGGCTGCACCCGAAGGCAATGCTTTTC
TTGATGTTTCTTACAAGGATTTCCCTTCTCGTTACCCTGGCGCTGTCATGATCAACAACCTCTTAC
AGAATGCTGATAAAAAGGCCACCTTTGAAAAATATTTGACTGAGACTGTGCGTGTGCTGTTCAATA
ATGTCACCTTGACTAACCGTGTCTTGGCCCTTCACAACTTCCTCTTGCCTGATCTTGAATGGGATC
GTTCGATCGTTCAACAATCTCCTGGTATTAACTTTGGTTGGACATTTGATCAAGTCACTCAAAACT
TGTGGCAAGGTGTCACTGCACCCAATAACAATGGAGGTGGTGCTGCTTTTGTTTAGTTGAATATA
TTGCTGCAAAGGCACAAGCTGTAGCTAAGGAATTTAATATTCTATCGTTTCCCAACCTGTTGGCC
CTCCTTCTGCTAATGGTACTACTGCTGCTGCTCCTGCTCCTGCTGCTGGCAATTCTACTGGAAAAG
GAGGAAATCAATCTATTTCTAGCAGTGCTTCATCCAACAAAACCTCGGCTCAAAGCACATCAGGTG
CTTCTCGTTCCAAGACTGCGCCCATCGTTTTAGCCATTTCCGCTTTAGCTCTCCTTGTATTCTAAA
```

FIGURE 30

CotH3 from Rhizopus oryzae 99-892 (exons only from Sequenced data)

```
ATGAAATTATCTATTATATCCGCTGCCTTTTTAGTGGCTATAACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTACTTCACTGGTTCAGCTGAAGTTGGTTCCTCAAAGACATACAAA
TATGTTGCAGGTGGAACAGAAGAAGGTTTTGATCGTTCTCTTGATGGAATCACAAACTCAACATTT
AATGATTTTTATAATCGCCCCATCACTTATGCTAACCTTCCTCAATTACCTTGGCCAATTGAAAAA
GACCCTCAGTGGACTCGTTCTGGAAACAAAGCCGACATTTTCGATGACAATTATATTCCCAGCATT
TTTTTCCACGGAGATGACAGTCAAGTCCAAAATGTGGTTAAAAACGTACCTGCTGACCGAATCAGT
GGTACACTGACCTTTATCGGATCTAATTACGTCTACTCTTTCCAGAATGTCTCATTTGGTATTCAC
GGTGCTGGCAAGAAACACAACAATGCAAAGCAATCTTGGAACTGGATCTTGTCTGGAAGTGATACG
ATGGGTAACCGTAATTTCTTTAAGCTTCGACATATGGAAGAAGATCCTACACAGATCCGTGAACGT
CTTTATTCTGACATTTTACATGCCATGGGTACTTATGCCAATGATGCTACCATGGTTCGATTGTTT
ATTAACAATCAAGGCTTCGGTACCTTCAACATGTTGGATGACATCACTCAATTCTCTTATATCAAT
GCTAAATTCTATAATGGCAAACCACCTGCTACCTTGGGTCCTCTCTATGATGGTGCCTCTGGTGCA
GATTTCTTATATCATCCTGGTAACCTCGATGGATACTCTTTCTTGGGTTGCCAACACAGCTAATCC
TAATGGTGAAGCTTATGAAGCTCTTGATCCTCTCTGTAAGGCCTGGAACGAGACGACCTATACCGA
TAATACAGCCATTGCGAACTTTGAAAAAATGTTTGATCTTGACCGTTTCATGCGTTTCATGGTTGT
TGAATACTTGGCTGCCGATTGGGATGGTTACTGGATGGGACAGACCAATGATGGTGCCTATCGTGA
TCCAACTGATAATAACAAGTGGTACTTTTAGATCAAGACTTTGATGGTACCTTTGGTGTCAACTT
GGCTGCACCCGAAGGCAATGCTTTTCTTGATATTTCTTACAAAGATTTCCCTTCTCGTTACCCTGG
CGCTGTCATGATCAACAACCTCTTACAGAATGCTGATAAAAAGGCCACCTTTGAAAAATACTTGAC
TGAGACTGTGCGTGTGCTGTTAATAATGTCACCTTGACTAACCGTGTCTTGGCCCTTCACAACTT
CCTCTTGCCTGACCTTGAATGGGATCGTTCGATCGTTCAACAATCTCCTGGTATTAACTTTGGTTG
GACATTTGATCAAGTCACTCAAAACTTGTGGCAAGGTGTCAATGCACCCAATAACAACGGAGGTGG
TGCTGCTATTGGTTTAGTTGAATATATTGCTACAAAGGCACAAGTTGTAGCTAAGAATTAATATTA
CTATCGTTCCCAACCTGTTGGCCCTCCTTCTGCTAATGGTACTACTACTGCTGCTAACTGCTCCTA
CTGCTGGTATCTACTGGAAAAGGAAGAAATCATCCCATTTCTAGCAGTGCTTCATCAACAAACTCG
CTCAAGTAACATCAAGTGCTTCTCGTCAAGACTGCGCCAATCATTTTAGGCAATTTCCGCTTAGCC
CTCCCCCGTTGTGATTCTCAAAA
```

FIGURE 31

>CotH3 from Rhizopus oryzae 99-892 (including intron from Sequenced data)

ATGAAATTATCTATTATATCCGCTGCCTTTTTAGTGGCTATAACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTACTTCACTGGTTCAGCTGAAGTTGGTTCCTCAAAGACATACAAA
GTAATCATAAATTTATTTTGAATTCAATCATATTAATCATCTTATTCTATAGTATGTTGCAGGTGG
AACAGAAGAAGGTTTTGATCGTTCTCTTGATGGAATCACAAACTCAACATTTAATGATTTTTATAA
TCGCCCCATCACTTATGCTAACCTTCCTCAATTACCTTGGCCAATTGAAAAAGACGTAAGTTATTT
TATTTTTATCTTTTCTCAGCTAAAATAAACATTGTCTTTCTCAGCCTCAGTGGACTCGTTCTGGAA
ACAAAGCCGACATTTTCGATGACAATTATATTCCCAGCATTTTTTTCCACGGAGATGACAGTCAAG
TCCAAAATGTGGTTAAAAACGTACCTGCTGACCGAATCAGTGGTACACTGACCTTTATCGGATCTA
ATTACGTCTACTCTTTCCAGAATGTCTCATTTGGTATTCACGGTGCTGGCAAGAAACACAACAATG
CAAAGCAATCTTGGAACTGGATCTTGTCTGGAAGTGATACGATGGGTAACCGTAATTTCTTTAAGC
TTCGACATATGGAAGAAGATCCTACACAGATCCGTGAACGTCTTTATTCTGACATTTTACATGCCA
TGGGTACTTATGCCAATGATGCTACCATGGTTCGATTGTTTATTAACAATCAAGGCTTCGGTACCT
TCAACATGTTGGATGACATCACTCAATTCTCTTATATCAATGCTAAATTCTATAATGGCAAACCAC
CTGCTACCTTGGGTCCTCTCTATGATGGTGCCTCTGGTGCAGATTTCTTATATCATCCTGGTAACC
TCGATGGATACTCTTTCTTGGGTTGCCAACACAGCTAATCCTAATGGTGAAGCTTATGAAGCTCTT
GATCCTCTCTGTAAGGCCTGGAACGAGACGACCTATACCGATAATACAGCCATTGCGAACTTTGAA
AAAATGTTTGATCTTGACCGTTTCATGCGTTTCATGGTTGTTGAATACTTGGCTGCCGATTGGGAT
GGTTACTGGATGGGACAGACCAATGATGGTGCCTATCGTGATCCAACTGATAATAACAAGTGGTAC
TTTTTAGATCAAGACTTTGATGGTACCTTTGGTGTCAACTTGGCTGCACCCGAAGGCAATGCTTTT
CTTGATATTTCTTACAAAGATTTCCCTTCTCGTTACCCTGGCGCTGTCATGATCAACAACCTCTTA
CAGAATGCTGATAAAAAGGCCACCTTTGAAAAATACTTGACTGAGACTGTGCGTGTGCTGTTCAAT
AATGTCACCTTGACTAACCGTGTCTTGGCCCTTCACAACTTCCTCTTGCCTGACCTTGAATGGGAT
CGTTCGATCGTTCAACAATCTCCTGGTATTAACTTTGGTTGGACATTTGATCAAGTCACTCAAAAC
TTGTGGCAAGGTGTCAATGCACCCAATAACAACGGAGGTGGTGCTGCTATTGGTTTAGTTGAATAT
ATTGCTACAAAGGCACAAGTTGTAGCTAAGAATTAATATTACTATCGTTCCCAACCTGTTGGCCCT
CCTTCTGCTAATGGTACTACTACTGCTGCTAACTGCTCCTACTGCTGGTATCTACTGGAAAAGGAA
GAAATCATCCCATTTCTAGCAGTGCTTCATCAACAAACTCGCTCAAGTAACATCAAGTGCTTCTCG
TCAAGACTGCGCCAATCATTTTAGGCAATTTCCGCTTAGCCCTCCTTGTGATTCTCAAAA

FIGURE 32

>Predicted amino acid sequence of CotH3 from *R. oryzae* 99-892 (excluding introns)

MKLSIISAAFLVAITHAASIKFNVIAPNATDVKVSVNGQQVTLTASDANVPYFTGSAEVGSSKTYK
VIINLF*IQSY*SSYSIVCCRWNRRRF*SFS*WNHKLNI**FL*SPHHLC*PSSITLAN*KRRKLF
YFYLFSAKINIVFLSLSGLVLETKPTFSMTIIFPAFFSTEMTVKSKMWLKTYLLTESVVH*PLSDL
ITSTLSRMSHLVFTVLARNTTMQSNLGTGSCLEVIRWVTVISLSFDIWKKILHRSVNVFILTFYMP
WVLMPMMLPWFDCLLTIKASVPSTCWMTSLNSLISMLNSIMANHLLPWVLSMMVPLVQISYIILVT
SMDTLSWVANTANPNGEAYEALDPLCKAWNETTYTDNTAIANFEKMFDLDRFMRFMVVEYLAADWD
GYWMGQTNDGAYRDPTDNNKWYFLDQDFDGTFGVNLAAPEGNAFLDISYKDFPSRYPGAVMINNLL
QNADKKATFEKYLTETVRVLFNNVTLTNRVLALHNFLLPDLEWDRSIVQQSPGINFGWTFDQVTQN
LWQGVNAPNNNGGGAAIGLVEYIATKAQVVAKN*YYYRSQPVGPPSANGTTTAANCSYCWYLLEKE
EIIPFLAVLHQQTRSSNIKCFSSRLRQSF*AISA*PSL*FSK

FIGURE 33

>Predicted amino acid sequence of CotH3 from *R. oryzae* 99-892 (including introns)

MKLSIISAAFLVAITHAASIKFNVIAPNATDVKVSVNGQQVTLTASDANVPYFTGSAEVGSSKTYK
VIINLF*IQSY*SSYSIVCCRWNRRRF*SFS*WNHKLNI**FL*SPHHLC*PSSITLAN*KRRKLF
YFYLFSAKINIVFLSLSGLVLETKPTFSMTIIFPAFFSTEMTVKSKMWLKTYLLTESVVH*PLSDL
ITSTLSRMSHLVFTVLARNTTMQSNLGTGSCLEVIRWVTVISLSFDIWKKILHRSVNVFILTFYMP
WVLMPMMLPWFDCLLTIKASVPSTCWMTSLNSLISMLNSIMANHLLPWVLSMMVPLVQISYIILVT
SMDTLSWVANTANPNGEAYEALDPLCKAWNETTYTDNTAIANFEKMFDLDRFMRFMVVEYLAADWD
GYWMGQTNDGAYRDPTDNNKWYFLDQDFDGTFGVNLAAPEGNAFLDISYKDFPSRYPGAVMINNLL
QNADKKATFEKYLTETVRVLFNNVTLTNRVLALHNFLLPDLEWDRSIVQQSPGINFGWTFDQVTQN
LWQGVNAPNNNGGGAAIGLVEYIATKAQVVAKN*YYYRSQPVGPPSANGTTTAANCSYCWYLLEKE
EIIPFLAVLHQQTRSSNIKCFSSRLRQSF*AISA*PSPVVILK

FIGURE 34

>CotH3 sequence from Mucor sp. 99-932(exons only from sequenced data)

ATGAAATTATCTATTATATCCGCTGCCTTTTTAGTGGCTATAACACACGCTGCTTCATAAAGTTTA
ATGTAATTGCTCCTAATGCAACTGATGTCAAAGTATCTGTAAATGGACAGCAAGTGACACTTACTG
CTTCAGATGCAAATGTCCCTTACTTCACTGGTTCAGCTGAAGTTGGTTCCTCAAAGACATACAAAT
ATGTTGCAGGTGGAACAGAAGAAGGTTTTGATCGTTCTCTTGATGGAATCACAAACTCAACATTTA
ATGATTTTTATAATCGCCCCATCACTTATGCTAACCTTCCTCAATTACCTTGGCCAATTGAAAAAG
ACCCTCAGTGGACTCGTTCTGGAAACAAAGCCGACATTTTCGATGACAATTATATTCCCAGCATTT
TTTTCCACGGAGATGACAGTCAAGTCCAAAATGTGGTTAAAAACGTACCTGCTGACCGAATCAGTG
GTACACTGACCTTTATCGGATCTAATTACGTCTACTCTTTCCAGAATGTCTCATTTGGTATTCACG
GTGCTGGCAAGAAACACAACAATGCAAAGCAATCTTGGAACTGGATCTTGTCTGGAAGTGATACGA
TGGGTAACCGTAATTTCTTTAAGCTTCGACATATGGAAGAAGATCCTACACAGATCCGTGAACGTC
TTTATTCTGACATTTTACATGCCATGGGTACTTATGCCAATGATGCTACCATGGTTCGATTGTTTA
TTAACAATCAAGGCTTCGGTACCTTCAACATGTTGGATGACATCACTCAATTCTCTTATATCAATG
CTAAATTCTATAATGGCAAACCACCTGCTACCTTGGGTCCTCTCTATGATGGTGCCTCTGGTGCAG
ATTTCTTATATCATCCTGGTAACCTCGATGGATACTCTTCTTGGGTTGCCAACACAGCTAATCCTA
ATGGTGAAGCTTATGAAGCTCTTGATCCTTCTCTGTAAGGCCTGGAAACGAGACGACCTATTACCG
ATAATACAGCCAATTGCGAACTTTGAAAAAATGTTTGATCTGACGTTTCATGCGTTCCATGCTGGT
GATACTGGGCTGCCGAATGAATGCTACTGCAATGGAAGACATGAATCGTGTCTATTCGTGATCCAA
CTGAATAATACCAGTCGGGTACTTTTAGATCAAGACTTTGATGGTACTTTTGGTGTCAACTTGGC
TGCACCCGAAGGCAATGCTTTTCTTGATGTTTCTTACAAGGATTTCCCTTCTCGTTACCCTGGCGC
TGTCATGATCAACAACCTCTTACAGAATGCTGATAAAAAGGCCACCTTTGAAAAATATTTGACTGA
GACTGTGCGTGTGCTGTTCAATAATGTCACCTTGACTAACCGTGTCTTGGCCCTTCACAACTTCCT
CTTGCCTGATCTTGAATGGGATCGTTCGATCGTTCAACAATCTCCTGGTATTAACTTTGGTTGGAC
ATTTGATCAAGTCACTCAAAACTTGTGGCAAGGTGTCACTGCACCCAATAACAATGGAGGTGGTGC
TGCTTTTGGTTTAGTTGAATATATTGCTGCAAAGGCACAAGCTGTAGCTAAGGAATTTAATATTTC
TATCGTTTCCCAACCTGTTGGCCCTCCTTCTGCTAATGGTACTACTGCTGCTGCTCCTGCTCCTGC
TGCTGGCAATTCTACTGGAAAAGGAGGAAATCAATCTATTTCTAGCAGTGCTTCATCCAACAAAAC
CTCGGCTCAAAGCACATCAGGTGCTTCTCGTTCCAAGACTGCGCCCATCGTTTTAGCCATTTCCGC
TTTAGCTCTCCTTGGTATTCTAAA

FIGURE 35

>Predicted amino acid sequence of CotH3 from Mucor 99-932(AA exons only)

MKLSIISAAFLVAITHAAS*SLM*LLLMQLMSKYL*MDSK*HLLLQMQMSLTSLVQLKLVPQRHTN
MLQVEQKKVLIVLLMESQTQHLMIFIIAPSLMLTFLNYLGQLKKTLSGLVLETKPTFSMTIIFPAF
FSTEMTVKSKMWLKTYLLTESVVH*PLSDLITSTLSRMSHLVFTVLARNTTMQSNLGTGSCLEVIR
WVTVISLSFDIWKKILHRSVNVFILTFYMPWVLMPMMLPWFDCLLTIKASVPSTCWMTSLNSLISM
LNSIMANHLLPWVLSMMVPLVQISYIILVTSMDTLLGLPTQLILMVKLMKLLILLCKAWKRDDLLP
IIQPIANFEKMFDLTFHAFHAGDTGLPNECYCNGRHESCLFVIQLNNTSRVLFRSRL*WYFWCQLG
CTRRQCFS*CFLQGFPFSLPWRCHDQQPLTEC**KGHL*KIFD*DCACAVQ*CHLD*PCLGPSQLP
LA*S*MGSFDRSTISWY*LWLDI*SSHSKLVARCHCTQ*QWRWCCFWFS*IYCCKGTSCS*GI*YF
YRFPTCWPSFC*WYYCCCSCSCCWQFYWKRRKSIYF*QCFIQQNLGSKHIRCFSFQDCAHRFSHFR
FSSPWYSK

FIGURE 36

>DNA sequence of CotH3 from Mucor 99-932(including introns)

```
ATGAAATTATCTATTATATCCGCTGCCTTTTTAGTGGCTATAACACACGCTGCTTCATAAAGTTTA
ATGTAATTGCTCCTAATGCAACTGATGTCAAAGTATCTGTAAATGGACAGCAAGTGACACTTACTG
CTTCAGATGCAAATGTCCCTTACTTCACTGGTTCAGCTGAAGTTGGTTCCTCAAAGACATACAAAG
TAATCATAAATTTATTTTGAATTCAATCATATTAATCATCTTATTCTATAGTATGTTGCAGGTGGA
ACAGAAGAAGGTTTTGATCGTTCTCTTGATGGAATCACAAACTCAACATTTAATGATTTTTATAAT
CGCCCCATCACTTATGCTAACCTTCCTCAATTACCTTGGCCAATTGAAAAGACGTAAGTTATTTT
ATTTTTATCTTTTCTCAGCTAAAATAAACATTGTCTTTCTCAGCCTCAGTGGACTCGTTCTGGAAA
CAAAGCCGACATTTTCGATGACAATTATATTCCAGCATTTTTTTCCACGGAGATGACAGTCAAGT
CCAAAATGTGGTTAAAAACGTACCTGCTGACCGAATCAGTGGTACACTGACCTTTATCGGATCTAA
TTACGTCTACTCTTTCCAGAATGTCTCATTTGGTATTCACGGTGCTGGCAAGAAACACAACAATGC
AAAGCAATCTTGGAACTGGATCTTGTCTGGAAGTGATACGATGGGTAACCGTAATTTCTTTAAGCT
TCGACATATGGAAGAAGATCCTACACAGATCCGTGAACGTCTTTATTCTGACATTTTACATGCCAT
GGGTACTTATGCCAATGATGCTACCATGGTTCGATTGTTTATTAACAATCAAGGCTTCGGTACCTT
CAACATGTTGGATGACATCACTCAATTCTCTTATATCAATGCTAAATTCTATAATGGCAAACCACC
TGCTACCTTGGGTCCTCTCTATGATGGTGCCTCTGGTGCAGATTTCTTATATCATCCTGGTAACCT
CGATGGATACTCTTCTTGGGTTGCCAACACAGCTAATCCTAATGGTGAAGCTTATGAAGCTCTTGA
TCCTTCTCTGTAAGGCCTGGAAACGAGACGACCTATTACCGATAATACAGCCAATTGCGAACTTTG
AAAAATGTTTGATCTGACGTTTCATGCGTTCCATGCTGGTGATACTGGGCTGCCGAATGAATGCT
ACTGCAATGGAAGACATGAATCGTGTCTATTCGTGATCCAACTGAATAATACCAGTCGGGTACTTT
TTAGATCAAGACTTTGATGGTACTTTTGGTGTCAACTTGGCTGCACCCGAAGGCAATGCTTTTCTT
GATGTTTCTTACAAGGATTTCCCTTCTCGTTACCCTGGCGCTGTCATGATCAACAACCTCTTACAG
AATGCTGATAAAAAGGCCACCTTTGAAAAATATTTGACTGAGACTGTGCGTGTGCTGTTCAATAAT
GTCACCTTGACTAACCGTGTCTTGGCCCTTCACAACTTCCTCTTGCCTGATCTTGAATGGGATCGT
TCGATCGTTCAACAATCTCCTGGTATTAACTTTGGTTGGACATTTGATCAAGTCACTCAAAACTTG
TGGCAAGGTGTCACTGCACCCAATAACAATGGAGGTGGTGCTGCTTTTGGTTTAGTTGAATATATT
GCTGCAAAGGCACAAGCTGTAGCTAAGGAATTTAATATTTCTATCGTTTCCCAACCTGTTGGCCCT
CCTTCTGCTAATGGTACTACTGCTGCTGCTCCTGCTCCTGCTGCTGGCAATTCTACTGGAAAAGGA
GGAAATCAATCTATTTCTAGCAGTGCTTCATCCAACAAAACCTCGGCTCAAAGCACATCAGGTGCT
TCTCGTTCCAAGACTGCGCCCATCGTTTTAGCCATTTCCGCTTTAGCTCTCCTTGGTATTCTAAA
```

FIGURE 37

>Predicted amino acid sequence of CotH3 from Mucor 99-932(including introns)

MKLSIISAAFLVAITHAAS*SLM*LLLMQLMSKYL*MDSK*HLLLQMQMSLTSLVQLKLVPQRHTK
*S*IYFEFNHINHLIL*YVAGGTEEGFDRSLDGITNSTFNDFYNRPITYANLPQLPWPIEKDVSYF
IFIFSQLK*TLSFSASVDSFWKQSRHFR*QLYSQHFFPRR*QSSPKCG*KRTC*PNQWYTDLYRI*
LRLLFPECLIWYSRCWQETQQCKAILELDLVWK*YDG*P*FL*ASTYGRRSYTDP*TSLF*HFTCH
GYLCQ*CYHGSIVY*QSRLRYLQHVG*HHSILLYQC*IL*WQTTCYLGSSL*WCLWCRFLISSW*P
RWILFLGCQHS*S*W*SL*SS*SFSVRPGNETTYYR*YSQLRTLKKCLI*RFMRSMLVILGCRMNA
TAMEDMNRVYS*SN*IIPVGYFLDQDFDGTFGVNLAAPEGNAFLDVSYKDFPSRYPGAVMINNLLQ
NADKKATFEKYLTETVRVLFNNVTLTNRVLALHNFLLPDLEWDRSIVQQSPGINFGWTFDQVTQNL
WQGVTAPNNNGGGAAFGLVEYIAAKAQAVAKEFNISIVSQPVGPPSANGTTAAAPAPAAGNSTGKG
GNQSISSSASSNKTSAQSTSGASRSKTAPIVLAISALALLGIL

FIGURE 38

>CotH3 sequence from Lichtheimia corymbifera(exons only from
sequenced data)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTTCCTCAAAGACATACAAA
TATGTTGCAGGTGGAACAGAAGAAAGTTTTGATCGTTCTCTTGATGGAATCACAAACTCAACACTT
AATGATTTTTATAATCGCCCCGTCACTTATGCTAACCTTCCTCAATTACCTTGGCCAATTGAAAAA
GACCCTCAGTGGACTCGTTCTGGAAACAAAGCCGACATTTTCGATGACAATTATATTCCCAGCGTT
TTTTTCCACGGAGATGACAGTCAAGTCCAAAATGTGGTTAAAAACGTACCTGCTGACCGAATCAGT
GGTACACTGACCTTTATTGGATCTAATTACGTCTACTCTTTCCAGAATGTCTCATTTGGTATTCAC
GGTGCTGGCAAGAAACACAACAATGCAAAACAATCTTGGAACTGGATATTGTCTGGAAGTGATACG
ATGGGTAACCGCAATTTCTTTAAGCTTCGACATATGGAAGAAGATCCTACACAGATCCGTGAACGT
CTTTATTCTGACATTTTACATGCCATGGGTACTTATGCCAATGATGCTACCATGGTTCGATTGTTT
ATTAACAACCAAGGCTTCGGTACCTTCAACATGTTGGATGATATCACTCAATTCTCTTATATCAAT
GCTAAATTTTATAATGGCAAACCACCTGCTACCTTGGGTCCTCTCTATGATGGTGCCTCTGGTGCA
GATTTCTTATATCATCCTGGTAACCTCATGGATACTCTTCTTGGGTTGCCAACACAGCCAATCCT
AATGGTGAAGCTTATGAAGCTCTTGATCCTCTCTGTAAGGCCTGGAACGAGACGACCTATACCGAT
AATACAGCCATTGCAAACTTTGAAAAAATGTTTGATCTCGACCGTTTCATGCGTTTCATGGTTATT
GAATACTTGACTGCCGATTGGGATGGTTACTGGATGGGACAGACCAATGATGGTGCCTATCGTGAT
CCAACTGATAATAACAAGTGGTACTTTTAGATCAAGACTTTGATGGTACTTTTGGTGTCAACTTG
GCTGCACCCGAAGGCAATGCTTTTCTTGATGTTTCTTACAAGGATTTCCCTTCTCGTTACCCTGGC
GCTGTCATGATCAACAACCTCTTACAGAATGCTGATAAAAAGGCCACCTATGAAAATATTTGACT
GAGACTGTGCGTGTGCTGTTCAATAATGTCACCTTGACTAACCGTGTCTTGGCCCTTCACAACTTC
CTCTTGCCTGATCTTGAATGGGATCGTTCGATCGTTCAACAATCTCCTGGTATTAACTTTGGTTGG
ACATTTGATCAAGTCACTCAAAACTTGTGGCAAGGTGTCACTGCACCCAATAACAATGGAGGTGGT
GCTGCTTTTGGTTTAGTTGAATATATTGCTACAAAGGCACAAGCTGTAGCTAAGGAATTTAATATT
TCTATCGTTTCCCAACCTGTTGGCCCTCCTTCTGCTAATGGTACTACTGCTGCTGCTCCTGCTCCT
GCTGCTGGCAATTCTACTGGAAAAGGAGGAAATCAATCTATTTCTAGCAGTGCTTCATCCAACAAA
ACCTCGGCTCAAAGCACATCAGGTGCTTCTCGTTCCAAGACTGCGCCCATCATTTTTAGCCATTTC
CGCTTTAGCTCTCCCTTGTATTCTAAA

FIGURE 39

>Predicted amino acid sequence of CotH3 from Lichtheimia corymbifera (exons only from sequenced data)

MKLSIISAAFLVAITHAASIKFNVIAPNATDVKVSVNGQQVTLTASDANVPYFTGSAEVGSSKTYK
YVAGGTEESFDRSLDGITNSTLNDFYNRPVTYANLPQLPWPIEKDPQWTRSGNKADIFDDNYIPSV
FFHGDDSQVQNVVKNVPADRISGTLTFIGSNYVYSFQNVSFGIHGAGKKHNNAKQSWNWILSGSDT
MGNRNFFKLRHMEEDPTQIRERLYSDILHAMGTYANDATMVRLFINNQGFGTFNMLDDITQFSYIN
AKFYNGKPPATLGPLYDGASGADFLYHPGNLDGYSSWVANTANPNGEAYEALDPLCKAWNETTYTD
NTAIANFEKMFDLDRFMRFMVIEYLTADWDGYWMGQTNDGAYRDPTDNNKWYFLDQDFDGTFGVNL
AAPEGNAFLDVSYKDFPSRYPGAVMINNLLQNADKKATYEKYLTETVRVLFNNVTLTNRVLALHNF
LLPDLEWDRSIVQQSPGINFGWTFDQVTQNLWQGVTAPNNNGGGAAFGLVEYIATKAQAVAKEFNI
SIVSQPVGPPSANGTTAAAPAPAAGNSTGKGGNQSISSSASSNKTSAQSTSGASRSKTAPIIFSHF
RFSSPLYSK

FIGURE 40

>CotH3 sequence from Lichtheimia corymbifera(including introns)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTTCCTCAAAGACATACAAA
GTAATCATAAATTTAGTTTGAATTCAATGAGATTAATCATCTTATTCTATAGTATGTTGCAGGTGG
AACAGAAGAAAGTTTTGATCGTTCTCTTGATGGAATCACAAACTCAACACTTAATGATTTTTATAA
TCGCCCCGTCACTTATGCTAACCTTCCTCAATTACCTTGGCCAATTGAAAAGACGTAAGTTATTT
TATTTTTATCTTTTCTCAGCTAAAATAAACATTGTCTTTCTCAGCCTCAGTGGACTCGTTCTGGAA
ACAAAGCCGACATTTTCGATGACAATTATATTCCCAGCGTTTTTTTCCACGGAGATGACAGTCAAG
TCCAAAATGTGGTTAAAAACGTACCTGCTGACCGAATCAGTGGTACACTGACCTTTATTGGATCTA
ATTACGTCTACTCTTTCCAGAATGTCTCATTTGGTATTCACGGTGCTGGCAAGAAACACAACAATG
CAAAACAATCTTGGAACTGGATATTGTCTGGAAGTGATACGATGGGTAACCGCAATTTCTTTAAGC
TTCGACATATGGAAGAAGATCCTACACAGATCCGTGAACGTCTTTATTCTGACATTTTACATGCCA
TGGGTACTTATGCCAATGATGCTACCATGGTTCGATTGTTTATTAACAACCAAGGCTTCGGTACCT
TCAACATGTTGGATGATATCACTCAATTCTCTTATATCAATGCTAAATTTTATAATGGCAAACCAC
CTGCTACCTTGGGTCCTCTCTATGATGGTGCCTCTGGTGCAGATTTCTTATATCATCCTGGTAACC
TCGATGGATACTCTTCTTGGGTTGCCAACACAGCCAATCCTAATGGTGAAGCTTATGAAGCTCTTG
ATCCTCTCTGTAAGGCCTGGAACGAGACGACCTATACCGATAATACAGCCATTGCAAACTTTGAAA
AAATGTTTGATCTCGACCGTTTCATGCGTTTCATGGTTATTGAATACTTGACTGCCGATTGGGATG
GTTACTGGATGGGACAGACCAATGATGGTGCCTATCGTGATCCAACTGATAATAACAAGTGGTACT
TTTTAGATCAAGACTTTGATGGTACTTTTGGTGTCAACTTGGCTGCACCCGAAGGCAATGCTTTTC
TTGATGTTTCTTACAAGGATTTCCCTTCTCGTTACCCTGGCGCTGTCATGATCAACAACCTCTTAC
AGAATGCTGATAAAAAGGCCACCTATGAAAATATTTGACTGAGACTGTGCGTGTGCTGTTCAATA
ATGTCACCTTGACTAACCGTGTCTTGGCCCTTCACAACTTCCTCTTGCCTGATCTTGAATGGGATC
GTTCGATCGTTCAACAATCTCCTGGTATTAACTTTGGTTGGACATTTGATCAAGTCACTCAAAACT
TGTGGCAAGGTGTCACTGCACCCAATAACAATGGAGGTGGTGCTGCTTTTGGTTTAGTTGAATATA
TTGCTACAAAGGCACAAGCTGTAGCTAAGGAATTTAATATTTCTATCGTTTCCCAACCTGTTGGCC
CTCCTTCTGCTAATGGTACTACTGCTGCTGCTCCTGCTCCTGCTGCTGGCAATTCTACTGGAAAAG
GAGGAAATCAATCTATTTCTAGCAGTGCTTCATCCAACAAAACCTCGGCTCAAAGCACATCAGGTG
CTTCTCGTTCCAAGACTGCGCCCATCATTTTTAGCCATTTCCGCTTTAGCTCTCCCTTGTATTCTA
AA

FIGURE 41

>Predicted amino acid sequence of CotH3 from Lichtheimia
corymbifera (including introns)

MKLSIISAAFLVAITHAASIKFNVIAPNATDVKVSVNGQQVTLTASDANVPYFTGSAEVGSSKTYK
VIINLV*IQ*D*SSYSIVCCRWNRRKF*SFS*WNHKLNT**FL*SPRHLC*PSSITLAN*KRRKLF
YFYLFSAKINIVFLSLSGLVLETKPTFSMTIIFPAFFSTEMTVKSKMWLKTYLLTESVVH*PLLDL
ITSTLSRMSHLVFTVLARNTTMQNNLGTGYCLEVIRWVTAISLSFDIWKKILHRSVNVFILTFYMP
WVLMPMMLPWFDCLLTTKASVPSTCWMISLNSLISMLNFIMANHLLPWVLSMMVPLVQISYIILVT
SMDTLLGLPTQPILMVKLMKLLILSVRPGTRRPIPIIQPLQTLKKCLISTVSCVSWLLNT*LPIGM
VTGWDRPMMVPIVIQLIITSGTF*IKTLMVLLVSTWLHPKAMLFLMFLTRISLLVTLALS*STTSY
RMLIKRPPMKNI*LRLCVCCSIMSP*LTVSWPFTTSSCLILNGIVRSFNNLLVLTLVGHLIKSLKT
CGKVSLHPITMEVVLLLV*LNILLQRHKL*LRNLIFLSFPNLLALLLMVLLLLLLLLAILLEK
EEINLFLAVLHPTKPRLKAHQVLLVPRLRPSFLAISALALPCIL

FIGURE 42

>CotH3 sequence from Cunninghamella bertholetiae(exons only)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
TATGTTGCAGGTGGAACAGAAGAAAGTTTTGATCGTTCTCTTGATGGAATCACAAACTCAACACTT
AATGATTTTTATAACCGCCCCGTCACTTATGCTAACCTTCCTCAATTACCTTGGCCAATTGAAAAA
GACCCTCAGTGGACTCGTTCTGGAAGCAAAGCCGACATTTTCGATGACAATTATATTCCCAGCGTT
TTTTTCCACGGAGATGACAGTCAAGTCCAAAATGTGGTTAAAAACGTACCTGCTGACCGAATCAGT
GGTACACTGACCTTTATTGGATCTAATTACGTCTACTCTTTCCAGAATGTCTCATTTGGTATTCAC
GGTGCTGGCAAGAAACACAACAATGCAAAACAATCTTGGAACTGGATATTGTCTGGAAGTGATACG
ATGGGTAACCGCAATTTCTTTAAGCTTCGACATATGGAAGAAGATCCTACACAGATTCGTGAACGT
CTTTATTCTGACATTTTACATGCCATGGGTACTTATGCCAATGATGCTACCATGGTTCGATTGTTT
ATTAACAACCAAGGCTTCGGTACCTTCAACATGTTGGATGATATCACTCAATTCTCCTATATCAAT
GCTAAATTTTATAATGGCAAACCACCTGCTACCTTGGGTCCTCTCTATGATGGTGCCTCTGGTGCA
GACTTCTTATATCATCCTGGTAACCTCGATGGATACTCTTCTTGGGTTGCCAACACAGCCAATCCT
AATGTGAAGCTTATGAAGCCTCTTGATCCTCTCTGTAGCCTGGAACGAGACGACCTAATACCGATA
ATACAGCCATTGCAAACTTTGAAAAATGTTTGATCTCGACCGTTTCATGCGTTTCATGGTTATTG
AATACTTGACTGCCGATTGGGATGGTTACTGGATGGGACAGACCAATGATGGTGCCTATCGTGATC
CAACTGATAATAACAAGTGGTACTTTTAGATCAAGACTTTGATGGTACTTTTGGTGTCAACTTGG
CTGCACCCGAAGGCAATGCTTTTCTTGATGTTTCTTACAAGGATTTCCCTTCTCGTTACCCTGGCG
CTGTCATGATCAACAACCTCTTACAGAATGCTGATAAAAAGGCCACCTTTGAAAAATATTTGACTG
AGACTGTGCGTGTGCTGTTCAATAATGTCACCTTGACTAACCGTGTCTTGGCCCTTCACAACTTCC
TCTTGCCTGATCTTGAATGGGATCGTTCGATCGTTCAACAATCTCCTGGTATTAACTTTGGTTGGA
CATTTGATCAAGTCACTCAAAACTTGTGGCAAGGTGTCACTGCACCCAATAACAATGGAGGTGGTG
CTGCTTTTGGTTTAGTTGAATATATTGCTGCAAAGGCACAAGCTGTAGCTAAGGAATTTAATATTT
CTATCGTTTCCCAACCTGTTGGCCCTCCTTCTGCTAATGGTACTACTGCTGCTGCTCTGCTCTGCT
GCTGCAATTCTACTGGAAAAGAGAAATCAATCTATTTCTAGCAGTGCTTCATCAACAAAGCTCGG
CTCAAGGCACATCAGTGCCTTCTCGATCAAGACTGCGCCCATCGATTAAGCAGTTCGCTTTAGCTT
CCCTGGGGTAATCTCCAAAAA

FIGURE 43

>Predicted amino acid sequence of CotH3 from Cunninghamella
bertholetiae (exons only from sequenced data)

MKLSIISAAFLVAITHAASIKFNVIAPNATDVKVSVNGQQVTLTASDANVPYFTGSAEVGASKTYK
VIINLV*IQ*D*SSYSIVCCRWNRRKF*SFS*WNHKLNT**FL*PPRHLC*PSSITLAN*KRRKLF
YFYLFSAKINIVFSASVDSFWKQSRHFR*QLYSQRFFPRR*QSSPKCG*KRTC*PNQWYTDLYWI*
LRLLFPECLIWYSRCWQETQQCKTILELDIVWK*YDG*PQFL*ASTYGRRSYTDS*TSLF*HFTCH
GYLCQ*CYHGSIVY*QPRLRYLQHVG*YHSILLYQC*IL*WQTTCYLGSSL*WCLWCRLLISSW*P
RWILFLGCQHSQS*CEAYEAS*SSL*PGTRRPNTDNTAIANFEKMFDLDRFMRFMVIEYLTADWDG
YWMGQTNDGAYRDPTDNNKWYFLDQDFDGTFGVNLAAPEGNAFLDVSYKDFPSRYPGAVMINNLLQ
NADKKATFEKYLTETVRVLFNNVTLTNRVLAHNFLLPDLEWDRSIVQQSPGINFGWTFDQVTQNL
WQGVTAPNNNGGGAAFGLVEYIAAKAQAVAKEFNISIVSQPVGPPSANGTTAAALLCCCNSTGKEK
SIYFLAVLHQQSSAQGTSVPSRSRLRPSIKQFALASLG*SPK

FIGURE 44

>CotH3 sequence from Cunninghamella bertholetiae (including introns)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
GTAATCATAAATTTAGTTTGAATTCAATGAGATTAATCATCTTATTCTATAGTATGTTGCAGGTGG
AACAGAAGAAAGTTTTGATCGTTCTCTTGATGGAATCACAAACTCAACACTTAATGATTTTTATAA
CCGCCCCGTCACTTATGCTAACCTTCCTCAATTACCTTGGCCAATTGAAAAGACGTAAGTTATTT
TATTTTTATCTTTTCTCAGCTAAAATAAACATTGTCTTCTCAGCCTCAGTGGACTCGTTCTGGAAG
CAAAGCCGACATTTTCGATGACAATTATATTCCCAGCGTTTTTTTCCACGGAGATGACAGTCAAGT
CCAAAATGTGGTTAAAAACGTACCTGCTGACCGAATCAGTGGTACACTGACCTTTATTGGATCTAA
TTACGTCTACTCTTTCCAGAATGTCTCATTTGGTATTCACGGTGCTGGCAAGAAACACAACAATGC
AAAACAATCTTGGAACTGGATATTGTCTGGAAGTGATACGATGGGTAACCGCAATTTCTTTAAGCT
TCGACATATGGAAGAAGATCCTACACAGATTCGTGAACGTCTTTATTCTGACATTTTACATGCCAT
GGGTACTTATGCCAATGATGCTACCATGGTTCGATTGTTTATTAACAACCAAGGCTTCGGTACCTT
CAACATGTTGGATGATATCACTCAATTCTCCTATATCAATGCTAAATTTTATAATGGCAAACCACC
TGCTACCTTGGGTCCTCTCTATGATGGTGCCTCTGGTGCAGACTTCTTATATCATCCTGGTAACCT
CGATGGATACTCTTCTTGGGTTGCCAACACAGCCAATCCTAATGTGAAGCTTATGAAGCCTCTTGA
TCCTCTCTGTAGCCTGGAACGAGACGACCTAATACCGATAATACAGCCATTGCAAACTTTGAAAAA
ATGTTTGATCTCGACCGTTTCATGCGTTTCATGGTTATTGAATACTTGACTGCCGATTGGGATGGT
TACTGGATGGGACAGACCAATGATGGTGCCTATCGTGATCCAACTGATAATAACAAGTGGTACTTT
TTAGATCAAGACTTTGATGGTACTTTTGGTGTCAACTTGGCTGCACCCGAAGGCAATGCTTTTCTT
GATGTTTCTTACAAGGATTTCCCTTCTCGTTACCCTGGCGCTGTCATGATCAACAACCTCTTACAG
AATGCTGATAAAAGGCCACCTTTGAAAAATATTTGACTGAGACTGTGCGTGTGCTGTTCAATAAT
GTCACCTTGACTAACCGTGTCTTGGCCCTTCACAACTTCCTCTTGCCTGATCTTGAATGGGATCGT
TCGATCGTTCAACAATCTCCTGGTATTAACTTTGGTTGGACATTTGATCAAGTCACTCAAAACTTG
TGGCAAGGTGTCACTGCACCCAATAACAATGGAGGTGGTGCTGCTTTTGGTTTAGTTGAATATATT
GCTGCAAAGGCACAAGCTGTAGCTAAGGAATTTAATATTTCTATCGTTTCCCAACCTGTTGGCCCT
CCTTCTGCTAATGGTACTACTGCTGCTGCTCTGCTCTGCTGCTGCAATTCTACTGGAAAAGAGAAA
TCAATCTATTTTCTAGCAGTGCTTCATCAACAAAGCTCGGCTCAAGGCACATCAGTGCCTTCTCGA
TCAAGACTGCGCCCATCGATTAAGCAGTTCGCTTTAGCTTCCCTGGGGTAATCTCCAAAAA

FIGURE 45

>Predicted amino acid sequence of CotH3 from Cunninghamella
bertholetiae (including introns from sequenced data)

MKLSIISAAFLVAITHAASIKFNVIAPNATDVKVSVNGQQVTLTASDANVPYFTGSAEVGASKTYK
VIINLV*IQ*D*SSYSIVCCRWNRRKF*SFS*WNHKLNT**FL*PPRHLC*PSSITLAN*KRRKLF
YFYLFSAKINIVFSASVDSFWKQSRHFR*QLYSQRFFPRR*QSSPKCG*KRTC*PNQWYTDLYWI*
LRLLFPECLIWYSRCWQETQQCKTILELDIVWK*YDG*PQFL*ASTYGRRSYTDS*TSLF*HFTCH
GYLCQ*CYHGSIVY*QPRLRYLQHVG*YHSILLYQC*IL*WQTTCYLGSSL*WCLWCRLLISSW*P
RWILFLGCQHSQS*CEAYEAS*SSL*PGTRRPNTDNTAIANFEKMFDLDRFMRFMVIEYLTADWDG
YWMGQTNDGAYRDPTDNNKWYFLDQDFDGTFGVNLAAPEGNAFLDVSYKDFPSRYPGAVMINNLLQ
NADKKATFEKYLTETVRVLFNNVTLTNRVLALHNFLLPDLEWDRSIVQQSPGINFGWTFDQVTQNL
WQGVTAPNNNGGGAAFGLVEYIAAKAQAVAKEFNISIVSQPVGPPSANGTTAAALLCCCNSTGKEK
SIYFLAVLHQQSSAQGTSVPSRSRLRPSIKQFALASLG*SPK

FIGURE 46

>CotH3 sequence from R. mirosporus(exons only from sequenced data)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
TATGTTGCAGGTGGAACAGAAGAAAGTTTTGATCGTTCTCTTGATGGAATCACAAACTCAACACTT
AATGATTTTTATAACCGCCCCGTCACTTATGCTAACCTTCCTCAATTACCTTGGCCAATTGAAAAA
GACCCTCAGTGGACTCGTTCTGGAAGCAAAGCCGACATTTTCGATGACAATTATATTCCCAGCGTT
TTTTTCCACGGAGATGACAGTCAAGTCCAAAATGTGGTTAAAAACGTACCTGCTGACCGAATCAGT
GGTACACTGACCTTTATTGGATCTAATTACGTCTACTCTTTCCAGAATGTCTCATTTGGTATTCAC
GGTGCTGGCAAGAAACACAACAATGCAAAACAATCTTGGAACTGGATATTGTCTGGAAGTGATACG
ATGGGTAACCGCAATTTCTTTAAGCTTCGACATATGGAAGAAGATCCTACACAGATTCGTGAACGT
CTTTATTCTGACATTTTACATGCCATGGGTACTTATGCCAATGATGCTACCATGGTTCGATTGTTT
ATTAACAACCAAGGCTTCGGTACCTTCAACATGTTGGATGATATCACTCAATTCTCCTATATCAAT
GCTAAATTTTATAATGGCAAACCACCTGCTACCTTGGGTCCTCTCTATGATGGTGCCTCTGGTGCA
GACTTCTTATATCATCCTGGTAACCTCGATGGATACTCTTCTTGGGTTGCCAACACAGCCAATCCT
AATGGTGAAGCTTATGAAGCTCTTGATCCTCTCTGTAAGGCCTGGAACGAGACGACCTATACCGAT
AATACAGCCATTGCAAACTTTGAAAAATGTTTGATCTCGACCGTTTCATGCGTTTCATGGTTATT
GAATACTTGACTGCCGATTGGGATGGTTACTGGATGGGACAGACCAATGATGGTGCCTATCGTGAT
CCAACTGATAATAACAAGTGGTACTTTTAGATCAAGACTTTGATGGTACTTTTGGTGTCAACTTG
GCTGCACCCGAAGGCAATGCTTTTCTTGATGTTTCTTACAAGGATTTCCCTTCTCGTTACCCTGGC
GCTGTCATGATCAACAACCTCTTACAGAATGCTGATAAAAAGGCCACCTTTGAAAAATATTTGACT
GAGACTGTGCGTGTGCTGTTCAATAATGTCACCTTGACTAACCGTGTCTTGGCCCTTCACAACTTC
CTCTTGCCTGATCTTGAATGGATCGTTCGATCGTTCAACAATCTCCTGGTATTAACTTTGGTTGG
ACATTTGATCAAGTCACTCAAAACTTGTGGCAAGGTGTCACTGCACCCAATAACAATGGAGGTGGT
GCTGCTTTTGGTTTAGTTGAATATATTGCTGCAAAGGCACAAGCTGTAGCTAAGGAATTTAATATT
TCTATCGTTTCCCAACCTGTTGGCCCTCCTTCTGCTAATGGTACTACTGCTGCTGCTCCTGCTCCT
GCTGCTGGCAATTCTACTGGAAAAGGAGGAAATCAATCTATTTCTAGCAGTGCTTCATCCAACAAA
ACCTCGGCTCAAAGCACATCAGGTGCTTCTCGTTCCAAGACTGCGCCCATCGTTTTAGCCATTTCC
GCTTTAGCTCTCCTTGTATTCTAAA

FIGURE 47

>Predicted amino acid sequence of CotH3 from R. mirosporus(exons only from sequenced data)

MKLSIISAAFLVAITHAASIKFNVIAPNATDVKVSVNGQQVTLTASDANVPYFTGSAEVGASKTYK
YVAGGTEESFDRSLDGITNSTLNDFYNRPVTYANLPQLPWPIEKDPQWTRSGSKADIFDDNYIPSV
FFHGDDSQVQNVVKNVPADRISGTLTFIGSNYVYSFQNVSFGIHGAGKKHNNAKQSWNWILSGSDT
MGNRNFFKLRHMEEDPTQIRERLYSDILHAMGTYANDATMVRLFINNQGFGTFNMLDDITQFSYIN
AKFYNGKPPATLGPLYDGASGADFLYHPGNLDGYSSWVANTANPNGEAYEALDPLCKAWNETTYTD
NTAIANFEKMFDLDRFMRFMVIEYLTADWDGYWMGQTNDGAYRDPTDNNKWYFLDQDFDGTFGVNL
AAPEGNAFLDVSYKDFPSRYPGAVMINNLLQNADKKATFEKYLTETVRVLFNNVTLTNRVLALHNF
LLPDLEWDRSIVQQSPGINFGWTFDQVTQNLWQGVTAPNNNGGGAAFGLVEYIAAKAQAVAKEFNI
SIVSQPVGPPSANGTTAAAPAPAAGNSTGKGGNQSISSSASSNKTSAQSTSGASRSKTAPIVLAIS
ALALLVF*

FIGURE 48

>CotH3 sequence from R. mirosporus(including introns, has only one intron)

ATGAAATTATCTATTATATCCGCTGCCTTTTTAGTGGCTATTACACACGCTGCTTCAATAAAGTTT
AATGTAATTGCTCCTAATGCAACTGATGTCAAAGTATCTGTAAATGGACAGCAAGTGACACTTACT
GCTTCAGATGCAAATGTCCCTTATTTCACTGGTTCAGCTGAAGTTGGTGCCTCAAAGACATACAAA
TATGTTGCAGGTGGAACAGAAGAAAGTTTTGATCGTTCTCTTGATGGAATCACAAACTCAACACTT
AATGATTTTTATAACCGCCCCGTCACTTATGCTAACCTTCCTCAATTACCTTGGCCAATTGAAAAA
GACGTAAGTTATTTTATTTTTATCTTTCTCAGCTAAAATAAACATTGTCTTTCTCAGCCTCAGTG
GACTCGTTCTGGAAGCAAAGCCGACATTTTCGATGACAATTATATTCCCAGCGTTTTTTTCCACGG
AGATGACAGTCAAGTCCAAAATGTGGTTAAAAACGTACCTGCTGACCGAATCAGTGGTACACTGAC
CTTTATTGGATCTAATTACGTCTACTCTTTCCAGAATGTCTCATTTGGTATTCACGGTGCTGGCAA
GAAACACAACAATGCAAACAATCTTGGAACTGGATATTGTCTGGAAGTGATACGATGGGTAACCG
CAATTTCTTTAAGCTTCGACATATGGAAGAAGATCCTACACAGATTCGTGAACGTCTTTATTCTGA
CATTTTACATGCCATGGGTACTTATGCCAATGATGCTACCATGGTTCGATTGTTTATTAACAACCA
AGGCTTCGGTACCTTCAACATGTTGGATGATATCACTCAATTCTCCTATATCAATGCTAAATTTTA
TAATGGCAAACCACCTGCTACCTTGGGTCCTCTCTATGATGGTGCCTCTGGTGCAGACTTCTTATA
TCATCCTGGTAACCTCGATGGATACTCTTCTTGGGTTGCCAACACAGCCAATCCTAATGGTGAAGC
TTATGAAGCTCTTGATCCTCTCTGTAAGGCCTGGAACGAGACGACCTATACCGATAATACAGCCAT
TGCAAACTTTGAAAAATGTTTGATCTCGACCGTTTCATGCGTTTCATGGTTATTGAATACTTGAC
TGCCGATTGGGATGGTTACTGGATGGGACAGACCAATGATGGTGCCTATCGTGATCCAACTGATAA
TAACAAGTGGTACTTTTTAGATCAAGACTTTGATGGTACTTTTGGTGTCAACTTGGCTGCACCCGA
AGGCAATGCTTTTCTTGATGTTTCTTACAAGGATTTCCCTTCTCGTTACCCTGGCGCTGTCATGAT
CAACAACCTCTTACAGAATGCTGATAAAAAGGCCACCTTTGAAAAATATTTGACTGAGACTGTGCG
TGTGCTGTTCAATAATGTCACCTTGACTAACCGTGTCTTGGCCCTTCACAACTTCCTCTTGCCTGA
TCTTGAATGGGATCGTTCGATCGTTCAACAATCTCCTGGTATTAACTTTGGTTGGACATTTGATCA
AGTCACTCAAAACTTGTGGCAAGGTGTCACTGCACCCAATAACAATGGAGGTGGTGCTGCTTTTGG
TTTAGTTGAATATATTGCTGCAAAGGCACAAGCTGTAGCTAAGGAATTTAATATTTCTATCGTTTC
CCAACCTGTTGGCCCTCCTTCTGCTAATGGTACTACTGCTGCTGCTCCTGCTCCTGCTGCTGGCAA
TTCTACTGGAAAAGGAGGAAATCAATCTATTTCTAGCAGTGCTTCATCCAACAAAACCTCGGCTCA
AAGCACATCAGGTGCTTCTCGTTCCAAGACTGCGCCCATCGTTTTAGCCATTTCCGCTTTAGCTCT
CCTTGTATTCTAAA

FIGURE 49

>Predicted amino acid sequence of CotH3 from R.
mirosporus(including introns)

MKLSIISAAFLVAITHAASIKFNVIAPNATDVKVSVNGQQVTLTASDANVPYFTGSAEVGASKTYK
VIINLV*IQ*D*SSYSIVCCRWNRRKF*SFS*WNHKLNT**FL*PPRHLC*PSSITLAN*KRRKLF
YFYLFSAKINIVFLSLSGLVLEAKPTFSMTIIFPAFFSTEMTVKSKMWLKTYLLTESVVH*PLLDL
ITSTLSRMSHLVFTVLARNTTMQNNLGTGYCLEVIRWVTAISLSFDIWKKILHRFVNVFILTFYMP
WVLMPMMLPWFDCLLTTKASVPSTCWMISLNSPISMLNFIMANHLLPWVLSMMVPLVQTSYIILVT
SMDTLLGLPTQPILMVKLMKLLILSVRPGTRRPIPIIQPLQTLKKCLISTVSCVSWLLNT*LPIGM
VTGWDRPMMVPIVIQLIITSGTF*IKTLMVLLVSTWLHPKAMLFLMFLTRISLLVTLALS*STTSY
RMLIKRPPLKNI*LRLCVCCSIMSP*LTVSWPFTTSSCLILNGIVRSFNNLLVLTLVGHLIKSLKT
CGKVSLHPITMEVVLLLV*LNILLQRHKL*LRNLIFLSFPNLLALLLLMVLLLLLLLLLAILLEK
EEINLFLAVLHPTKPRLKAHQVLLVPRLRPSF*PFPL*LSLYSK

FIGURE 50

IMMUNOTHERAPY AND DIAGNOSIS OF MUCORMYCOSIS USING COTH

This application claims the benefit of priority of U.S. Provisional application Ser. No. 61/535,257, filed Sep. 15, 2011, the entire contents of which is incorporated herein by reference.

This invention was made with government support under NIH grant numbers 011671 and 013377 awarded by NIAID. The government has certain rights in the invention.

The instant application contains a Sequence Listing which has been submitted in ASCII format via EFS-Web and is hereby incorporated by reference in its entirety. Said ASCII copy, created on Oct. 18, 2012, is named 12959-037-999_Sequence_Listing.txt and is 183,987 bytes in size.

BACKGROUND OF THE INVENTION

The present invention relates generally to compositions and methods for detecting, treating and preventing infectious diseases in a patient, and more specifically to compositions and methods that target specific proteins or nucleic acids unique to fungi that cause mucormycosis.

About 180 of the 250,000 known fungal species are recognized to cause disease (mycosis) in man and animal. Some of fungi can establish an infection in all exposed subjects, e.g., the systemic pathogens *Histoplasma capsulatum* and *Coccidioides immitis*. Others, such as *Candida, Asergillus* species and Zygomycetes are opportunist pathogens which ordinarily cause disease only in a compromised host. Fungi of the class Zygomycetes, order Mucorales, can cause mucormycosis, a potentially deadly fungal infection in human. Fungi belonging to the order Mucorales are distributed into at least six families, all of which can cause mucormycosis (Ibrahim et al. *Zygomycosis*, p. 241-251, In W. E. Dismukes, P. G. Pappas, and J. D. Sobel (ed.), *Clinical Mycology*, Oxford University Press, New York (2003); Kwon-Chung, K. J., and J. E. Bennett, *Mucormycosis*, p. 524-559, *Medical Mycology*, Lea & Febiger, Philadelphia (1992), and Ribes et al. *Zygomycetes in Human Disease, Clin Microbiol Rev* 13:236-301 (2000)). However, fungi belonging to the family Mucoraceae, and specifically the species *Rhizopus oryzae* (*Rhizopus arrhizus*), are by far the most common cause of infection (Ribes et al., supra). Increasing cases of mucormycosis have been also reported due to infection with *Cunninghamella* spp. in the Cunninghamellaceae family (Cohen-Abbo et al., *Clinical Infectious Diseases* 17:173-77 (1993); Kontoyianis et al., *Clinical Infectious Diseases* 18:925-28 (1994); Kwon-Chung et al., *American Journal of Clinical Pathology* 64:544-48 (1975), and Ventura et al., *Cancer* 58:1534-36 (1986)). The remaining four families of the Mucorales order are less frequent causes of disease (Bearer et al., *Journal of Clinical Microbiology* 32:1823-24 (1994); Kamalam and Thambiah, *Sabouraudia* 18:19-20 (1980); Kemna et al., *Journal of Clinical Microbiology* 32:843-45 (1994); Lye et al., *Pathology* 28:364-65 (1996), and Ribes et al., (supra)).

The agents of mucormycosis almost uniformly affect immunocompromised hosts (Spellberg et al., *Clin. Microbiol. Rev.* 18:556-69 (2005)). The major risk factors for mucormycosis include uncontrolled diabetes mellitus in ketoacidosis known as diabetes ketoacidosis (DKA), other forms of metabolic acidosis, treatment with corticosteroids, organ or bone marrow transplantation, neutropenia, trauma and burns, malignant hematological disorders, and deferoxamine chelation-therapy in subjects receiving hemodialysis.

Recent reports have demonstrated a striking increase in the number of reported cases of mucormycosis over the last two decades (Gleissner et al., *Leuk. Lymphoma* 45(7):1351-60 (2004)). There has also been an alarming rise in the incidence of mucormycosis at major transplant centers. For example, at the Fred Hutchinson Cancer Center, Marr et al. have described a greater than doubling in the number of cases from 1985-1989 to 1995-1999 (Marr et al., *Clin. Infect. Dis.* 34(7): 909-17 (2002)). Similarly, Kontoyiannis et al. have described a greater than doubling in the incidence of mucormycosis in transplant subjects over a similar time-span (Kontoyiannis et al, *Clin. Infect. Dis.* 30(6):851-6 (2000)). Given the increasing prevalence of diabetes, cancer, and organ transplantation in the aging United States population, the rise in incidence of mucormycosis is anticipated to continue unabated for the foreseeable future.

Therefore, there exists a need for compounds and methods that can reduce the risk of mucormycosis pathogenesis and provide effective therapies without adverse effects. The present invention satisfies this need and provides related advantages as well.

SUMMARY OF INVENTION

In accordance with the present invention, there are provided Mucorales CotH polypeptides and encoding nucleic acid molecules. The Mucorales CotH polypeptides and encoding nucleic acids can be advantageously used to diagnose, treat or prevent fungal conditions, in particular mucormycosis. Furthermore, the Mucorales CotH polypeptides and encoding nucleic acids are useful to generate or screen for agents that can alter Mucorales CotH activity or expression, which can further be used to treat or prevent fungal conditions.

The invention also provides vectors containing Mucorales CotH nucleic acids, host cells containing such vectors, Mucorales CotH anti-sense nucleic acids and related compositions. The invention additionally provides Mucorales CotH oligonucleotides that can be used to hybridize to or amplify a Mucorales CotH nucleic acid. Anti-Mucorales CotH specific antibodies are also provided. Further provided are kits containing Mucorales CotH nucleic acids or Mucorales CotH specific antibodies. Such kits and reagents can be used to diagnose fungal infection cause by Mucorales organisms. Also provided are pharmaceutical and vaccine compositions.

BRIEF DESCRIPTION OF THE DRAWINGS

FIG. 8, panels A and B, show *S. cerevisiae* expressing CotH2 or CotH3 adhere to and invades endothelial cells or CHO cells overexpressing GRP78 but not CHO parent cells.

FIG. 9 shows the amino acid sequence (SEQ ID NO. 1) and the nucleic acid coding sequence (SEQ ID NO. 2) of CotH1 from *R. oryzae*.

FIG. 10 shows the amino acid sequence (SEQ ID NO. 3) and the nucleic acid coding sequence (SEQ ID NO. 4) of CotH2 from *R. oryzae*.

FIG. 11 shows the amino acid sequence (SEQ ID NO. 5) and the nucleic acid coding sequence (SEQ ID NO. 6) of CotH3 from *R. oryzae*.

FIG. 12 shows the amino acid sequence (SEQ ID NO. 7) and the nucleic acid coding sequence (SEQ ID NO. 8) of RO3G_16295 from *R. oryzae*.

FIG. 17 shows the highest homology of any of the CotH predicted proteins (in this case CotH3 [R03G_11882] SEQ ID NO: 5) with an amino acid sequence of a protein from *Stigmatella aurantiaca* (ZP 01460584) (SEQ ID NO: 65).

FIG. 18 shows an amino acid sequence alignment between the RO3G_16295 protein from *R. oryzae* (SEQ ID NO: 66) and *Talaromyces stipitatus* ATCC 10500 (EED23986) protein (SEQ ID NO: 67).

FIG. 19 shows an amino acid sequence alignment between the RO3G_16295 protein from *R. oryzae* (SEQ ID NO: 66) and *Penicillium marneffei* ATCC 18224 (XP 002144175) protein (SEQ ID NO: 68).

FIG. 20 shows an amino acid sequence alignment between the RO3G_16295 protein from *R. oryzae* (SEQ ID NO: 66) and *Aspergillus niger* (XP_001392236) protein (SEQ ID NO: 69).

FIG. 21 shows an amino acid sequence alignment between the RO3G_16295 protein from *R. oryzae* (SEQ ID NO: 66) and *Aspergillus nidulans* (XP_658934) protein (SEQ ID NO: 70).

FIG. 22 shows an amino acid sequence alignment between the RO3G_16295 protein from *R. oryzae* (SEQ ID NO: 66) and *Ustilago maydis* (XP_760027) protein (SEQ ID NO: 71).

FIG. 23 shows an amino acid sequence alignment between the RO3G_16295 protein from *R. oryzae* (SEQ ID NO: 66) and *Coccidioides immitis* (XP_001243211) protein (SEQ ID NO: 72).

FIG. 24 shows an amino acid sequence alignment between the RO3G_16295 protein from *R. oryzae* (SEQ ID NO: 66) and *Neurospora crassa* (XP_956792) protein (SEQ ID NO: 73).

FIG. 25 shows an amino acid sequence alignment between the RO3G_16295 protein from *R. oryzae* (SEQ ID NO: 66) and *Cryptococcus neoformans* (XP_775558) protein (SEQ ID NO: 74).

FIG. 26 shows an amino acid sequence alignment between the RO3G_16295 protein from *R. oryzae* (SEQ ID NO: 66) and *Streptomyces lividans* (EFD65170) protein (SEQ ID NO: 75).

FIG. 27 shows a nucleic acid sequence of CotH3 from *Rhizopus oryzae* 99-880 (including introns from Data base) (SEQ ID NO: 9).

FIG. 28 shows a nucleic acid sequence of CotH3 from *Rhizopus oryzae* 99-880 (exon only from Data base) (SEQ ID NO: 10).

FIG. 29 shows an amino acid sequence of CotH3 from *Rhizopus oryzae* 99-880 (predicted amino acids) (SEQ ID NO: 11).

FIG. 30 shows a nucleic acid sequence of CotH3 from *Rhizopus oryzae* 99-880 (including introns from sequenced data) (SEQ ID NO: 12).

FIG. 31 shows a nucleic acid sequence of CotH3 from *Rhizopus oryzae* 99-892 (exons only from Sequenced data) (SEQ ID NO: 13).

FIG. 32 shows a nucleic acid sequence of CotH3 from *Rhizopus oryzae* 99-892 (including intron from Sequenced data) (SEQ ID NO: 14).

FIG. 33 shows the predicted amino acid sequence of CotH3 from *R. oryzae* 99-892 (excluding introns) (SEQ ID NO: 15).

FIG. 34 shows the predicted amino acid sequence of CotH3 from *R. oryzae* 99-892 (including introns) (SEQ ID NO: 16).

FIG. 35 shows a nucleic acid sequence of CotH3 sequence from *Mucor* sp. 99-932 (exons only from sequenced data) (SEQ ID NO: 17).

FIG. 36 shows the predicted amino acid sequence of CotH3 from *Mucor* 99-932 (AA exons only) (SEQ ID NO: 18).

FIG. 37 shows a nucleic acid sequence of CotH3 from *Mucor* 99-932 (including introns) (SEQ ID NO: 19).

FIG. 38 shows the predicted amino acid sequence of CotH3 from *Mucor* 99-932 (including introns) (SEQ ID NO: 20).

FIG. 39 shows a nucleic acid sequence of CotH3 from *Lichtheimia corymbifera* (exons only from sequenced data) (SEQ ID NO: 21).

FIG. 40 shows the predicted amino acid sequence of CotH3 from *Lichtheimia corymbifera* (exons only from sequenced data) (SEQ ID NO: 22).

FIG. 41 shows a nucleic acid sequence of CotH3 from *Lichtheimia corymbifera* (including introns) (SEQ ID NO: 23).

FIG. 42 shows the predicted amino acid sequence of CotH3 from *Lichtheimia corymbifera* (including introns) (SEQ ID NO: 24).

FIG. 43 shows a nucleic acid sequence of CotH3 sequence from *Cunninghamella bertholetiae* (exons only) (SEQ ID NO: 25).

FIG. 44 shows the predicted amino acid sequence of CotH3 from *Cunninghamella bertholetiae* (exons only from sequenced data) (SEQ ID NO: 26).

FIG. 45 shows a nucleic acid sequence of CotH3 from *Cunninghamella bertholetiae* (including introns) (SEQ ID NO: 27).

FIG. 46 shows the predicted amino acid sequence of CotH3 from *Cunninghamella bertholetiae* (including introns from sequenced data) (SEQ ID NO: 28).

FIG. 47 shows a nucleic acid sequence of CotH3 from *R. microsporus* (exons only from sequenced data) (SEQ ID NO: 29).

FIG. 48 shows the predicted amino acid sequence of CotH3 from *R. microsporus* (exons only from sequenced data) (SEQ ID NO: 30).

FIG. 49 shows a nucleic acid sequence of CotH3 from *R. microsporus* (including introns, has only one intron) (SEQ ID NO: 31).

FIG. 50 shows the predicted amino acid sequence of CotH3 from *R. microsporus* (including introns) (SEQ ID NO: 32).

DETAILED DESCRIPTION OF THE INVENTION

Figure 1:
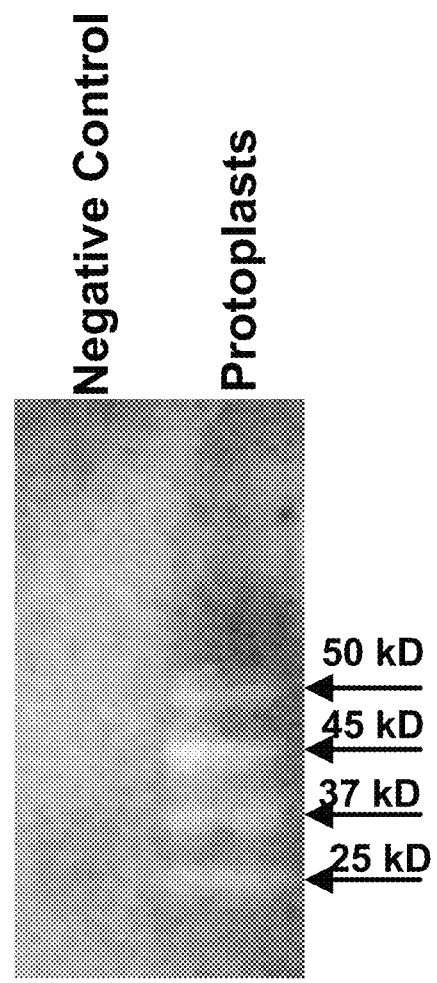
FIG. 1 shows a FAR-western blot of four open reading frames (ORF) predicted to be cell surface proteins.
Figure 2:
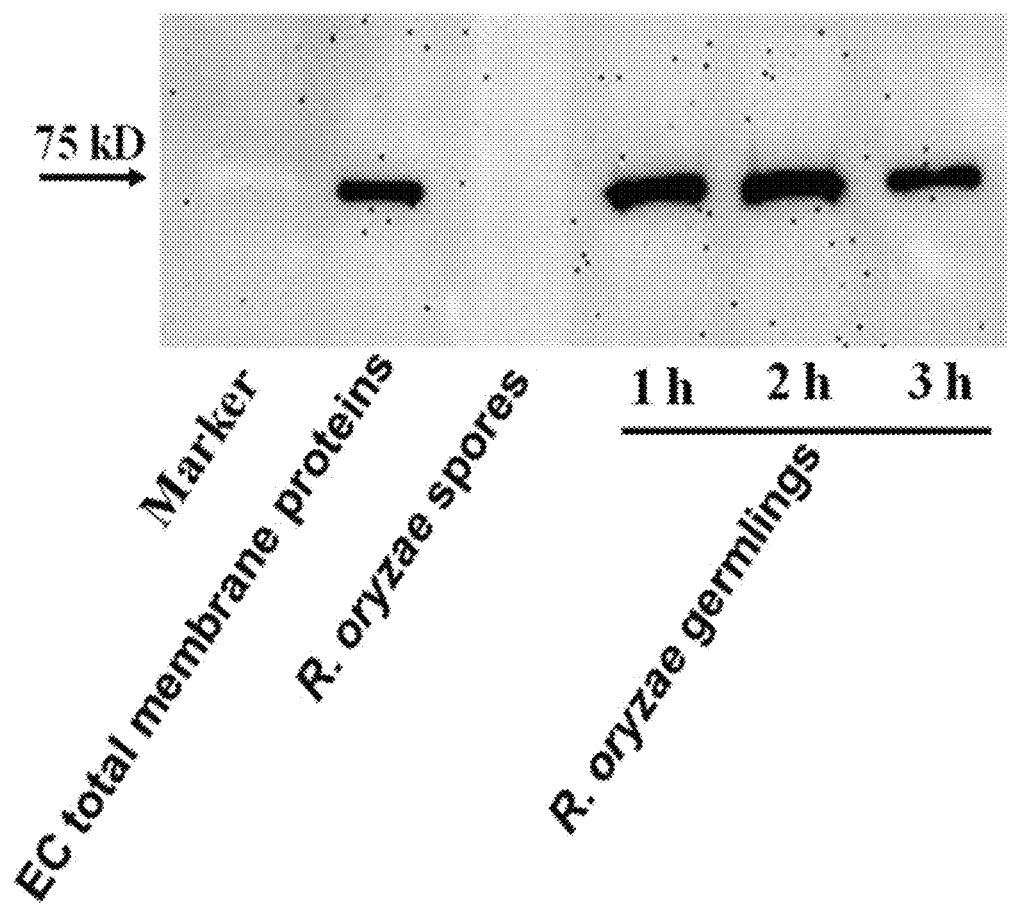
FIG. 2 shows GRP78 binds to germlings but not to spores of *R. oryzae*.

The compositions and methods disclosed herein are based, at least in part, on the identification and characterization of cell surface proteins that are uniquely expressed by fungi of the Mucorales order and can facilitate binding of endothelial cells during fungal infections. mucormycosis, which is mainly caused by *Rhizopus oryzae*, is characterized by angio-invasion and vascular thrombosis. Interactions between Mucorales and endothelial cells is an important factor in establishing a fungal condition. The recently identified Glucose Regulated Protein 78 (GRP78), a novel host receptor that mediates invasion and subsequent damage of human umbilical vein endothelial cells by *R. oryzae* germlings, provides a likely target ligand for *R. oryzae* and other Mucorales species to bind during invasion (Liu et al., J. Clin. Invest. 120:1914-24 (2010)).

In accordance with the present invention, provided are nucleic acids encoding Mucorales CotH polypeptides and other polypeptides disclosed herein, or functional polypeptide fragments thereof.

As used herein, the term "Mucorales CotH" refers to subfamily members of the CotH family of proteins, wherein the Mucorales CotH proteins include cell surface proteins expressed by fungi in the Mucorales order that are involved in the process of adherence and invasion of host cells, such as endothelial cell. Because Mucorales CotH proteins are unique to Mucorales, the presence or absence of Mucorales CotH nucleic acid or polypeptide or changes in Mucorales CotH nucleic acid or polypeptide expression can serve as a marker for infection by a Mucorales species, for example, mucormycosis. Thus, the invention includes Mucorales CotH nucleic acids and/or polypeptides that can be used for screening for a fungal condition and/or for developing drug candidates for the treatment of a fungal condition.

The term "functional," when used herein as a modifier of an Mucorales CotH polypeptide, or polypeptide fragment thereof, refers to a polypeptide that exhibits functional characteristics similar to CotH1, CotH2 and CotH3 as disclosed herein. For example, when CotH3 or CotH2 were expressed in *S. cerevisae*, the *S. cerevisae* cells adhere to and invade endothelial cells or CHO cells overexpressing GRP78. Therefore, one function of Mucorales CotH is a pro-adherance and/or pro-invasion function. In another aspect, a functional Murcorales CotH polypeptide or fragment thereof can also include in vivo or in vitro binding to a GRP78 protein, variant or fragment thereof.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention Mucorales CotH gene or mRNA transcript in a given sample. The nucleic acid molecules described herein, and fragments thereof, are also useful as primers and/or templates in a PCR reaction for amplifying genes encoding invention proteins described herein.

The term "nucleic acid", also referred to as polynucleotides, encompasses ribonucleic acid (RNA) or deoxyribonucleic acid (DNA), probes, oligonucleotides, and primers and can be single stranded or double stranded. DNA can be either complementary DNA (cDNA) or genomic DNA, and can represent the sense strand, the anti-sense strand or both. Examples of nucleic acids are RNA, cDNA, or isolated genomic DNA encoding an Mucorales CotH polypeptide. Such nucleic acids include, but are not limited to, nucleic acids comprising substantially the same nucleotide sequence as set forth in 2, 4, 6, 9, 10, 12-14, 17, 19, 21, 23, 25, 27, 29 or 31. In general, a genomic sequence of the invention includes regulatory regions such as promoters, enhancers, and introns that are outside of the exons encoding a Mucorales CotH but does not include proximal genes that do not encode Mucorales CotH.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment.

The term substantially the same nucleotide sequence refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID NOS: 2, 4, 6, 9, 10, 12-14, 17, 19, 21, 23, 25, 27, 29 or 31. In another embodiment, DNA having substantially the same nucleotide sequence as the reference nucleotide sequence has at least 65% identity with respect to the reference nucleotide sequence. DNA having substantially the same nucleotide sequence can have at least 65% identity, at least 70% identity, at least 75% identity, at least 80% identity, at least 85% identity, at least 90% identity, at least 95% identity, at least 98% identity, or at least 99% identity to the reference nucleotide sequence.

As used herein, a "modification" of a nucleic acid can also include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication.

Exemplary modifications of the recited Mucorales CotH sequences include sequences that correspond to homologs of other species, including species of the Mucorales order such as *A. corymbifera, A. elegans, A. rouxii, B. circina, B. multispora, C. brefeldii, C. angarensis, C. recurvatus, D. fulva, E. anomalus, H. elegans, H. assamensis, K. cordensis, M. amphibiorum, P. parasitica, P. agaricine, P. anomala, P. circinans, R. endophyticus, R. javensis, S. umbellata, S. megalocarpus, T. elegans, T. indicae-seudaticae, Z. californiensis, R. azygosporus, R. caespitosus, R. homothallicus, R. oryzae, R. microspores, R. microsporus* var. *rhizopodiformis, R. schipperae*, or any other species of the Mucorales order disclosed herein. The corresponding Mucorales CotH sequences of Mucorales species can be determined by methods known in the art, such as by PCR or by screening genomic, cDNA or expression libraries.

Another exemplary modification of the invention Mucorales CotH can correspond to splice variant forms of the Mucorales CotH nucleotide sequence. Additionally, a modification of a nucleotide sequence can include one or more non-native nucleotides, having, for example, modifications to the base, the sugar, or the phosphate portion, or having a modified phosphodiester linkage. Such modifications can be advantageous in increasing the stability of the nucleic acid molecule.

The invention also encompasses nucleic acids which differ from the nucleic acids shown in SEQ ID NOS: 2, 4, 6, 9, 10, 12-14, 17, 19, 21, 23, 25, 27, 29 or 31, but which have the same phenotype. Phenotypically similar nucleic acids are also referred to as functionally equivalent nucleic acids. As used herein, the phrase functionally equivalent nucleic acids encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding Mucorales CotH polypeptides that, by virtue of the degeneracy of the genetic code, do not necessarily hybridize to the invention nucleic acids under specified hybridization conditions. As used herein, the term degenerate refers to codons that differ in at least one nucleotide from a reference nucleic acid, but encode the same amino acids as the reference nucleic acid. Nucleic acids encoding the invention Mucorales CotH polypeptides can be comprised of nucleotides that encode substantially the same amino acid sequence as set forth in SEQ ID NOS: 1, 3, 5, 11, 15, 16, 18, 20, 22, 24, 26, 28, 30 or 32.

In one embodiment, the invention provides an isolated nucleic acid encoding a polypeptide as disclosed herein including a Mucorales CotH polypeptide, an immunogenic fragment thereof, or a functional fragment thereof. The invention also provides an isolated nucleic acid encoding a Mucorales CotH polypeptide, an immunogenic fragment thereof, or a functional fragment thereof, comprising a nucleic acid selected from: (a) nucleic acid encoding an amino acid sequence set forth in SEQ ID NOS: 1, 3, 5, 11, 15, 16, 18, 20, 22, 24, 26, 28, 30 or 32, or (b) nucleic acid that hybridizes to the nucleic acid of (a) under low, moderately or highly stringent conditions, wherein said nucleic acid contiguously encodes biologically active Mucorales CotH polypeptide, or (c) nucleic acid degenerate with respect to either (a) or (b) above, wherein said nucleic acid encodes biologically active Mucorales CotH polypeptide. In one aspect, the nucleic acid of the invention hybridizes under highly stringent conditions.

Hybridization refers to the binding of complementary strands of nucleic acid, for example, sense: antisense strands or probe:target-nucleic acid to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, at least about 75% identity, or at least about 85% identity; or at least about 90% identity. Moderately stringent conditions are conditions equivalent to hybridization in 50% formamide, 5×Denhart's solution, 5×SSPE, 0.2% SDS at 42EC, followed by washing in 0.2×SSPE, 0.2% SDS, at 42EC.

The phrase "highly stringent hybridization" refers to conditions that permit hybridization of only those nucleic acid sequences that form stable hybrids in 0.018M NaCl at 65EC, for example, if a hybrid is not stable in 0.018M NaCl at 65EC, it will not be stable under high stringency conditions, as contemplated herein. High stringency conditions can be provided, for example, by hybridization in 50% formamide, 5×Denhart's solution, 5×SSPE, 0.2% SDS at 42EC, followed by washing in 0.1×SSPE, and 0.1% SDS at 65EC.

The phrase "low stringency hybridization" refers to conditions equivalent to hybridization in 10% formamide, 5×Denhart's solution, 6×SSPE, 0.2% SDS at 22EC, followed by washing in 1×SSPE, 0.2% SDS, at 37EC. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, Cold Spring Harbor Laboratories, Cold Spring Harbor, N.Y., 1989; and Ausubel et al., *Current Protocols in Molecular Biology*, John Wiley and Sons, Baltimore, Md. (1999)). Nucleic acids encoding polypeptides hybridize under moderately stringent or high stringency conditions to substantially the entire sequence, or substantial portions, for example, typically at least 15-30 nucleotides of the nucleic acid sequence set forth in SEQ ID NOS: 2, 4, 6, 9, 10, 12-14, 17, 19, 21, 23, 25, 27, 29 or 31.

The invention also provides a modification of a Mucorales CotH nucleotide sequence that hybridizes to a Mucorales CotH nucleic acid molecule, for example, a nucleic acid molecule set forth in SEQ ID NOS: 2, 4, 6, 9, 10, 12-14, 17, 19, 21, 23, 25, 27, 29 or 31, under moderately stringent conditions. Modifications of Mucorales CotH nucleotide sequences, where the modification has at least 65% identity to a Mucorales CotH nucleotide sequence, are also provided. The invention also provides modification of a Mucorales CotH nucleotide sequence having at least 65% identity, at least 70% identity, at least 75% identity, at least 80% identity, at least 85% identity, at least 90% identity, at least 95% identity, at least 98% identity, or at least 99% identity. The invention also provides modification of Mucorales CotH nucleotide sequences, wherein the amino acid sequence encoded by the modified nucleic acid has 65% identity, at least 70% identity, at least 75% identity, at least 80% identity, at least 85% identity, at least 90% identity, at least 95% identity, at least 98% identity, or at least 99% identity to the amino acid sequence set forth in SEQ ID NOS: 1, 3, 5, 11, 15, 16, 18, 20, 22, 24, 26, 28, 30 or 32.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al., supra. Preferably, default parameters are used for alignment. One alignment program is BLAST, using default parameters. In particular, programs are BLASTN and BLASTP, using the following default parameters: Genetic code=standard; filter=none; strand=both; cut-off=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity.

One means of isolating a nucleic acid encoding a Mucorales CotH polypeptide is to probe a cDNA library or genomic library with a natural or artificially designed nucleic acid probe using methods well known in the art. Nucleic acid probes derived from the Mucorales CotH gene are particularly useful for this purpose. DNA and cDNA molecules that encode Mucorales CotH polypeptides can be used to obtain complementary genomic DNA, cDNA or RNA from any number of Mucorales species sources, or to isolate related cDNA or genomic clones by the screening of cDNA or genomic libraries, by methods well known in the art (see, for example, Sambrook et al., supra, 1989; Ausubel et al., supra, 1999).

The invention additionally provides a Mucorales CotH oligonucleotide comprising between 15 and 300 contiguous nucleotides of SEQ ID NOS: 2, 4, 6, 9, 10, 12-14, 17, 19, 21, 23, 25, 27, 29 or 31, or the anti-sense strand thereof. As used herein, the term "oligonucleotide" refers to a nucleic acid molecule that includes at least 15 contiguous nucleotides from a reference nucleotide sequence, and can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence. The reference nucleotide sequence can be the sense strand or the anti-sense strand. Accordingly, in one aspect of the inventions, CotH oligonucleotides can comprise the nucleic acid sequence of ATGAAATTATCTATTATATCCGCTGCC (SEQ ID NO: 33), GCTGGGAATATAATTGTCATCGA (SEQ ID NO: 34), GATGACAATTATATTCCCAGC (SEQ ID NO: 35), GAGTAGACGTAATTAGATCCAA (SEQ ID NO: 36) AAACGTACCTGCTGACCGAATC (SEQ ID NO: 37) or oligonucleotide disclosed herein.

The Mucorales CotH oligonucleotides of the invention that contain at least 15 contiguous nucleotides of a reference Mucorales CotH nucleotide sequence are able to hybridize to Mucorales CotH under moderately stringent hybridization conditions and thus can be advantageously used, for example, as probes to detect Mucorales CotH DNA or RNA in a sample, and to detect splice variants thereof; as sequencing or PCR primers; as antisense reagents to block transcription of Mucorales CotH RNA in cells; or in other applications known to those skilled in the art in which hybridization to a Mucorales CotH nucleic acid molecule is desirable.

The isolated Mucorales CotH nucleic acid molecules of the invention can be used in a variety of diagnostic and therapeutic applications. For example, the isolated Mucorales CotH nucleic acid molecules of the invention can be used as probes, as described above; as templates for the recombinant expression of Mucorales CotH polypeptides; or in screening assays to identify cellular molecules that bind Mucorales CotH.

Another useful method for producing a Mucorales CotH nucleic acid molecule of the invention involves amplification of the nucleic acid molecule using PCR and Mucorales CotH oligonucleotides and, optionally, purification of the resulting product by gel electrophoresis. Either PCR or RT-PCR can be used to produce a Mucorales CotH nucleic acid molecule having any desired nucleotide boundaries. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention thus provides methods for detecting Mucorales CotH nucleic acid in a sample. The methods of detecting Mucorales CotH nucleic acid in a sample can be either qualitative or quantitative, as desired. For example, the presence, abundance, integrity or structure of a Mucorales CotH can be determined, as desired, depending on the assay format and the probe used for hybridization or primer pair chosen for application.

Useful assays for detecting Mucorales CotH nucleic acid based on specific hybridization with an isolated Mucorales CotH nucleic acid molecule are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A Mucorales CotH hybridization probe can be labeled with any suitable detectable moiety, such as a radioisotope, fluorochrome, chemiluminescent marker, biotin, or other detectable moiety known in the art that is detectable by analytical methods.

Useful assays for detecting a Mucorales CotH nucleic acid in a sample based on amplifying a Mucorales CotH nucleic acid with two or more Mucorales CotH oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified Mucorales CotH nucleic acid can be sequenced to detect mutations and mutational hot-spots, and specific assays for large-scale screening of samples to identify such mutations can be developed.

The invention further provides an isolated Mucorales CotH polypeptides, immunogenic fragment thereof, or a functional fragment thereof, encoded by a Mucorales CotH nucleic acid of the invention. For example, the invention provides a polypeptide comprising the same or substantially the same amino acid sequence as set forth in SEQ ID NOS: 1, 3, 5, 11, 15, 16, 18, 20, 22, 24, 26, 28, 30 or 32. Also provided is a Mucorales CotH polypeptide encoded by a nucleotide sequence comprising the same or substantially the same nucleotide sequence as set forth in SEQ ID NOS: 2, 4, 6, 9, 10, 12-14, 17, 19, 21, 23, 25, 27, 29 or 31.

As employed herein, the term substantially the same amino acid sequence refers to amino acid sequences having at least about 65% identity with respect to the reference amino acid sequence, and retaining comparable functional and biological activity characteristic of the protein defined by the reference amino acid sequence. In one aspect, proteins having substantially the same amino acid sequence will have at least 65% identity, at least 70% identity, at least 75% identity, at least 80% identity, at least 85% identity, at least 90% identity, at least 95% identity, at least 98% identity, or at least 99% identity. It is recognized, however, that polypeptides, or encoding nucleic acids, containing less than the described levels of sequence identity arising as splice variants or that are modified by conservative amino acid substitutions, or by substitution of degenerate codons are also encompassed within the scope of the present invention.

Also encompassed by the term Mucorales CotH are functional fragments or polypeptide analogs thereof. The term "functional fragment" refers to a peptide fragment that is a portion of a full length Mucorales CotH protein, provided that the portion has a biological activity, as defined herein, that is characteristic of the corresponding full length protein. For example, in aspect of the invention, the functional fragments of the invention can bind to the GRP78 protein or more specifically the functional fragments of the invention can bind to the GRP78 protein expressed by epithelial cells. Thus, the invention also provides functional fragments of invention Mucorales CotH proteins, which can be identified using the binding and routine methods, such as bioassays described herein.

As used herein, the term "polypeptide" when used in reference to Mucorales CotH is intended to refer to a peptide or polypeptide of two or more amino acids. The term polypeptide analog includes any polypeptide having an amino acid residue sequence substantially the same as a sequence specifically described herein in which one or more residues have been conservatively substituted with a functionally similar residue and which displays the ability to functionally mimic a Mucorales CotH as described herein. A "modification" of a Mucorales CotH polypeptide also encompasses conservative substitutions of a Mucorales CotH polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within Mucorales CotH polypeptides so long as the polypeptide retains some or all of its function as described herein.

The amino acid length of functional fragments or polypeptide analogs of the present invention can range from about 5 amino acids up to the full-length protein sequence of an invention Mucorales CotH. In certain embodiments, the amino acid lengths include, for example, at least about 10 amino acids, at least about 15, at least about 20, at least about 25, at least about 30, at least about 35, at least about 40, at least about 45, at least about 50, at least about 75, at least about 100, at least about 150, at least about 200, at least about 250 or more amino acids in length up to the full-length Mucorales CotH protein sequence. The functional fragments can be contiguous amino acid sequences of a Mucorales CotH polypeptide, including contiguous amino acid sequences of SEQ ID NOS: 1, 3, 5, 11, 15, 16, 18, 20, 22, 24, 26, 28, 30 or 32.

In another embodiment, the invention provides an immunogenic fragment of the Mucorales CotH polypeptides disclosed herein. The immunogenic fragments of the invention can include immunogenic epitopes, which can be identified using experimental methods well known in the art. Additionally, computational modeling can also be used to identify immunogenic epitopes. See, for example, Tong et al. (*Brief Bioinform.* 8(2):96-108 (2006)) and Ponomarenko et al. (2008) "B-cell epitope prediction," in *Structural Bioinformatics*, Bourne P E and Gu J (eds) Wiley-Liss; 2 edition, pgs. 849-879. Once an epitope bearing reactivity with an antibody raised against the intact protein is identified, the polypeptide can be tested for specificity by amino acid substitution at every position and/or extension at both C and/or N terminal ends. Such epitope bearing polypeptides typically contain at least six to fourteen amino acid residues, and can be produced, for example, by polypeptide synthesis using methods well known in the art or by fragmenting an existing protein. Accordingly, in some aspects of the invention, an immunogenic fragment of the Mucorales CotH polypeptides disclosed herein can include the amino acid sequence GAGKKHNNAKQSWNW (SEQ ID NO: 39) or MGQTNDGAYRDPTDNNK (SEQ ID NO: 40).

With respect to the molecule used as immunogens pursuant to the present invention, those skilled in the art will recognize that the protein can be truncated or fragmented without losing the essential qualities as an immunogenic vaccine. For example, a protein can be truncated to yield an N-terminal fragment by truncation from the C-terminal end with preservation of the functional properties of the molecule as an immunogenic. Similarly, C-terminal fragments can be generated by truncation from the N-terminal end with preservation of the functional properties of the molecule as an immunogenic. Other modifications in accordance with the teachings and guidance provided herein can be made pursuant to this invention to create other polypeptide functional fragments, immunogenic fragments, variants, analogs or derivatives thereof, to achieve the therapeutically useful properties described herein with the native proteins.

Accordingly, the term "immunogenic fragment" as it is used herein refers to a portion of a protein that is recognized by a T-cell and/or B-cell antigen receptor. The immunogenic portion generally includes at least 5 amino acid residues, or alternatively at least 6, or alternatively at least 7, or alternatively at least 8, or alternatively at least 9, or alternatively at least 10, or alternatively at least 11, or alternatively at least 12, or alternatively at least 13, or alternatively at least 14, or alternatively at least 15, or alternatively at least 16, or alternatively at least 17, or alternatively at least 18, or alternatively at least 18, or alternatively at least 19, or alternatively at least 20, or alternatively at least 25, or alternatively at least 30, or alternatively at least 50, or alternatively at least 100 amino acid residues of a CotH polypeptide disclosed herein. Alternatively, the immunogenic portion can include at most 5 amino acid residues, or alternatively at most 6, or alternatively at most 7, or alternatively at most 8, or alternatively at most 9, or alternatively at most 10, or alternatively at most 11, or alternatively at most 12, or alternatively at most 13, or alternatively at most 14, or alternatively at most 15, or alternatively at most 16, or alternatively at most 17, or alternatively at most 18, or alternatively at most 18, or alternatively at most 19, or alternatively at most 20, or alternatively at most 25, or alternatively at most 30, or alternatively at most 50, or alternatively at most 100 amino acid residues of a CotH polypeptide disclosed herein. In some aspects, immunogenic portions can contain a small N- and/or C-terminal fragment (e.g., 5-30 amino acids, preferably 10-25 amino acids).

A modification of a polypeptide can also include derivatives, analogues and functional mimetics thereof, provided that such polypeptide displays the Mucorales CotH biological activity. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as Mucorales CotH activity is maintained.

The invention provides an isolated Mucorales CotH polypeptides, immunogenic fragment thereof, or functional fragment thereof. The invention Mucorales CotH polypeptides can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology*, Vol. 182, (Academic Press, (1990)). Alternatively, the isolated polypeptides of the present invention can be obtained using well-known recombinant methods (see, for example, Sambrook et al., supra, 1989; Ausubel et al., supra, 1999). The methods and conditions for biochemical purification of a polypeptide of the invention can be chosen by those skilled in the art, and purification monitored, for example, by an immunological assay or a functional assay.

An example of the means for preparing the invention polypeptide(s) is to express nucleic acids encoding Mucorales CotH in a suitable host cell, such as a bacterial cell, a yeast cell, an amphibian cell such as an oocyte, or a mammalian cell, using methods well known in the art, and recovering the expressed polypeptide, again using well-known purification methods, so described herein. Invention polypeptides can be isolated directly from cells that have been transformed with expression vectors as described herein. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by chemical synthesis. For example, synthetic polypeptides can be produced using Applied Biosystems, Inc.

Model 430A or 431A automatic peptide synthesizer (Foster City, Calif.) employing the chemistry provided by the manufacturer.

The present invention also provides compositions containing an acceptable carrier and any of an isolated, purified Mucorales CotH mature protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil and water emulsion, and various types of wetting agents.

The invention thus provides a pharmaceutical composition comprising a pharmaceutically acceptable carrier and a compound selected from the group consisting of a Mucorales CotH polypeptide, an immunogenic fragment thereof, or a functional fragment thereof as described herein, an antisense nucleic acid as described herein or an anti-Mucorales CotH antibody as described herein. The invention additionally provides a method of treating or preventing mucormycosis in a subject in need thereof by administering a therapeutically effective amount of a pharmaceutical composition containing a pharmaceutically acceptable carrier and a compound selected from the group consisting of a Mucorales CotH polypeptide, an immunogenic fragment thereof, or a functional fragment thereof as described herein, an antisense nucleic acid as described herein or an anti-Mucorales CotH antibody as described herein. The invention additionally provides a method of treating or preventing mucormycosis in a subject in need thereof by administering an therapeutically effective amount of a vaccine composition as disclosed herein.

Also provided are antisense-nucleic acids having a sequence capable of binding specifically with full-length or any portion of an mRNA that encodes Mucorales CotH polypeptides so as to prevent translation of the mRNA. The antisense-nucleic acid can have a sequence capable of binding specifically with any portion of the sequence of the cDNA encoding Mucorales CotH polypeptides. As used herein, the phrase binding specifically encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

The present invention provides means to modulate levels of expression of Mucorales CotH polypeptides by recombinantly expressing Mucorales CotH anti-sense nucleic acids or employing synthetic anti-sense nucleic acid compositions (hereinafter SANC) that inhibit translation of mRNA encoding these polypeptides. Synthetic oligonucleotides, or other antisense-nucleic acid chemical structures designed to recognize and selectively bind to mRNA are constructed to be complementary to full-length or portions of an Mucorales CotH coding strand, including nucleotide sequences set forth in SEQ ID NOS: 2, 4, 6, 9, 10, 12-14, 17, 19, 21, 23, 25, 27, 29 or 31.

The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC, which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed above. The SANC is also designed to recognize and selectively bind to target mRNA sequence, which can correspond to a sequence contained within the sequences shown in SEQ ID NOS: 2, 4, 6, 9, 10, 12-14, 17, 19, 21, 23, 25, 27, 29 or 31. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp. 40).

Compositions comprising an amount of the antisense-nucleic acid of the invention, effective to reduce expression of Mucorales CotH polypeptides by entering a cell and binding specifically to mRNA encoding Mucorales CotH polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type.

Antisense-nucleic acid compositions are useful to inhibit translation of mRNA encoding invention polypeptides. Synthetic oligonucleotides, or other antisense chemical structures are designed to bind to mRNA encoding Mucorales CotH polypeptides and inhibit translation of mRNA and are useful as compositions to inhibit expression of Mucorales CotH associated genes in a tissue sample or in a subject.

The invention also provides a method for expression of a Mucorales CotH polypeptide by culturing cells containing a Mucorales CotH nucleic acid under conditions suitable for expression of Mucorales CotH. Thus, there is provided a method for the recombinant production of a Mucorales CotH of the invention by expressing the nucleic acid sequences encoding Mucorales CotH in suitable host cells. Recombinant DNA expression systems that are suitable to produce Mucorales CotH described herein are well-known in the art (see, for example, Ausubel et al., supra, 1999). For example, the above-described nucleotide sequences can be incorporated into vectors for further manipulation. As used herein, vector refers to a recombinant DNA or RNA plasmid or virus containing discrete elements that are used to introduce heterologous DNA into cells for either expression or replication thereof.

The invention also provides vectors containing the Mucorales CotH nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

The terms "vector", "cloning vector" and "expression vector" mean the vehicle by which a nucleic acid can be introduced into a host cell. The vector can be used for propagation or harboring a nucleic acid or for polypeptide expression of an encoded sequence. A wide variety of vectors are known in the art and include, for example, plasmids, phages and viruses. Exemplary vectors can be found described in, for example, Sambrook et al., supra; Ausubel et al., supra.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra, 1999). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a Mucorales CotH nucleic acid molecule and for recombinantly expressing a Mucorales CotH polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing Mucorales CotH nucleic acids of the invention. The recombinant cells are generated by introducing into a host cell a vector containing a Mucorales CotH nucleic acid molecule. The recombinant cells are transducted, transfected or otherwise genetically modified. Exemplary host cells that can be used to express recombinant Mucorales CotH molecules include mammalian primary cells; established mammalian cell lines, such as COS, CHO, HeLa, NIH3T3, HEK 293 and PC12 cells; amphibian cells, such as *Xenopus* embryos and oocytes; and other vertebrate cells. Exemplary host cells also include insect cells such as *Drosophila*, yeast cells such as *Saccharomyces cerevisiae, Saccharomyces pombe*, or *Pichia pastoris*, and prokaryotic cells such as *Escherichia coli*.

In one embodiment, the invention provides a vaccine composition having an immunogenic amount of a Mucorales CotH polypeptide, an immunogenic fragment thereof or a variant of the polypeptide. The vaccine composition also can include an adjuvant. The formulation of the vaccine composition of the invention is effective in inducing protective immunity in a subject by stimulating both specific humoral (neutralizing antibodies) and effector cell mediated immune responses against Mucorales CotH polypeptide. The vaccine composition of the invention is also used in the treatment or prophylaxis of fungal infections such as, for example, mucormycosis.

The vaccine of the present invention will contain an immunoprotective quantity of Mucorales CotH polypeptide antigens and is prepared by methods well known in the art. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Ajuvants: Preparation Methods and Research Protocols (Methods in Molecular Medicine)," Humana Press (2000).

Mucorales CotH polypeptide, and peptide fragments or variants thereof can include immunogenic epitopes, which can be identified using methods known in the art and described in, for example, Geysen et al. *Proc. Natl. Acad. Sci. USA* 81:3998 (1984)). Briefly, hundreds of overlapping short peptides, e.g., hexapeptides, can be synthesized covering the entire amino acid sequence of the target polypeptide (i.e., Mucorales CotH). The peptides while still attached to the solid support used for their synthesis are then tested for antigenicity by an ELISA method using a variety of antisera. Antiserum against Mucorales CotH protein can be obtained by known techniques, Kohler and Milstein, *Nature* 256: 495-499 (1975), and can be humanized to reduce antigenicity, see, for example, U.S. Pat. No. 5,693,762, or produced in transgenic mice leaving an unrearranged human immunoglobulin gene, see, for example, U.S. Pat. No. 5,877,397. Once an epitope bearing hexapeptide reactive with antibody raised against the intact protein is identified, the peptide can be further tested for specificity by amino acid substitution at every position and/or extension at both C and/or N terminal ends. Such epitope bearing polypeptides typically contain at least six to fourteen amino acid residues, and can be produced, for example, by polypeptide synthesis using methods well known in the art or by fragmenting an Mucorales CotH polypeptide. With respect to the molecule used as immunogens pursuant to the present invention, those skilled in the art will recognize that the Mucorales CotH polypeptide can be truncated or fragmented without losing the essential qualities as an immunogenic vaccine. For example, Mucorales CotH polypeptide can be truncated to yield an N-terminal fragment by truncation from the C-terminal end with preservation of the functional properties of the molecule as an immunogen. Similarly, C-terminal fragments can be generated by truncation from the N-terminal end with preservation of the functional properties of the molecule as an immunogen. Other modifications in accord with the teachings and guidance provided herein can be made pursuant to this invention to create other Mucorales CotH polypeptide functional fragments, immunogenic fragments, variants, analogs or derivatives thereof, to achieve the therapeutically useful properties described herein with the native protein.

The vaccine compositions of the invention further contain conventional pharmaceutical carriers. Suitable carriers are well known to those of skill in the art. These vaccine compositions can be prepared in liquid unit dose forms. Other optional components, e.g., pharmaceutical grade stabilizers, buffers, preservatives, excipients and the like can be readily selected by one of skill in the art. However, the compositions can be lyophilized and reconstituted prior to use. Alternatively, the vaccine compositions can be prepared in any manner appropriate for the chosen mode of administration, e.g., intranasal administration, oral administration, etc. The preparation of a pharmaceutically acceptable vaccine, having due regard to pH, isotonicity, stability and the like, is within the skill of the art.

The immunogenicity of the vaccine compositions of the invention can further be enhanced if the vaccine further comprises an adjuvant substance. Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein.

Preferred adjuvants facilitate uptake of the vaccine molecules by antigen presenting cells (APCs), such as dendritic cells, and activate these cells. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM® matrix); a particle; DDA (dimethyldioctadecylammonium bromide); aluminium adjuvants; DNA adjuvants; and an encapsulating adjuvant. Liposome formulations are also known to confer adjuvant effects, and therefore liposome adjuvants are included according to the invention.

In addition to vaccination of subjects susceptible to fungal infections such as mucormycosis, the vaccine compositions of the present invention can be used to treat, immunotherapeutically, subjects suffering from a variety of fungal infections. Accordingly, vaccines that contain one or more of Mucorales CotH polynucleotides, polypeptides and/or antibody compositions described herein in combination with adjuvants, and that act for the purposes of prophylactic or therapeutic use, are also within the scope of the invention. In an embodiment, vaccines of the present invention will induce the body's own immune system to seek out and inhibit Mucorales CotH molecules.

The term "vaccine", as used herein, refers to a composition that can be administered to an individual to protect the individual against an infectious disease. Vaccines protect against diseases by inducing or increasing an immune response in an animal against the infectious disease. An exemplary infectious disease amenable to treatment with the vaccines of the invention is mucormycosis. The vaccine-mediated protection can be humoral and/or cell mediated immunity induced in host when a subject is challenged with, for example, Mucorales CotH or an immunogenic portion or fragment thereof.

The term "adjuvant" is intended to mean a composition with the ability to enhance an immune response to an antigen generally by being delivered with the antigen at or near the site of the antigen. Ability to increase an immune response is manifested by an increase in immune mediated protection. Enhancement of humoral immunity can be determined by, for example, an increase in the titer of antibody raised to the antigen. Enhancement of cellular immunity can be measured by, for example, a positive skin test, cytotoxic T-cell assay, ELISPOT assay for IFN-gamma or IL-2. Adjuvants are well known in the art. Exemplary adjuvants include, for example, Freud's complete adjuvant, Freud's incomplete adjuvant, aluminum adjuvants, MF59 and QS21.

The term "treating" or "treatment," as it is used herein is intended to mean an amelioration of a clinical symptom indicative of a fungal condition. Amelioration of a clinical symptom includes, for example, a decrease or reduction in at least one symptom of a fungal condition in a treated individual compared to pretreatment levels or compared to an individual with a fungal condition. The term "treating" also is intended to include the reduction in severity of a pathological condition, a chronic complication or an opportunistic fungal infection which is associated with a fungal condition. Such pathological conditions, chronic complications or opportunistic infections are exemplified below with reference to mucormycosis. mucormycosis and other such pathological conditions, chronic complications and opportunistic infections also can be found described in, for example, Merck Manual, Sixteenth Edition, 1992, and Spellberg et al., Clin. Microbio. Rev. 18:556-69 (2005).

The term "preventing" or "prevention," as it is used herein is intended to mean a forestalling of a clinical symptom indicative of a fungal condition. Such forestalling includes, for example, the maintenance of normal physiological indicators in an individual at risk of infection by a fungus or fungi prior to the development of overt symptoms of the condition or prior to diagnosis of the condition. Therefore, the term "preventing" includes the prophylactic treatment of individuals to guard them from the occurrence of a fungal condition. Preventing a fungal condition in an individual also is intended to include inhibiting or arresting the development of the fungal condition. Inhibiting or arresting the development of the condition includes, for example, inhibiting or arresting the occurrence of abnormal physiological indicators or clinical symptoms such as those described above and/or well known in the art. Therefore, effective prevention of a fungal condition would include maintenance of normal body temperature, weight, psychological state as well as lack of lesions or other pathological manifestations in an individual predisposed to a fungal condition. Individuals predisposed to a fungal condition include an individual who is immunocompromised, for example, but not limited to, an individual with AIDS, azotemia, diabetes mellitus, diabetic ketoacidosis, neutropenia, bronchiectasis, emphysema, TB, lymphoma, leukemia, or burns, or an individual undergoing chemotherapy, bone marrow-, stem cell- and/or solid organ transplantation or an individual with a history of susceptibility to a fungal condition. Inhibiting or arresting the development of the condition also includes, for example, inhibiting or arresting the progression of one or more pathological conditions, chronic complications or susceptibility to an opportunistic infection associated with a fungal condition.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

The term "fungal condition" as used herein refers to fungal diseases, infection, or colonization including superficial mycoses (i.e., fungal diseases of skin, hair, nail and mucous membranes; for example, ringworm or yeast infection), subcutaneous mycoses (i.e., fungal diseases of subcutaneous tissues, fascia and bone; for example, mycetoma, chromomycosis, or sporotichosis), and systemic mycoses (i.e., deep-seated fungal infections generally resulting from the inhalation of air-borne spores produced by causal moulds; for example, zygomycosis, aspergillosis, cryptococcosis, candidiasis, histoplasmosis, coccidiomycosis, paracoccidiomycosis, fusariosis (hyalohyphomycoses), blastomycosis, penicilliosis or sporotrichosis.

As used herein, the term "zygomycosis" is intended to mean a fungal condition caused by fungi of the class Zygomycetes, comprised of the orders Mucorales and Entomophthorales. The Entomophthorales are causes of subcutaneous and mucocutaneous infections known as entomophthoromycosis, which largely afflict immunocompetent hosts in developing countries. Zygomycosis is also referred to as mucormycosis and the two terms are used interchangeably to refer to similar types of fungal infections.

As used herein, the term "mucormycosis" is intended to mean a fungal condition caused by fungi of the order Mucorales. mucormycosis is a life-threatening fungal infection almost uniformly affecting immunocompromised hosts in either developing or industrialized countries. Fungi belonging to the order Mucorales are distributed into at least six families, all of which can cause cutaneous and deep infections. Species belonging to the family Mucoraceae are isolated more frequently from patients with mucormycosis than any other family. Among the Mucoraceae, *Rhizopus oryzae* (*Rhizopus arrhizus*) is a common cause of infection. Other exemplary species of the Mucoraceae family that cause a similar spectrum of infections include, for example, *Rhizopus microsporus* var. *rhizopodiformis*, *Absidia corymbifera*, *Apophysomyces elegans*, *Mucor* species, *Rhizomucor pusillus* and *Cunninghamella* spp (Cunninghamellaceae family). mucormycosis is well known in the art and includes, for example, rinocerebral mucormycosis, pulmonary mucormycosis, gastrointestinal mucormycosis, disseminated mucormycosis, bone mucormycosis, mediastinum mucormycosis, trachea mucormycosis, kidney mucormycosis, peritoneum mucormycosis, superior vena cava mucormycosis or external otitis mucormycosis.

Fungi belonging to the order Mucorales are currently distributed into the families of Choanephoraceae; Cunninghamellaceae; Mucoraceae; Mycotyphaceae; Phycomycetaceae; Pilobolaceae; Saksenaeaceae; Syncephalastraceae; and Umbelopsidaceae. Each of these fungi families consists of one or more genera. For example, fungi belonging to the order Mucorales, family Mucoraceae, are further classified into the genera of *Absidia* (e.g., *A. corymbifera*); *Actinomucor* (e.g., *A. elegans*); *Amylomyces* (e.g., *A. rouxii*); *Apophysomyces*; *Backusella* (e.g., *B. circina*); *Benjaminiella* (e.g., *B. multispora*); *Chaetocladium* (e.g., *C. brefeldii*); *Circinella* (e.g., *C. angarensis*); *Cokeromyces* (e.g., *C. recurvatus*); *Dicranophora* (e.g., *D. fulva*); *Ellisomyces* (e.g., *E. anomalus*; *Helicostylum* (e.g., *H. elegans*); *Hyphomucor* (e.g., *H. assamensis*); *Kirkomyces* (e.g., *K. cordensis*); *Mucor* (e.g., *M. amphibiorum*); *Parasitella* (e.g., *P. parasitica*); *Philophora* (e.g., *P. agaricine*); *Pilaira* (e.g., *P. anomala*); *Pirella* (e.g., *P. circinans*); *Rhizomucor* (e.g., *R. endophyticus*); *Rhizopodopsis* (e.g., *R. javensis*); *Rhizopus*; *Sporodiniella* (e.g., *S. umbellata*); *Syzygites* (e.g., *S. megalocarpus*); *Thamnidium* (e.g., *T. elegans*); *Thermomucor* (e.g., *T. indicae-seudaticae*); and *Zygorhynchus* (e.g., *Z. californiensis*). The genus *Rhizopus*, for example, consists of *R. azygosporus*; *R. caespitosus*; *R. homothallicus*; *R. oryzae*; *R. microsporus*, *R. microsporus* var. *rhizopodiformis* and *R. schipperae* species.

The term "immunogenic amount" as used herein refers an effective amount of a particular epitope of a polypeptide of the invention or a fragment or variant thereof that can induce the host immune response against the polypeptide or the infectious agent expressing the polypeptide. This amount is generally in the range of 20 μg to 10 mg of antigen per dose of vaccine and depends on the subject to be treated, capacity of the subject's immune system to synthesize antibodies, and the degree of protection desired. The precise amount of immunogen required can be calculated by various methods such as, for example, antibody titration. The term effective amount refers to an amount of a compound or compositions that is sufficient to provide a desired result. Thus, as used to describe a vaccine, an effective amount refers to an amount of a compound or composition (e.g., an antigen) that is sufficient to produce or elicit a protective immune response. An effective amount with respect to an immunological composition is an amount that is sufficient to elicit an immune response, whether or not the response is protective.

The "therapeutically effective amount" will vary depending on the polypeptide, polynucleotide, antibody, antibody fragment or compositions, the disease and its severity and the age, weight, etc., of the patient to be treated all of which is within the skill of the attending clinician. It is contemplated that a therapeutically effective amount of one or more of a polynucleotide, polypeptide, antibody, antibody fragment or composition described herein will alter a fungal pathogen penetration through and damage of endothelial cells in the patient as compared to the absence of treatment. As such, fungal pathogenesis is decreased. A therapeutically effective amount is distinguishable from an amount having a biological effect (a "biologically effective amount"). A polypeptide, polynucleotide, antibody, antibody fragment or compositions of the present invention may have one or more biological effects in vitro or even in vivo, such as reducing function of a Mucorales CotH polypeptide. A biological effect, however, may not result in any clinically measurable therapeutically effect as described herein as determined by methods within the skill of the attending clinician.

In one embodiment, nucleic acids encoding the invention Mucorales CotH polypeptides can be delivered into mammalian cells, either in vivo or in vitro using suitable vectors well-known in the art. Suitable vectors for delivering a Mucorales CotH polypeptide, an immunogenic fragment thereof, or a functional fragment thereof to a mammalian cell, include viral vectors such as retroviral vectors, adenovirus, adeno-associated virus, lentivirus, herpesvirus, as well as non-viral vectors such as plasmid vectors. Such vectors are useful for providing therapeutic or immunogenic amounts of a Mucorales CotH polypeptide (see, for example, U.S. Pat. No. 5,399, 346, issued Mar. 21, 1995). Delivery of Mucorales CotH polypeptides or nucleic acids therapeutically can be particularly useful when targeted to a muscel cell, bone marrow cell or B-cell, thereby presenting the encoded mucorales CotH polypeptide for development of an immune response. Such presentation is commonly known in the art as a DNA vaccination.

Viral based systems provide the advantage of being able to introduce relatively high levels of the heterologous nucleic acid into a variety of cells. Suitable viral vectors for introducing invention nucleic acid encoding an Mucorales CotH protein into mammalian cells are well known in the art. These viral vectors include, for example, Herpes simplex virus vectors (Geller et al., *Science*, 241:1667-1669 (1988)); vaccinia virus vectors (Piccini et al., *Meth. Enzymology*, 153:545-563 (1987)); cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., *Proc. Natl. Acad. Sci. USA*, 85:6460-6464 (1988); Blaese et al., *Science*, 270:475-479 (1995); Onodera et al., *J. Virol.*, 72:1769-1774 (1998)); adenovirus vectors (Berkner, *Biotechniques*, 6:616-626 (1988); Cotten et al., *Proc. Natl. Acad. Sci. USA*, 89:6094-6098 (1992); Graham et al., *Meth. Mol. Biol.*, 7:109-127 (1991); Li et al., *Human Gene Therapy*, 4:403-409 (1993); Zabner et al., *Nature Genetics*, 6:75-83 (1994)); adeno-associated virus vectors (Goldman et al., *Human Gene Therapy*, 10:2261-2268 (1997); Greelish et al., *Nature Med.*, 5:439-443 (1999); Wang et al., *Proc. Natl. Acad. Sci. USA*, 96:3906-3910 (1999); Snyder et al., *Nature Med.*, 5:64-70 (1999); Herzog et al., *Nature Med.*, 5:56-63 (1999)); retrovirus vectors (Donahue et al., *Nature Med.*, 4:181-186 (1998); Shackleford et al., *Proc. Natl. Acad. Sci. USA*, 85:9655-9659 (1988); U.S. Pat. Nos. 4,405,712, 4,650, 764 and 5,252,479, and WIPO publications WO 92/07573, WO 90/06997, WO 89/05345, WO 92/05266 and WO 92/14829; and lentivirus vectors (Kafri et al., *Nature Genetics*, 17:314-317 (1997)).

Vectors useful for therapeutic administration of a Mucorales CotH polypeptide of nucleic acid can contain a regulatory element that provides tissue specific or inducible expression of an operatively linked nucleic acid. One skilled in the art can readily determine an appropriate tissue-specific promotor or enhancer that allows exparssion of a Mucorales CotH polypeptide or nucleic acid in a desired tissue or cell. Any of a variety of inducible promoters or enhancers can also be included in the vector for regulatable expression of a Mucorales CotH polypeptide or nucleic acid. Such inducible systems, include, for example, tetracycline inducible system (Gossen & Bizard, *Proc. Natl. Acad. Sci. USA*, 89:5547-5551 (1992); Gossen et al., *Science,* 268:1766-1769 (1995); Clontech, Palo Alto, Calif.); metalothionein promoter induced by heavy metals; insect steroid hormone responsive to ecdysone or related steroids such as muristerone (No et al., *Proc. Natl. Acad. Sci. USA,* 93:3346-3351 (1996); Yao et al., *Nature,* 366:476-479 (1993); Invitrogen, Carlsbad, Calif.); mouse mammory tumor virus (MMTV) induced by steroids such as glucocortocoid and estrogen (Lee et al., *Nature,* 294:228-232 (1981); and heat shock promoters inducible by temperature changes.

An inducible system particularly useful for therapeutic administration utilizes an inducible promotor that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., *Proc. Natl. Acad. Sci. USA,* 96:355-360 (1999). Another such inducible system utilizes the drug rapamycin to induce reconstitution of a transcriptional activator containing rapamycin binding domains of FKBP12 and FRAP in an adeno-associated virus vector (Ye et al., *Science,* 283:88-91 (1999)). It is understood that any combination of an inducible system can be combined in any suitable vector, including those disclosed herein. Such a regulatable inducible system is advantageous because the level of expression of the therapeutic product can be controlled by the amount of drug administered to the individual or, if desired, expression of the therapeutic product can be terminated by stopping administration of the drug.

The invention additionally provides an isolated anti-Mucorales CotH antibody having specific reactivity with a Mucorales CotH polypeptide, an immunogenic fragment thereof, or functional fragment thereof. For example, an anti-Mucorales CotH antibody of the invention can have specific reactivity to a polypeptide having the amino acid sequence GAGKKHNNAKQSWNW (SEQ ID NO: 39) or MGQTND-GAYRDPTDNNK (SEQ ID NO: 40). The anti-Mucorales CotH antibody can be a monoclonal antibody or a polyclonal antibody. The invention further provides cell lines producing monoclongal antibodies having specific reactivity with a Mucorales CotH polypeptide, an immunogenic fragment thereof, or functional fragment thereof.

The invention thus provides antibodies that specifically bind a Mucorales CotH polypeptide. As used herein, the term "antibody" is used in its broadest sense to include polyclonal and monoclonal antibodies, as well as antigen binding fragments of such antibodies. With regard to an anti-Mucorales CotH antibody of the invention, the term "antigen" means a native or synthesized Mucorales CotH polypeptide or fragment thereof. An anti-Mucorales CotH antibody, or antigen binding fragment of such an antibody, is characterized by having specific binding activity for a Mucorales CotH polypeptide or a peptide portion thereof of at least about $1 \times 10^5$ $M^{-1}$. Thus, Fab, $F(ab')_2$, Fd and Fv fragments of an anti-Mucorales CotH antibody, which retain specific binding activity for a Mucorales CotH polypeptide, are included within the definition of an antibody. Specific binding activity of a Mucorales CotH polypeptide can be readily determined by one skilled in the art, for example, by comparing the binding activity of an anti-Mucorales CotH antibody to a Mucorales CotH polypeptide versus a control polypeptide that is not a Mucorales CotH polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, antibodies of the invention can be naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (Huse et al., *Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineering: A practical approach* (IRL Press 1992); Borrabeck, *Antibody Engineering,* 2d ed. (Oxford University Press 1995)).

Anti-Mucorales CotH antibodies can be raised using a Mucorales CotH immunogen such as an isolated Mucorales CotH polypeptide having the amino acid sequence of SEQ ID NOS: 1, 3, 5, 11, 15, 16, 18, 20, 22, 24, 26, 28, 30 or 32, or an immunogenic fragment thereof, which can be prepared from natural sources or produced recombinantly, or a peptide portion of the Mucorales CotH polypeptide. Such peptide portions of a Mucorales CotH polypeptide are functional antigenic fragments if the antigenic peptides can be used to generate a Mucorales CotH-specific antibody. A non-immunogenic or weakly immunogenic Mucorales CotH polypeptide or portion thereof can be made immunogenic by coupling the hapten to a carrier molecule such as bovine serum albumin (BSA) or keyhole limpet hemocyanin (KLH). Accordingly, in some aspects of the invention, an immunogenic fragment of the CotH polypeptides disclosed herein can be conjugated to a carrier molecule, such as, but not limited to KLH or BSA. Various other carrier molecules and methods for coupling a hapten to a carrier molecule are well known in the art (see, for example, Harlow and Lane, supra, 1988). An immunogenic Mucorales CotH polypeptide fragment can also be generated by expressing the peptide portion as a fusion protein, for example, to glutathione S transferase (GST), polyHis or the like. Methods for expressing peptide fusions are well known to those skilled in the art (Ausubel et al., supra).

The invention further provides a method for detecting the presence of a Mucorales organism in a sample by contacting a sample with a Mucorales CotH-specific antibody, and detecting the presence of specific binding of the antibody to the sample, thereby detecting the presence of a Mucorales CotH polypeptide in the sample. Mucorales CotH specific antibodies can be used in diagnostic methods and systems to detect the level of Mucorales CotH present in a sample. As used herein, the term "sample" is intended to mean any biological fluid, cell, tissue, organ or portion thereof, that includes or potentially includes Mucorales CotH nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation.

Mucorales CotH-specific antibodies can also be used for the immunoaffinity or affinity chromatography purification of the invention Mucorales CotH. In addition, methods are contemplated herein for detecting the presence of an invention Mucorales CotH protein in a cell, comprising contacting the cell with an antibody that specifically binds to Mucorales CotH polypeptides under conditions permitting binding of the antibody to the Mucorales CotH polypeptides, detecting the presence of the antibody bound to the Mucorales CotH polypeptide, and thereby detecting the presence of invention polypeptides in a cell. With respect to the detection of such polypeptides, the antibodies can be used for in vitro diagnostic or in vivo imaging methods.

Immunological procedures useful for in vitro detection of target Mucorales CotH polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the Mucorales CotH specific antibody. Useful markers include, for example, radionucleotides, enzymes, binding proteins such as biotin, fluorogens, chromogens and chemiluminescent labels.

As used herein, the terms label and indicating means in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189-231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3-46 (1981). Conventional means of protein conjugation or coupling by activated functional groups are particularly applicable. See, for example, Aurameas et al., *Scand. J. Immunol.*, Vol. 8, Suppl. 7:7-23 (1978), Rodwell et al., *Biotech.*, 3:889-894 (1984), and U.S. Pat. No. 4,493,795.

Invention nucleic acids, oligonucleotides, including antisense, vectors containing invention nucleic acids, transformed host cells, polypeptides and combinations thereof, as well as antibodies of the present invention, can be used to screen compounds to determine whether a compound functions as a potential agonist or antagonist of invention polypeptides. These screening assays provide information regarding the function and activity of invention polypeptides, which can lead to the identification and design of compounds that are capable of specific interaction with one or more types of polypeptides, peptides or proteins.

Thus, the invention provides methods for identifying compounds which bind to Mucorales CotH polypeptides. The invention proteins can be employed in a competitive binding assay. Such an assay can accommodate the rapid screening of a large number of compounds to determine which compounds, if any, are capable of binding to Mucorales CotH polypeptides. Subsequently, more detailed assays can be carried out with those compounds found to bind, to further determine whether such compounds act as modulators, agonists or antagonists of invention Mucorales CotH polypeptides. Compounds that bind to and/or modulate invention Mucorales CotH polypeptides can be used to treat a variety of pathologies mediated by invention Mucorales CotH polypeptides.

Various binding assays to identify cellular proteins that interact with protein binding domains are known in the art and include, for example, yeast two-hybrid screening assays (see, for example, U.S. Pat. Nos. 5,283,173, 5,468,614 and 5,667,973; Ausubel et al., supra, 1999; Luban et al., *Curr. Opin. Biotechnol.* 6:59-64 (1995)) and affinity column chromatography methods using cellular extracts. By synthesizing or expressing polypeptide fragments containing various Mucorales CotH sequences or deletions, the Mucorales CotH binding interface can be readily identified.

In another embodiment of the invention, there is provided a bioassay for identifying compounds which modulate the activity of invention Mucorales CotH polypeptides. According to this method, invention polypeptides are contacted with an "unknown" or test substance, for example, in the presence of a reporter gene construct responsive to a Mucorales CotH signaling pathway, the activity of the polypeptide is monitored subsequent to the contact with the "unknown" or test substance, and those substances which cause the reporter gene construct to be expressed are identified as functional ligands for Mucorales CotH polypeptides. Such reporter gene assays and systems are well known to those skilled in the art (Ausubel et al., supra, 1999). In addition, a reporter gene constrict can be generated using the promoter region of Mucorales CotH and screened for compounds that increase or decrease Mucorales CotH gene promoter activity. Such compounds can also be used to alter Mucorales CotH expression.

In accordance with another embodiment of the present invention, transformed host cells that recombinantly express invention polypeptides can be contacted with a test compound, and the modulating effect(s) thereof can then be evaluated by comparing the Mucorales CotH-mediated response, for example, via reporter gene expression in the presence and absence of test compound, or by comparing the response of test cells or control cells, to the presence of the compound.

As used herein, a compound or a signal that modulates the activity of invention polypeptides refers to a compound or a signal that alters the activity of Mucorales CotH polypeptides so that the activity of the invention polypeptide is different in the presence of the compound or signal than in the absence of the compound or signal. In particular, such compounds or signals include agonists and antagonists. An agonist encompasses a compound or a signal that activates Mucorales CotH protein expression or biological activity. Alternatively, an antagonist includes a compound or signal that interferes with Mucorales CotH expression or biological activity. Typically, the effect of an antagonist is observed as a blocking of agonist-induced protein activation. Antagonists include competitive and non-competitive antagonists.

Assays to identify compounds that modulate Mucorales CotH polypeptide expression can involve detecting a change in Mucorales CotH polypeptide abundance in response to contacting the cell with a compound that modulates Mucorales CotH activity. Assays for detecting changes in polypeptide expression include, for example, immunoassays with Mucorales CotH-specific Mucorales CotH antibodies, such as immunoblotting, immunofluorescence, immunohistochemistry and immunoprecipitation assays, as described above.

As understood by those of skill in the art, assay methods for identifying compounds that modulate Mucorales CotH activity generally require comparison to a control. One type of a "control" is a cell or culture that is treated substantially the same as the test cell or test culture exposed to the compound, with the distinction that the "control" cell or culture is not exposed to the compound. Another type of "control" cell or culture can be a cell or culture that is identical to the test cells, with the exception that the "control" cells or culture do not express a Mucorales CotH polypeptide. Accordingly, the response of the transfected cell to a compound is compared to the response, or lack thereof, of the "control" cell or culture to the same compound under the same reaction conditions.

The invention further provides a method for modulating an activity mediated by a Mucorales CotH polypeptide by contacting the Mucorales CotH polypeptide with an effective, modulating amount of an agent that modulates Mucorales CotH activity. The Mucorales CotH activity can be, for example, binding to GRP78. The invention additionally provides a method of modulating the level of adhesion to a cell.

In some embodiment, the invention provides a method of detecting a Mucorales CotH nucleic acid molecule in a sample. Such methods of the invention can include the steps of contacting a sample with two or more oligonucleotides disclosed herein, amplifying a nucleic acid molecule, and detecting the amplification. It is understood that methods for amplifying a nucleic acid are well known to one of skill in the art, which can be readily selected and applied to the methods of the invention. For example, in some aspects, the amplification is performed using polymerase chain reaction (PCR). In some aspects of the invention, at least one of the two or more oligonucleotides used in the method of the invention includes an oligonucleotide having the nucleic acid sequence of ATGAAATTATCTATTATATCCGCTGCC (SEQ ID NO: 33), GCTGGGAATATAATTGTCATCGA (SEQ ID NO: 34), GATGACAATTATATTCCCAGC (SEQ ID NO: 35), GAGTAGACGTAATTAGATCCAA (SEQ ID NO: 36), AAACGTACCTGCTGACCGAATC (SEQ ID NO: 37) or any oligonucleotide disclosed herein.

The invention further provides a method of diagnosing mucormycosis infection in a subject by detecting the presence of a Mucorales organism in a sample from the patient. The method can include the steps of (a) providing a test sample from the subject; (b) contacting the sample with an agent that can binds a nucleic acid or a polypeptide of the invention under suitable conditions, wherein the conditions allow specific binding of the agent to the nucleic acid or polypeptide; and (c) comparing the amount of the specific binding in the test sample with the amount of specific binding in a control sample, wherein an increased or decreased amount of the specific binding in the test sample as compared to the control sample is diagnostic of mucormycosis infection. In some aspects of the invention, the agent is selected from the group consisting of an anti-Mucorales CotH antibody or a CotH oligonucleotide as described herein.

In accordance with another embodiment of the present invention, there are provided diagnostic systems, preferably in kit form, comprising at least one invention nucleic acid or antibody in a suitable packaging material. The diagnostic kits containing nucleic acids are derived from the Mucorales CotH-encoding nucleic acids described herein. In one embodiment, for example, the diagnostic nucleic acids are derived from any of SEQ ID NOS: 2, 4, 6, 9, 10, 12-14, 17, 19, 21, 23, 25, 27, 29 or 31 and can be oligonucleotides of the invention. In some aspects of the invention, at least one oligonucleotide comprises a nucleic acid seqeunce selected from ATGAAATTATCTATTATATCCGCTGCC (SEQ ID NO: 33), GCTGGGAATATAATTGTCATCGA (SEQ ID NO: 34), GATGACAATTATATTCCCAGC (SEQ ID NO: 35), GAGTAGACGTAATTAGATCCAA (SEQ ID NO: 36), AAACGTACCTGCTGACCGAATC (SEQ ID NO: 37) or any oligonucleotide disclosed herein. Invention diagnostic systems are useful for assaying for the presence or absence of nucleic acid encoding Mucorales CotH in either genomic DNA or mRNA.

A suitable diagnostic system includes at least one invention nucleic acid or antibody, as a separately packaged chemical reagent(s) in an amount sufficient for at least one assay. For a diagnostic kit containing nucleic acid of the invention, the kit will generally contain two or more nucleic acids. When the diagnostic kit is to be used in PCR, the kit will contain at least two oligonucleotides that can serve as primers for PCR. Those of skill in the art can readily incorporate invention nucleic probes and/or primers or invention antibodies into kit form in combination with appropriate buffers and solutions for the practice of the invention methods as described herein. A kit containing a Mucorales CotH antibody can contain a reaction cocktail that provides the proper conditions for performing an assay, for example, an ELISA or other immunoassay, for determining the level of expression of a Mucorales CotH polypeptide in a sample, and can contain control samples that contain known amounts of a Mucorales CotH polypeptide and, if desired, a second antibody specific for the anti-Mucorales CotH antibody.

The contents of the kit of the invention, for example, Mucorales CotH nucleic acids or antibodies, are contained in packaging material, preferably to provide a sterile, contaminant-free environment. In addition, the packaging material contains instructions indicating how the materials within the kit can be employed both to detect the presence or absence of a particular Mucorales CotH sequence or Mucorales CotH polypeptide or to diagnose the presence of, or a predisposition for a condition associated with mucormycosis. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

It is understood that modifications which do not substantially affect the activity of the various embodiments of this invention are also provided within the definition of the invention provided herein. Accordingly, the following examples are intended to illustrate but not limit the present invention.

EXAMPLE I

Cell Surface CotH3 Protein Facilitates Binding to Host GRP78 During Fungal Invasion of Endothelial Cells Cell wall material was collected from supernatants of protoplasts of *R. oryzae* germlings. *R. oryzae* ligands bound to rGrp78 were isolated by FAR Western blot analysis using anti-Grp78 Ab and identified by MALDI-TOF-MS/MS analysis (FIG. 1). Briefly, protein spots of interest were excised and sent to the UCLA W. M. Keck Proteomic Center for identification on a Thermo LTQ-Orbitrap XL mass spectrometer (San Jose, Calif.) equipped with an Eksigent (Dublin, Calif.) NanoLiquid chromatography-1D plus system and an Eksigent autosampler. Proteins within the spots were in-gel tryptic digested as described by Shevchenko et al. (Shevchenko et al. (1996). Proc Natl Acad Sci USA 93: 14440-14445; Shevchenko et al., *Anal. Chem.*, 68(5):850-8 (1996)). The eluted peptides were loaded onto a CVC Microtech (Fontana, Calif.) 35 mm length, 100 µm ID C18 pre-Trap column and washed for 10 min with 100% Buffer A (2% acetonitrile containing 0.1% formic acid) at a flow rate of 5 µl/min. The peptides were separated on a 15 cm New Objective ProteoPep IntegraFrit column (Woburn, Mass.) using a flow rate of 300 nl/min. The following elution gradient was used: 0-15 min 0-30% Buffer B (98% acetonitrile containing 0.1% formic acid), 15-20 min 30-80% Buffer B and 20-22 min 80% Buffer B. The column was then re-equilibrated for 13 min with Buffer A. The eluting analytes were sprayed in positive mode into the LTQ-Orbitrap MS using electrospray ionization voltage of 2300 V, capillary voltage of 45 V, tube lens of 130 V, and capillary temperature of 200° C. Information dependent acquisition was performed where the 6 most intense ions were selected in the m/z range of 300-1600 using a 60 K resolution FTMS scan and subjecting them to MS-MS using broadband collision induced disassociation of normalized collision energy of 35 and LTQ detection. Peaks were excluded from further MS-MS for a period of 60 sec.

The resulting MS/MS spectra was searched against the *Rhizopus oryzae* 99-880 database (http://www.broad-institute.org/annotation/genome/rhizopus_oryzae/Multi-Home.html) using the Matrix Science MASCOT Daemon search engine (Boston, Mass.). The following search parameters were used: peptide tolerance: ±10 ppm, MS/MS tolerance ±0.3 Da, maximum missed cleavages: 2, fixed modifications: carboxymethyl (C) and variable modifications: deamidization (ND) and oxidation (M). Proteins identified within a particular included those with a minimum of two unique peptides that are ranked as number 1 and with an ion scores with a p<0.05.

Figure 4:
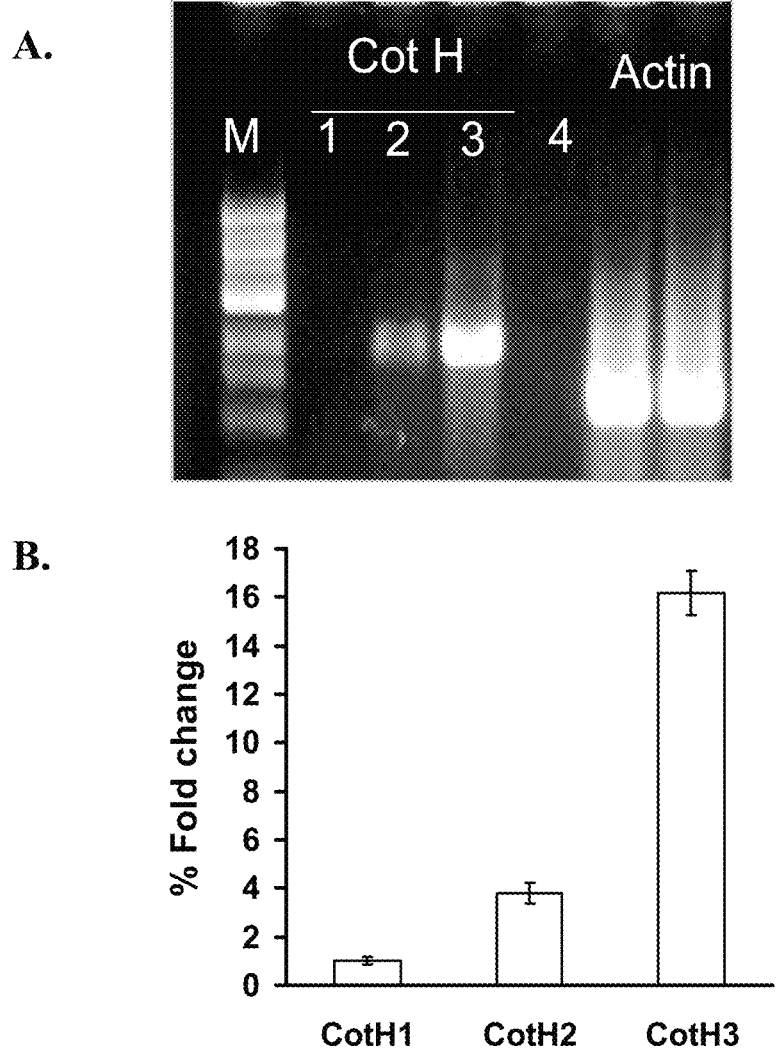
FIG. 4, panels A and B, show expression of CotH genes in *R. oryzae* germlings incubated with endothelial cells.
Figure 5:
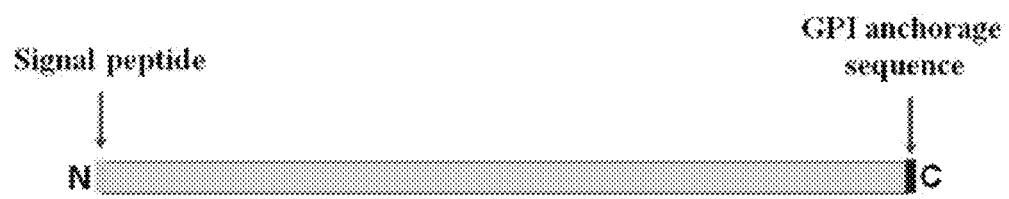
FIG. 5 shows homology of the 4 putative GPI-anchored proteins to each other and the number of predicted N- and O-glycosylation sites in CotH3.

Expression of the putative ligands in *R. oryzae* incubated with endothelial cells was detected by RT-PCR (FIG. 4). Interaction of the ligand with GRP78 was confirmed by heterologously expressing the ligand in *Saccharomyces cerevisiae* (FIG. 6) and comparing its adherence to and invasion of endothelial cells and CHO cells overexpressing GRP78 to *S. cerevisiae* transformed with empty plasmid (control) (FIG. 8).

Three of the ORF had homology to CotH family of proteins implicated in spore coat formation from several bacteria:
RO3G_05018, CotH1
RO3G_08029, CotH2
RO3G_11882, CotH3

A fourth ORF (RO3G_16295) is widely present in other pathogenic fungi, but none of these ORFs appear to encode a protein that has an identified function. As sequence comparison between the identified CotH polypeptides and other bacterial CotH proteins shows very little sequence identity (FIG. 17 and Table 1).

TABLE 1

Sequence similarity of *Rhizopus* CotH and bacterial CotH (different sizes)

|  | *Flammeovirga yaeyamensis* (ACY02060) | *Desulfotomaculum reducens* (YP_001112853) | *Bacillus amyloliquefaciens* (YP_001422883) | *Bacillus cereus* (ZP_04217292) |
|---|---|---|---|---|
| RO3G_05018 | 18.5 | 13.6 | 12.9 | 14.5 |
| RO3G_08029 | 18.6 | 15.8 | 13.8 | 13.6 |
| RO3G_11882 | 18 | 14.1 | 13 | 13.6 |

RO3G_16295 appears to be a common protein, it's homologues (usually ~25% identity at amino acid) can be seen from many different fungi as well as a few bacteria (FIGS. 18-26). All these proteins are not characterized. To name a few:

*Talaromyces stipitatus* ATCC 10500 (EED23986);

*Penicillium marneffei* ATCC 18224 (XP_002144175);

*Aspergillus niger* (XP_001392236);

*Aspergillus nidulans* (XP_658934);

*Ustilago maydis* (XP_760027);

*Coccidioides immitis* (XP_001243211);

*Neurospora crassa* (XP_956792);

*Cryptococcus neoformans* (XP_775558); and

*Streptomyces lividans* (EFD65170).

Figure 3:
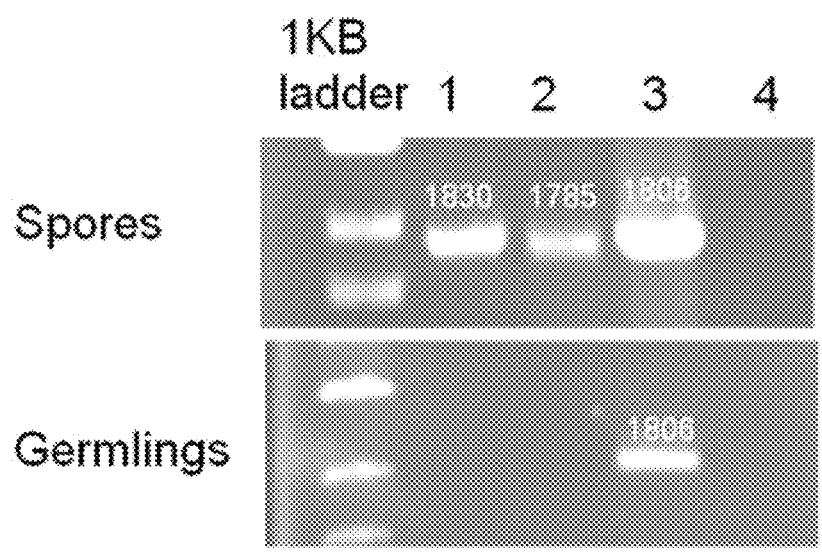
FIG. 3 shows expression of the four glycosylphosphatidylinisotol (GPI) anchored predicted to act as ligands to GRP78.
Figure 6:
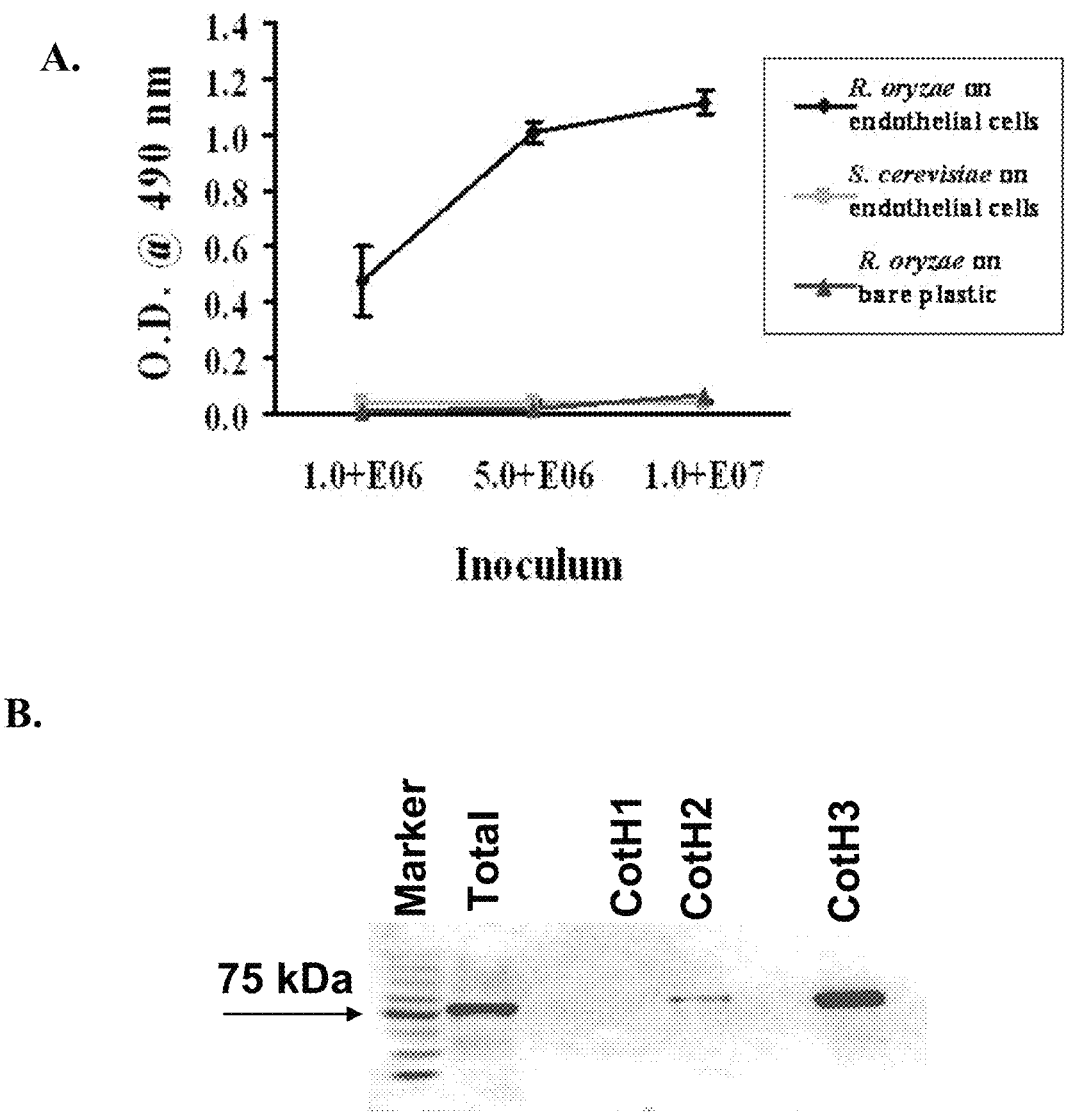
FIG. 6, panel A demonstrates the ability of *R. oryzae* to adhere to human umbilical endothelial cells but not plastic. Further, *Saccharomyces cerevisiae* doesn't adhere to endothelial cells. Panel B, showing *R. oryzae* CotH2 and CotH3 enabling *S. cerevisiae* to bind endothelial cells expressing GRP78.
Figure 7:
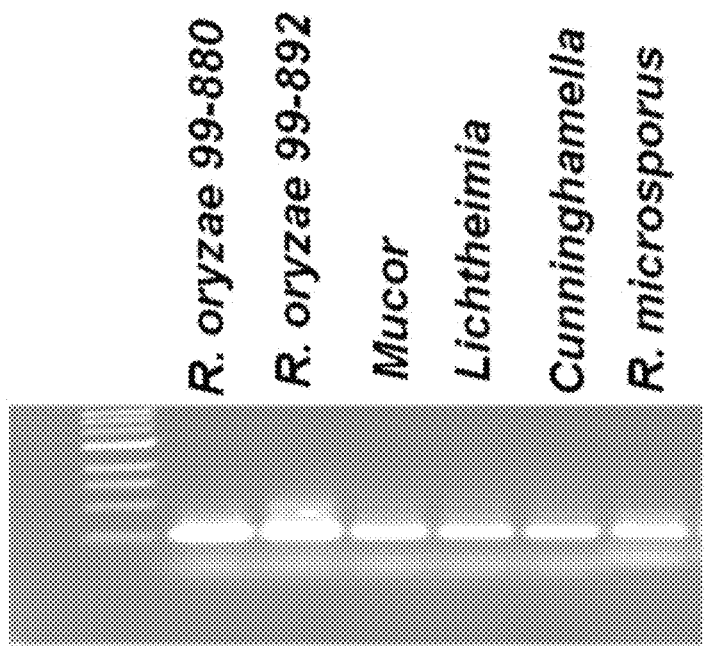
FIG. 7 shows CotH3 is conserved among various Mucorales including *R. oryzae* 99-880, *R. oryzae* 99-892, *Mucor* sp., *Lichtheimia corymbifera, Cunninghamella bertholetiae* and *R. microsporus*.
Figure 13:
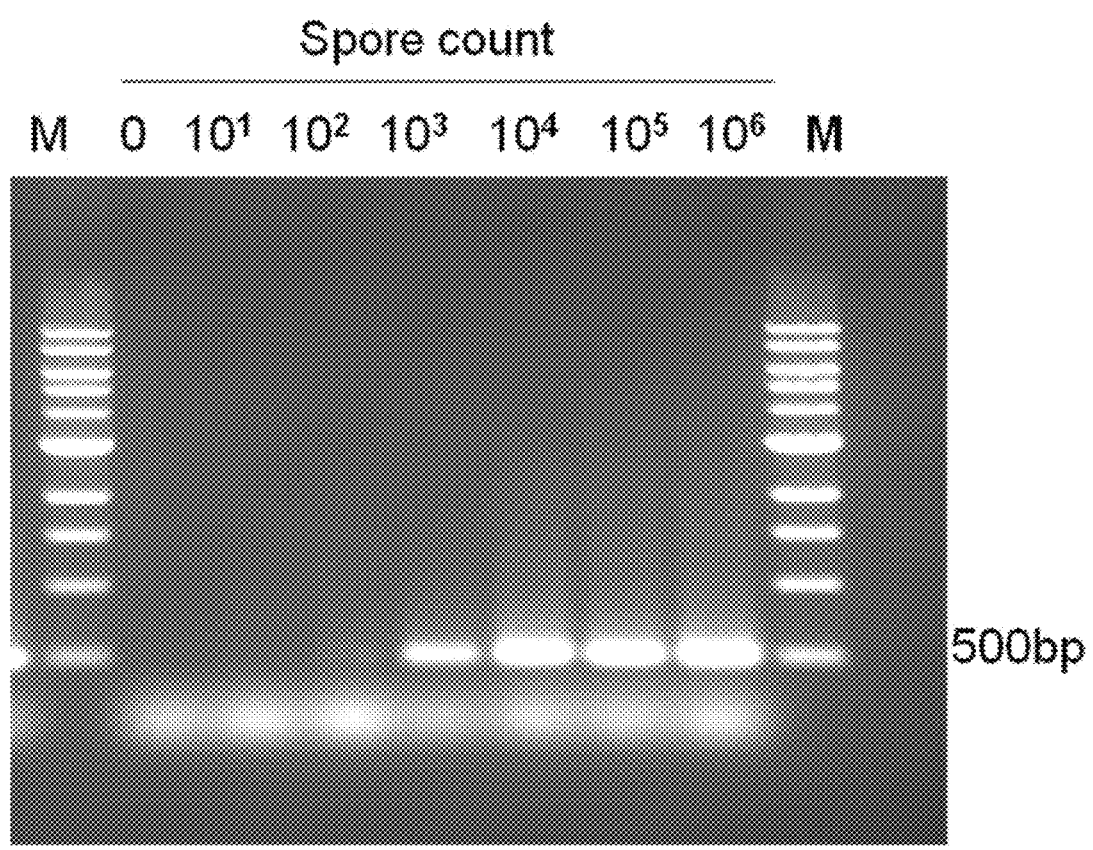
FIG. 13 shows detection of CotH3 in sheep's blood spiked with *R. oryzae* by PCR using oligonucleotide primers having the nucleic acid sequence of SEQ ID NO: 33 and SEQ ID NO: 34.
Figure 14:
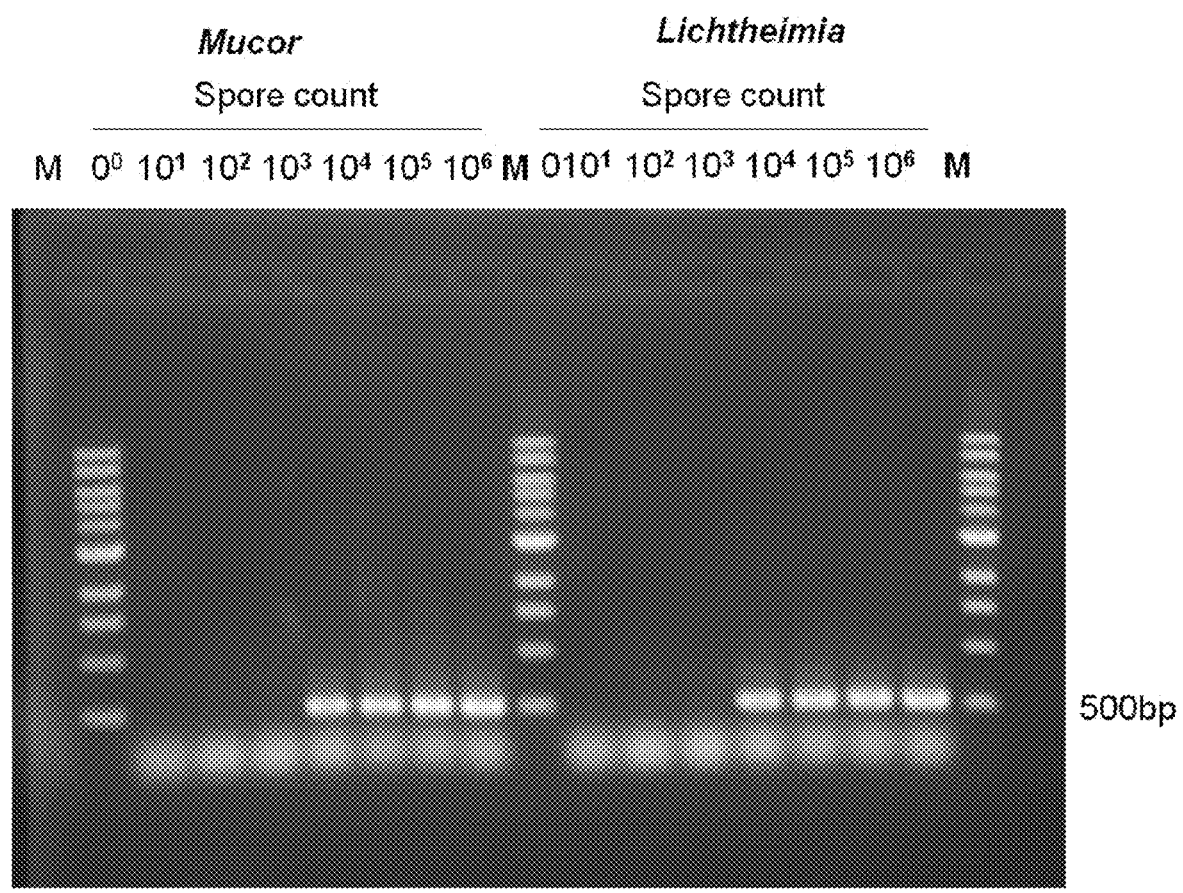
FIG. 14 shows detection of CotH3 in sheep's blood spiked with *Mucor* sp. or *Lichtheimia corymbifera* by PCR using oligonucleotide primers having the nucleic acid sequence of SEQ ID NO: 33 and SEQ ID NO: 34.
Figure 15:
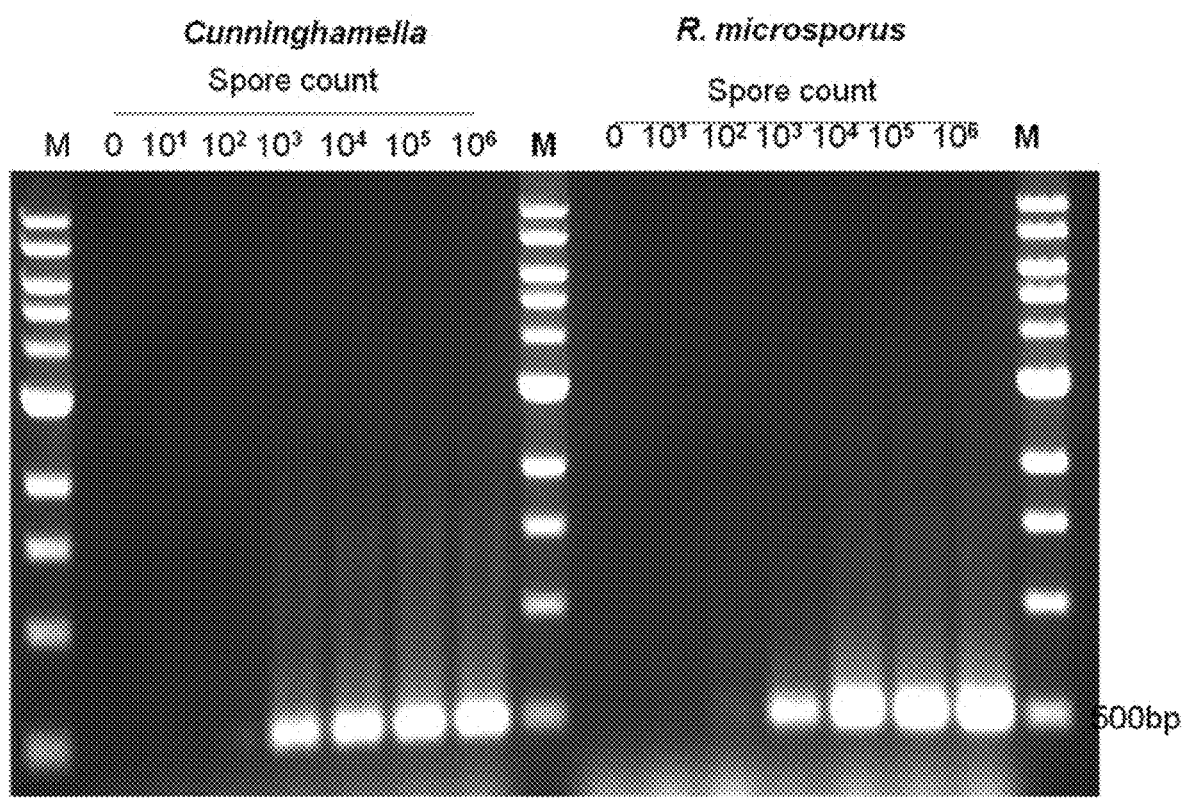
FIG. 15 shows detection of CotH3 in sheep's blood spiked with *Cunninghamella bertholetiae* or *R. microsporus* by PCR using oligonucleotide primers having the nucleic acid sequence of SEQ ID NO: 33 and SEQ ID NO: 34.
Figure 16:
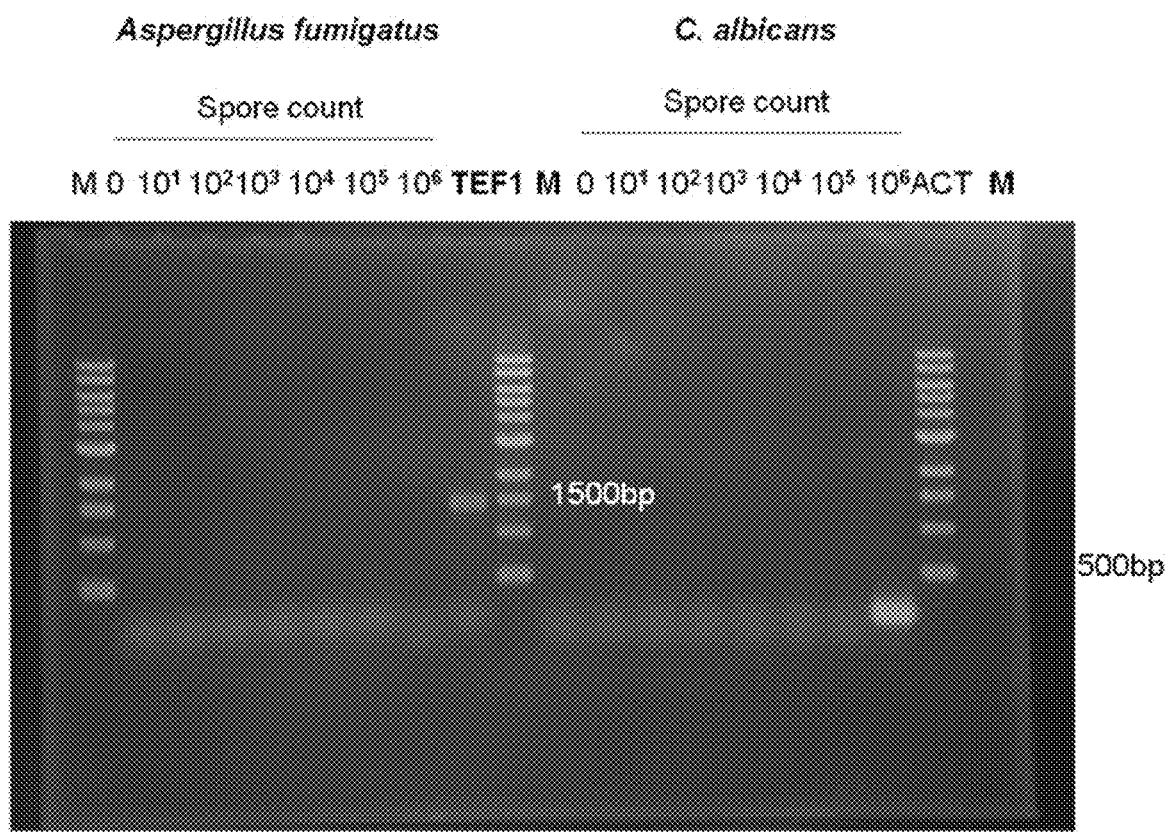
FIG. 16 shows no detection of CotH3 in sheep's blood spiked with *Aspergillus* fumigates or *Candida albicans* by PCR using oligonucleotide primers having the nucleic acid sequence of SEQ ID NO: 33 and SEQ ID NO: 34.
Figure 58:
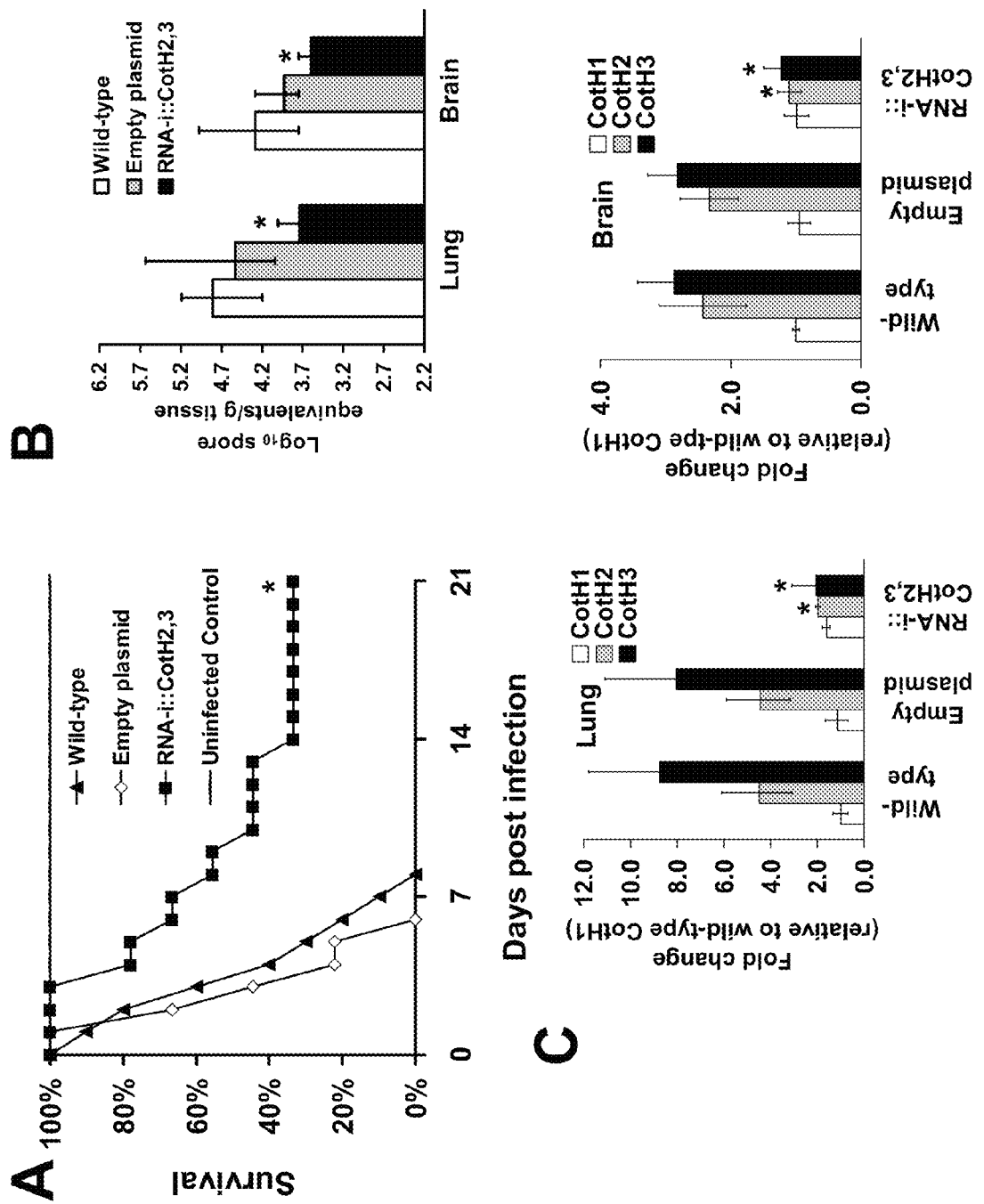
FIG. 58, panels A-C, show inhibition of CotH2 and CotH3 expression attenuates virulence of *R. oryzae* in diabetic ketoacidotic mice. Panel A shows the survival of mice (n=10 for wild type or 9 for RNA-i or empty plasmid transformants) infected intratracheally with one of the three strains. Inhaled inocula were $2.4\times10^3$, $2.8\times10^3$, and $2.5\times10^3$ spores, for wild type, empty plasmid, or RNA-i cells, respectively. *P<0.003 vs. wild type or empty plasmid infected mice by log Rank test. Panel B shows the lung and brain fungal burden of diabetic ketoacidotic mice (n=9 per group) infected intratracheally with wild type ($1.7\times10^3$), empty plasmid ($3.0\times10^3$) or RNA-i (3.1×10³) cells. Mice were sacrificed on day +2 relative to infection and their organs processed for tissue fungal burden using SYBR green assay. Data are expressed as median±interquartile range. *P<0.001 compared to wild type or empty plasmid infected mice by Wilcoxon Rank Sum test. Panel C shows in vivo expression of CotH genes in lungs and brains harvested from mice infected with wild type, empty plasmid or RNA-i construct as determined by qRT-PCR using specific primers to each of the CotH genes. Data are expressed as mean±SD. *P<0.001 vs. wild type or empty plasmid.

CotH3 and to a lesser extent CotH2 were expressed in *R. oryzae* germlings interacting with human umbilical vein endothelial cells (FIG. 4). CotH1 was expressed by *R. oryzae* spores but not germlings interacting with endothelial cells (FIG. 3). Although FAR-Western analysis identified the 4th ORF (RO3G_16295), this gene was not expressed by *R. oryzae* germlings interacting with endothelial cells. *S. cerevisiae* expressing CotH3, and to a lesser extent CotH2, specifically bound endothelial cell GRP78 (FIG. 6). Heterologous expression of CotH3 in the non-adherent *S. cerevisiae* promoted adherence and subsequent invasion of endothelial cells and CHO cells overexpressing GRP78 (FIG. 58). A sequence alignment between CotH3 polypeptides from various Mucorales species show an >90% sequence identity between the various species (FIG. 7 and Table 2)

These results show that *R. oryzae* invasion of endothelial cells is facilitated by CotH3, or CotH2 binding to GRP78.

TABLE 2

Alignamaent of Nucleotide (CotH3 and other genera exons only)

| CotH 3 | R. oryzae 99-880 | R. oryzae 99-892 | Mucor 99-932 | Absidia Corymbifera | Cunninghamela bertholetiae | R. microsporus |
|---|---|---|---|---|---|---|
| R. oryzae 99-880 | 100% | 95.82 | 96.42% | 99.34% | 97.80% | 99.94 |
| R. oryzae 99-892 | 95.82 | 100% | 100.00% | 96.53% | 94.51% | 96.47% |
| Mucor 99-932 | 96.42% | 100.00% | 100% | 96.53% | 94.51% | 96.47% |
| Absidia Corymbifera | 99.34% | 96.53% | 96.53% | 100% | 97.36% | 99.39% |
| Cunninghamela bertholetiae | 97.80% | 94.51% | 94.51% | 97.36% | 100% | 97.85% |
| R. microsporus | 99.94 | 96.47% | 96.47% | 99.39% | 97.85% | 100% |

EXAMPLE II

CotH3 and CotH2 are Unique Mucorales Invasins that Bind to Endothelial Cell GRP78

*R. oryzae* and Culture Conditions

Several clinical Mucorales isolates were used in the experiments disclosed herein. For example, *R. oryzae* 99-880 and *Mucor* sp. 99-932 were isolated from brain samples, whereas *R. oryzae* 99-892 and *Rhizopus* sp 99-1150 were isolated from lungs samples of infected patients (samples were obtained from the Fungus Testing Laboratory, University of Texas Health Science Center at San Antonio). *Cunninghamella bertholletiae* 182 is also a clinical isolate, which was a kind gift from Dr. Tomas Walsh (NIH). *Lichtheimia corymbifera* is also a clinical isolate obtained from the DEFEAT Mucor clinical study (Spellberg et al. (2102), J Antimicorbiol Chemother 67(3):715-22)

Mucorales were grown on potato dextrose agar (PDA, BD Diagnostic) plates for 3-5 days at 37° C., while *A. fumigatus* and *C. albicans* were grown on Sabouraud dextrose agar (SDA) plates for 2 weeks and 48 h at 37° C., respectively. The sporangiospores were collected in endotoxin free Dulbecco's phosphate buffered saline (PBS) containing 0.01% Tween 80, washed with PBS, and counted with a hemocytometer to prepare the final inocula. For *C. albicans*, blastospores were collected in PBS after growing the organisms in YPD medium [1% yeast extract (Difco Laboratories), 2% bacto-peptone (Difco) and 2% glucose (Sigma)] at 30° C. for overnight. To form germlings, spores were incubated in liquid YPD medium at 37° C. with shaking for 1-3 h based on the assay under study. Germlings were washed twice with RPMI 1640 without glutamine (Irvine Scientific) for all assays used except for isolating the endothelial cell receptor experiments in which the germlings were washed twice with PBS (plus $Ca^{2+}$ and $Mg^{2+}$).

Heterologous Expression of CotH Genes in *S. cerevisiae*

The entire ORF of CotH1, CotH2, and CotH3 were PCR amplified from cDNA extracted from *R. oryzae* spores grown on PDA plates by using Phusion high fidelity PCR Kit (New England Biolabs) and the primers listed in Table 3. The pESC-LEU yeast dual expression vector (Stratagene) was used to clone and express these genes under the Gall promoter. The vector was digested with BamHI and SalI. PCR amplified inserts from each of the CotH genes were cloned into pESC-LEU by using In-Fusion 2.0 Dry-Down PCR Cloning Kit, per the manufacturer's instructions (Clontech Laboratories). The generated yeast expression vectors were independently transformed into yeast strain LL-20 by the polyethylene glycol-LiOAc method, and transformants were screened on the solid synthetic dextrose minimal medium lacking leucine. *S. cerevisiae* transformed with the empty plasmid served as control.

TABLE 3

Primers used in this study

| Primer Name | Primer Sequence (SEQ ID NOS 41-64, respectively, in order of apperance) | Reaction/Use |
|---|---|---|
| CotH1-F | AAAAAACCCCGGATCCTATGAAATCCCTACTTTTTGTTGTATTC | RT-PCR and to clone CotH1 in to expression vector pESC-Leu |
| CotH1-R | TCTGTTCCATGTCGACCTAGAAGAAAGAGGCAAATAAAGTGC | RT-PCR and to clone CotH2 in to expression vector |
| CotH2-F | AAAAAACCCCGGATCCTATGAAATTATCACTCACTATAGTATCCTCT | RT-PCR to clone CotH3 in to expression vector |
| CotH2-R | TCTGTTCCATGTCGACTTAAAAGATAGCAGTGGCAACTAAAG | RT-PCR to clone CotH3 in to expression vector |
| CotH3-F | AAAAAACCCCGGATCCTATGAAATTATCTATTATATCCGCTGCC | RT-PCR to clone CotH3 in to expression vector |
| CotH3-R | TCTGTTCCATGTCGACTTAGAATACAAGGAGAGCTAAAGCG | Detection in mucorales |
| Ligand#4-F RO3G_16295 | AAAAAACCCCGGATCCTATGATTGCTACCCCTTTTGAAA | RT-PCR |
| Ligand#4-R RO3G_16295 | TCTGTTCCATGTCGACTTAAAAGAAAATAAAGAATGTTGCAGC | RT-PCR |

TABLE 3-continued

Primers used in this study

| Primer Name | Primer Sequence (SEQ ID NOS 41-64, respectively, in order of apperance) | Reaction/Use |
|---|---|---|
| CotH3-F-ORF | ATGAAATTATCTATTATATCCGCTGCC | Detection IN OTHER MUCORALS1.9Kb |
| CotH3-R-ORF | TTAGAATACAAGGAGAGCTAAAGCG | Detection IN OTHER MUCORALS1.9Kb |
| RNAi-cotHF-F | GCATGCTAGAACAGAAGAAAGTTTTGATCGTTC | RNAi-forward |
| RNAi-ccoHF-R | GTACGACGTTCACGAATCTGTGTAGG | RNAi-forward |
| RNAi-I-F | CCGCGGGACGTTCACGAATCTGTGTAGG | RNAi-Reverse |
| RNAi-I-R | GCTAGCAGAACAGAAGAAAGTTTTGATCGTTC | RNAi-Reverse |
| CotH1-F | CAAACAAATGATGGGGCCTA | qRT-PCR for Expression |
| CotH1-R | CGTTTTTGTTCAAGATTTACACCA | qRTPCR for Expression |
| CotH2-F | CCTAATAAGGACAACGCAAACG | qRT-PCR for Expression |
| CotH2-R | TTGGCAATGGCTGTGTTATC | qRT-PCR for Expression |
| CotH3-F | GCCAATCCTAATGGTGAAGC | qRT-PCR for Expression |
| CotH3-R | CATGAAACGGTCGAGATCAA | qRT-PCR for Expression |
| RO Actin-F | AGCTCCTTTGAACCCCAAGT | qRT-PCR for Expression |
| RO Actin-R | ACGACCAGAGGCATACAAGG | qRT-PCR for Expression |
| RO 18sRNA-F | GCGGATCGCATGGCC | qRTPCR for CFU |
| RO 18sRNA-R | CCATGATAGGGCAGAAAATCG | qRTPCR for CFU |

Anti-CotH Antibody Production and Cell Surface Localization

Rabbit polyclonal antibodies were raised against two peptides predicted to be antigenic. The peptides GAGKKHNNA-KQSWNW (SEQ ID NO: 39), and MGQTND-GAYRDPTDNNK (SEQ ID NO: 40) were coupled with KLH and used to commercially vaccinate rabbits (ProMab Biotechnologies Inc., Richmond, Calif.). Purified IgG from the vaccinated rabbits were used to detect cell surface localization of CotH proteins on S. cerevisiae and on R. oryzae interacting with endothelial cells (Liu et al., J. Clin. Invest., 120: 1914-1924 (2010)).

For localizing the CotH proteins to the cell surface of S. cerevisiae, blastospores expressing individual CotH genes were incubated first with the anti-CotH IgG at 1:50, followed by fluorescein isothiocyanate (FITC)-labeled goat anti-rabbit IgG at 1:100. The stained cells were imaged with Leica confocal microscope and the entire yeast cells were visualized with differential interference contract (DIC).

For detecting the expression of the CotH proteins on R. oryzae, spores were germinated in YPD for 3 hours at 37° C. Germlings were stained with the anti-CotH IgG at 1:50, followed by FITC-labeled goat anti-rabbit IgG at 1:100. A FACSCaliber (Becton Dickinson) instrument equipped with an argon laser emitting at 488 nm was used for flow cytometric analysis. Fluorescence emission was read with a 515/40 bandpass filter. Fluorescence data were collected with logarithmic amplifiers. The mean fluorescence intensities of $10^4$ events were calculated using the CELLQUEST software.

Endothelial Cells and Chinese Hamster Ovary (CHO) Cells

Endothelial cells were collected from umbilical vein endothelial cells by the method of Jaffe et al. (Jaffe et al., J. Clin. Invest. 52:2745-2756 (1973)). The cells were harvested by using collagenase and were grown in M-199 (Gibco BRL) enriched with 10% fetal bovine serum, 10% defined bovine calf serum, L-glutamine, penicillin, and streptomycin (all from Gemini Bio-Products, CA). Second-passage cells were grown to confluency in 96-well tissue culture plates (Costar, Van Nuys, Calif.) on fibronectin (BD Biosciences). All incubations were in 5% $CO_2$ at 37° C. The reagents were tested for endotoxin using a chromogenic limulus amebocyte lysate assay (BioWhittaker, Inc., Walkersville, Md.), and the endotoxin concentrations were less than 0.01 IU/ml. Endothelial cell collection was approved by Institutional Review Board at Los Angeles Biomedical Research Institute at Harbor-UCLA Medical Center. CHO cell line C.1 which was derived from parental DHFR-deficient CHO cells engineered to overexpress GRP78s were kind gifts of Dr. Randall Kaufman (Morris et al., J. Biol. Chem., 272:4327-4334 (1997); Reddy et al., J. Biol. Chem., 278:20915-20924 (2003)).

Extraction of Endothelial Cell Membrane Proteins

Endothelial cell membrane proteins were extracted according to the method of Isberg and Leong (Isberg and Leong, Cell 60:861-871 (1990)). Briefly, confluent endothelial cells in 100-mm diameter tissue culture dishes were rinsed twice with warm DPBS containing $Ca^{2+}$ and $Mg^{2+}$ (PBS-CM) and then incubated with Ez-Link Sulfo-NHS-LS Biotin (0.5 mg/ml, Pierce) in PBS-CM for 12 min at 37° C. in 5% $CO_2$. The cells were then rinsed extensively with cold PBS-CM and scraped from the tissue culture dishes. The endothelial cells were collected by centrifugation at 500×g for 5 min at 4° C. and then lysed by incubation for 20 min on ice in PBS-CM containing 5.8% n-octyl-β-D-glucopyranoside (w/v) (Cal Bio-Chem) and protease inhibitors (1 mM phenylmethylsulfonyl fluoride, 1 µg/ml pepstatin A, 1 µg/ml leupeptin, and 1 µg/ml aprotinin) (Sigma). The cell debris was removed by centrifugation at 5000×g for 5 min at 4° C. The supernatant was collected and centrifuged at 100,000×g for 1 h at 4° C. The concentration of the endothelial cell proteins in the resulting supernatant was determined using Bradford method (Bio-Rad).

RNA Interference of CotH2/CotH3

Previously described RNA interference (RNAi) technology (Ibrahim et al., Mol. Microbiol., 77:587-604 (2010)) was utilized to inhibit the expression of CotH2 and CotH3 in *R. oryzae*. A 450 bp fragment commonly shared between CotH2 and CotH3 ORF was PCR amplified and cloned as an inverted repeat under control of the *Rhizopus* expression vector pPdcA-Ex (Mertens et al., Archives of microbiology 186:41-50 (2006)). Additionally, an intron from the *Rhizopus* pdcA gene (Skory, Curr. Microbiol., 47: 59-64 (2003)) was included between repeat to serve as a linker for stabilization of the intended dsRNA structure (Nakayashiki et al., Fungal Genet. Biol., 42:275-283 (2005); Wesley et al., Plant J., 27:581-590 (2001)). The generated plasmid was transformed into *R. oryzae* pyrF mutant using the biolistic delivery system (Skory, Mol. Genet. Genomics 268: 397-406 (2002)) (Bio-Rad) and transformants were selected on minimal medium lacking uracil.

Binding of GRP78 by *S. cerevisiae* Expressing CotH.

*S. cerevisiae* cells ($8 \times 10^8$) expressing CotH1, CotH2, CotH3, or empty plasmid were incubated for 1 h on ice with 250 µg of biotin-labeled endothelial cell surface proteins in PBS-CM plus 1.5% n-octyl-β-D-glucopyranoside and protease inhibitors. The unbound endothelial cell proteins were washed away by three rinses with this buffer. The endothelial cell proteins that remained bound to the fungal cells were eluted twice with 6M urea (Fluka) and the supernatant was combined and concentrated to appropriate volume with a Microcon centrifugal filter (10,000 MWCO, Millipore). The proteins were then separated on 10% SDS-PAGE, and transferred to PVDF-plus membranes (GE Water& Process Technologies). The membrane was then treated with Western Blocking Reagent (Roche) and probed with a rabbit anti-GRP78 antibody (Abcam) followed with secondary antibodies of HRP-conjugated goat anti-rabbit IgG (Pierce), respectively. After incubation with SuperSignal West Dura Extended Duration Substrate (Pierce), the signals were detected using a CCD camera.

Interactions of Fungi with Endothelial or CHO Cells

The number of organisms endocytosed by endothelial cells or CHO cells was determined using a modification of a previously described differential fluorescence assay (Ibrahim et al., Infect. Immun., 63:4368-4374 (1995)). Briefly, 12-mm glass coverslips in a 24-well cell culture plate were coated with fibronectin for at least 4 hrs, and seeded with endothelial or CHO cells until confluency. After washing twice with prewarmed HBSS, the cells were then infected with $10^5$ cells of *S. cerevisiae* expressing CotH or *R. oryzae* in RPMI 1640 medium that has been germinated for 1 h. Following incubation for 3 h, the cells were fixed in 3% paraformaldehyde and the cells were stained with 1% Uvitex (a kind gift from Jay Isharani, Ciba-Geigy, Greensboro, N.C.) for 1 hr, which specifically binds to the chitin of fungal cell wall. After washing 3 times with PBS, the coverslips were mounted on a glass slide with a drop of ProLong Gold antifade reagent (Molecular Probes) and sealed with nail polish. The total number of cell associated organisms (i.e. germlings adhering to monolayer) was determined by phase-contrast microscopy. The same field was examined by epifluorescence microscopy, and the number of uninternalized germlings (which were brightly fluorescent) was determined. The number of endocytosed organisms was calculated by subtracting the number of fluorescent organisms from the total number of visible organisms. At least 400 organisms were counted in 20-40 different fields on each slide. Two slides per arm were used for each experiment and the experiment was performed in triplicate on different days.

*R. oryzae*-induced endothelial or CHO cell damage was quantified by using a chromium ($^{51}$Cr) release assay (Ibrahim et al., J. Infect. Dis., 198:1083-1090 (2008)). Briefly, endothelial cells or CHO cells grown in 96-well tissue culture plates containing detachable wells were incubated with 1 µCi per well of Na$_2$$^{51}$CrO$_4$ (ICN, Irvine, Calif.) in M-199 medium (for endothelial cells) or Alpha minimum Eagle's medium (for CHO cells) for 16 h. On the day of the experiment, the unincorporated $^{51}$Cr was aspirated, and the wells were washed twice with warmed Hanks' balanced salt solution (Irvine Scientific, Irvine, Calif.). Cells were infected with fungal germlings ($1.5 \times 10^5$ germinated for 1 h) suspended in 150 µl of RPMI 1640 medium (Irvine Scientific) supplemented with glutamine. Spontaneous $^{51}$Cr release was determined by incubating endothelial or CHO cells in RPMI 1640 medium supplemented with glutamine without *R. oryzae*. After 3 h of incubation at 37° C. in a 5% CO$_2$ incubator, 50% of the medium was aspirated from each well and transferred to glass tubes, and the cells were manually detached and placed into another set of tubes. The amount of $^{51}$Cr in the aspirate and the detached well was determined by gamma counting. The total amount of $^{51}$Cr incorporated by endothelial cells in each well equaled the sum of radioactive counts per minute of the aspirated medium plus the radioactive counts of the corresponding detached wells. After the data were corrected for variations in the amount of tracer incorporated in each well, the percentage of specific endothelial cell release of $^{51}$Cr was calculated by the following formula: [(experimental release×2)-(spontaneous release×2)]/[total incorporation-(spontaneous release×2)]. Each experimental condition was tested at least in triplicate and the experiment repeated at least once.

For antibody blocking of adherence, endocytosis, or damage caused by *R. oryzae*, the assays were carried out as described above except for incubating endothelial cells with 50 µg of anti-CotH antibodies (purified IgG) or with serum obtained from the same rabbit prior to vaccination with CotH3 peptide predicted to be antigenic for 1 h prior to adding *R. oryzae* germlings.

In Vivo Virulence Studies

For in vivo studies, ICR male mice (≥20 g) (Taconic Farms) were rendered DKA with a single i.p. injection of 190 mg/kg streptozotocin in 0.2 ml citrate buffer 10 days prior to fungal challenge (Ibrahim et al., Antimicrob. Agents Chemother., 47:3343-3344 (2003)). Glycosuria and ketonuria were confirmed in all mice 7 days after streptozotocin treatment. Diabetic ketoacidotic mice were infected with fungal spores by intratracheal route after sedating the mice with ketamine (66 mg/kg) and xylazine (4.8 mg/kg) with a target inoculum of $2.5 \times 10^5$ spores. To confirm the inoculum, the lungs from three mice that were sacrificed immediately following inoculation, were homogenized in PBS and quantitatively cultured on PDA plates containing 0.1% triton and colonies were counted following a 24 h incubation period at 37° C. The primary efficacy endpoint was time to moribundity. In some experiments, as a secondary endpoint, fungal burden in the lungs and brains (primary target organs) was determined on day +2 post infection by qPCR assay as previously described (Ibrahim et al., Antimicrob. Agents Chemother., 49:721-727 (2005)). Values were expressed as $\log_{10}$ spore equivalent/g of tissue. Histopathological examination was carried out on sections of the harvested organs after fixing in 10% zinc formalin. The fixed organs were embedded in paraffin, and 5 mm sections were stained with hematoxylin and eosin (H&E) or Periodic acid-Schiff stains to detect R. oryzae hyphae (Ibrahim et al., J. Clin. Invest., 117:2649-2657 (2007)).

For in vivo expression of the CotH genes, lungs and brains collected from mice 48 h post infection intratracheally with wild-type R. oryzae, or transformants with empty plasmid or with RNA-i construct were flash frozen in liquid nitrogen and process for RNA extraction using a Tri Reagent solution (Ambion). Reverse transcription was performed with RETROscript (Ambion) using primers listed in Table 3. For quantitative RT-PCR, SYBR green assays were performed. Constitutively expressed ACT1 was used as a control for all reactions. Calculations and statistical analyses were performed using ABI PRISM 7000 Sequence Detection System User Bulletin 2 (Applied Biosystems).

Passive Immunization

To detect if antibodies against CotH proteins protect mice from mucormycosis, diabetic ketoacidotic mice were immunized with 1 mg of rabbit purified anti-CotH IgG raised against GAGKKHNNAKQSWNW (SEQ ID NO: 39) or MGQTNDGAYRDPTDNNK (SEQ ID NO: 40) by intraperitoneal injection 2 hours prior to infecting the mice intratracheally as outlined above. Control mice were infected similarly but received a similar dose from the same rabbit prior to vaccinating with the CotH3 peptide. Three days post infection a repeated dose of the antibody or the control serum (prior to vaccination) was introduced. The primary efficacy endpoint was time to moribundity.

Statistical Analysis

Differences in CotH expression and fungi-endothelial cell interactions were compared by the non-parametric Wilcoxon Rank Sum test. The non-parametric log-rank test was used to determine differences in survival times. Comparisons with P values of <0.05 were considered significant.

Results

Isolation of Putative R. oryzae Ligand(s) that Bind to Endothelial Cell GRP78.

Figure 51:
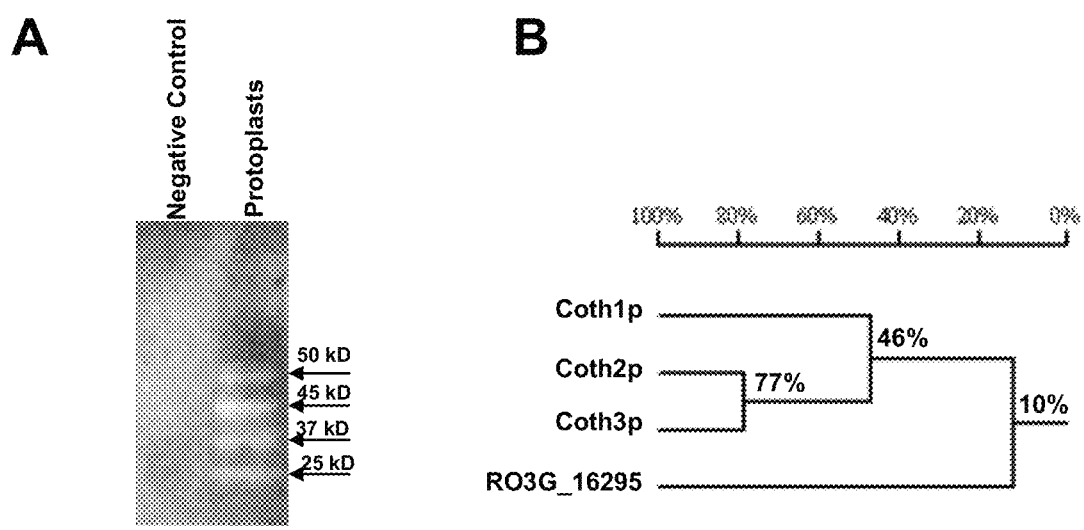
FIG. 51, panels A and B, show a FAR western blot of *R. oryzae* surface proteins that bound to GRP78 (Panel A) and a dendrogram showing the close identity between CotH2 and CotH3 predicated proteins and the divergence of the CotH proteins from the fourth identified ORF widely present in fungi without an identified function (i.e. RO3G_16295) (Panel B).

To identify the R. oryzae ligand that binds to endothelial cell GRP78, cell wall material from supernatants of protoplasts of R. oryzae germlings were collected (Michielse et al., Mol. Genet. Genomics, 271:499-510 (2004)). Incubating protoplasts in the presence of an osmotic stabilizer (e.g. sorbitol) enables regeneration of the cell wall, and during regeneration cell wall constituents are released into the supernatant (Pitarch et al., Mol. Cell. Proteomics, 5:79-96 (2006); Pitarch et al., Electrophoresis, 20:1001-1010 (1999)). After a 2 h incubation period, (Michielse et al., Mol. Genet. Genomics, 271: 499-510 (2004)) protoplasts were pelleted and the supernatant was sterilized in the presence of protease inhibitors. The supernatant was concentrated and protein concentration was measured. Negative control samples were processed similarly with the exception of absence of protoplasts. FAR Western blot analysis (Wu et al., Nat. Protoc., 2:3278-3284 (2007)) using recombinant human Grp78 and anti-Grp78 Ab revealed the presence of 4 bands collected from the supernatant of R. oryzae protoplasts that bound to Grp78p (FIG. 51A). These bands were excised for protein identification by MALDI-TOF-MS/MS analysis. Only 4 ORFs predicted to be cell surface proteins were identified with GPI anchor sequence at the c-terminus, signal peptides at the N-terminus and multiple predicted N- and O-glycosylation sites. Three of the ORF (i.e. RO3G__05018, RO3G__08029, and RO3G__11882) had limited homology of 17% at the amino acid level to CotH family of proteins implicated in spore coat formation from several bacteria (Giorno et al., J. Bacteriol., 189:691-705 (2007); Naclerio et al., J. Bacteriol., 178:6407 (1996)). These were named CotH1 (RO3G__05018), CotH2 (RO3G__08029) and CotH3 (RO3G__11882). The fourth ORF RO3G__16295 is widely present in many fungi and some bacteria without an identified function.

CotH2 and CotH3 are closely related to each other with 77% identity at the amino acid level, while CotH1 is more distantly related (FIG. 51b). The fourth ORF had an overall identity of 10% to the three CotH proteins at the amino acid level. Upon searching the R. oryzae (delemar) 99-880 genome data base, two more related ORFs were found (66% homology at the amino acid level) and were predicted to encode GPI-anchored proteins. These two ORFS (RO3G__09276; and RO3G__01139) had distant homology to CotH1, CotH2, CotH3 proteins (20-24% at the amino acid level). These ORFs were named CotH4 and CotH5, respectively.

The possibility of the presence of this family of genes in other Mucorales known to cause human mucormycosis was also examined. Using primers that span the entire CotH3 ORF (1.9 kb), bands were amplified from clinical isolates including R. oryzae 99-892, Mucor sp. 99-932, Lichtheimia corymbifera, Cunninghamella bertholletiae, and Rhizomucor. Sequence analysis of these PCR-amplified bands revealed more than 90% identity at the nucleotide and predicted amino acid level with R. oryzae 99-880 CotH3. Collectively, these studies show the uniqueness of CotH family of genes to agents of mucormycosis.

CotH2 and CotH3 are Expressed During Interaction of R. oryzae with Endothelial Cells.

Figure 52:
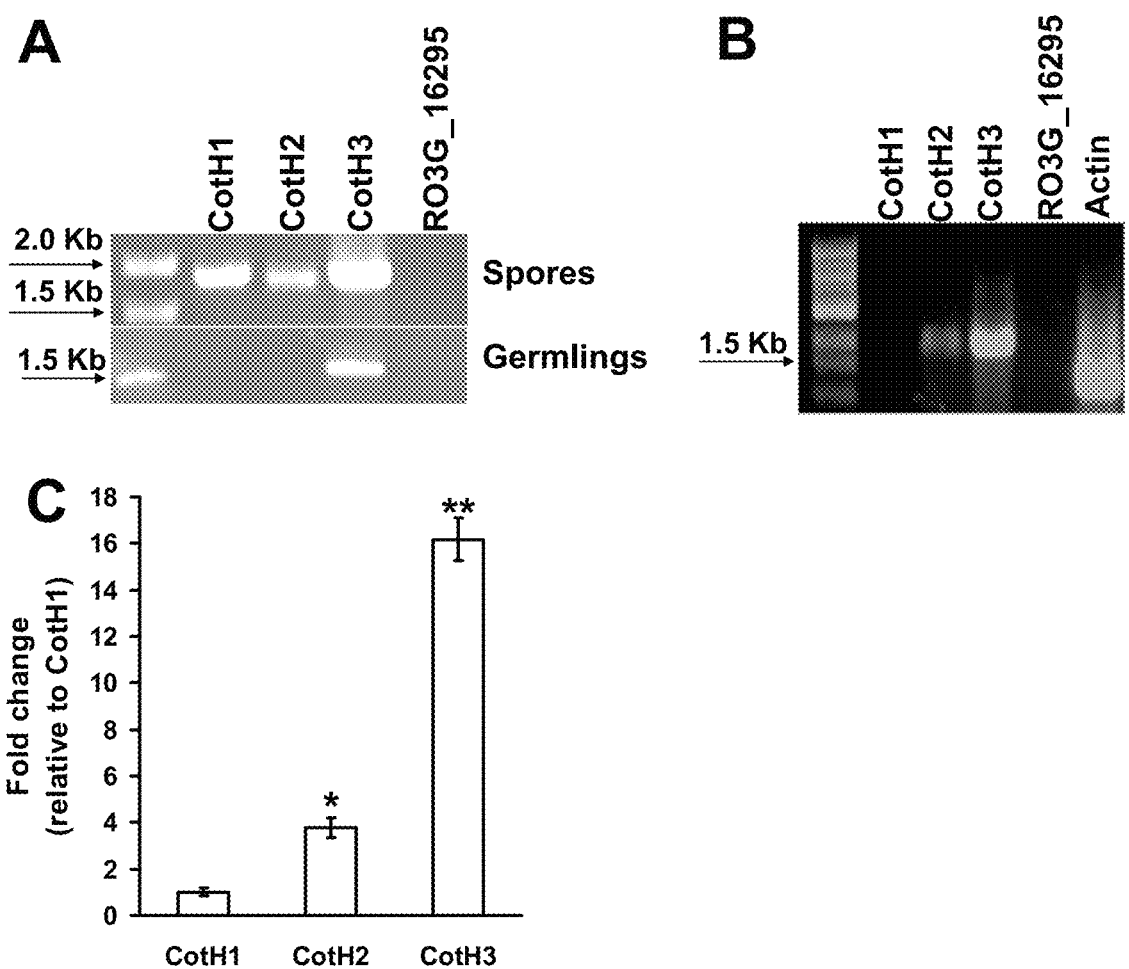
FIG. 52, panels A-C, show expression of CotH genes and RO3G_16295 in response to germination and to host cell interaction. All CotH genes were expressed in resting spores but only CotH3 was expressed in germlings of *R. oryzae* grown in YPD at 37° C. (Panel A). Exposure of *R. oryzae* germlings to endothelial cells induced expression of only CotH2 and CotH3 genes as determined by RT-PCR (Panel B). Quantification of gene expression of CotH genes in *R. oryzae* germlings on endothelial cells by qRT-PCR demonstrated 16 and 4 fold increase in expression of CotH3 and CotH2 relative to the non expressed CotH1, respectively. RO3G_16295 was not expressed under any of the conditions tested. *P<0.001 vs. CotH1 expression and **P<0.001 vs. CotH1 and CotH2 expression, by Wilcoxon Rank Sum test (Panel C). N=9 from three independent experiments.

Based on the results disclosed herein, it was hypothesizes that, if any of the isolated proteins represented a fungal ligand to GRP78, then the proteins must be expressed during R. oryzae interaction with endothelial cells. Since R. oryzae binds endothelial cell GRP78 while in germlings, the expression of these four ORFs in spores or germlings were studied. All CotH genes were expressed in the spore form while only CotH3 was expressed in germlings of R. oryzae. Importantly, when R. oryzae germlings were incubated with endothelial cells, both CotH2 and CotH3 were expressed (FIG. 52B) with CotH3 having 16 fold and 4 fold increase compared to CotH1 and CotH2, respectively (FIG. 52C). Finally, the fourth ORF RO3G__16295 was not expressed R. oryzae spores or germlings (FIG. 52A) or in R. oryzae germlings interacting with endothelial cells (FIG. 52B). These results showed that CotH3 and to a lesser extent CotH2 are putative candidates for interacting with GRP78 during invasion of human cells.

S. cerevisiae Cells Expressing CotH2 or CotH3 Bound GRP78 and Adhered to and Invaded Endothelial Cells and CHO Cells Overexpressing GRP78.

Figure 53:
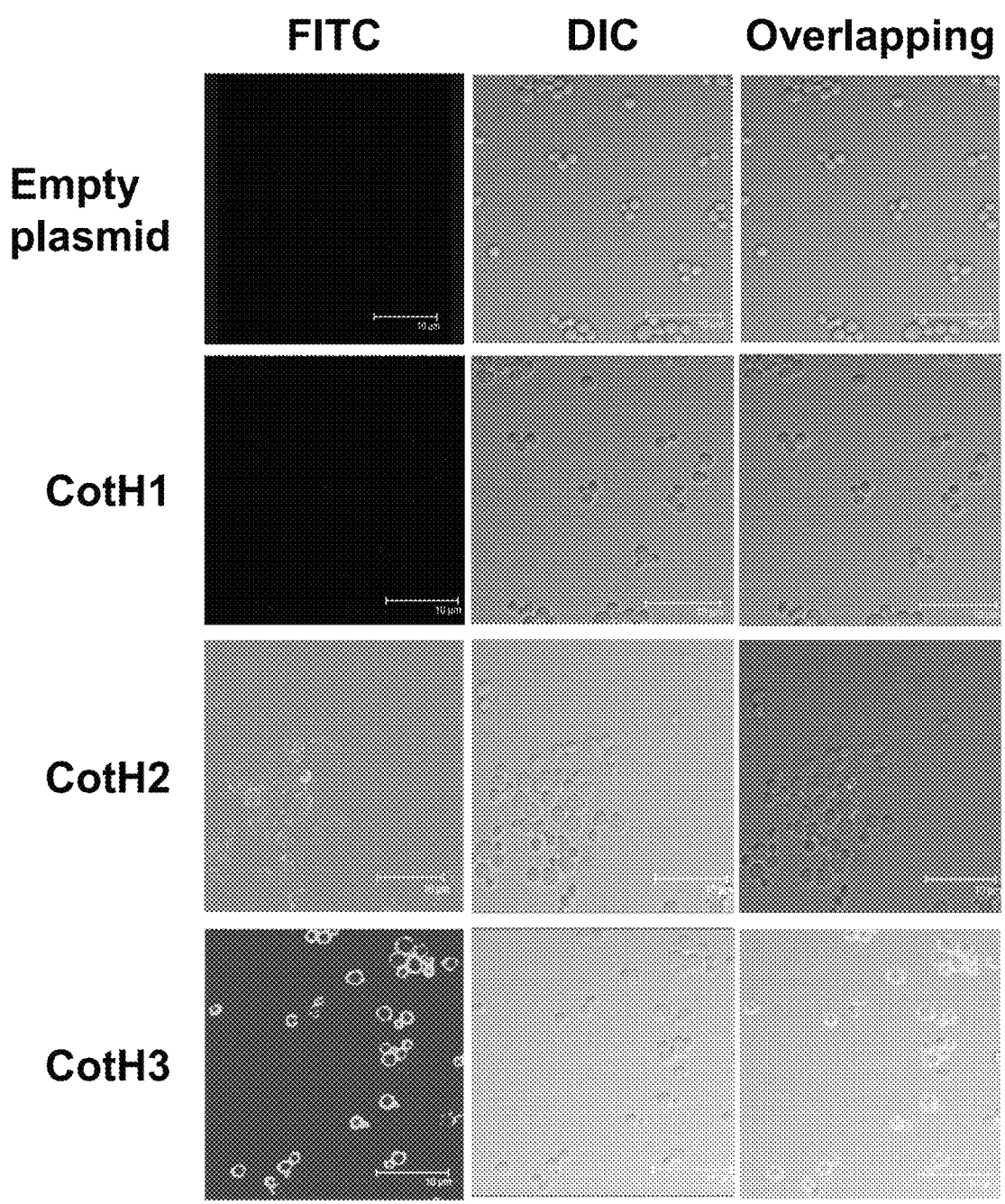
FIG. 53 shows antibodies raised against peptide GAGKKHNNAKQSWNW (SEQ ID NO: 39) recognized CotH2 and CotH3 but not CotH1 proteins heterologously expressed by *S. cerevisiae*. Peptide was coupled with KLH and used to raise rabbit antibodies commercially. *S. cerevisiae* heterologously expressing CotH proteins were stained with the antibodies then counter stained with FITC labeled anti-rabbit goat antibody prior to visualizing the cells with confocal microscopy.
Figure 54:
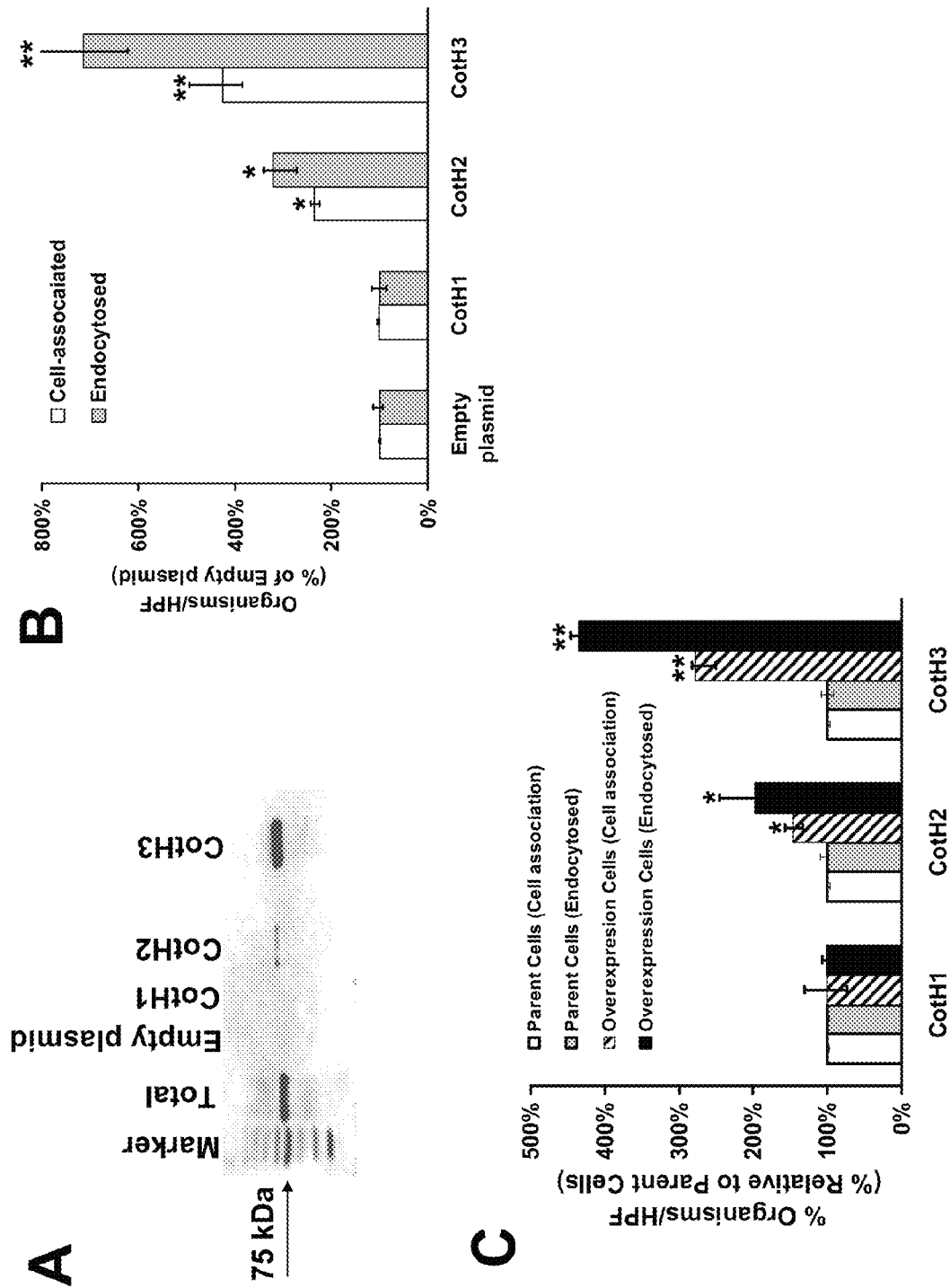
FIG. 54, panels A-C, show endothelial cell surface GRP78 binds to *S. cerevisiae* cells heterologously expressing CotH2 or CotH3 but not CotH1 and *S. cerevisiae* expressing CotH2 or CotH3 adhered and invaded endothelial cells or CHO cells overexpressing GRP78 but not *S. cerevisiae* expressing CotH1 or empty plasmid. Endothelial cell surface proteins were labeled with NHS-biotin and then extracted with n-octyl-β-d-glucopyranoside in PBS containing $Ca^{2+}$ and $Mg^{2+}$ and protease inhibitors. The labeled proteins (250 µg) were incubated with yeast cells ($2\times10^8$), then the unbound proteins were removed by extensive rinsing with PBS containing $Ca^{2+}$ and $Mg^{2+}$. The membrane proteins that remained bound to the organisms were eluted with 6 M urea, separated on 10% SDS-PAGE, and identified by immunoblotting with anti-GRP78 Ab (Panel A). Adherence and endocytosis (determined by differential fluorescence) assays were carried out using endothelial cells (Panel B), or CHO parent cells or those overexpressing GRP78 (Panel C) split on 12-mm glass coverslips. *P<0.001 vs. *S. cerevisiae* expressing empty plasmid or CotH1 and **P<0.001 vs. CotH1 and CotH2 expression, by Wilcoxon Rank Sum test. N=9 from three independent experiments. Data are expressed as median±interquartile range.

To study the role of CotH1, CotH2 and CotH3 in interacting with the GRP78 receptor, CotH2 or CotH3 were heterologously expressed in the none-adherent none invading S. cerevisiae. The transformed yeast cells were tested for their ability to specifically bind endothelial cell GRP78. Antibodies raised against two CotH3 peptides predicted to be antigenic and surface expressed (GAGKKHNNAKQSWNW (SEQ ID NO: 39), and MGQTNDGAYRDPTDNNK (SEQ ID NO: 40)) recognized S. cerevisiae expressing CotH3, and to a lesser extent CotH2, but not cells expressing CotH1 (FIG. 53). S. cerevisiae cells expressing CotH3 primarily bound GRP78 from endothelial cell membrane protein extracts. CotH2 expressing yeast cells also bound GRP78 from the same extract but S. cerevisiae expressing CotH1 (FIG. 54A). These results indicated that CotH3, and to lesser extent CotH2, interact with endothelial cell GRP78 during invasion of R. oryzae of the endothelium. To confirm this hypothesis, the ability of the transformed yeast cells to adhere to and invade endothelial cells in vitro was examined.

Compared to empty plasmid, *S. cerevisiae* expressing CotH1 had no enhancement in adherence to or endocytosis (invasion) of endothelial cells. In contrast, yeast cells expressing CotH2 or CotH3 had multiple fold increase in adherence to and invasion of endothelial cells compared to *S. cerevisiae* expressing CotH1 or those transformed with empty plasmid (FIG. 54B). Importantly, cells expressing CotH3 had significantly higher ability to adhere to and invade endothelial cells compared to yeast cells expressing CotH2. To examine if this enhanced adherence to and invasion of endothelial cells was due to interactions with GRP78, the ability of *S. cerevisiae* expressing CotH1, CotH2, CotH3 or empty plasmid to adhere to and invade parent CHO cells were compared to CHO cells overexpressing GRP78 (Morris et al., *J. Biol. Chem.*, 272: 4327-4334 (1997); Reddy et al., *J. Biol. Chem.*, 278:20915-20924 (2003)).

Only yeast cells expressing CotH2 or CotH3 had significant enhancement in their adhering to and invading CHO cells overexpressing GRP78 (FIG. 54C). Yeast cells expressing CotH1, CotH2 or CotH3 demonstrated no increased ability to bind to and invade parent CHO cells. Collectively, these data show that CotH3, and to a lesser extent CotH2, represents an adhesin/invasion of *R. oryzae* during interacting with endothelial cell GRP78.

CotH3 Protein is a *R. oryzae* Invasin.

Figure 55:
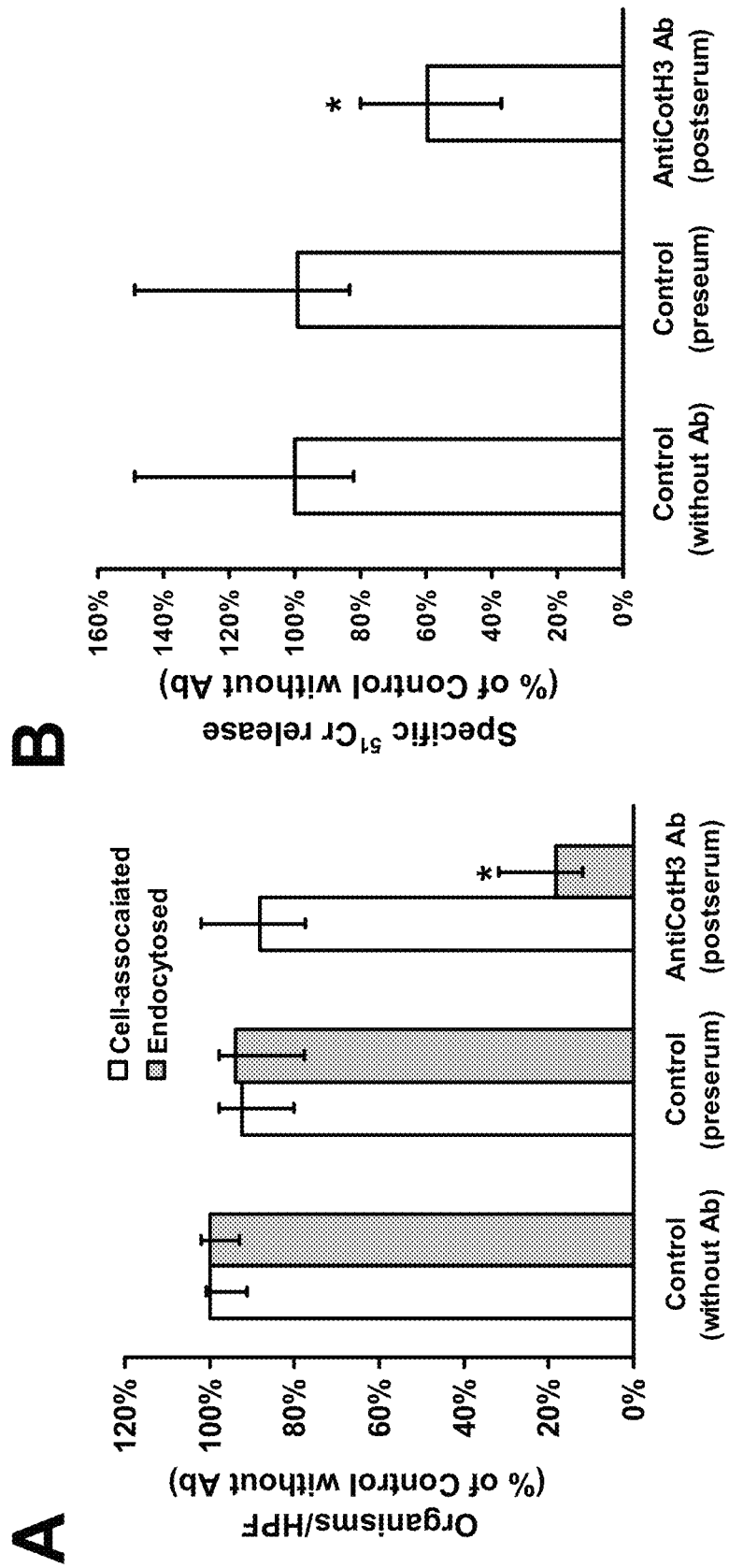
FIG. 55, panels A and B, show anti-CotH3 Abs (raised against peptide GAGKKHNNAKQSWNW (SEQ ID NO: 39) block endothelial cell endocytosis of and damage by *R. oryzae*. Adherence and endocytosis (determined by differential fluorescence) assays were carried out using endothelial cells split on 12-mm glass coverslips, while damage was carried out using the 96-well plate $^{51}Cr$-release method. Endothelial cells were incubated with 50 µg/ml anti-CotH3 or with serum from the same rabbit prior to vaccination (control) for 1 hour prior to addition of *R. oryzae* germlings. Blocking of CotH3 and CotH2 (since the antibodies react to CotH2 proteins) abrogates endocytosis of *R. oryzae* by endothelial cells (data derived from >700 fungal cells interacting with approximately 200 endothelial cells/each group/experiment, with an average of 59% cells being endocytosed in the control) (Panel A) and reduces the ability of the fungus to cause endothelial cell damage (Panel B). *P<0.01 compared with pre-vaccinated serum or with no serum by Wilcoxon rank-sum test. n=6 slides per group from 3 independent experiments for endocytosis, and n=6 wells per group from 2 independent experiments for damage assay. Data are expressed as median±interquartile range.

Because endocytosis of the fungus was previously shown to be a prerequisite for *R. oryzae* to cause endothelial cell damage, (Ibrahim et al., *Infect. Immun.* 73:778-783 (2005); Liu et al., *J. Clin. Invest.*, 120:1914-1924 (2010)) blocking the function or expression of CotH3 to protect endothelial cells from *R. oryzae*-induced endocytosis and subsequent damage was investigated. Endocytosis, but not adherence, of *R. oryzae* germlings was abrogated by addition of rabbit anti-CotH3 polyclonal antibodies, but not pre-immune serum collected from the same animal (FIG. 55A). The damage to endothelial cells caused by *R. oryzae* germlings was reduce by >40% using anti-CotH3 antibodies (FIG. 55B)

To complement the antibody blocking studies, suppression of CotH3 and CotH2 expression was investigated to determine their impact on adherence, endocytosis, and endothelial cell damage. Using a previously described RNA-i method (Ibrahim et al., *Mol. Microbiol.*, 77:587-604 (2010)), a ~400 bp fragment was used to suppress both genes in one construct. CotH2 and CotH3 expression in two clones of *R. oryzae* pyrf mutant (Skory and Ibrahim, *Curr. Genet.* 52:23-33 (2007)) transformed with the RNA-i construct harboring PyrF as a selection marker (i.e. Trans 2 and Trans 6) were almost entirely abrogated compared to *R. oryzae* pyrf mutant transformed with empty plasmid (FIG. 56A).

Figure 56:
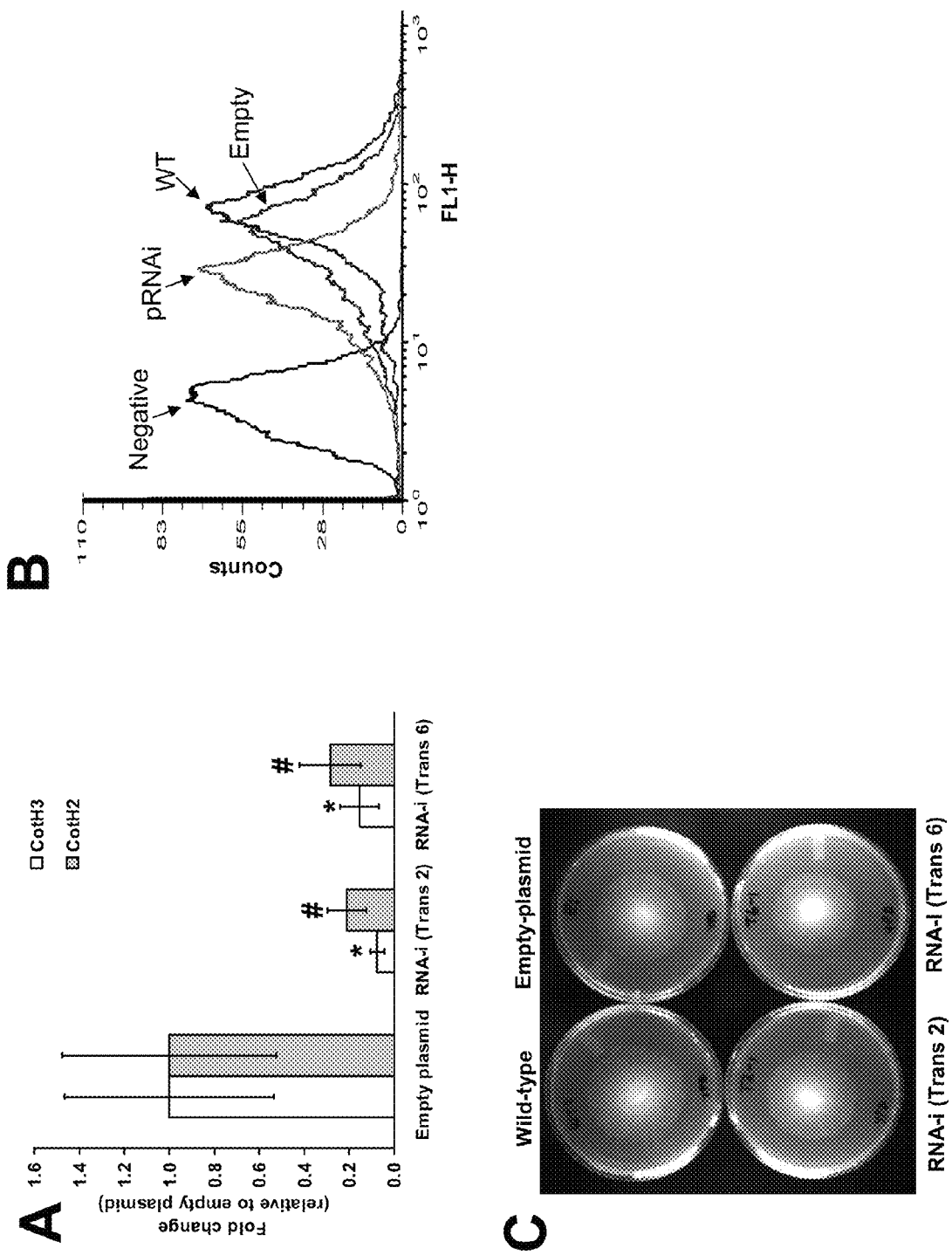
FIG. 56, panels A-C, show RNA-i construct targeting CotH2 and CotH3 inhibits the expression of both genes, reduces CotH2 and CotH3 protein synthesis on the cell surface and has no effect on the growth or the pattern of germination of *R. oryzae*. *R. oryzae* was transformed with an RNA-i construct (pRNAi) targeting CotH2 and CotH3 expression or with empty plasmid. Two transformants were shown to have >80% reduction in the expression of CotH2 and CotH3 relative to cells transformed with the empty plasmid as determined by qRT-PCR (Panel A). Flow cytometry testing using anti-CotH antibodies demonstrated reduction in cell surface expression of CotH proteins on *R. oryzae* cells transformed with the RNA-i construct compared to those transformed with the empty plasmid, wild type cells or negative control (i.e. wild type *R. oryzae* stained with commercial IgG instead of anti-CotH antibodies) (Panel B). The two transformants with reduced CotH2 and CotH3 expression had similar growth rate (Panel C) as the wild type cells or cells transformed with the empty plasmid.
Figure 57:
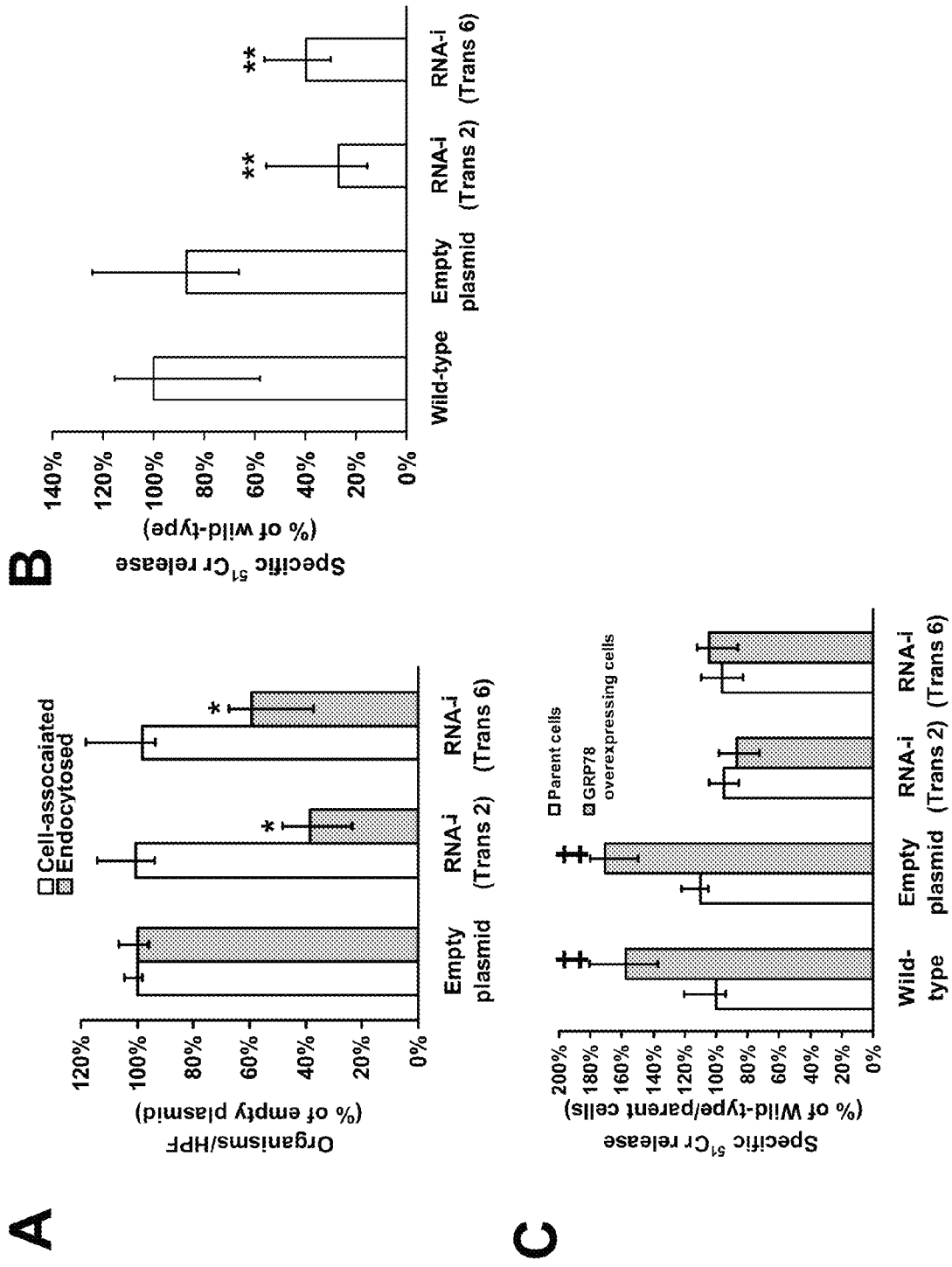
FIG. 57, panels A-C, show inhibition of CotH2 and CotH3 expression compromise the ability of *R. oryzae* to invade and damage endothelial cells and CHO cells overexpressing GRP78. Adherence and endocytosis (determined by differential fluorescence) assays were carried out using endothelial cells split on 12-mm glass coverslips, while damage was carried out using the 96-well plate $^{51}Cr$-release method. *R. oryzae* germlings transformed with the RNA-i construct caused less invasion (Panel A) and damage (Panel B) to endothelial cells when compared to cells transformed with empty plasmid. Transformants with RNA-i targeting CotH2 and CotH3 caused equivalent damage to CHO cells overexpressing GRP78 when compared to CHO parent cells. In contrast, *R. oryzae* germlings transformed with the empty plasmid or wild type *R. oryzae* caused significantly more damage to CHO cell overexpressing GRP78 vs. CHO parent cells (Panel C). *P<0.005 compared with empty plasmid, **P<0.01 vs. wild type or empty plasmid, and ‡P<0.01 vs. CHO parent cells by Wilcoxon rank-sum test. n=6 slides per group from 3 independent experiments for endocytosis, and n=9 wells per group from 3 independent experiments for damage assay. Data are expressed as median±interquartile range.

Next, the cell surface expression of CotH2 and CotH3 on the constructed mutants was assayed by flow cytometry using anti-CotH3 polyclonal antibodies as described herein. *R. oryzae* transformed with the RNA-i construct expressed less cell surface CotH2 and CotH3 proteins compared to wild-type or *R. oryzae* transformed with the empty plasmid (FIG. 56B). These RNA-i transformants had no difference in growth rate, cell size or germination when compared to the wild-type or empty plasmid transformed cells (FIG. 56C). However, the reduction of *R. oryzae* cell surface expression of CotH2 and CotH3 resulted in significant reduction of endothelial cell endocytosis of *R. oryzae* germlings and subsequent endothelial cell damage (FIGS. 57A and 57B). These results show that CotH3 and CotH2 are required for maximal invasion of endothelial cells by *R. oryzae*.

To further demonstrate that CotH3 and CotH2 function as invasins via binding to GRP78, the ability of *R. oryzae* germlings with CotH3 and CotH2 RNA-i construct to cause damage to CHO cells overexpressing GRP78 or parent CHO cells (which do not overexpress GRP78) were compared to *R. oryzae* transformed with the empty plasmid or wild type *R. oryzae* cells (Morris et al., *J. Biol. Chem.*, 272:4327-4334 (1997); Reddy et al., J. Biol. Chem., 278:20915-20924 (2003)). As previously shown (Liu et al., *J. Clin. Invest.*, 120:1914-1924 (2010)), wild type *R. oryzae* caused considerably more damage to CHO cells overexpressing GRP78 when compared to CHO parent cells. These results were further confirmed by a similar pattern of cell damage caused by *R. oryzae* germlings transformed with the empty plasmid. In contrast, CHO cells overexpressing GRP78 and CHO parent cells were equally susceptible to damage caused by *R. oryzae* germlings with reduced cell surface expression of CotH3 and CotH2 (FIG. 57C). Collectively, these results indicate that CotH3 and CotH2 are cell surface proteins that mediate invasion (endocytosis) of endothelial cells via binding to GRP78.

CotH2 and CotH3 are Required for Full Virulence of *R. oryzae* In Vivo.

Because CotH3 and CotH2 function as invasins of endothelial cells, it was hypothesized that these two genes are critical determinants of virulence. To test this hypothesis, the virulence of *R. oryzae* with reduced cell surface expression of CotH2 and CotH3 was compared to wild-type or to *R. oryzae* transformed with empty plasmid using an intratracheally infected diabetic ketoacidotic mouse model. Despite the initial infection being initiated by inoculating the lungs in this model, the infection hematogenously disseminates to other target organs such as the brain. Empty plasmid harboring cells were as virulent as wild type *R. oryzae* cells (median survival time of 3 vs. 4 days of the wild type and the empty plasmid infected mice, respectively, P=0.33). In contrast, mice infected with the RNAi-transformant had attenuated virulence, which was shown by a 10 day median survival time and ⅓ of the mice surviving the lethal infection (P=0.003) (FIG. 58A). Additionally, mice infected with the RNA-i transformant had significantly less fungal burden in the lungs and brains (primary and secondary target organs) when compared to the same organs recovered from mice infected with wild type cells or those infected with the empty plasmid transformant (FIG. 58B).

To further demonstrate that the attenuated virulence observed with mice infected with *R. oryzae* transformed with the RNA-i construct was due to actual inhibition of CotH2 and CotH3, the pattern of in vivo expression of these genes was assessed in fungal hyphae recovered from the mouse target organs. CotH1 was not expressed in mice infected with wild type *R. oryzae*, or *R. oryzae* transformed with the empty plasmid or RNA-i constructs. In contrast, CotH2 showed a four fold and two fold increase in expression in the lungs and brains of mice infected with either the wild type *R. oryzae* or *R. oryzae* transformed with the empty plamid, receptively (FIG. 58C) compared to CotH1. Additionally, CotH3 had significantly higher expression than CotH2 in the lungs, but not brains, of mice infected with wild type the empty plasmid transformant. Finally, fungal cells recovered from mice infected with *R. oryzae* transformed with the RNA-i construct had no expression of any of the CotH genes (FIG. 58C). These results indicate that CotH2 and CotH3 are expressed in vivo and the reduced virulence in mice infected with *R. oryzae* transformed with the RNA-i is due to a lack of expression of any of the CotH genes.

Figure 59:
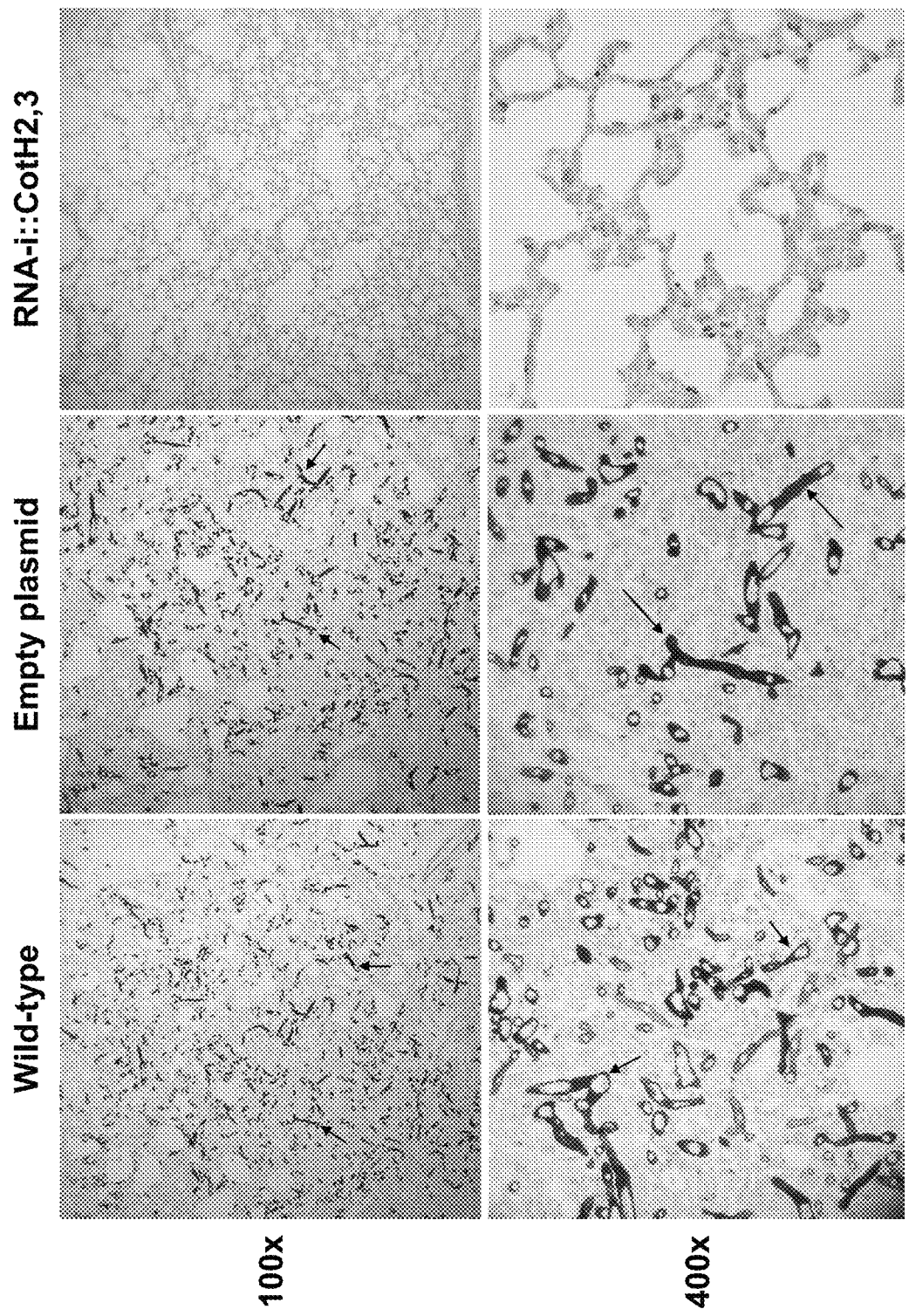
FIG. 59 shows histopathological examination of lungs harvested from diabetic ketoacidotic mice infected with wild type or *R. oryzae* transformed with empty plasmid or RNA-i. Periodic acid Schieff (PAS) stained sections demonstrating extensive hyphal elements (arrows) from organs collected from mice infected with wild type or *R. oryzae* transformed with empty plasmid but not *R. oryzae* transformed with RNA-i construct.

To compare the severity of infection, histopathological examination of mice organs infected with the three different strains was conducted. Lungs harvested from mice infected with *R. oryzae* transformed with RNA-i construct had normal histology compared with lungs taken from mice infected with the wild type or *R. oryzae* transformed with the empty plasmid, which had an abundance of fungal abscesses characterized by phagocyte infiltration and substantial edema (FIG. 59).

Anti-CotH3p Antibodies Protect Diabetic Ketoacidotic Mice from *R. oryzae* Infection.

Figure 60:
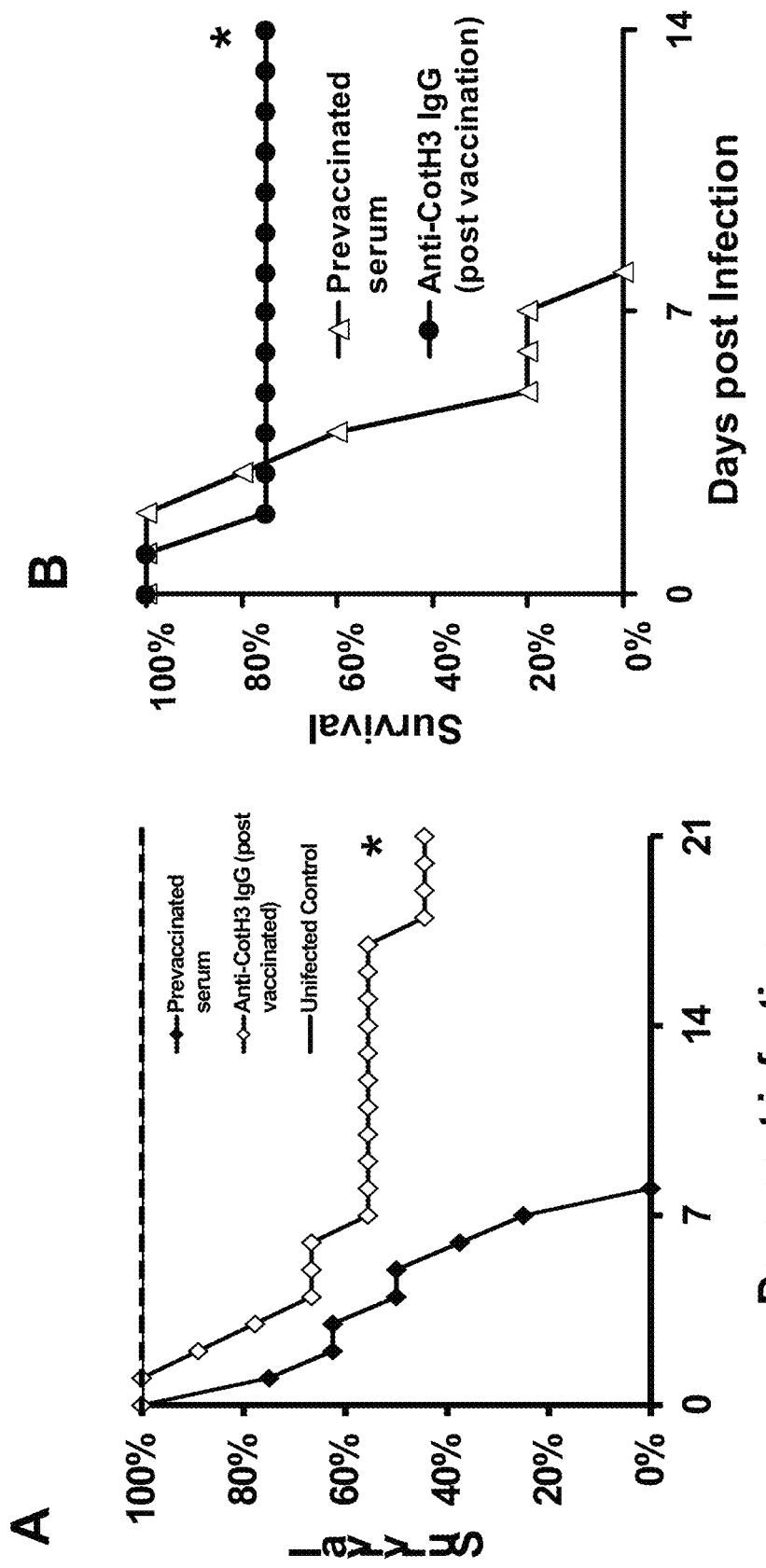
FIG. 60 shows passive immunization with antiCotH antibodies raise against peptide GAGKKHNNAKQSWNW (SEQ ID NO: 39) (A) or peptide MGQTND-GAYRDPTDNNK (SEQ ID NO: 40) (B) protect mice from *R. oryzae* infection. Diabetic ketoacidotic mice were given 1 mg of antiCotH IgG or pre-vaccination serum (control) 2 hr prior to infecting intratracheally with 2.4×10³ spores of *R. oryzae* 99-880 (wild type). A second dose of the polyclonal antibody or the pre-vaccination serum was given on day +3 relative to infection. *P<0.03 vs. mice receiving pre-vaccination serum.

Because the above data showed that CotH2 and CotH3 proteins act as invasins to mammalian cells in vitro and because CotH2 and Cot3 were required for full virulence of *R. oryzae* in the hematogenously disseminated murine model infection initiated by intratracheal inoculation, the use of anti-CotH3 and CotH2 antibodies raised against peptide GAGKKHNNAKQSWNW (SEQ ID NO: 39) or peptide MGQTNDGAYRDPTDNNK (SEQ ID NO: 40) were investigated for their protective affect against the disease (antibodies raised against these 2 peptides recognized *S. cerevisiae* expressing either CotH2 or CotH3 proteins). 1 mg of the polyclonal antibodies was administered to diabetic ketoacidotic mice two hours prior to and three days post infecting intratracheally with *R. oryzae* spores. Mice receiving the anti-CotH2 and anti-CotH3 rabbit IgG had a significantly enhanced survival time compared to mice receiving pre-vaccination serum from the same rabbit. Survival at day 21 post infection was 44% for the mice receiving antibodies raised against peptide GAGKKHNNAKQSWNW (SEQ ID NO: 39) vs. 0% survival for the mice receiving the control pre-vaccination IgG (FIG. 60A). Further, Survival at day 14 post infection was 75% for mice receiving antibodies raised against peptide MGQTNDGAYRDPTDNNK (SEQ ID NO: 40) vs. 0% survival for mice receiving the control pre-vaccination IgG (FIG. 60B). These results demonstrate that antibodies targeting CotH proteins can be used to treat mucormycosis.

EXAMPLE III

Diagnostic Methods for Detecting Mucormycosis

A series of experiments were performed to determine the detection capability of Nucleic Acid Sequence-Based Amplification (NASBA). A NASBA primer pair was designed to amplify a 127 bp CotH3 using *Rhizopus oryzae* total RNA as a template.

```
CotH3 forward primer
                                      (SEQ ID NO: 35)
5'-GATGACAATTATATTCCCAGC-3', CotH3 reverse primer
                                      (SEQ ID NO: 36)
5'-GAGTAGACGTAATTAGATCCAA-3', Molecular beacon probe:
                                      (SEQ ID NO: 38)
5'-CGCGATCAAACGTACCTGCTGACCGAATCGATCGCG-3'
```

RNAs from *Aspergillus fumigatus*, *Candida albicans*, and *Rhizopus oryzae* were isolated using an RNeasy® Plant Mini Kit (Qiagen) according to manufacturer's instructions. Total RNA isolated from four different *R. oryzae* spores (10, 100, 1000, 10000 spores, respectively) were added to the NASBA reactions.

To test the specificity of the molecular beacon for *Rhizopus* spp., RNAs isolated from *C. albicans* and *A. fumigatus* were used as controls. 300 ng total RNA was added to each reaction. NASBA reactions were performed with NucliSENS EasyQ Basic kit v2 (bioMerieux bv, Boxtel, NL) according to manufacturer's instructions. In brief, The NASBA reaction volume was 20 µl (per reaction) in MicroAmp® 96-Well Reaction Plate (Applied Biosystems) and contained 5.4 µl of sterile water, 0.4 µl of each primer, 0.2 µl probe, 4 µl of 5×NASBA buffer. Then 5 µl of purified RNA (300 ng) or water (when preparing no template controls) was added to the premix. Reaction mixtures were subsequently incubated at 65° C. for 5 min, cooled down to 41° C. for 5 min, after which 5 µl of enzyme mix from the NucliSENS EasyQ Basic kit v2 was added. This mix consisted of containing T7 RNA polymerase, AMV-RT (avian myeloblastosis virus reverse transcriptase), RNase H, and BSA (bovine serum albumin). Reactions were incubated at 41° C. for 90 min. The fluorescence signal was measured with StepOnePlus Real-Time PCR machine (Applied Biosystems).

Figure 61:
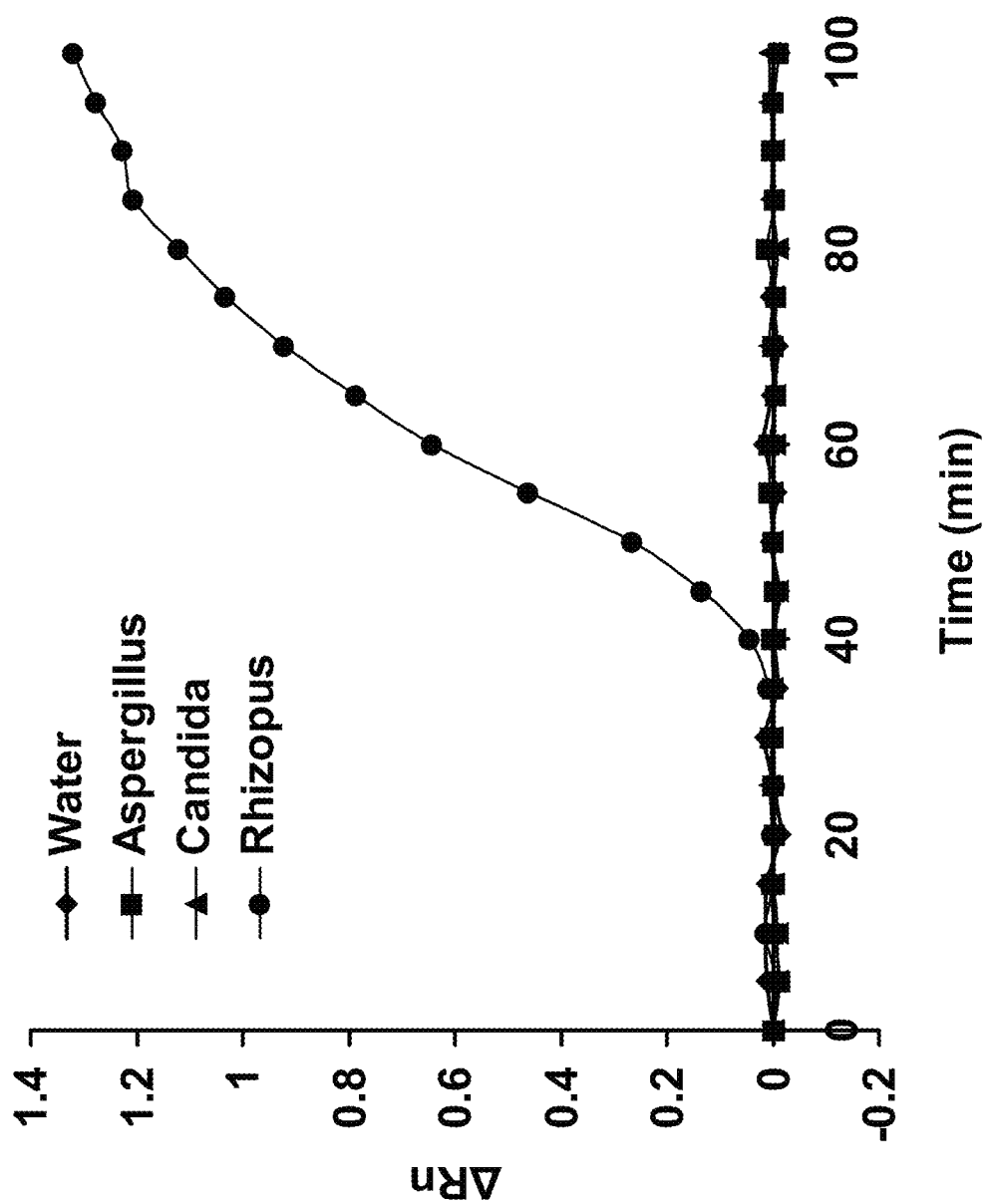
FIG. 61 shows the specificities of the CotH3 molecular beacon detection of different fungal species. The amplification plot was generated in StepOnePlus Real-Time PCR machine (Applied Biosystems). The x axis is the time from the initiation of amplification; the y axis is the increase in fluorescence (ΔRn); threshold fluorescence is shown as the bold horizontal line (It is equal to the average plus 2 times SD for the water negative control samples). Signals can be amplified from water samples (0.5 ml) spiked with 10⁵ spores of *R. oryzae* but not *Candida albicans* or *Aspergillus fumigatus*.

Using the NASBA amplification assay described above, the CotH3 molecular beacon primers/probe showed differential detection of fungal species, i.e. specificity for *R. oryzae*. Application products from samples spiked with *R. oryzae* readily show amplification, whereas amplification products from samples spiked with *A. fumigants* or *C. albicans* were not detected (FIG. 61).

Figure 62:
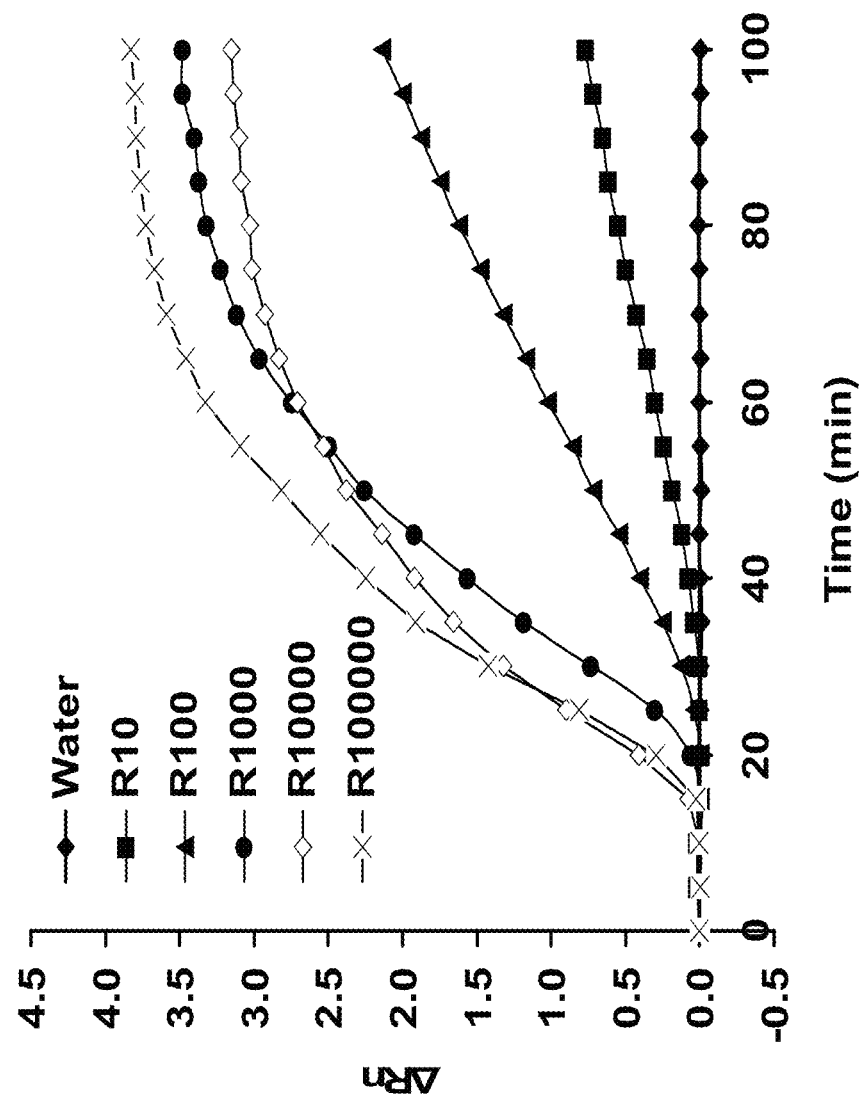
FIG. 62 shows the sensitivity of the CotH3 molecular beacon detection of water samples (0.5 ml) spiked with different inocula of *R. oryzae* 99-880. The amplification plot was generated in StepOnePlus Real-Time PCR machine (Applied Biosystems). The x axis is the time from the initiation of amplification; the y axis is the increase in fluorescence (ΔRn); threshold fluorescence is shown as the bold horizontal line (It is equal to the average plus 2 times SD for the water negative control samples).

The CotH3 molecular beacon primers/probe showed highly sensitive detection of *R. oryzae*. Fungal spores were germinated in YPD broth for 3 hours at 37° C. shaker. 10 µl of samples containing 10 to $10^5$ of germlings were aliquoted into 250 µl of sheep blood. Total RNA was isolated from the spiked blood samples with RNeasy Plant Mini Kit (Qiagen) and eluted in 30 µl elution buffer. Five microliter of the total RNA was added to each NASBA reaction. Applification products were detected in all samples, include samples inoculated with only 10 germlings (FIG. 62).

Figure 63:
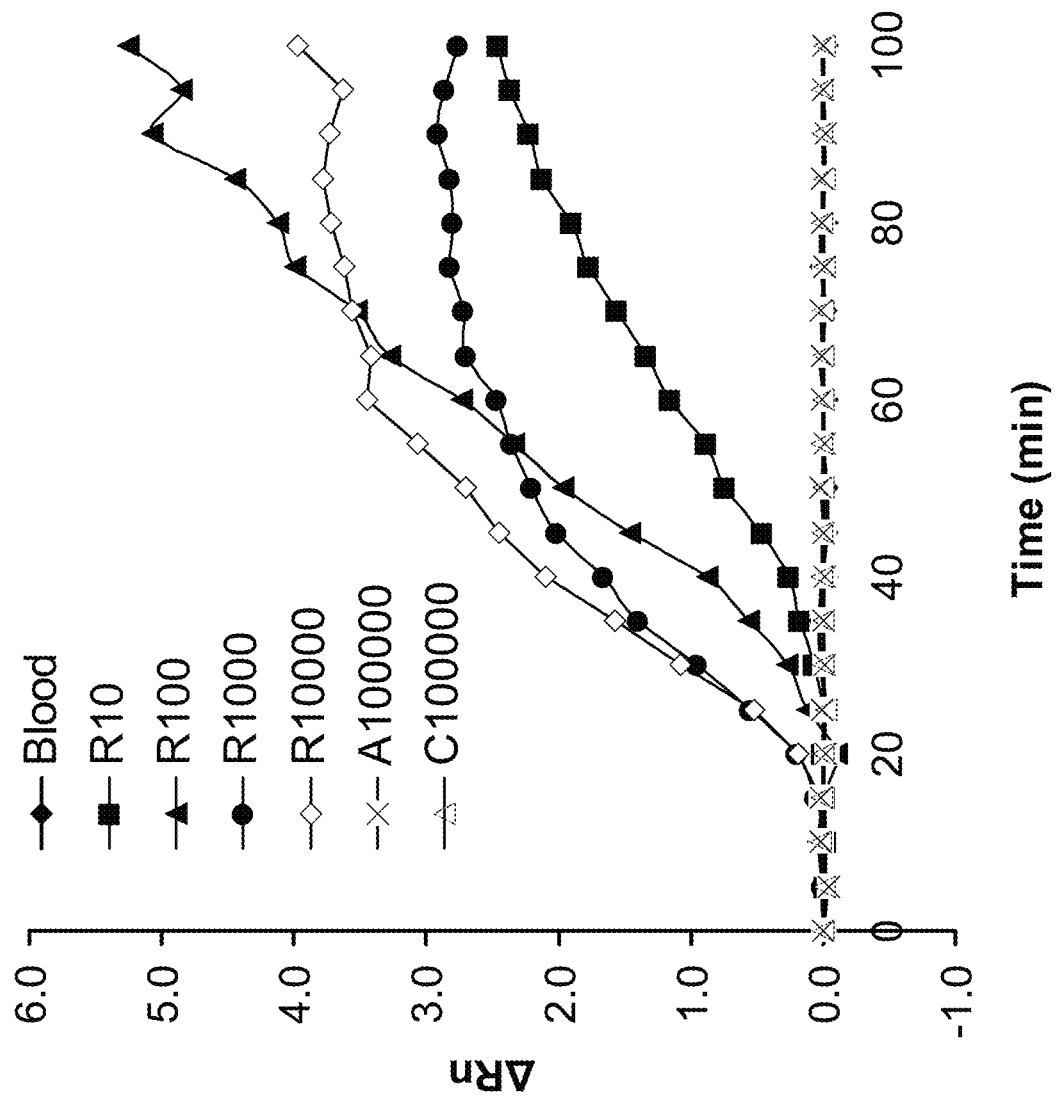
FIG. 63 shows the sensitivity and specificity of the CotH3 molecular beacon probe in detection of *Rhizopus oryzae* spores in blood. The amplification plot was generated in StepOnePlus Real-Time PCR machine (Applied Biosystems). The x axis is the time from the initiation of amplification; the y axis is the increase in fluorescence (ΔRn); threshold fluorescence is shown as the bold horizontal line (It is equal to the average plus 2 times SD for the water negative control samples). Blood, is inoculated control. R: *R. oryzae* 99-880 at different inocula (e.g. R10=*R. oryzae* 10 spores used to spike 350 μl of blood), A: *A. fumigants*, C: *C. albicans* each used to spike 350 μl of blood at 10⁵ cells.

The CotH3 molecular beacon primers showed not only highly sensitive detection of *R. oryzae*, but also a robust specificity. Fresh *R. oryzae*, *A. fumigatus* and *C. albicans* spores were collected, counted and aliquoted into 10 µl of YPD broth each. 350 µl of sheep blood was added into each tube and incubated for 24 hours at 37° C. shaker. Total RNA was isolated with RNeasy Plant Mini Kit (Qiagen) and eluted in 30 µl in elution buffer. Five microliter of the RNA was added to each NASBA reaction. No amplification products were detected in samples inoculated with $10^6$ spores of *A. fumigatus* or *C. albicans*, whereas each sample inoculated with 10 to $10^4$ spores of *R. oryzae* were detectable (FIG. 63).

Figure 64:
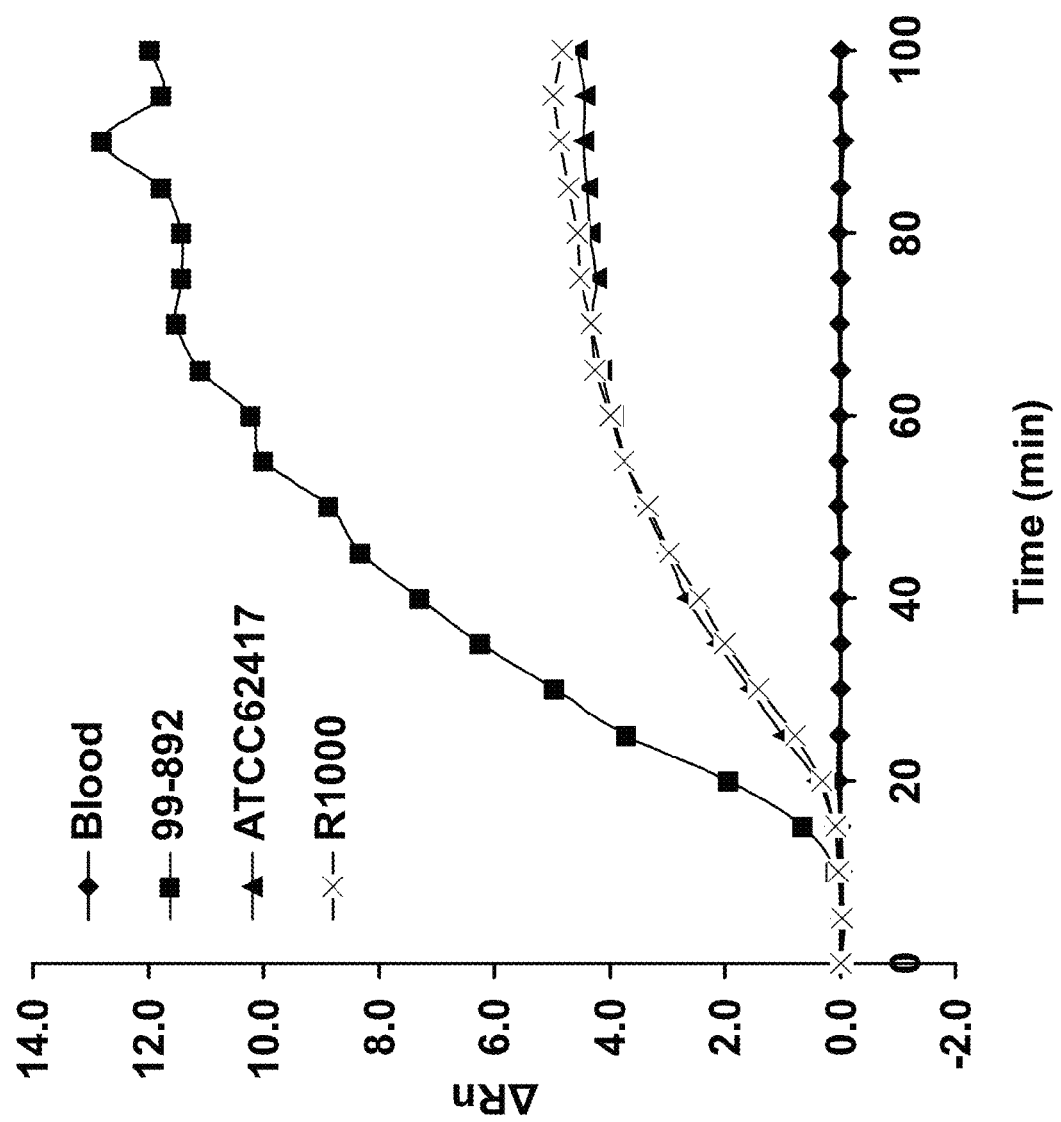
FIG. 64 shows the specificity of the CotH3 molecular beacon probe in detection of *Rhizopus*. The amplification plot was generated in a StepOnePlus Real-Time PCR machine (Applied Biosystems). The x axis is the time from the initiation of amplification; the y axis is the increase in fluorescence (ΔRn); threshold fluorescence is shown as the bold horizontal line (It is equal to the average plus 2 times SD for the water negative control samples). Blood: uninoculated blood sample; 99-892: *R. oryzae* 99-892; ATCC62417: *R. microspores* ATCC62417; R1000: *R. oryzae* 99-880. All strains were used to spike blood (350 μl) with 10³ spores.

The CotH3 molecular beacon primers/probe showed detection of multiple *Rhizopus* species. Fresh *R. oryzae* (99-880 and 99-892 isolates) and *R. microsporus* spores (1000 spores each) were aliquoted into 10 µl of YPD broth. 350 µl of sheep blood was added into each tube and incubated for 24 hours at 37° C. shaker. Total RNA was isolated with RNeasy Plant Mini Kit (Qiagen) and eluted in 30 µl in elution buffer. Five microliter of the RNA was added to each NASBA reaction. Not only were samples containing *R. oryzae* 99-892 spores detectable, but samples containing *R. oryzae* 99-880 (R1000) and *R. microspores* (ATCC62417) showed amplification (FIG. 64). These results show that primers designed from CotH genes of *R. oryzae* can detect other strains of *R. oryzae* as well as other species of *Rhizopus* confirming the conserved nature of CotH genes among Mucorales.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

---

What is claimed is:

1. An isolated anti-Mucorales CotH antibody that abrogates endocytosis of a fungus belonging to the species *Rhizopus oryzae* by a mammalian cell, wherein the antibody specifically binds to a Mucorales CotH polypeptide consisting of the amino acid sequence of SEQ ID NO: 39 or SEQ ID NO: 40.

2. A pharmaceutical composition comprising a pharmaceutically acceptable carrier and the anti-Mucorales CotH antibody of claim 1.

3. The antibody of claim 1, wherein said antibody is a monoclonal antibody.

4. The antibody of claim 1, wherein said antibody is a polyclonal antibody.

5. The antibody of claim 1, wherein the antibody is a non-naturally occurring antibody.

6. The antibody of claim 5, wherein the antibody is a chimeric antibody.

7. The antibody of claim 5, wherein the antibody is a humanized antibody.

8. The antibody of claim 5, wherein the antibody is a single chain antibody.

9. The antibody of claim 5, wherein the antibody comprises a detectable marker or label.

10. The antibody of claim 5, wherein the antibody is an antibody fragment that retains the binding specificity to the Mucorales CotH polypeptides consisting of the amino acid sequence of SEQ ID NO: 39 or SEQ ID NO: 40.

* * * * *

SEQUENCE LISTING

```
<160> NUMBER OF SEQ ID NOS: 75

<210> SEQ ID NO 1
<211> LENGTH: 610
<212> TYPE: PRT
<213> ORGANISM: Rhizopus oryzae
<220> FEATURE:
<221> NAME/KEY: MOD_RES
<222> LOCATION: (610)..(610)
<223> OTHER INFORMATION: Any amino acid

<400> SEQUENCE: 1

Met Lys Ser Leu Leu Phe Val Val Phe Ile Phe Leu Thr Thr Thr Tyr
1               5                   10                  15

Ala Ala Lys Val Ser Phe Lys Val Ile Ala Pro Asp Ala Lys Asn Arg
            20                  25                  30

Val His Val Asn Ile Asn Gly Val Leu Val Glu Leu Lys Ala Ser Asp
        35                  40                  45

Pro Asp Val Pro Tyr Tyr Thr Gly Phe Ala Glu Leu Lys His Gly Gln
    50                  55                  60

Ser Tyr Asn Tyr Val Val Asp Gly Asn Ala Glu Pro Phe Lys Arg Leu
65                  70                  75                  80

Leu Asn Gly Ser Ser Thr Lys Asn Glu Phe Phe Asn Arg Pro Val Thr
                85                  90                  95

Tyr Ala Thr Asn Ile Pro Glu Leu Pro Ser Ile Leu Thr Glu Gly Ser
            100                 105                 110

Trp Thr Arg Gly Asp Thr Ser Asn Pro Ile Trp Asp Ser Asn Tyr Val
        115                 120                 125

Pro Ser Ile Phe Val Thr Gly Asn Pro Arg Glu Met Asn Glu Leu Ile
    130                 135                 140

Glu Asn Val Lys Lys Asn Thr Tyr Lys Thr Lys Ile Thr Phe Ile Gly
145                 150                 155                 160

Pro Glu Thr Ile Asn Thr Phe Glu Gly Cys Thr Leu Gly Leu His Lys
                165                 170                 175

Pro Gly Arg Lys His Asn Asp Ala Lys Gln Ser Trp Ile Trp Ala Leu
            180                 185                 190

Pro Glu Gly Gln Phe Met Ala Asn Arg Asn Trp Phe Lys Ile Arg His
        195                 200                 205

Met Glu Glu Asp Pro Thr Gln Leu Arg Glu Lys Leu Tyr Ala Asp Ile
    210                 215                 220

Leu Arg Lys Met Gly Thr Tyr Ala Asn Glu Ala Asn Met Val Arg Phe
225                 230                 235                 240

Phe Ile Asn Lys Glu Gly Met Gly Ile Phe Asn Met Leu Asp Asp Val
                245                 250                 255

Ile Met Tyr Ser Tyr Ile Asn Ala Met Phe Tyr His Gly Asp Thr Pro
            260                 265                 270

Glu Gln Leu Gly Gly Leu Tyr Asp Gly Ala Ser Gly Ala Ser Phe Asn
        275                 280                 285

Phe Pro Gly Asp Phe Asp Ser Phe Ile Pro Asn Val Glu Ser Pro Leu
    290                 295                 300

Asp Gln Asp Ala Ile Glu Pro Phe Ser Lys Ala Phe Thr Ser Ile Asp
305                 310                 315                 320
```

```
Phe Leu Glu Asp Glu Gln Val Lys Thr Ile Gly Lys Tyr Phe Asp Tyr
            325                 330                 335

Asp Gln Phe Leu Arg Phe Met Val Met Glu Phe Leu Thr Gly Asp Trp
        340                 345                 350

Asp Gly Tyr Trp Gln Glu Gln Thr Asn Asp Gly Ala Tyr Ile Asp Ile
    355                 360                 365

Asn Asp His Asn Lys Ile Tyr Tyr Leu Gly Gln Asp Phe Asp Ala Thr
370                 375                 380

Phe Gly Val Asn Leu Glu Gln Lys Arg Glu Phe Val Asn Val Ser Tyr
385                 390                 395                 400

Thr Glu Tyr Pro Lys Leu Phe Pro Gly Gly Val Leu Ile Asn Arg Leu
                405                 410                 415

Leu Gln Asn Pro Gly Val Lys Lys Thr Phe Glu Asn Tyr Leu Lys Ile
            420                 425                 430

Thr Val Gln Glu Ile Phe Asn Asn Ala Thr Leu Gly Pro Tyr Val Thr
        435                 440                 445

Ala Arg His Glu Phe Leu Ala Pro Asp Leu Gln Trp Asp Arg Ser Ile
    450                 455                 460

Lys Gln Arg Ser Pro Gly Asn Ile Phe Gly Trp Thr Phe Glu Gln Thr
465                 470                 475                 480

Tyr Glu Asn Leu Phe Glu Gly Val Thr Ala Pro Gly Lys Asn Ser Gly
                485                 490                 495

Gly Ala Asp Trp Gly Leu Leu Glu Trp Val Ala Ala Lys Glu Lys Ala
            500                 505                 510

Val Lys Ser Tyr Leu Ser Ser Ser Glu Ala Ala Asp Ala Ala Thr Val
        515                 520                 525

Thr Gln Val Pro Glu Ala Pro Gly Thr Asp Gly Thr Pro Ser Glu Ser
    530                 535                 540

Thr Ala Trp Pro His Ala Asn Thr Arg Phe Arg Gln Ala Glu Ala Ser
545                 550                 555                 560

Asn Thr His Lys Ile Gly Thr Ser Ser Pro Ser Asn Phe Ile Val Lys
                565                 570                 575

Ile Lys Gln Gly Thr Val Ser Ser Ser Ser Ile Lys Arg Thr Pro
            580                 585                 590

Cys Ile Leu Pro Leu Val Ile Leu Ala Ser Thr Leu Phe Ala Ser Phe
        595                 600                 605

Phe Xaa
    610

<210> SEQ ID NO 2
<211> LENGTH: 1830
<212> TYPE: DNA
<213> ORGANISM: Rhizopus oryzae

<400> SEQUENCE: 2
atgaaatccc tacttttgt tgtattcatc tttttaacaa caacatatgc cgctaaagta      60
tcatttaaag ttatcgctcc tgatgctaaa acagagttc atgtcaatat caatggagta     120
cttgtcgaat taaggccag tgatccagat gttccttact caccggtttt gctgaacta     180 aagcatggac aaagttataa ttacgttgtc gatggaaatg cagagccatt caaacgtcta     240
ttgaatggct cttctactaa aaacgagttc ttcaatcgac ctgtaaccta cgctaccaac     300
attcccgagc tacccagcat tcttactgaa ggtagctgga ctcgtggaga tacgagtaat     360
cctatttggg atagtaacta tgtccttct atctttgtca ctggaaatcc aagggaaatg     420
```

-continued

```
aatgaattaa ttgagaatgt gaaaaagaac acatataaaa caaaaatcac ttttattgga     480
cctgagacta tcaacacatt tgagggttgt acccttggac ttcataaacc tgggcgtaaa     540
cataatgatg ctaaacaatc ttggatatgg gctctccctg aaggtcaatt tatggcgaat     600
cgaaattggt ttaagattcg acatatggaa gaagatccta cacaacttcg tgaaaagctt     660
tatgcagata tccttcgaaa gatgggaacc tatgcgaatg aggccaatat ggttcgattc     720
tttataaaca aggaaggcat gggtatcttt aatatgttgg acgatgttat tatgtattct     780
tatattaatg ccatgtttta ccacggtgat actcctgaac agctcggtgg tctttacgac     840
ggtgcctctg gtgcctcatt caattttcct ggtgactttg atagcttcat cccgaatgtc     900
gaatccccgc ttgaccaaga tgctatcgag cctttttcta aagcctttac tagtattgac     960
tttttggaag acgaacaggt caagacgatc ggaaagtatt ttgattatga ccaattcctt    1020
cgtttcatgg tcatggagtt ccttaccggt gactgggatg gctactggca agagcaaaca    1080
aatgatgggg cctatattga tatcaacgac acaacaaaaa tttattactt ggggcaggat    1140
tttgacgcca cctttggtgt aaatcttgaa caaaaacgag agtttgtcaa tgtgtcttat    1200
actgaatacc ccaaactgtt tcctggaggt gtcttgatca acagacttct tcaaaaccca    1260
ggtgtcaaga aaacgtttga aaactatctg aaaatcacag tacaagagat cttcaacaac    1320
gccacgctcg gccccctatgt cactgctcgc cacgaattcc ttgctccaga tcttcagtgg    1380
gatcgttcga taaaacaacg gtctcctgga aatatctttg gttggacgtt cgagcagaca    1440
tatgaaaatc tatttgaagg tgtcactgct cctggaaaaa actcgggtgg tgctgattgg    1500
ggtcttcttg aatgggtggc tgcaaaggaa aaagcagtca aaagttacct cagttcgtct    1560
gaagccgctg atgctgccac tgttacgcaa gtaccagaag ctcctggtac agatggcact    1620
ccttccgaat caactgcctg gcctcatgcc aatacaaggt tcagacaagc cgaagcttct    1680
aatactcata aaataggcac ctcatcgcct tctaatttta ttgttaaaat caagcaaggt    1740
actgtgtcat cgtcttcatc tatcaaaaga acccatgta ttctacctct tgttatcttg    1800
gctagcactt tatttgcctc tttcttctag                                     1830
```

<210> SEQ ID NO 3
<211> LENGTH: 595
<212> TYPE: PRT
<213> ORGANISM: Rhizopus oryzae
<220> FEATURE:
<221> NAME/KEY: MOD_RES
<222> LOCATION: (595)..(595)
<223> OTHER INFORMATION: Any amino acid

<400> SEQUENCE: 3

```
Met Lys Leu Ser Leu Thr Ile Val Ser Ser Phe Leu Val Ala Ile
1               5                   10                  15

Ala His Ala Ala Ser Val Gln Phe Asn Leu Ile Ala Pro Ser Ala Thr
            20                  25                  30

Asp Val Lys Val Ser Val Asn Gly Gln Gln Val Ala Leu Thr Ala Ser
                35                  40                  45

Asp Pro Asn Val Pro Tyr Phe Thr Gly Ser Ala Glu Val Gly Gly Thr
        50                  55                  60

Glu Glu Ser Phe Glu Arg Ser Leu Ala Gly Ile Thr Asn Ser Thr Phe
65                  70                  75                  80

Asn Asp Phe Tyr Asn Arg Pro Val Thr Tyr Ala Asn Leu Pro Gln Leu
                85                  90                  95
```

```
Pro Trp Pro Ile Glu Asn Asp Pro Gln Trp Thr Arg Lys Gly Lys Lys
            100                 105                 110

Ala Glu Ile Phe Asp Asp Asn Tyr Ile Pro Ser Val Phe Phe His Gly
        115                 120                 125

Asp Asp Ser Gln Val Gln Asp Leu Val Lys Asn Val Pro Lys Asp Lys
    130                 135                 140

Val Thr Gly Thr Leu Thr Phe Ile Gly Ser Asn Tyr Val His Ser Phe
145                 150                 155                 160

Ala Asn Val Ser Phe Gly Ile His Gly Ala Gly Lys Lys His Asn Asn
                165                 170                 175

Ala Lys Gln Ser Trp Lys Trp Thr Leu Ser Gly Thr Asp Thr Met Gly
            180                 185                 190

Asn Arg Asn His Phe Lys Leu Arg His Met Glu Glu Asp Pro Thr Gln
        195                 200                 205

Ile Arg Glu Arg Leu Tyr Ala Asp Ile Leu His Ala Met Gly Thr Tyr
    210                 215                 220

Ala Asn Glu Thr Thr Met Val Arg Leu Phe Ile Asn Gly Gln Gly Phe
225                 230                 235                 240

Gly Thr Phe Asn Met Leu Asp Asp Ile Thr Glu Phe Ser Tyr Ile Asn
                245                 250                 255

Ala Met Phe Tyr Gly Gly Asn Pro Pro Ala Thr Leu Gly Pro Leu Phe
            260                 265                 270

Asp Gly Ala Ser Gly Ala Asp Phe Ile Tyr His Pro Gly Asn Leu Asp
        275                 280                 285

Gly Tyr Ser Ser Trp Lys Pro Asn Lys Asp Asn Ala Asn Gly Glu Gly
    290                 295                 300

Tyr Glu Ala Phe Asp Pro Leu Cys Lys Ala Trp Asn Glu Thr Asp Tyr
305                 310                 315                 320

Thr Asp Asn Thr Ala Ile Ala Asn Phe Glu Lys Met Phe Asp Thr Glu
                325                 330                 335

His Phe Leu Arg Phe Met Val Ile Glu Tyr Leu Thr Ala His Trp Asp
            340                 345                 350

Gly Tyr Trp Met Gly Gln Thr Asn Asp Gly Ala Tyr Arg Asp Pro Ser
        355                 360                 365

Asp Asn Asn Lys Trp Tyr Phe Leu Asp Gln Asp Phe Asp Ala Thr Phe
    370                 375                 380

Gly Val Asn Leu Asp Val Pro Glu Asn Lys Asp Phe Ile Ser Val Ser
385                 390                 395                 400

Tyr Lys Asp Phe Pro Ser Arg Tyr Pro Ala Gly Val Met Ala Asn Gly
                405                 410                 415

Leu Leu Gln Asn Ala Asp Lys Lys Ala Lys Phe Glu Gln Tyr Leu Thr
            420                 425                 430

Glu Thr Val Arg Val Leu Phe Asn Asn Val Thr Leu Thr Asn Arg Val
        435                 440                 445

Leu Ala Ile His Asn Phe Leu Ser Pro Asp Leu Glu Trp Asp Arg Ser
    450                 455                 460

Ile Val Gln Gln Ser Pro Gly Thr Asn Phe Gly Trp Thr Phe Glu Gln
465                 470                 475                 480

Thr Ser Gln Asn Leu Trp Gln Gly Val Ser Ala Pro Asn Asn Asn Gly
                485                 490                 495

Gly Gly Ala Glu Trp Gly Leu Val Glu Tyr Ile Ala Ala Lys Ser Gln
            500                 505                 510

Ala Met Ala Lys Glu Phe Asn Ile Thr Ile Val Ser Glu Pro Val Gly
```

|  |  | 515 |  |  | 520 |  |  | 525 |  |  |

Pro Pro Ala Ala Asn Gly Thr Ala Thr Ser Thr Asn Asp Gly Gly Asn
530                     535                 540

Thr His Thr Ala Ala Gly Glu Ser Lys Pro Ala Ser Ser Ser Glu Ser
545                 550                 555                 560

Ser Gly Ser Lys Ile Ala Ser Gln Ser Val Ser Gly Ala Ser Arg Ser
                565                 570                 575

Ala Val Ser Thr Val Leu Leu Gly Val Thr Ala Leu Val Ala Thr Ala
            580                 585                 590

Ile Phe Xaa
      595

<210> SEQ ID NO 4
<211> LENGTH: 1785
<212> TYPE: DNA
<213> ORGANISM: Rhizopus oryzae

<400> SEQUENCE: 4

```
atgaaattat cactcactat agtatcctct tcattttag tagccattgc acatgctgct     60
tcagtacaat tcaatttaat tgctccaagt gcaactgatg tcaaagtatc tgtaaatgga    120
cagcaggttg cccttacagc ttcagaccct aatgtgcctt atttcaccgg atctgctgaa    180
gttggtggaa ctgaagaaag ctttgagcgt tctctcgctg gtattacaaa ctccacattc    240
aatgattttt ataaccgtcc tgttacttac gctaaccttc tcaattacc atggccaatt     300 gaaaatgatc cacaatggac tcgcaaagga agaaagctg aaatatttga cgacaactac     360
atcccctccg tattctttca cggtgatgat agccaagtcc aagatttggt taaaaatgtg    420
cccaaagaca agttactgg caccttgact tcattgggt ccaattacgt tcattctttc     480
gcaaatgtct cctttggaat tcatggtgca ggaaagaagc acaacaatgc aaagcaatcc    540
tggaagtgga ccttgtctgg tactgatact atgggcaacc gtaaccattt taagcttcgt    600
catatggaag aagatcctac acagatccgt gaacgtcttt atgctgatat attgcatgct    660 atgggaaccct atgccaatga ccactatg gtccgattgt ttattaacgg tcaaggtttt    720
ggtaccttca acatgctaga cgatattact gaattttctt acatcaatgc catgttctat    780
ggtggtaatc ctcctgctac tttaggacct ctatttgatg gtgcaagcgg tgcagacttt    840
atttaccatc ctggtaatct cgatggttat tcctcttgga accctaataa ggacaacgca    900
aacggtgaag ctatgaggc ctttgatcct ctatgtaagg cttggaacga accgactat    960 accgataaca cagccattgc caactttgaa aaaatgtttg ataccgagca cttttacga   1020 ttcatggtga ttgaatatct aactgctcac tgggatggtt attggatggg acagaccaac   1080
gatggtgctt atcgtgaccc aagtgacaat aacaagtggt actttttgga tcaagatttt   1140
gatgccacat ttggtgtcaa tttggacgtt cctgagaata aagactttat cagtgtctcc   1200
tacaaggatt tccatctcg ttaccctgct ggtgtcatgg ccaatggtct cttacagaat   1260
gctgataaaa aagccaagtt tgaacagtac ttgactgaaa ctgttcgcgt cttgttcaat   1320
aatgtcactt tgactaatcg tgtcttggct atccacaact tcctctctcc tgatcttgaa   1380
tgggatcgat ccatcgttca acagtcgcct ggtactaatt ttggatggac ctttgagcaa   1440
acttctcaaa acttatggca aggtgtctca gccccaaata caacggagg tggtgctgag   1500 tgggggcttgg ttgaatatat cgcagcaaaa tcccaagcca tggctaagga atttaatatc   1560
actattgtct ctgaacctgt aggtcctcct gctgctaatg gaactgcaac ttctactaat   1620
```

```
gatggtggta acactcatac cgctgccgga gaaagtaagc ctgcctcaag ttctgaatct   1680
tccggttcga aaattgcttc tcaaagcgta tcaggtgctt cccgttctgc tgtatctacc   1740
gtcttattag gtgttacagc tttagttgcc actgctatct tttaa                  1785
```

<210> SEQ ID NO 5
<211> LENGTH: 602
<212> TYPE: PRT
<213> ORGANISM: Rhizopus oryzae
<220> FEATURE:
<221> NAME/KEY: MOD_RES
<222> LOCATION: (602)..(602)
<223> OTHER INFORMATION: Any amino acid

<400> SEQUENCE: 5

```
Met Lys Leu Ser Ile Ile Ser Ala Ala Phe Leu Val Ala Ile Thr His
1               5                   10                  15

Ala Ala Ser Ile Lys Phe Asn Val Ile Ala Pro Asn Ala Thr Asp Val
                20                  25                  30

Lys Val Ser Val Asn Gly Gln Gln Val Thr Leu Thr Ala Ser Asp Ala
            35                  40                  45

Asn Val Pro Tyr Phe Thr Gly Ser Ala Glu Val Gly Ala Ser Lys Thr
        50                  55                  60

Tyr Lys Tyr Val Ala Gly Gly Thr Glu Glu Ser Phe Asp Arg Ser Leu
65                  70                  75                  80

Asp Gly Ile Thr Asn Ser Thr Leu Asn Asp Phe Tyr Asn Arg Pro Val
                85                  90                  95

Thr Tyr Ala Asn Leu Pro Gln Leu Pro Trp Pro Ile Glu Lys Asp Pro
            100                 105                 110

Gln Trp Thr Arg Ser Gly Ser Lys Ala Asp Ile Phe Asp Asp Asn Tyr
        115                 120                 125

Ile Pro Ser Val Phe Phe His Gly Asp Asp Ser Gln Val Gln Asn Val
    130                 135                 140

Val Lys Asn Val Pro Ala Asp Arg Ile Ser Gly Thr Leu Thr Phe Ile
145                 150                 155                 160

Gly Ser Asn Tyr Val Tyr Ser Phe Gln Asn Val Ser Phe Gly Ile His
                165                 170                 175

Gly Ala Gly Lys Lys His Asn Asn Ala Lys Gln Ser Trp Asn Trp Ile
            180                 185                 190

Leu Ser Gly Ser Asp Thr Met Gly Asn Arg Asn Phe Phe Lys Leu Arg
        195                 200                 205

His Met Glu Glu Asp Pro Thr Gln Ile Arg Glu Arg Leu Tyr Ser Asp
    210                 215                 220

Ile Leu His Ala Met Gly Thr Tyr Ala Asn Asp Ala Thr Met Val Arg
225                 230                 235                 240

Leu Phe Ile Asn Asn Gln Gly Phe Gly Thr Phe Asn Met Leu Asp Asp
                245                 250                 255

Ile Thr Gln Phe Ser Tyr Ile Asn Ala Lys Phe Tyr Asn Gly Lys Pro
            260                 265                 270

Pro Ala Thr Leu Gly Pro Leu Tyr Asp Gly Ala Ser Gly Ala Asp Phe
        275                 280                 285

Leu Tyr His Pro Gly Asn Leu Asp Gly Tyr Ser Ser Trp Val Ala Asn
    290                 295                 300

Thr Ala Asn Pro Asn Gly Glu Ala Tyr Glu Ala Leu Asp Pro Leu Cys
305                 310                 315                 320

Lys Ala Trp Asn Glu Thr Thr Tyr Thr Asp Asn Thr Ala Ile Ala Asn
```

-continued

```
              325                 330                 335
Phe Glu Lys Met Phe Asp Leu Asp Arg Phe Met Arg Phe Met Val Ile
            340                 345                 350
Glu Tyr Leu Thr Ala Asp Trp Asp Gly Tyr Trp Met Gly Gln Thr Asn
            355                 360                 365
Asp Gly Ala Tyr Arg Asp Pro Thr Asp Asn Asn Lys Trp Tyr Phe Leu
            370                 375                 380
Asp Gln Asp Phe Asp Gly Thr Phe Gly Val Asn Leu Ala Ala Pro Glu
385                 390                 395                 400
Gly Asn Ala Phe Leu Asp Val Ser Tyr Lys Asp Phe Pro Ser Arg Tyr
                405                 410                 415
Pro Gly Ala Val Met Ile Asn Asn Leu Leu Gln Asn Ala Asp Lys Lys
                420                 425                 430
Ala Thr Phe Glu Lys Tyr Leu Thr Glu Thr Val Arg Val Leu Phe Asn
                435                 440                 445
Asn Val Thr Leu Thr Asn Arg Val Leu Ala Leu His Asn Phe Leu Leu
            450                 455                 460
Pro Asp Leu Glu Trp Asp Arg Ser Ile Val Gln Gln Ser Pro Gly Ile
465                 470                 475                 480
Asn Phe Gly Trp Thr Phe Asp Gln Val Thr Gln Asn Leu Trp Gln Gly
                485                 490                 495
Val Thr Ala Pro Asn Asn Asn Gly Gly Ala Ala Phe Gly Leu Val
            500                 505                 510
Glu Tyr Ile Ala Ala Lys Ala Gln Ala Val Ala Lys Glu Phe Asn Ile
            515                 520                 525
Ser Ile Val Ser Gln Pro Val Gly Pro Ser Ala Asn Gly Thr Thr
            530                 535                 540
Ala Ala Ala Pro Ala Pro Ala Ala Gly Asn Ser Thr Gly Lys Gly Gly
545                 550                 555                 560
Asn Gln Ser Ile Ser Ser Ser Ala Ser Ser Asn Lys Thr Ser Ala Gln
                565                 570                 575
Ser Thr Ser Gly Ala Ser Arg Ser Lys Thr Ala Pro Ile Val Leu Ala
            580                 585                 590
Ile Ser Ala Leu Ala Leu Leu Val Phe Xaa
            595                 600
```

<210> SEQ ID NO 6
<211> LENGTH: 1806
<212> TYPE: DNA
<213> ORGANISM: Rhizopus oryzae

<400> SEQUENCE: 6

```
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc ccttatttca ctggttcagc tgaagttggt     180
gcctcaaaga catacaaata tgttgcaggt ggaacagaag aaagttttga tcgttctctt     240
gatggaatca caactcaac acttaatgat tttttataacc gccccgtcac ttatgctaac     300
cttcctcaat taccttggcc aattgaaaaa gaccctcagt ggactcgttc tggaagcaaa     360
gccgacattt tcgatgacaa ttatattccc agcgttttt tccacggaga tgacagtcaa     420
gtccaaaatg tggttaaaaa cgtacctgct gaccgaatca gtggtacact gacctttatt     480
ggatctaatt acgtctactc tttccagaat gtctcatttg gtattcacgg tgctggcaag     540
```

```
aaacacaaca atgcaaaaca atcttggaac tggatattgt ctggaagtga tacgatgggt    600
aaccgcaatt tctttaagct tcgacatatg gaagaagatc ctacacagat cgtgaacgt    660 ctttattctg acattttaca tgccatgggt acttatgcca atgatgctac catggttcga    720
ttgtttatta acaaccaagg cttcggtacc ttcaacatgt tggatgatat cactcaattc    780
tcctatatca atgctaaatt ttataatggc aaaccacctg ctaccttggg tcctctctat    840
gatggtgcct ctggtgcaga cttcttatat catcctggta acctcgatgg atactcttct    900
tgggttgcca acacagccaa tcctaatggt gaagcttatg aagctcttga tcctctctgt    960
aaggcctgga acgagacgac ctataccgat aatacagcca ttgcaaactt tgaaaaaatg   1020
tttgatctcg accgtttcat gcgtttcatg gttattgaat acttgactgc cgattgggat   1080
ggttactgga tgggacagac caatgatggt gcctatcgtg atccaactga taataacaag   1140
tggtactttt tagatcaaga ctttgatggt acttttggtg tcaacttggc tgcacccgaa   1200
ggcaatgctt tccttgatgt ttcttacaag gatttccctt ctcgttaccc tggcgctgtc   1260
atgatcaaca acctcttaca gaatgctgat aaaaaggcca cctttgaaaa atatttgact   1320
gagactgtgc gtgtgctgtt caataatgtc accttgacta accgtgtctt ggcccttcac   1380
aacttcctct tgcctgatct tgaatgggat cgttcgatcg ttcaacaatc tcctggtatt   1440
aactttggtt ggacatttga tcaagtcact caaaacttgt ggcaaggtgt cactgcaccc   1500
aataacaatg gaggtggtgc tgcttttggt ttagttgaat atattgctgc aaaggcacaa   1560
gctgtagcta aggaatttaa tatttctatc gtttcccaac ctgttggccc tccttctgct   1620
aatggtacta ctgctgctgc tcctgctcct gctgctggca attctactgg aaaaggagga   1680
aatcaatcta tttctagcag tgcttcatcc aacaaaacct cggctcaaag cacatcaggt   1740
gcttctcgtt ccaagactgc gcccatcgtt ttagccattt ccgctttagc tctccttgta   1800
ttctaa                                                              1806
```

<210> SEQ ID NO 7
<211> LENGTH: 366
<212> TYPE: PRT
<213> ORGANISM: Rhizopus oryzae
<220> FEATURE:
<221> NAME/KEY: MOD_RES
<222> LOCATION: (366)..(366)
<223> OTHER INFORMATION: Any amino acid

<400> SEQUENCE: 7

```
Met Ile Ala Thr Pro Phe Glu Met Phe Gln Cys Gln Met Tyr Ile Leu
1               5                   10                  15

Cys Leu Val Leu Ile Ala Phe Ser Phe Thr Cys Val Asn Thr Gln Gln
            20                  25                  30

Leu Cys Asn Gly Tyr Ala Glu Tyr Cys Asn Lys Pro Tyr Asn Ser Leu
        35                  40                  45

Thr Tyr Leu Leu Thr His Asn Ser Tyr Gly Tyr Val Ser Asn Pro Ala
    50                  55                  60

Ala Asn Gln Leu Cys Pro Ile Thr Thr Gln Leu Ala Asp Gly Val Arg
65                  70                  75                  80

Gly Ile Lys Leu Ser Ala Val Lys Ala Thr Asn Ala Thr Thr Asp Gly
                85                  90                  95

Thr Ile Thr Ala Asp Ser Ile Tyr Leu Cys His Thr Ser Cys Ile Ile
            100                 105                 110

Leu Asn Ala Gly Pro Ala Val Asn Thr Leu Arg Thr Ile Lys Glu Trp
        115                 120                 125
```

Val Glu Gln Asn Pro Asn Glu Val Val Thr Ile Met Trp Asn Asn Val
         130                 135                 140

Asp Ala Phe Asp Gly Asn Ala Phe Glu Ala Ala Tyr Asn Ala Ser Gly
145                 150                 155                 160

Ile Ile Glu Tyr Ser Tyr Gln Gln Pro Lys Lys Asn Tyr Thr Trp Pro
                165                 170                 175

Thr Leu Gly Glu Leu Ile Ala Ser Gly Lys Arg Val Ile Asn Phe Gly
            180                 185                 190

Asp Thr Tyr Gln Gln Asp Leu Pro Trp Leu Leu Thr Glu Tyr Asp
        195                 200                 205

Tyr Val Phe Glu Thr Pro Tyr Glu Asn His Asn Glu Ser Ser Phe Ser
    210                 215                 220

Cys Thr Ile Asp Arg Pro Gln Asp Pro Ala Ser Pro Thr Glu Phe Leu
225                 230                 235                 240

Tyr Val Met Asn His Phe Leu Tyr Gly Ser Leu Gln Leu Gly Ser Leu
                245                 250                 255

Pro Ile Glu Ile Pro Gln Lys Gly Ile Ala Asn Thr Thr Asn Ser Asp
            260                 265                 270

Asn Ser Leu Met Lys Gln Ala Lys Thr Cys Thr Glu Lys Phe Gly Arg
        275                 280                 285

Gln Pro Asn Phe Leu Glu Ile Asp Phe Tyr Asn Leu Gly Asp Ala Leu
    290                 295                 300

Lys Ile Thr Ala Glu Leu Asn Asn Val Thr Tyr Lys Gly Ser Gly Ser
305                 310                 315                 320

Leu Gln Cys Asp Thr Tyr Ala Ala Gln Gln Ala Ser Ser Ser Ser Thr
                325                 330                 335

Asp Ser Ser Glu Ala Ile Gln Thr Ile Ser Ile Ser Ser Val Ser Leu
            340                 345                 350

Leu Leu Thr Leu Ile Ala Ala Thr Phe Phe Ile Phe Phe Xaa
        355                 360                 365

<210> SEQ ID NO 8
<211> LENGTH: 1098
<212> TYPE: DNA
<213> ORGANISM: Rhizopus oryzae

<400> SEQUENCE: 8
atgattgcta ccccttttga aatgtttcaa tgtcaaatgt atattttatg tttagtactc    60
attgcatttt catttacttg tgtcaatact caacagctct gtaatgggta tgcagagtat   120
tgtaataagc cttacaactc gctcacctac ctcttgacac ataattcata tggttatgta   180
tctaaccctg ctgctaatca actctgtcct atcactactc aacttgcaga tggtgttcga   240
ggcatcaagc tgtcagccgt taaagcaaca atgcaactac agatggtac cattacagcg   300 gacagcattt atctttgtca cacatcgtgt attatattaa atgctggtcc agcagtcaat   360
acccttcgta cgattaaaga tgggtcgag caaaacccta tgaagtagt gacaatcatg   420 tggaataatg tggatgcctt tgatgggaat gcatttgagg ctgcttataa tgcaagtggt   480
atcattgaat atagttatca gcaacctaaa aaaaactata cttggccaac gttaggtgaa   540
ttaattgcta gtggaaaaag agtaattaat tttggtgata cttattatca acaggatctt   600
ccctggttat taacagaata tgattatgtg ttcgagacac cttatgaaaa tcataacgaa   660
agttcattta gttgcactat tgatcgacct caagatcctg ccagcccaac cgaattctta   720
tacgtcatga accatttttt gtatggttca cttcaattgg gttcactacc tatcgagata   780

```
cctcaaaaag gcatagccaa cacaaccaac tctgataatt cgctcatgaa acaagctaaa      840
acatgtaccg agaaatttgg tcgtcaaccc aacttttag aaatagattt ttataacctg      900
ggtgatgcac tcaagattac tgcagaatta acaatgtca cctacaaagg ttcaggaagt      960
ttgcagtgtg atacatatgc tgctcaacaa gcaagtagtt caagtacaga ctcatccgaa     1020
gcaattcaaa caattagtat tagttcagtt agtttactat aactttaat gctgcaaca      1080 ttctttattt tcttttaa                                                   1098
```

<210> SEQ ID NO 9
<211> LENGTH: 1913
<212> TYPE: DNA
<213> ORGANISM: Rhizopus oryzae

<400> SEQUENCE: 9

```
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc ccttatttca ctggttcagc tgaagttggt     180
gcctcaaaga catacaaagt aatcataaat ttagtttgaa ttcaatgaga ttaatcatct     240
tattctatag tatgttgcag gtggaacaga agaaagtttt gatcgttctc ttgatggaat     300
cacaaactca acacttaatg attttttataa ccgccccgtc acttatgcta accttcctca     360 attccttgg ccaattgaaa aagacgtaag ttattttatt tttatctttt ctcagctaaa     420
ataaacattg tctttctcag cctcagtgga ctcgttctgg aagcaaagcc gacatttccg     480
atgacaatta tattcccagc gttttttcc acggagatga cagtcaagtc caaaatgtgg     540
ttaaaaacgt acctgctgac cgaatcagtg gtacactgac ctttattgga tctaattacg     600
tctactcttt ccagaatgtc tcatttggta ttcacggtgc tggcaagaaa cacaacaatg     660
caaaacaatc ttggaactgg atattgtctg gaagtgatac gatgggtaac cgcaatttct     720
ttaagcttcg acatatggaa gaagatccta cacagattcg tgaacgtctt tattctgaca     780
ttttacatgc catgggtact tatgccaatg atgctaccat ggttcgattg tttattaaca     840
accaaggctt cggtaccttc aacatgttgg atgatatcac tcaattctcc tatatcaatg     900
ctaaatttta taatggcaaa ccacctgcta ccttgggtcc tctctatgat ggtgcctctg     960
gtgcagactt cttatatcat cctggtaacc tcgatggata ctcttcttgg gttgccaaca    1020
cagccaatcc taatggtgaa gcttatgaag ctcttgatcc tctctgtaag gcctggaacg    1080
agacgaccta taccgataat acagccattg caaactttga aaaaatgttt gatctcgacc    1140
gtttcatgcg tttcatggtt attgaatact tgactgccga ttgggatggt tactggatgg    1200
gacagaccaa tgatggtgcc atccgtgatc caactgataa taacaagtgg tacttttag    1260 atcaagactt tgatggtact tttggtgtca acttggctgc acccgaaggc aatgcttttc    1320
ttgatgtttc ttacaaggat ttccttctc gttaccctgg cgctgtcatg atcaacaacc    1380
tcttacagaa tgctgataaa aaggccacct ttgaaaaata tttgactgag actgtgcgtg    1440
tgctgttcaa taatgtcacc ttgactaacc gtgtcttggc ccttcacaac ttcctcttgc    1500
ctgatcttga atgggatcgt tcgatcgttc aacaatctcc tggtattaac tttggttgga    1560
catttgatca agtcactcaa aacttgtggc aaggtgtcac tgcacccaat aacaatggag    1620
gtggtgctgc ttttggttta gttgaatata ttgctgcaaa ggcacaagct gtagctaagg    1680
aatttaatat ttctatcgtt tcccaacctg ttggccctcc ttctgctaat ggtactactg    1740
```

```
ctgctgctcc tgctcctgct gctggcaatt ctactggaaa aggaggaaat caatctattt    1800
ctagcagtgc ttcatccaac aaaacctcgg ctcaaagcac atcaggtgct tctcgttcca    1860
agactgcgcc atcgttttta gccatttccg ctttagctct ccttgtattc taa           1913
```

<210> SEQ ID NO 10
<211> LENGTH: 1806
<212> TYPE: DNA
<213> ORGANISM: Rhizopus oryzae

<400> SEQUENCE: 10

```
atgaaattat ctattatatc cgctgccttt ttagtggcta ttacacacgc tgcttcaata     60
aagtttaatg taattgctcc taatgcaact gatgtcaaag tatctgtaaa tggacagcaa    120
gtgacactta ctgcttcaga tgcaaatgtc cctatttca ctggttcagc tgaagttggt     180
gcctcaaaga catacaaata tgttgcaggt ggaacagaag aaagttttga tcgttctctt    240
gatggaatca caaactcaac acttaatgat ttttataacc gccccgtcac ttatgctaac    300
cttcctcaat taccttggcc aattgaaaaa gaccctcagt ggactcgttc tggaagcaaa    360
gccgacattt tcgatgacaa ttatattccc agcgtttttt tccacggaga tgacagtcaa    420
gtccaaaatg tggttaaaaa cgtacctgct gaccgaatca gtggtacact gacctttatt    480
ggatctaatt acgtctactc tttccagaat gtctcatttg gtattcacgg tgctggcaag    540
aaacacaaca atgcaaaaca atcttggaac tggatattgt ctggaagtga tacgatgggt    600
aaccgcaatt tctttaagct tcgacatatg gaagaagatc ctacacagat tcgtgaacgt    660
ctttattctg acatttaca tgccatgggt acttatgcca atgatgctac catggttcga    720
ttgttttatta caaccaaggc ttcggtacct tcaacatgt tggatgatat cactcaattc    780
tcctatatca atgctaaatt ttataatggc aaaccacctg ctaccttggg tcctctctat    840
gatggtgcct ctggtgcaga cttcttatat catcctggta acctcgatgg atactcttct    900
tggggttgcca acacagccaa tcctaatggt gaagcttatg aagctcttga tcctctctgt    960
aaggcctgga acgagacgac ctataccgat aatacagcca ttgcaaactt tgaaaaaatg   1020
tttgatctcg accgtttcat gcgtttcatg gttattgaat acttgactgc cgattgggat   1080
ggttactgga tgggacagac caatgatggt gcctatcgtg atccaactga taataacaag   1140
tggtactttt tagatcaaga ctttgatggt acttttggtg tcaacttggc tgcacccgaa   1200
ggcaatgctt ttcttgatgt ttcttacaag gatttcccct tctcgttaccc tggcgctgtc   1260
atgatcaaca acctcttaca gaatgctgat aaaaaggcca cctttgaaaa atatttgact   1320
gagactgtgc gtgtgctgtt caataatgtc accttgacta accgtgtctt ggcccttcac   1380
aacttcctct tgcctgatct tgaatgggat cgttcgatcg ttcaacaatc tcctggtatt   1440
aactttggtt ggacatttga tcaagtcact caaaacttgt ggcaaggtgt cactgcaccc   1500
aataacaatg gaggtggtgc tgcttttggt ttagttgaat atattgctgc aaaggcacaa   1560
gctgtagcta aggaatttaa tatttctatc gtttcccaac tgttggccc tccttctgct   1620
aatggtacta ctgctgctgc tcctgctcct gctgctggca attctactgg aaaaggagga   1680
aatcaatcta tttctagcag tgcttcatcc aacaaaacct cggctcaaag cacatcaggt   1740
gcttctcgtt ccaagactgc gcccatcgtt ttagccattt ccgctttagc tctccttgta   1800
ttctaa                                                              1806
```

<210> SEQ ID NO 11
<211> LENGTH: 602

<212> TYPE: PRT
<213> ORGANISM: Rhizopus oryzae
<220> FEATURE:
<221> NAME/KEY: MOD_RES
<222> LOCATION: (602)..(602)
<223> OTHER INFORMATION: Any amino acid

<400> SEQUENCE: 11

```
Met Lys Leu Ser Ile Ser Ala Ala Phe Leu Val Ala Ile Thr His
1               5                   10                  15

Ala Ala Ser Ile Lys Phe Asn Val Ile Ala Pro Asn Ala Thr Asp Val
            20                  25                  30

Lys Val Ser Val Asn Gly Gln Gln Val Thr Leu Thr Ala Ser Asp Ala
        35                  40                  45

Asn Val Pro Tyr Phe Thr Gly Ser Ala Glu Val Gly Ala Ser Lys Thr
    50                  55                  60

Tyr Lys Tyr Val Ala Gly Gly Thr Glu Glu Ser Phe Asp Arg Ser Leu
65                  70                  75                  80

Asp Gly Ile Thr Asn Ser Thr Leu Asn Asp Phe Tyr Asn Arg Pro Val
                85                  90                  95

Thr Tyr Ala Asn Leu Pro Gln Leu Pro Trp Pro Ile Glu Lys Asp Pro
            100                 105                 110

Gln Trp Thr Arg Ser Gly Ser Lys Ala Asp Ile Phe Asp Asp Asn Tyr
        115                 120                 125

Ile Pro Ser Val Phe Phe His Gly Asp Asp Ser Gln Val Gln Asn Val
    130                 135                 140

Val Lys Asn Val Pro Ala Asp Arg Ile Ser Gly Thr Leu Thr Phe Ile
145                 150                 155                 160

Gly Ser Asn Tyr Val Tyr Ser Phe Gln Asn Val Ser Phe Gly Ile His
                165                 170                 175

Gly Ala Gly Lys Lys His Asn Asn Ala Lys Gln Ser Trp Asn Trp Ile
            180                 185                 190

Leu Ser Gly Ser Asp Thr Met Gly Asn Arg Asn Phe Phe Lys Leu Arg
        195                 200                 205

His Met Glu Glu Asp Pro Thr Gln Ile Arg Glu Arg Leu Tyr Ser Asp
    210                 215                 220

Ile Leu His Ala Met Gly Thr Tyr Ala Asn Asp Ala Thr Met Val Arg
225                 230                 235                 240

Leu Phe Ile Asn Asn Gln Gly Phe Gly Thr Phe Asn Met Leu Asp Asp
                245                 250                 255

Ile Thr Gln Phe Ser Tyr Ile Asn Ala Lys Phe Tyr Asn Gly Lys Pro
            260                 265                 270

Pro Ala Thr Leu Gly Pro Leu Tyr Asp Gly Ala Ser Gly Ala Asp Phe
        275                 280                 285

Leu Tyr His Pro Gly Asn Leu Asp Gly Tyr Ser Ser Trp Val Ala Asn
    290                 295                 300

Thr Ala Asn Pro Asn Gly Glu Ala Tyr Glu Ala Leu Asp Pro Leu Cys
305                 310                 315                 320

Lys Ala Trp Asn Glu Thr Thr Tyr Thr Asp Asn Thr Ala Ile Ala Asn
                325                 330                 335

Phe Glu Lys Met Phe Asp Leu Asp Arg Phe Met Arg Phe Met Val Ile
            340                 345                 350

Glu Tyr Leu Thr Ala Asp Trp Asp Gly Tyr Trp Met Gly Gln Thr Asn
        355                 360                 365

Asp Gly Ala Tyr Arg Asp Pro Thr Asp Asn Asn Lys Trp Tyr Phe Leu
```

```
                    370              375              380
Asp Gln Asp Phe Asp Gly Thr Phe Gly Val Asn Leu Ala Ala Pro Glu
385              390              395              400

Gly Asn Ala Phe Leu Asp Val Ser Tyr Lys Asp Phe Pro Ser Arg Tyr
                405              410              415

Pro Gly Ala Val Met Ile Asn Asn Leu Leu Gln Asn Ala Asp Lys Lys
            420              425              430

Ala Thr Phe Glu Lys Tyr Leu Thr Glu Thr Val Arg Val Leu Phe Asn
        435              440              445

Asn Val Thr Leu Thr Asn Arg Val Leu Ala Leu His Asn Phe Leu Leu
    450              455              460

Pro Asp Leu Glu Trp Asp Arg Ser Ile Val Gln Gln Ser Pro Gly Ile
465              470              475              480

Asn Phe Gly Trp Thr Phe Asp Gln Val Thr Gln Asn Leu Trp Gln Gly
                485              490              495

Val Thr Ala Pro Asn Asn Gly Gly Gly Ala Ala Phe Gly Leu Val
            500              505              510

Glu Tyr Ile Ala Ala Lys Ala Gln Ala Val Ala Lys Glu Phe Asn Ile
        515              520              525

Ser Ile Val Ser Gln Pro Val Gly Pro Ser Ala Asn Gly Thr Thr
    530              535              540

Ala Ala Ala Pro Ala Pro Ala Ala Gly Asn Ser Thr Gly Lys Gly Gly
545              550              555              560

Asn Gln Ser Ile Ser Ser Ala Ser Ser Asn Lys Thr Ser Ala Gln
                565              570              575

Ser Thr Ser Gly Ala Ser Arg Ser Lys Thr Ala Pro Ile Val Leu Ala
            580              585              590

Ile Ser Ala Leu Ala Leu Leu Val Phe Xaa
        595              600

<210> SEQ ID NO 12
<211> LENGTH: 1914
<212> TYPE: DNA
<213> ORGANISM: Rhizopus oryzae

<400> SEQUENCE: 12
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc cctatttca ctggttcagc tgaagttggt     180
gcctcaaaga catacaaagt aatcataaat ttagtttgaa ttcaatgaga ttaatcatct     240
tattctatag tatgttgcag gtggaacaga agaaagtttt gatcgttctc ttgatggaat     300
cacaaactca acacttaatg attttttataa ccgccccgtc actatgcta accttcctca     360 attaccttgg ccaattgaaa aagacgtaag ttattttatt tttatctttt ctcagctaaa     420
ataaacattg tctttctcag cctcagtgga ctcgttctgg aagcaaagcc gacattttcg     480
atgacaatta tattcccagc gtttttttcc acggagatga cagtcaagtc caaatgtgg      540 ttaaaaacgt acctgctgac cgaatcagtg gtacactgac ctttattgga tctaattacg     600
tctactcttt ccagaatgtc tcatttggta ttcacggtgc tggcaagaaa cacaacaatg     660
caaaacaatc ttggaactgg atattgtctg gaagtgatac gatgggtaac cgcaatttct     720
ttaagcttcg acatatggaa gaagatccta cacagattcg tgaacgtctt tattctgaca     780
ttttacatgc catgggtact tatgccaatg atgctaccat ggttcgattg tttattaaca     840
```

```
accaaggctt cggtaccttc aacatgttgg atgatatcac tcaattctcc tatatcaatg    900
ctaaatttta taatggcaaa ccacctgcta ccttgggtcc tctctatgat ggtgcctctg    960
gtgcagactt cttatatcat cctggtaacc tcgatggata ctcttcttgg gttgccaaca   1020
cagccaatcc taatggtgaa gcttatgaag ctcttgatcc tctctgtaag gcctggaacg   1080
agacgaccta taccgataat acagccattg caaactttga aaaaatgttt gatctcgacc   1140
gtttcatgcg tttcatggtt attgaatact tgactgccga ttgggatggt tactggatgg   1200
gacagaccaa tgatggtgcc tatcgtgatc aactgataa taacaagtgg tacttttag    1260 atcaagactt tgatggtact tttggtgtca acttggctgc acccgaaggc aatgcttttc   1320
ttgatgtttc ttacaaggat ttcccttctc gttaccctgg cgctgtcatg atcaacaacc   1380
tcttacagaa tgctgataaa aaggccacct ttgaaaaata tttgactgag actgtgcgtg   1440
tgctgttcaa taatgtcacc ttgactaacc gtgtcttggc ccttcacaac ttcctcttgc   1500
ctgatcttga atgggatcgt tcgatcgttc aacaatctcc tggtattaac tttggttgga   1560
catttgatca agtcactcaa aacttgtggc aaggtgtcac tgcacccaat aacaatggag   1620
gtggtgctgc ttttggttta gttgaatata ttgctgcaaa ggcacaagct gtagctaagg   1680
aatttaatat ttctatcgtt tcccaacctg ttggccctcc ttctgctaat ggtactactg   1740
ctgctgctcc tgctcctgct gctggcaatt ctactggaaa aggaggaaat caatctattt   1800
ctagcagtgc ttcatccaac aaaacctcgg ctcaaagcac atcaggtgct tctcgttcca   1860
agactgcgcc catcgtttta gccatttccg ctttagctct ccttgtattc taaa          1914

<210> SEQ ID NO 13
<211> LENGTH: 1805
<212> TYPE: DNA
<213> ORGANISM: Rhizopus oryzae

<400> SEQUENCE: 13
atgaaattat ctattatatc cgctgccttt ttagtggcta taacacacgc tgcttcaata     60
aagtttaatg taattgctcc taatgcaact gatgtcaaag tatctgtaaa tggacagcaa    120
gtgacactta ctgcttcaga tgcaaatgtc ccttacttca ctggttcagc tgaagttggt    180
tcctcaaaga catacaaata tgttgcaggt ggaacagaag aaggttttga tcgttctctt    240
gatggaatca caaactcaac atttaatgat ttttataatc gccccatcac ttatgctaac    300
cttcctcaat taccttggcc aattgaaaaa gaccctcagt ggactcgttc tggaaacaaa    360
gccgacattt tcgatgacaa ttatattccc agcattttt tccacggaga tgacagtcaa    420
gtccaaaatg tggttaaaaa cgtacctgct gaccgaatca gtggtacact gacctttatc    480
ggatctaatt acgtcactc tttccagaat gtctcatttg gtattcacgg tgctggcaag    540
aaacacaaca atgcaaagca atcttggaac tggatcttgt ctggaagtga tacgatgggt    600
aaccgtaatt tctttaagct tcgacatatg gaagaagatc ctacacagat ccgtgaacgt    660
ctttattctg acatttttaca tgccatgggt acttatgcca atgatgctac catggttcga    720
ttgtttatta caatcaagg cttcggtacc ttcaacatgt tggatgacat cactcaattc    780
tcttatatca atgctaaatt ctataatggc aaaccacctg ctaccttggg tcctctctat    840
gatggtgcct ctggtgcaga tttcttatat catcctggta acctcgatgg atactctttc    900
ttgggttgcc aacacagcta atcctaatgg tgaagcttat gaagctcttg atcctctctg    960
taaggcctgg aacgagacga cctataccga ataatacagcc attgcgaact tgaaaaaat   1020
```

```
gtttgatctt gaccgtttca tgcgtttcat ggttgttgaa tacttggctg ccgattggga      1080
tggttactgg atgggacaga ccaatgatgg tgcctatcgt gatccaactg ataataacaa      1140
gtggtacttt ttagatcaag actttgatgg tacctttggt gtcaacttgg ctgcacccga      1200
aggcaatgct tttcttgata tttcttacaa agatttccct tctcgttacc ctggcgctgt      1260
catgatcaac aacctcttac agaatgctga taaaaaggcc acctttgaaa aatacttgac      1320
tgagactgtg cgtgtgctgt tcaataatgt caccttgact aaccgtgtct ggcccttca      1380 caacttcctc ttgcctgacc ttgaatggga tcgttcgatc gttcaacaat ctcctggtat      1440
taactttggt tggacatttg atcaagtcac tcaaaacttg tggcaaggtg tcaatgcacc      1500
caataacaac ggaggtggtg ctgctattgg tttagttgaa tatattgcta caaaggcaca      1560
agttgtagct aagaattaat attactatcg ttcccaacct gttggccctc cttctgctaa      1620
tggtactact actgctgcta actgctccta ctgctggtat ctactggaaa aggaagaaat      1680
catcccattt ctagcagtgc ttcatcaaca aactcgctca gtaacatca agtgcttctc       1740 gtcaagactg cgccaatcat tttaggcaat ttccgcttag ccctcccccg ttgtgattct      1800
caaaa                                                                  1805

<210> SEQ ID NO 14
<211> LENGTH: 1908
<212> TYPE: DNA
<213> ORGANISM: Rhizopus oryzae

<400> SEQUENCE: 14
atgaaattat ctattatatc cgctgccttt ttagtggcta taacacacgc tgcttcaata       60
aagtttaatg taattgctcc taatgcaact gatgtcaaag tatctgtaaa tggacagcaa      120
gtgacactta ctgcttcaga tgcaaatgtc ccttacttca ctggttcagc tgaagttggt      180
tcctcaaaga catacaaagt aatcataaat ttattttgaa ttcaatcata ttaatcatct      240
tattctatag tatgttgcag gtggaacaga agaaggtttt gatcgttctc ttgatggaat      300
cacaaactca acatttaatg atttttataa tcgccccatc acttatgcta accttcctca      360
attaccttgg ccaattgaaa aagacgtaag ttattttatt tttatctttt ctcagctaaa      420
ataaacattg tctttctcag cctcagtgga ctcgttctgg aaacaaagcc gacattttcg      480
atgacaatta tattcccagc attttttttcc acggagatga cagtcaagtc caaaatgtgg      540
ttaaaaacgt acctgctgac cgaatcagtg gtacactgac ctttatcgga tctaattacg      600
tctactcttt ccagaatgtc tcatttggta ttcacggtgc tggcaagaaa cacaacaatg      660
caaagcaatc ttggaactgg atcttgtctg gaagtgatac gatgggtaac cgtaatttct      720
ttaagcttcg acatatggaa gaagatccta cacagatccg tgaacgtctt tattctgaca      780
ttttacatgc catgggtact tatgccaatg atgctaccat ggttcgattg tttattaaca      840
atcaaggctt cggtaccttc aacatgttgg atgacatcac tcaattctct tatatcaatg      900
ctaaattcta taatggcaaa ccacctgcta ccttgggtcc tctctatgat ggtgcctctg      960
gtgcagattt cttatatcat cctggtaacc tcgatggata ctctttcttg ggttgccaac     1020
acagctaatc ctaatggtga agcttatgaa gctcttgatc ctctctgtaa ggcctggaac     1080
gagacgacct ataccgataa tacagccatt gcgaactttg aaaaaatgtt tgatcttgac     1140
cgtttcatgc gtttcatggt tgttgaatac ttggctgccg attgggatgg ttactggatg     1200
ggacagacca atgatggtgc ctatcgtgat ccaactgata taacaagtg gtacttttta     1260 gatcaagact ttgatggtac ctttggtgtc aacttggctg caccgaagg caatgctttt     1320
```

```
cttgatattt cttacaaaga tttcccttct cgttaccctg gcgctgtcat gatcaacaac    1380
ctcttacaga atgctgataa aaaggccacc tttgaaaaat acttgactga gactgtgcgt    1440
gtgctgttca ataatgtcac cttgactaac cgtgtcttgg cccttcacaa cttcctcttg    1500
cctgaccttg aatgggatcg ttcgatcgtt caacaatctc ctggtattaa ctttggttgg    1560
acatttgatc aagtcactca aaacttgtgg caaggtgtca atgcacccaa taacaacgga    1620
ggtggtgctg ctattggttt agttgaatat attgctacaa aggcacaagt tgtagctaag    1680
aattaatatt actatcgttc ccaacctgtt ggccctcctt ctgctaatgg tactactact    1740
gctgctaact gctcctactg ctggtatcta ctggaaaagg aagaaatcat cccatttcta    1800
gcagtgcttc atcaacaaac tcgctcaagt aacatcaagt gcttctcgtc aagactgcgc    1860
caatcatttt aggcaatttc cgcttagccc tccttgtgat tctcaaaa                1908
```

```
<210> SEQ ID NO 15
<211> LENGTH: 636
<212> TYPE: PRT
<213> ORGANISM: Rhizopus oryzae
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (193)..(193)
<223> OTHER INFORMATION: Any amino acid
<220> FEATURE:
<221> NAME/KEY: MOD_RES
<222> LOCATION: (562)..(562)
<223> OTHER INFORMATION: Any amino acid
<220> FEATURE:
<221> NAME/KEY: MOD_RES
<222> LOCATION: (624)..(624)
<223> OTHER INFORMATION: Any amino acid
<220> FEATURE:
<221> NAME/KEY: MOD_RES
<222> LOCATION: (629)..(629)
<223> OTHER INFORMATION: Any amino acid
<220> FEATURE:
<221> NAME/KEY: MOD_RES
<222> LOCATION: (633)..(633)
<223> OTHER INFORMATION: Any amino acid
```

<400> SEQUENCE: 15

```
Met Lys Leu Ser Ile Ile Ser Ala Ala Phe Leu Val Ala Ile Thr His
1               5                   10                  15

Ala Ala Ser Ile Lys Phe Asn Val Ile Ala Pro Asn Ala Thr Asp Val
            20                  25                  30

Lys Val Ser Val Asn Gly Gln Gln Val Thr Leu Thr Ala Ser Asp Ala
        35                  40                  45

Asn Val Pro Tyr Phe Thr Gly Ser Ala Glu Val Gly Ser Ser Lys Thr
    50                  55                  60

Tyr Lys Val Ile Ile Asn Leu Phe Xaa Ile Gln Ser Tyr Xaa Ser Ser
65                  70                  75                  80

Tyr Ser Ile Val Cys Cys Arg Trp Asn Arg Arg Phe Xaa Ser Phe
                85                  90                  95

Ser Xaa Trp Asn His Lys Leu Asn Ile Xaa Xaa Phe Leu Xaa Ser Pro
            100                 105                 110

His His Leu Cys Xaa Pro Ser Ser Ile Thr Leu Ala Asn Xaa Lys Arg
        115                 120                 125

Arg Lys Leu Phe Tyr Phe Tyr Leu Phe Ser Ala Lys Ile Asn Ile Val
    130                 135                 140

Phe Leu Ser Leu Ser Gly Leu Val Leu Glu Thr Lys Pro Thr Phe Ser
145                 150                 155                 160

Met Thr Ile Ile Phe Pro Ala Phe Phe Ser Thr Glu Met Thr Val Lys
                165                 170                 175

Ser Lys Met Trp Leu Lys Thr Tyr Leu Leu Thr Glu Ser Val Val His
            180                 185                 190

Xaa Pro Leu Ser Asp Leu Ile Thr Ser Thr Leu Ser Arg Met Ser His
        195                 200                 205

Leu Val Phe Thr Val Leu Ala Arg Asn Thr Thr Met Gln Ser Asn Leu
    210                 215                 220

Gly Thr Gly Ser Cys Leu Glu Val Ile Arg Trp Val Thr Val Ile Ser
225                 230                 235                 240

Leu Ser Phe Asp Ile Trp Lys Lys Ile Leu His Arg Ser Val Asn Val
                245                 250                 255

Phe Ile Leu Thr Phe Tyr Met Pro Trp Val Leu Met Pro Met Met Leu
            260                 265                 270

Pro Trp Phe Asp Cys Leu Leu Thr Ile Lys Ala Ser Val Pro Ser Thr
        275                 280                 285

Cys Trp Met Thr Ser Leu Asn Ser Leu Ile Ser Met Leu Asn Ser Ile
    290                 295                 300

Met Ala Asn His Leu Leu Pro Trp Val Leu Ser Met Val Pro Leu
305                 310                 315                 320

Val Gln Ile Ser Tyr Ile Ile Leu Val Thr Ser Met Asp Thr Leu Ser
                325                 330                 335

Trp Val Ala Asn Thr Ala Asn Pro Asn Gly Glu Ala Tyr Glu Ala Leu
            340                 345                 350

Asp Pro Leu Cys Lys Ala Trp Asn Glu Thr Thr Tyr Thr Asp Asn Thr
        355                 360                 365

Ala Ile Ala Asn Phe Glu Lys Met Phe Asp Leu Asp Arg Phe Met Arg
    370                 375                 380

Phe Met Val Val Glu Tyr Leu Ala Ala Asp Trp Asp Gly Tyr Trp Met
385                 390                 395                 400

Gly Gln Thr Asn Asp Gly Ala Tyr Arg Asp Pro Thr Asn Asn Lys
                405                 410                 415
```

```
Trp Tyr Phe Leu Asp Gln Asp Phe Asp Gly Thr Phe Gly Val Asn Leu
            420                 425                 430

Ala Ala Pro Glu Gly Asn Ala Phe Leu Asp Ile Ser Tyr Lys Asp Phe
        435                 440                 445

Pro Ser Arg Tyr Pro Gly Ala Val Met Ile Asn Asn Leu Leu Gln Asn
    450                 455                 460

Ala Asp Lys Lys Ala Thr Phe Glu Lys Tyr Leu Thr Glu Thr Val Arg
465                 470                 475                 480

Val Leu Phe Asn Asn Val Thr Leu Thr Asn Arg Val Leu Ala Leu His
                485                 490                 495

Asn Phe Leu Leu Pro Asp Leu Glu Trp Asp Arg Ser Ile Val Gln Gln
                500                 505                 510

Ser Pro Gly Ile Asn Phe Gly Trp Thr Phe Asp Gln Val Thr Gln Asn
            515                 520                 525

Leu Trp Gln Gly Val Asn Ala Pro Asn Asn Gly Gly Gly Ala Ala
        530                 535                 540

Ile Gly Leu Val Glu Tyr Ile Ala Thr Lys Ala Gln Val Val Ala Lys
545                 550                 555                 560

Asn Xaa Tyr Tyr Tyr Arg Ser Gln Pro Val Gly Pro Pro Ser Ala Asn
                565                 570                 575

Gly Thr Thr Thr Ala Ala Asn Cys Ser Tyr Cys Trp Tyr Leu Leu Glu
            580                 585                 590

Lys Glu Glu Ile Ile Pro Phe Leu Ala Val Leu His Gln Gln Thr Arg
        595                 600                 605

Ser Ser Asn Ile Lys Cys Phe Ser Ser Arg Leu Arg Gln Ser Phe Xaa
610                 615                 620

Ala Ile Ser Ala Xaa Pro Ser Leu Xaa Phe Ser Lys
625                 630                 635

<210> SEQ ID NO 16
<211> LENGTH: 637
<212> TYPE: PRT
<213> ORGANISM: Rhizopus oryzae
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Any amino acid
<220> FEATURE:
<221> NAME/KEY: MOD_RES
<222> LOCATION: (126)..(126)
```

```
<223> OTHER INFORMATION: Any amino acid
<220> FEATURE:
<221> NAME/KEY: MOD_RES
<222> LOCATION: (193)..(193)
<223> OTHER INFORMATION: Any amino acid
<220> FEATURE:
<221> NAME/KEY: MOD_RES
<222> LOCATION: (562)..(562)
<223> OTHER INFORMATION: Any amino acid
<220> FEATURE:
<221> NAME/KEY: MOD_RES
<222> LOCATION: (624)..(624)
<223> OTHER INFORMATION: Any amino acid
<220> FEATURE:
<221> NAME/KEY: MOD_RES
<222> LOCATION: (629)..(629)
<223> OTHER INFORMATION: Any amino acid

<400> SEQUENCE: 16
```

| Met | Lys | Leu | Ser | Ile | Ile | Ser | Ala | Ala | Phe | Leu | Val | Ala | Ile | Thr | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ala Ala Ser Ile Lys Phe Asn Val Ile Ala Pro Asn Ala Thr Asp Val
                20                  25                  30

Lys Val Ser Val Asn Gly Gln Gln Val Thr Leu Thr Ala Ser Asp Ala
            35                  40                  45

Asn Val Pro Tyr Phe Thr Gly Ser Ala Glu Val Gly Ser Ser Lys Thr
 50                  55                  60

Tyr Lys Val Ile Ile Asn Leu Phe Xaa Ile Gln Ser Tyr Xaa Ser Ser
 65                  70                  75                  80

Tyr Ser Ile Val Cys Cys Arg Trp Asn Arg Arg Phe Xaa Ser Phe
                85                  90                  95

Ser Xaa Trp Asn His Lys Leu Asn Ile Xaa Xaa Phe Leu Xaa Ser Pro
                100                 105                 110

His His Leu Cys Xaa Pro Ser Ser Ile Thr Leu Ala Asn Xaa Lys Arg
            115                 120                 125

Arg Lys Leu Phe Tyr Phe Tyr Leu Phe Ser Ala Lys Ile Asn Ile Val
        130                 135                 140

Phe Leu Ser Leu Ser Gly Leu Val Leu Glu Thr Lys Pro Thr Phe Ser
145                 150                 155                 160

Met Thr Ile Ile Phe Pro Ala Phe Phe Ser Thr Glu Met Thr Val Lys
                165                 170                 175

Ser Lys Met Trp Leu Lys Thr Tyr Leu Leu Thr Glu Ser Val Val His
            180                 185                 190

Xaa Pro Leu Ser Asp Leu Ile Thr Ser Thr Leu Ser Arg Met Ser His
        195                 200                 205

Leu Val Phe Thr Val Leu Ala Arg Asn Thr Thr Met Gln Ser Asn Leu
    210                 215                 220

Gly Thr Gly Ser Cys Leu Glu Val Ile Arg Trp Val Thr Val Ile Ser
225                 230                 235                 240

Leu Ser Phe Asp Ile Trp Lys Lys Ile Leu His Arg Ser Val Asn Val
                245                 250                 255

Phe Ile Leu Thr Phe Tyr Met Pro Trp Val Leu Met Pro Met Met Leu
                260                 265                 270

Pro Trp Phe Asp Cys Leu Leu Thr Ile Lys Ala Ser Val Pro Ser Thr
            275                 280                 285

Cys Trp Met Thr Ser Leu Asn Ser Leu Ile Ser Met Leu Asn Ser Ile
        290                 295                 300

Met Ala Asn His Leu Leu Pro Trp Val Leu Ser Met Met Val Pro Leu
305                 310                 315                 320

Val Gln Ile Ser Tyr Ile Ile Leu Val Thr Ser Met Asp Thr Leu Ser
                    325                 330                 335

Trp Val Ala Asn Thr Ala Asn Pro Asn Gly Glu Ala Tyr Glu Ala Leu
                340                 345                 350

Asp Pro Leu Cys Lys Ala Trp Asn Glu Thr Thr Tyr Thr Asp Asn Thr
            355                 360                 365

Ala Ile Ala Asn Phe Glu Lys Met Phe Asp Leu Asp Arg Phe Met Arg
        370                 375                 380

Phe Met Val Val Glu Tyr Leu Ala Ala Asp Trp Asp Gly Tyr Trp Met
385                 390                 395                 400

Gly Gln Thr Asn Asp Gly Ala Tyr Arg Asp Pro Thr Asn Asn Lys
                    405                 410                 415

Trp Tyr Phe Leu Asp Gln Asp Phe Asp Gly Thr Phe Gly Val Asn Leu
                420                 425                 430

Ala Ala Pro Glu Gly Asn Ala Phe Leu Asp Ile Ser Tyr Lys Asp Phe
            435                 440                 445

Pro Ser Arg Tyr Pro Gly Ala Val Met Ile Asn Asn Leu Leu Gln Asn
        450                 455                 460

Ala Asp Lys Lys Ala Thr Phe Glu Lys Tyr Leu Thr Glu Thr Val Arg
465                 470                 475                 480

Val Leu Phe Asn Asn Val Thr Leu Thr Asn Arg Val Leu Ala Leu His
                    485                 490                 495

Asn Phe Leu Leu Pro Asp Leu Glu Trp Asp Arg Ser Ile Val Gln Gln
                500                 505                 510

Ser Pro Gly Ile Asn Phe Gly Trp Thr Phe Asp Gln Val Thr Gln Asn
            515                 520                 525

Leu Trp Gln Gly Val Asn Ala Pro Asn Asn Gly Gly Gly Ala Ala
        530                 535                 540

Ile Gly Leu Val Glu Tyr Ile Ala Thr Lys Ala Gln Val Val Ala Lys
545                 550                 555                 560

Asn Xaa Tyr Tyr Tyr Arg Ser Gln Pro Val Gly Pro Pro Ser Ala Asn
                    565                 570                 575

Gly Thr Thr Thr Ala Ala Asn Cys Ser Tyr Cys Trp Tyr Leu Leu Glu
                580                 585                 590

Lys Glu Glu Ile Ile Pro Phe Leu Ala Val Leu His Gln Gln Thr Arg
            595                 600                 605

Ser Ser Asn Ile Lys Cys Phe Ser Ser Arg Leu Arg Gln Ser Phe Xaa
        610                 615                 620

Ala Ile Ser Ala Xaa Pro Ser Pro Val Val Ile Leu Lys
625                 630                 635

<210> SEQ ID NO 17
<211> LENGTH: 1806
<212> TYPE: DNA
<213> ORGANISM: Mucor sp.

<400> SEQUENCE: 17
atgaaattat ctattatatc cgctgccttt ttagtggcta taacacacgc tgcttcataa     60
agtttaatgt aattgctcct aatgcaactg atgtcaaagt atctgtaaat ggacagcaag    120
tgacacttac tgcttcagat gcaaatgtcc cttacttcac tggttcagct gaagttggtt    180
cctcaaagac atacaaatat gttgcaggtg gaacagaaga aggttttgat cgttctcttg    240
atggaatcac aaactcaaca tttaatgatt tttataatcg ccccatcact tatgctaacc    300

```
ttcctcaatt accttggcca attgaaaaag accctcagtg gactcgttct ggaaacaaag      360
ccgacatttt cgatgacaat tatattccca gcattttttt ccacggagat gacagtcaag      420
tccaaaatgt ggttaaaaac gtacctgctg accgaatcag tggtacactg acctttatcg      480
gatctaatta cgtctactct ttccagaatg tctcatttgg tattcacggt gctggcaaga      540
aacacaacaa tgcaaagcaa tcttggaact ggatcttgtc tggaagtgat acgatgggta      600
accgtaattt ctttaagctt cgacatatgg aagaagatcc tacacagatc cgtgaacgtc      660
tttattctga cattttacat gccatgggta cttatgccaa tgatgctacc atggttcgat      720
tgtttattaa caatcaaggc ttcggtacct caacatgtt ggatgacatc actcaattct      780
cttatatcaa tgctaaattc tataatggca aaccacctgc taccttgggt cctctctatg      840
atggtgcctc tggtgcagat ttcttatatc atcctggtaa cctcgatgga tactcttctt      900
gggttgccaa cacagctaat cctaatggtg aagcttatga agctcttgat ccttctctgt      960
aaggcctgga aacgagacga cctattaccg ataatacagc caattgcgaa ctttgaaaaa     1020
atgtttgatc tgacgtttca tgcgttccat gctggtgata ctgggctgcc gaatgaatgc     1080
tactgcaatg gaagacatga atcgtgtcta ttcgtgatcc aactgaataa taccagtcgg     1140
gtacttttta gatcaagact ttgatggtac ttttggtgtc aacttggctg cacccgaagg     1200
caatgctttt cttgatgttt cttacaagga tttcccttct cgttaccctg cgctgtcat      1260 gatcaacaac ctcttacaga tgctgataa aaaggccacc tttgaaaaat atttgactga     1320
gactgtgcgt gtgctgttca ataatgtcac cttgactaac cgtgtcttgg cccttcacaa     1380
cttcctcttg cctgatcttg aatgggatcg ttcgatcgtt caacaatctc ctggtattaa     1440
ctttggttgg acatttgatc aagtcactca aaacttgtgg caaggtgtca ctgcacccaa     1500
taacaatgga ggtggtgctg cttttggttt agttgaatat attgctgcaa aggcacaagc     1560
tgtagctaag gaatttaata tttctatcgt ttcccaacct gttggccctc cttctgctaa     1620
tggtactact gctgctgctc ctgctcctgc tgctggcaat tctactggaa aaggaggaaa     1680
tcaatctatt tctagcagtg cttcatccaa caaaacctcg gctcaaagca catcaggtgc     1740
ttctcgttcc aagactgcgc ccatcgtttt agccatttcc gctttagctc tccttggtat     1800
tctaaa                                                                1806
```

<210> SEQ ID NO 18
<211> LENGTH: 602
<212> TYPE: PRT
<213> ORGANISM: Mucor sp.
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (157)..(157)
<223> OTHER INFORMATION: Any amino acid
<220> FEATURE:
<221> NAME/KEY: MOD_RES

```
<222> LOCATION: (388)..(388)
<223> OTHER INFORMATION: Any amino acid
<220> FEATURE:
<221> NAME/KEY: MOD_RES
<222> LOCATION: (405)..(405)
<223> OTHER INFORMATION: Any amino acid
<220> FEATURE:
<221> NAME/KEY: MOD_RES
<222> LOCATION: (429)..(430)
<223> OTHER INFORMATION: Any amino acid
<220> FEATURE:
<221> NAME/KEY: MOD_RES
<222> LOCATION: (435)..(435)
<223> OTHER INFORMATION: Any amino acid
<220> FEATURE:
<221> NAME/KEY: MOD_RES
<222> LOCATION: (440)..(440)
<223> OTHER INFORMATION: Any amino acid
<220> FEATURE:
<221> NAME/KEY: MOD_RES
<222> LOCATION: (448)..(448)
<223> OTHER INFORMATION: Any amino acid
<220> FEATURE:
<221> NAME/KEY: MOD_RES
<222> LOCATION: (453)..(453)
<223> OTHER INFORMATION: Any amino acid
<220> FEATURE:
<221> NAME/KEY: MOD_RES
<222> LOCATION: (465)..(465)
<223> OTHER INFORMATION: Any amino acid
<220> FEATURE:
<221> NAME/KEY: MOD_RES
<222> LOCATION: (467)..(467)
<223> OTHER INFORMATION: Any amino acid
<220> FEATURE:
<221> NAME/KEY: MOD_RES
<222> LOCATION: (480)..(480)
<223> OTHER INFORMATION: Any amino acid
<220> FEATURE:
<221> NAME/KEY: MOD_RES
<222> LOCATION: (486)..(486)
<223> OTHER INFORMATION: Any amino acid
<220> FEATURE:
<221> NAME/KEY: MOD_RES
<222> LOCATION: (501)..(501)
<223> OTHER INFORMATION: Any amino acid
<220> FEATURE:
<221> NAME/KEY: MOD_RES
<222> LOCATION: (512)..(512)
<223> OTHER INFORMATION: Any amino acid
<220> FEATURE:
<221> NAME/KEY: MOD_RES
<222> LOCATION: (523)..(523)
<223> OTHER INFORMATION: Any amino acid
<220> FEATURE:
<221> NAME/KEY: MOD_RES
<222> LOCATION: (526)..(526)
<223> OTHER INFORMATION: Any amino acid
<220> FEATURE:
<221> NAME/KEY: MOD_RES
<222> LOCATION: (540)..(540)
<223> OTHER INFORMATION: Any amino acid
<220> FEATURE:
<221> NAME/KEY: MOD_RES
<222> LOCATION: (565)..(565)
<223> OTHER INFORMATION: Any amino acid

<400> SEQUENCE: 18

Met Lys Leu Ser Ile Ile Ser Ala Ala Phe Leu Val Ala Ile Thr His
1               5                   10                  15

Ala Ala Ser Xaa Ser Leu Met Xaa Leu Leu Met Gln Leu Met Ser
            20                  25                  30

Lys Tyr Leu Xaa Met Asp Ser Lys Xaa His Leu Leu Leu Gln Met Gln
        35                  40                  45

Met Ser Leu Thr Ser Leu Val Gln Leu Lys Leu Val Pro Gln Arg His
```

```
                50                  55                  60
Thr Asn Met Leu Gln Val Glu Gln Lys Lys Val Leu Ile Val Leu Leu
 65                  70                  75                  80

Met Glu Ser Gln Thr Gln His Leu Met Ile Phe Ile Ile Ala Pro Ser
                 85                  90                  95

Leu Met Leu Thr Phe Leu Asn Tyr Leu Gly Gln Leu Lys Lys Thr Leu
                100                 105                 110

Ser Gly Leu Val Leu Glu Thr Lys Pro Thr Phe Ser Met Thr Ile Ile
                115                 120                 125

Phe Pro Ala Phe Phe Ser Thr Glu Met Thr Val Lys Ser Lys Met Trp
130                 135                 140

Leu Lys Thr Tyr Leu Leu Thr Glu Ser Val Val His Xaa Pro Leu Ser
145                 150                 155                 160

Asp Leu Ile Thr Ser Thr Leu Ser Arg Met Ser His Leu Val Phe Thr
                165                 170                 175

Val Leu Ala Arg Asn Thr Thr Met Gln Ser Asn Leu Gly Thr Gly Ser
                180                 185                 190

Cys Leu Glu Val Ile Arg Trp Val Thr Val Ile Ser Leu Ser Phe Asp
                195                 200                 205

Ile Trp Lys Lys Ile Leu His Arg Ser Val Asn Val Phe Ile Leu Thr
210                 215                 220

Phe Tyr Met Pro Trp Val Leu Met Pro Met Met Leu Pro Trp Phe Asp
225                 230                 235                 240

Cys Leu Leu Thr Ile Lys Ala Ser Val Pro Ser Thr Cys Trp Met Thr
                245                 250                 255

Ser Leu Asn Ser Leu Ile Ser Met Leu Asn Ser Ile Met Ala Asn His
                260                 265                 270

Leu Leu Pro Trp Val Leu Ser Met Met Val Pro Leu Val Gln Ile Ser
                275                 280                 285

Tyr Ile Ile Leu Val Thr Ser Met Asp Thr Leu Leu Gly Leu Pro Thr
                290                 295                 300

Gln Leu Ile Leu Met Val Lys Leu Met Lys Leu Leu Ile Leu Leu Cys
305                 310                 315                 320

Lys Ala Trp Lys Arg Asp Asp Leu Leu Pro Ile Ile Gln Pro Ile Ala
                325                 330                 335

Asn Phe Glu Lys Met Phe Asp Leu Thr Phe His Ala Phe His Ala Gly
                340                 345                 350

Asp Thr Gly Leu Pro Asn Glu Cys Tyr Cys Asn Gly Arg His Glu Ser
                355                 360                 365

Cys Leu Phe Val Ile Gln Leu Asn Asn Thr Ser Arg Val Leu Phe Arg
                370                 375                 380

Ser Arg Leu Xaa Trp Tyr Phe Trp Cys Gln Leu Gly Cys Thr Arg Arg
385                 390                 395                 400

Gln Cys Phe Ser Xaa Cys Phe Leu Gln Gly Phe Pro Phe Ser Leu Pro
                405                 410                 415

Trp Arg Cys His Asp Gln Gln Pro Leu Thr Glu Cys Xaa Xaa Lys Gly
                420                 425                 430

His Leu Xaa Lys Ile Phe Asp Xaa Asp Cys Ala Cys Ala Val Gln Xaa
                435                 440                 445

Cys His Leu Asp Xaa Pro Cys Leu Gly Pro Ser Gln Leu Pro Leu Ala
                450                 455                 460

Xaa Ser Xaa Met Gly Ser Phe Asp Arg Ser Thr Ile Ser Trp Tyr Xaa
465                 470                 475                 480
```

Leu Trp Leu Asp Ile Xaa Ser Ser His Ser Lys Leu Val Ala Arg Cys
            485                 490                 495

His Cys Thr Gln Xaa Gln Trp Arg Trp Cys Cys Phe Trp Phe Ser Xaa
            500                 505                 510

Ile Tyr Cys Cys Lys Gly Thr Ser Cys Ser Xaa Gly Ile Xaa Tyr Phe
            515                 520                 525

Tyr Arg Phe Pro Thr Cys Trp Pro Ser Phe Cys Xaa Trp Tyr Tyr Cys
            530                 535                 540

Cys Cys Ser Cys Ser Cys Cys Trp Gln Phe Tyr Trp Lys Arg Arg Lys
545                 550                 555                 560

Ser Ile Tyr Phe Xaa Gln Cys Phe Ile Gln Gln Asn Leu Gly Ser Lys
            565                 570                 575

His Ile Arg Cys Phe Ser Phe Gln Asp Cys Ala His Arg Phe Ser His
            580                 585                 590

Phe Arg Phe Ser Ser Pro Trp Tyr Ser Lys
            595                 600

<210> SEQ ID NO 19
<211> LENGTH: 1913
<212> TYPE: DNA
<213> ORGANISM: Mucor sp.

<400> SEQUENCE: 19
atgaaattat ctattatatc cgctgccttt ttagtggcta taacacacgc tgcttcataa      60
agtttaatgt aattgctcct aatgcaactg atgtcaaagt atctgtaaat ggacagcaag     120
tgacacttac tgcttcagat gcaaatgtcc cttacttcac tggttcagct gaagttggtt     180
cctcaaagac atacaaagta atcataaatt tattttgaat tcaatcatat taatcatctt     240
attctatagt atgttgcagg tggaacagaa gaaggttttg atcgttctct tgatggaatc     300
acaaactcaa catttaatga ttttttataat cgccccatca cttatgctaa ccttcctcaa     360
ttaccttggc caattgaaaa agacgtaagt tattttattt ttatcttttc tcagctaaaa     420
taaacattgt ctttctcagc ctcagtggac tcgttctgga aacaaagccg acattttcga     480
tgacaattat attcccagca ttttttttcca cggagatgac agtcaagtcc aaaatgtggt     540
taaaaacgta cctgctgacc gaatcagtgg tacactgacc tttatcggat ctaattacgt     600
ctactctttc cagaatgtct catttggtat tcacggtgct ggcaagaaac acaacaatgc     660
aaagcaatct tggaactgga tcttgtctgg aagtgatacg atgggtaacc gtaatttctt     720
taagcttcga catatggaag aagatcctac acagatccgt gaacgtcttt attctgacat     780
tttacatgcc atgggtactt atgccaatga tgctaccatg gttcgattgt ttattaacaa     840
tcaaggcttc ggtaccttca acatgttgga tgacatcact caattctctt atatcaatgc     900
taaattctat aatggcaaac cacctgctac cttgggtcct ctctatgatg gtgcctctgg     960
tgcagatttc ttatatcatc ctggtaacct cgatggatac tcttcttggg ttgccaacac    1020
agctaatcct aatggtgaag cttatgaagc tcttgatcct tctctgtaag gcctggaaac    1080
gagacgacct attaccgata atacagccaa ttgcgaactt tgaaaaaatg tttgatctga    1140
cgtttcatgc gttccatgct ggtgatactg ggctgccgaa tgaatgctac tgcaatggaa    1200
gacatgaatc gtgtctattc gtgatccaac tgaataatac cagtcgggta cttttttagat    1260 caagactttg atggtacttt tggtgtcaac ttggctgcac ccgaaggcaa tgcttttctt    1320
gatgtttctt acaaggattt cccttctcgt taccctggcg ctgtcatgat caacaacctc    1380

```
ttacagaatg ctgataaaaa ggccaccttt gaaaaatatt tgactgagac tgtgcgtgtg    1440
ctgttcaata atgtcacctt gactaaccgt gtcttggccc ttcacaactt cctcttgcct    1500
gatcttgaat gggatcgttc gatcgttcaa caatctcctg gtattaactt tggttggaca    1560
tttgatcaag tcactcaaaa cttgtggcaa ggtgtcactg cacccaataa caatggaggt    1620
ggtgctgctt ttggtttagt tgaatatatt gctgcaaagg cacaagctgt agctaaggaa    1680
tttaatattt ctatcgtttc ccaacctgtt ggccctcctt ctgctaatgg tactactgct    1740
gctgctcctg ctcctgctgc tggcaattct actggaaaag gaggaaatca atctatttct    1800
agcagtgctt catccaacaa aacctcggct caaagcacat caggtgcttc tcgttccaag    1860
actgcgccca tcgttttagc catttccgct ttagctctcc ttggtattct aaa           1913
```

```
<210> SEQ ID NO 20
<211> LENGTH: 637
<212> TYPE: PRT
<213> ORGANISM: Mucor sp.
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (67)..(67)
<223> OTHER INFORMATION: Any amino acid
<220> FEATURE:
<221> NAME/KEY: MOD_RES
<222> LOCATION: (69)..(69)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (173)..(173)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (198)..(198)
<223> OTHER INFORMATION: Any amino acid
<220> FEATURE:
<221> NAME/KEY: MOD_RES
<222> LOCATION: (232)..(232)
<223> OTHER INFORMATION: Any amino acid
```

```
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (238)..(238)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (259)..(259)
<223> OTHER INFORMATION: Any amino acid
<220> FEATURE:
<221> NAME/KEY: MOD_RES
<222> LOCATION: (270)..(270)
<223> OTHER INFORMATION: Any amino acid
<220> FEATURE:
<221> NAME/KEY: MOD_RES
<222> LOCATION: (279)..(279)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (304)..(304)
<223> OTHER INFORMATION: Any amino acid
<220> FEATURE:
<221> NAME/KEY: MOD_RES
<222> LOCATION: (316)..(316)
<223> OTHER INFORMATION: Any amino acid
<220> FEATURE:
<221> NAME/KEY: MOD_RES
<222> LOCATION: (329)..(329)
<223> OTHER INFORMATION: Any amino acid
<220> FEATURE:
<221> NAME/KEY: MOD_RES
<222> LOCATION: (342)..(342)
<223> OTHER INFORMATION: Any amino acid
<220> FEATURE:
<221> NAME/KEY: MOD_RES
<222> LOCATION: (344)..(344)
<223> OTHER INFORMATION: Any amino acid
<220> FEATURE:
<221> NAME/KEY: MOD_RES
<222> LOCATION: (346)..(346)
<223> OTHER INFORMATION: Any amino acid
<220> FEATURE:
<221> NAME/KEY: MOD_RES
<222> LOCATION: (349)..(349)
<223> OTHER INFORMATION: Any amino acid
<220> FEATURE:
<221> NAME/KEY: MOD_RES
<222> LOCATION: (352)..(352)
<223> OTHER INFORMATION: Any amino acid
<220> FEATURE:
<221> NAME/KEY: MOD_RES
<222> LOCATION: (367)..(367)
<223> OTHER INFORMATION: Any amino acid
<220> FEATURE:
<221> NAME/KEY: MOD_RES
<222> LOCATION: (380)..(380)
<223> OTHER INFORMATION: Any amino acid
<220> FEATURE:
<221> NAME/KEY: MOD_RES
<222> LOCATION: (408)..(408)
```

<223> OTHER INFORMATION: Any amino acid
<220> FEATURE:
<221> NAME/KEY: MOD_RES
<222> LOCATION: (411)..(411)
<223> OTHER INFORMATION: Any amino acid

<400> SEQUENCE: 20

```
Met Lys Leu Ser Ile Ser Ala Ala Phe Leu Val Ala Ile Thr His
1               5                   10                  15

Ala Ala Ser Xaa Ser Leu Met Xaa Leu Leu Met Gln Leu Met Ser
            20                  25                  30

Lys Tyr Leu Xaa Met Asp Ser Lys Xaa His Leu Leu Gln Met Gln
            35                  40                  45

Met Ser Leu Thr Ser Leu Val Gln Leu Lys Leu Val Pro Gln Arg His
50                  55                  60

Thr Lys Xaa Ser Xaa Ile Tyr Phe Glu Phe Asn His Ile Asn His Leu
65                  70                  75                  80

Ile Leu Xaa Tyr Val Ala Gly Gly Thr Glu Glu Gly Phe Asp Arg Ser
            85                  90                  95

Leu Asp Gly Ile Thr Asn Ser Thr Phe Asn Asp Phe Tyr Asn Arg Pro
            100                 105                 110

Ile Thr Tyr Ala Asn Leu Pro Gln Leu Pro Trp Pro Ile Glu Lys Asp
            115                 120                 125

Val Ser Tyr Phe Ile Phe Ile Phe Ser Gln Leu Lys Xaa Thr Leu Ser
130                 135                 140

Phe Ser Ala Ser Val Asp Ser Phe Trp Lys Gln Ser Arg His Phe Arg
145                 150                 155                 160

Xaa Gln Leu Tyr Ser Gln His Phe Phe Pro Arg Arg Xaa Gln Ser Ser
            165                 170                 175

Pro Lys Cys Gly Xaa Lys Arg Thr Cys Xaa Pro Asn Gln Trp Tyr Thr
            180                 185                 190

Asp Leu Tyr Arg Ile Xaa Leu Arg Leu Leu Phe Pro Glu Cys Leu Ile
            195                 200                 205

Trp Tyr Ser Arg Cys Trp Gln Glu Thr Gln Gln Cys Lys Ala Ile Leu
210                 215                 220

Glu Leu Asp Leu Val Trp Lys Xaa Tyr Asp Gly Xaa Pro Xaa Phe Leu
225                 230                 235                 240

Xaa Ala Ser Thr Tyr Gly Arg Arg Ser Tyr Thr Asp Pro Xaa Thr Ser
            245                 250                 255

Leu Phe Xaa His Phe Thr Cys His Gly Tyr Leu Cys Gly Xaa Cys Tyr
            260                 265                 270

His Gly Ser Ile Val Tyr Xaa Gln Ser Arg Leu Arg Tyr Leu Gln His
            275                 280                 285

Val Gly Xaa His His Ser Ile Leu Leu Tyr Gln Cys Xaa Ile Leu Xaa
            290                 295                 300

Trp Gln Thr Thr Cys Tyr Leu Gly Ser Ser Leu Xaa Trp Cys Leu Trp
305                 310                 315                 320

Cys Arg Phe Leu Ile Ser Ser Trp Xaa Pro Arg Trp Ile Leu Phe Leu
            325                 330                 335

Gly Cys Gln His Ser Xaa Ser Xaa Trp Xaa Ser Leu Xaa Ser Ser Xaa
            340                 345                 350

Ser Phe Ser Val Arg Pro Gly Asn Glu Thr Thr Tyr Tyr Arg Xaa Tyr
            355                 360                 365

Ser Gln Leu Arg Thr Leu Lys Lys Cys Leu Ile Xaa Arg Phe Met Arg
370                 375                 380
```

Ser Met Leu Val Ile Leu Gly Cys Arg Met Asn Ala Thr Ala Met Glu
385                 390                 395                 400

Asp Met Asn Arg Val Tyr Ser Xaa Ser Asn Xaa Ile Ile Pro Val Gly
                405                 410                 415

Tyr Phe Leu Asp Gln Asp Phe Asp Gly Thr Phe Gly Val Asn Leu Ala
            420                 425                 430

Ala Pro Glu Gly Asn Ala Phe Leu Asp Val Ser Tyr Lys Asp Phe Pro
        435                 440                 445

Ser Arg Tyr Pro Gly Ala Val Met Ile Asn Asn Leu Leu Gln Asn Ala
    450                 455                 460

Asp Lys Lys Ala Thr Phe Glu Lys Tyr Leu Thr Glu Thr Val Arg Val
465                 470                 475                 480

Leu Phe Asn Asn Val Thr Leu Thr Asn Arg Val Leu Ala Leu His Asn
                485                 490                 495

Phe Leu Leu Pro Asp Leu Glu Trp Asp Arg Ser Ile Val Gln Gln Ser
            500                 505                 510

Pro Gly Ile Asn Phe Gly Trp Thr Phe Asp Gln Val Thr Gln Asn Leu
        515                 520                 525

Trp Gln Gly Val Thr Ala Pro Asn Asn Asn Gly Gly Gly Ala Ala Phe
    530                 535                 540

Gly Leu Val Glu Tyr Ile Ala Ala Lys Ala Gln Ala Val Ala Lys Glu
545                 550                 555                 560

Phe Asn Ile Ser Ile Val Ser Gln Pro Val Gly Pro Pro Ser Ala Asn
                565                 570                 575

Gly Thr Thr Ala Ala Pro Ala Pro Ala Ala Gly Asn Ser Thr Gly
            580                 585                 590

Lys Gly Gly Asn Gln Ser Ile Ser Ser Ser Ala Ser Ser Asn Lys Thr
        595                 600                 605

Ser Ala Gln Ser Thr Ser Gly Ala Ser Arg Ser Lys Thr Ala Pro Ile
    610                 615                 620

Val Leu Ala Ile Ser Ala Leu Ala Leu Leu Gly Ile Leu
625                 630                 635

<210> SEQ ID NO 21
<211> LENGTH: 1809
<212> TYPE: DNA
<213> ORGANISM: Lichtheimia corymbifera

<400> SEQUENCE: 21
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc ccttatttca ctggttcagc tgaagttggt     180
tcctcaaaga catacaaata tgttgcaggt ggaacagaag aaagttttga tcgttctctt     240
gatggaatca caactcaac acttaatgat tttataatc gccccgtcac ttatgctaac      300
cttcctcaat taccttggcc aattgaaaaa gaccctcagt ggactcgttc tggaaacaaa     360
gccgacattt tcgatgacaa ttatattccc agcgttttt tccacggaga tgacagtcaa      420
gtccaaaatg tggttaaaaa cgtacctgct gaccgaatca gtggtacact gacctttatt     480
ggatctaatt acgtctactc tttccagaat gtctcatttg gtattcacgg tgctggcaag    540
aaacacaaca atgcaaaaca atcttggaac tggatattgt ctggaagtga tacgatgggt    600
aaccgcaatt tctttaagct tcgacatatg gaagaagatc ctacacagat ccgtgaacgt    660

```
cttattctg acatttaca tgccatgggt acttatgcca atgatgctac catggttcga    720
ttgttttta acaaccaagg cttcggtacc ttcaacatgt tggatgatat cactcaattc    780
tcttatatca atgctaaat ttataatggc aaaccacctg ctaccttggg tcctctctat    840
gatggtgcct ctggtgcaga tttcttatat catcctggta acctcgatgg atactcttct    900
tgggttgcca acacagccaa tcctaatggt gaagcttatg aagctcttga tcctctctgt    960
aaggcctgga acgagacgac ctataccgat aatacagcca ttgcaaactt tgaaaaaatg   1020
tttgatctcg accgtttcat gcgtttcatg gttattgaat acttgactgc cgattgggat   1080
ggttactgga tgggacagac caatgatggt gcctatcgtg atccaactga taataacaag   1140
tggtactttt tagatcaaga ctttgatggt acttttggtg tcaacttggc tgcacccgaa   1200
ggcaatgctt tcttgatgt ttcttacaag gatttcccct tctcgttacc tggcgctgtc   1260
atgatcaaca acctcttaca gaatgctgat aaaaaggcca cctatgaaaa atatttgact   1320
gagactgtgc gtgtgctgtt caataatgtc accttgacta accgtgtctt ggcccttcac   1380
aacttcctct tgcctgatct tgaatgggat cgttcgatcg ttcaacaatc tcctggtatt   1440
aactttggtt ggacatttga tcaagtcact caaaacttgt ggcaaggtgt cactgcaccc   1500
aataacaatg gaggtggtgc tgcttttggt ttagttgaat atattgctac aaaggcacaa   1560
gctgtagcta aggaattaa tatttctatc gtttcccaac ctgttggccc tccttctgct   1620
aatggtacta ctgctgctgc tcctgctcct gctgctggca attctactgg aaaaggagga   1680
aatcaatcta tttctagcag tgcttcatcc aacaaaacct cggctcaaag cacatcaggt   1740
gcttctcgtt ccaagactgc gcccatcatt tttagccatt ccgctttag ctctccttg   1800
tattctaaa                                                           1809
```

<210> SEQ ID NO 22
<211> LENGTH: 603
<212> TYPE: PRT
<213> ORGANISM: Lichtheimia corymbifera

<400> SEQUENCE: 22

```
Met Lys Leu Ser Ile Ile Ser Ala Ala Phe Leu Val Ala Ile Thr His
1               5                   10                  15

Ala Ala Ser Ile Lys Phe Asn Val Ile Ala Pro Asn Ala Thr Asp Val
                20                  25                  30

Lys Val Ser Val Asn Gly Gln Gln Val Thr Leu Thr Ala Ser Asp Ala
            35                  40                  45

Asn Val Pro Tyr Phe Thr Gly Ser Ala Glu Val Gly Ser Ser Lys Thr
        50                  55                  60

Tyr Lys Tyr Val Ala Gly Gly Thr Glu Glu Ser Phe Asp Arg Ser Leu
65                  70                  75                  80

Asp Gly Ile Thr Asn Ser Thr Leu Asn Asp Phe Tyr Asn Arg Pro Val
                85                  90                  95

Thr Tyr Ala Asn Leu Pro Gln Leu Pro Trp Pro Ile Glu Lys Asp Pro
            100                 105                 110

Gln Trp Thr Arg Ser Gly Asn Lys Ala Asp Ile Phe Asp Asp Asn Tyr
        115                 120                 125

Ile Pro Ser Val Phe Phe His Gly Asp Asp Ser Gln Val Gln Asn Val
    130                 135                 140

Val Lys Asn Val Pro Ala Asp Arg Ile Ser Gly Thr Leu Thr Phe Ile
145                 150                 155                 160

Gly Ser Asn Tyr Val Tyr Ser Phe Gln Asn Val Ser Phe Gly Ile His
```

```
                165                 170                 175
Gly Ala Gly Lys Lys His Asn Asn Ala Lys Gln Ser Trp Asn Trp Ile
            180                 185                 190

Leu Ser Gly Ser Asp Thr Met Gly Asn Arg Asn Phe Phe Lys Leu Arg
            195                 200                 205

His Met Glu Glu Asp Pro Thr Gln Ile Arg Glu Arg Leu Tyr Ser Asp
            210                 215                 220

Ile Leu His Ala Met Gly Thr Tyr Ala Asn Asp Ala Thr Met Val Arg
225                 230                 235                 240

Leu Phe Ile Asn Asn Gln Gly Phe Gly Thr Phe Asn Met Leu Asp Asp
                245                 250                 255

Ile Thr Gln Phe Ser Tyr Ile Asn Ala Lys Phe Tyr Asn Gly Lys Pro
                260                 265                 270

Pro Ala Thr Leu Gly Pro Leu Tyr Asp Gly Ala Ser Gly Ala Asp Phe
                275                 280                 285

Leu Tyr His Pro Gly Asn Leu Asp Gly Tyr Ser Ser Trp Val Ala Asn
                290                 295                 300

Thr Ala Asn Pro Asn Gly Glu Ala Tyr Glu Ala Leu Asp Pro Leu Cys
305                 310                 315                 320

Lys Ala Trp Asn Glu Thr Thr Tyr Thr Asp Asn Thr Ala Ile Ala Asn
                325                 330                 335

Phe Glu Lys Met Phe Asp Leu Asp Arg Phe Met Arg Phe Met Val Ile
                340                 345                 350

Glu Tyr Leu Thr Ala Asp Trp Asp Gly Tyr Trp Met Gly Gln Thr Asn
                355                 360                 365

Asp Gly Ala Tyr Arg Asp Pro Thr Asp Asn Asn Lys Trp Tyr Phe Leu
                370                 375                 380

Asp Gln Asp Phe Asp Gly Thr Phe Gly Val Asn Leu Ala Ala Pro Glu
385                 390                 395                 400

Gly Asn Ala Phe Leu Asp Val Ser Tyr Lys Asp Phe Pro Ser Arg Tyr
                405                 410                 415

Pro Gly Ala Val Met Ile Asn Asn Leu Leu Gln Asn Ala Asp Lys Lys
                420                 425                 430

Ala Thr Tyr Glu Lys Tyr Leu Thr Glu Thr Val Arg Val Leu Phe Asn
                435                 440                 445

Asn Val Thr Leu Thr Asn Arg Val Leu Ala Leu His Asn Phe Leu Leu
                450                 455                 460

Pro Asp Leu Glu Trp Asp Arg Ser Ile Val Gln Gln Ser Pro Gly Ile
465                 470                 475                 480

Asn Phe Gly Trp Thr Phe Asp Gln Val Thr Gln Asn Leu Trp Gln Gly
                485                 490                 495

Val Thr Ala Pro Asn Asn Gly Gly Ala Ala Phe Gly Leu Val
                500                 505                 510

Glu Tyr Ile Ala Thr Lys Ala Gln Ala Val Ala Lys Glu Phe Asn Ile
                515                 520                 525

Ser Ile Val Ser Gln Pro Val Gly Pro Ser Ala Asn Gly Thr Thr
                530                 535                 540

Ala Ala Ala Pro Ala Pro Ala Gly Asn Ser Thr Gly Lys Gly Gly
545                 550                 555                 560

Asn Gln Ser Ile Ser Ser Ser Ala Ser Ser Asn Lys Thr Ser Ala Gln
                565                 570                 575

Ser Thr Ser Gly Ala Ser Arg Ser Lys Thr Ala Pro Ile Ile Phe Ser
                580                 585                 590
```

His Phe Arg Phe Ser Ser Pro Leu Tyr Ser Lys
        595                 600

<210> SEQ ID NO 23
<211> LENGTH: 1916
<212> TYPE: DNA
<213> ORGANISM: Lichtheimia corymbifera

<400> SEQUENCE: 23

```
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc cctatttca ctggttcagc tgaagttggt     180
tcctcaaaga catacaaagt aatcataaat ttagtttgaa ttcaatgaga ttaatcatct     240
tattctatag tatgttgcag gtggaacaga agaaagtttt gatcgttctc ttgatggaat     300
cacaaactca acacttaatg attttttataa tcgccccgtc acttatgcta accttcctca     360
attaccttgg ccaattgaaa aagacgtaag ttattttatt tttatctttt ctcagctaaa     420
ataaacattg tctttctcag cctcagtgga ctcgttctgg aaacaaagcc gacattttcg     480
atgacaatta tattcccagc gtttttttcc acggagatga cagtcaagtc caaaatgtgg     540
ttaaaaacgt acctgctgac cgaatcagtg gtacactgac ctttattgga tctaattacg     600
tctactcttt ccagaatgtc tcatttggta ttcacggtgc tggcaagaaa cacaacaatg     660
caaaacaatc ttggaactgg atattgtctg gaagtgatac gatgggtaac cgcaatttct     720
ttaagcttcg acatatggaa gaagatccta cacagatccg tgaacgtctt tattctgaca     780
ttttacatgc catgggtact tatgccaatg atgctaccat ggttcgattg tttattaaca     840
accaaggctt cggtaccttc aacatgttgg atgatatcac tcaattctct tatatcaatg     900
ctaaatttta atggcaaa ccacctgcta ccttgggtcc tctctatgat ggtgcctctg     960
gtgcagattt cttatatcat cctggtaacc tcgatggata ctcttcttgg ttgccaaca    1020
cagccaatcc taatggtgaa gcttatgaag ctcttgatcc tctctgtaag gcctggaacg    1080
agacgaccta taccgataat acagccattg caaactttga aaaaatgttt gatctcgacc    1140
gtttcatgcg tttcatggtt attgaatact tgactgccga ttgggatggt tactggatgg    1200
gacagaccaa tgatggtgcc tatcgtgatc caactgataa taacaagtgg tactttttag    1260
atcaagactt tgatggtact tttggtgtca acttggctgc acccgaaggc aatgcttttc    1320
ttgatgtttc ttacaaggat ttcccttctc gttaccctgg cgctgtcatg atcaacaacc    1380
tcttacagaa tgctgataaa aaggccacct atgaaaata tttgactgag actgtgcgtg    1440
tgctgttcaa taatgtcacc ttgactaacc gtgtcttggc ccttcacaac ttcctcttgc    1500
ctgatcttga atgggatcgt tcgatcgttc aacaatctcc tggtattaac tttggttgga    1560
catttgatca agtcactcaa aacttgtggc aaggtgtcac tgcacccaat aacaatggag    1620
gtggtgctgc ttttggttta gttgaatata ttgctacaaa ggcacaagct gtagctaagg    1680
aatttaatat ttctatcgtt tcccaacctg ttggccctcc ttctgctaat ggtactactg    1740
ctgctgctcc tgctcctgct gctggcaatt ctactggaaa aggaggaaat caatctattt    1800
ctagcagtgc ttcatccaac aaaacctcgg ctcaaagcac atcaggtgct tctcgttcca    1860
agactgcgcc catcattttt agccatttcc gctttagctc tcccttgtat tctaaa       1916
```

<210> SEQ ID NO 24
<211> LENGTH: 638

```
<212> TYPE: PRT
<213> ORGANISM: Lichtheimia corymbifera
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (193)..(193)
<223> OTHER INFORMATION: Any amino acid
<220> FEATURE:
<221> NAME/KEY: MOD_RES
<222> LOCATION: (391)..(391)
<223> OTHER INFORMATION: Any amino acid
<220> FEATURE:
<221> NAME/KEY: MOD_RES
<222> LOCATION: (420)..(420)
<223> OTHER INFORMATION: Any amino acid
<220> FEATURE:
<221> NAME/KEY: MOD_RES
<222> LOCATION: (457)..(457)
<223> OTHER INFORMATION: Any amino acid
<220> FEATURE:
<221> NAME/KEY: MOD_RES
<222> LOCATION: (475)..(475)
<223> OTHER INFORMATION: Any amino acid
<220> FEATURE:
<221> NAME/KEY: MOD_RES
<222> LOCATION: (488)..(488)
<223> OTHER INFORMATION: Any amino acid
<220> FEATURE:
<221> NAME/KEY: MOD_RES
<222> LOCATION: (547)..(547)
<223> OTHER INFORMATION: Any amino acid
<220> FEATURE:
<221> NAME/KEY: MOD_RES
<222> LOCATION: (558)..(558)
<223> OTHER INFORMATION: Any amino acid

<400> SEQUENCE: 24

Met Lys Leu Ser Ile Ile Ser Ala Ala Phe Leu Val Ala Ile Thr His
1               5                   10                  15

Ala Ala Ser Ile Lys Phe Asn Val Ile Ala Pro Asn Ala Thr Asp Val
            20                  25                  30
```

-continued

```
Lys Val Ser Val Asn Gly Gln Gln Val Thr Leu Thr Ala Ser Asp Ala
             35                  40                  45

Asn Val Pro Tyr Phe Thr Gly Ser Ala Glu Val Gly Ser Ser Lys Thr
     50                  55                  60

Tyr Lys Val Ile Ile Asn Leu Val Xaa Ile Gln Xaa Asp Xaa Ser Ser
 65                  70                  75                  80

Tyr Ser Ile Val Cys Cys Arg Trp Asn Arg Arg Lys Phe Xaa Ser Phe
                 85                  90                  95

Ser Xaa Trp Asn His Lys Leu Asn Thr Xaa Xaa Phe Leu Xaa Ser Pro
            100                 105                 110

Arg His Leu Cys Xaa Pro Ser Ser Ile Thr Leu Ala Asn Xaa Lys Arg
            115                 120                 125

Arg Lys Leu Phe Tyr Phe Tyr Leu Phe Ser Ala Lys Ile Asn Ile Val
        130                 135                 140

Phe Leu Ser Leu Ser Gly Leu Val Leu Glu Thr Lys Pro Thr Phe Ser
145                 150                 155                 160

Met Thr Ile Ile Phe Pro Ala Phe Phe Ser Thr Glu Met Thr Val Lys
                165                 170                 175

Ser Lys Met Trp Leu Lys Thr Tyr Leu Leu Thr Glu Ser Val Val His
            180                 185                 190

Xaa Pro Leu Leu Asp Leu Ile Thr Ser Thr Leu Ser Arg Met Ser His
            195                 200                 205

Leu Val Phe Thr Val Leu Ala Arg Asn Thr Thr Met Gln Asn Asn Leu
        210                 215                 220

Gly Thr Gly Tyr Cys Leu Glu Val Ile Arg Trp Val Thr Ala Ile Ser
225                 230                 235                 240

Leu Ser Phe Asp Ile Trp Lys Lys Ile Leu His Arg Ser Val Asn Val
                245                 250                 255

Phe Ile Leu Thr Phe Tyr Met Pro Trp Val Leu Met Pro Met Met Leu
            260                 265                 270

Pro Trp Phe Asp Cys Leu Leu Thr Thr Lys Ala Ser Val Pro Ser Thr
            275                 280                 285

Cys Trp Met Ile Ser Leu Asn Ser Leu Ile Ser Met Leu Asn Phe Ile
        290                 295                 300

Met Ala Asn His Leu Leu Pro Trp Val Leu Ser Met Val Pro Leu
305                 310                 315                 320

Val Gln Ile Ser Tyr Ile Ile Leu Val Thr Ser Met Asp Thr Leu Leu
                325                 330                 335

Gly Leu Pro Thr Gln Pro Ile Leu Met Val Lys Leu Met Lys Leu Leu
            340                 345                 350

Ile Leu Ser Val Arg Pro Gly Thr Arg Arg Pro Ile Pro Ile Ile Gln
            355                 360                 365

Pro Leu Gln Thr Leu Lys Lys Cys Leu Ile Ser Thr Val Ser Cys Val
        370                 375                 380

Ser Trp Leu Leu Asn Thr Xaa Leu Pro Ile Gly Met Val Thr Gly Trp
385                 390                 395                 400

Asp Arg Pro Met Met Val Pro Ile Val Ile Gln Leu Ile Ile Thr Ser
                405                 410                 415

Gly Thr Phe Xaa Ile Lys Thr Leu Met Val Leu Leu Val Ser Thr Trp
            420                 425                 430

Leu His Pro Lys Ala Met Leu Phe Leu Met Phe Leu Thr Arg Ile Ser
            435                 440                 445

Leu Leu Val Thr Leu Ala Leu Ser Xaa Ser Thr Thr Ser Tyr Arg Met
```

```
                450              455              460
Leu Ile Lys Arg Pro Pro Met Lys Asn Ile Xaa Leu Arg Leu Cys Val
465                 470                 475                 480

Cys Cys Ser Ile Met Ser Pro Xaa Leu Thr Val Ser Trp Pro Phe Thr
                485                 490                 495

Thr Ser Ser Cys Leu Ile Leu Asn Gly Ile Val Arg Ser Phe Asn Asn
            500                 505                 510

Leu Leu Val Leu Thr Leu Val Gly His Leu Ile Lys Ser Leu Lys Thr
            515                 520                 525

Cys Gly Lys Val Ser Leu His Pro Ile Thr Met Glu Val Val Leu Leu
    530                 535                 540

Leu Val Xaa Leu Asn Ile Leu Leu Gln Arg His Lys Leu Xaa Leu Arg
545                 550                 555                 560

Asn Leu Ile Phe Leu Ser Phe Pro Asn Leu Leu Ala Leu Leu Leu Leu
                565                 570                 575

Met Val Leu Leu Leu Leu Leu Leu Leu Leu Leu Ala Ile Leu Leu
            580                 585                 590

Glu Lys Glu Glu Ile Asn Leu Phe Leu Ala Val Leu His Pro Thr Lys
            595                 600                 605

Pro Arg Leu Lys Ala His Gln Val Leu Leu Val Pro Arg Leu Arg Pro
    610                 615                 620

Ser Phe Leu Ala Ile Ser Ala Leu Ala Leu Pro Cys Ile Leu
625                 630                 635

<210> SEQ ID NO 25
<211> LENGTH: 1803
<212> TYPE: DNA
<213> ORGANISM: Cunninghamella bertholetiae

<400> SEQUENCE: 25
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc cctatttca  ctggttcagc tgaagttggt     180
gcctcaaaga catacaaata tgttgcaggt ggaacagaag aaagttttga tcgttctctt     240
gatggaatca caaactcaac acttaatgat ttttataacc gccccgtcac ttatgctaac     300
cttcctcaat taccttggcc aattgaaaaa gaccctcagt ggactcgttc tggaagcaaa     360
gccgacattt tcgatgacaa ttatattccc agcgtttttt tccacggaga tgacagtcaa     420
gtccaaaatg tggttaaaaa cgtacctgct gaccgaatca gtggtacact gacctttatt     480
ggatctaatt acgtctactc tttccagaat gtctcatttg gtattcacgg tgctggcaag     540
aaacacaaca atgcaaaaca atcttggaac tggatattgt ctggaagtga tacgatgggt     600
aaccgcaatt tctttaagct tcgacatatg gaagaagatc ctacacagat tcgtgaacgt     660
ctttattctg acattttaca tgccatgggt acttatgcca atgatgctac catggttcga     720
ttgtttatta acaaccaagg cttcggtacc ttcaacatgt ggatgatat cactcaattc     780 tcctatatca atgctaaatt ttataatggc aaaccacctg ctaccttggg tcctctctat     840
gatggtgcct ctggtgcaga cttcttatat catcctggta acctcgatgg atactcttct     900
tgggttgcca acacagccaa tcctaatgtg aagcttatga agcctcttga tcctctctgt     960
agcctggaac gagacgacct aataccgata atacagccat gcaaactttt gaaaaaatgt    1020
ttgatctcga ccgtttcatg cgtttcatgg ttattgaata cttgactgcc gattgggatg    1080
```

-continued

```
gttactggat gggacagacc aatgatggtg cctatcgtga tccaactgat aataacaagt    1140
ggtacttttt agatcaagac tttgatggta cttttggtgt caacttggct gcacccgaag    1200
gcaatgcttt tcttgatgtt tcttacaagg atttcccttc tcgttaccct ggcgctgtca    1260
tgatcaacaa cctcttacag aatgctgata aaaaggccac ctttgaaaaa tatttgactg    1320
agactgtgcg tgtgctgttc aataatgtca ccttgactaa ccgtgtcttg gcccttcaca    1380
acttcctctt gcctgatctt gaatgggatc gttcgatcgt tcaacaatct cctggtatta    1440
actttggttg acatttgat caagtcactc aaaacttgtg gcaaggtgtc actgcaccca    1500
ataacaatgg aggtggtgct gcttttggtt tagttgaata tattgctgca aaggcacaag    1560
ctgtagctaa ggaatttaat atttctatcg tttcccaacc tgttggccct ccttctgcta    1620
atggtactac tgctgctgct ctgctctgct gctgcaattc tactggaaaa gagaaatcaa    1680 tctatttct agcagtgctt catcaacaaa gctcggctca aggcacatca gtgccttctc    1740
gatcaagact gcgcccatcg attaagcagt tcgctttagc ttccctgggg taatctccaa    1800
aaa                                                                 1803
```

```
<210> SEQ ID NO 26
<211> LENGTH: 636
<212> TYPE: PRT
<213> ORGANISM: Cunninghamella bertholetiae
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (173)..(173)
<223> OTHER INFORMATION: Any amino acid
<220> FEATURE:
<221> NAME/KEY: MOD_RES
<222> LOCATION: (181)..(181)
<223> OTHER INFORMATION: Any amino acid
```

```
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (198)..(198)
<223> OTHER INFORMATION: Any amino acid
<220> FEATURE:
<221> NAME/KEY: MOD_RES
<222> LOCATION: (232)..(232)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (259)..(259)
<223> OTHER INFORMATION: Any amino acid
<220> FEATURE:
<221> NAME/KEY: MOD_RES
<222> LOCATION: (270)..(270)
<223> OTHER INFORMATION: Any amino acid
<220> FEATURE:
<221> NAME/KEY: MOD_RES
<222> LOCATION: (279)..(279)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (304)..(304)
<223> OTHER INFORMATION: Any amino acid
<220> FEATURE:
<221> NAME/KEY: MOD_RES
<222> LOCATION: (316)..(316)
<223> OTHER INFORMATION: Any amino acid
<220> FEATURE:
<221> NAME/KEY: MOD_RES
<222> LOCATION: (329)..(329)
<223> OTHER INFORMATION: Any amino acid
<220> FEATURE:
<221> NAME/KEY: MOD_RES
<222> LOCATION: (344)..(344)
<223> OTHER INFORMATION: Any amino acid
<220> FEATURE:
<221> NAME/KEY: MOD_RES
<222> LOCATION: (352)..(352)
<223> OTHER INFORMATION: Any amino acid
<220> FEATURE:
<221> NAME/KEY: MOD_RES
<222> LOCATION: (356)..(356)
<223> OTHER INFORMATION: Any amino acid
<220> FEATURE:
<221> NAME/KEY: MOD_RES
<222> LOCATION: (633)..(633)
<223> OTHER INFORMATION: Any amino acid

<400> SEQUENCE: 26

Met Lys Leu Ser Ile Ile Ser Ala Ala Phe Leu Val Ala Ile Thr His
1               5                   10                  15

Ala Ala Ser Ile Lys Phe Asn Val Ile Ala Pro Asn Ala Thr Asp Val
```

```
                 20                  25                  30
Lys Val Ser Val Asn Gly Gln Gln Val Thr Leu Thr Ala Ser Asp Ala
             35                  40                  45

Asn Val Pro Tyr Phe Thr Gly Ser Ala Glu Val Gly Ala Ser Lys Thr
         50                  55                  60

Tyr Lys Val Ile Ile Asn Leu Val Xaa Ile Gln Xaa Asp Xaa Ser Ser
 65                  70                  75                  80

Tyr Ser Ile Val Cys Cys Arg Trp Asn Arg Arg Lys Phe Xaa Ser Phe
                 85                  90                  95

Ser Xaa Trp Asn His Lys Leu Asn Thr Xaa Xaa Phe Leu Xaa Pro Pro
            100                 105                 110

Arg His Leu Cys Xaa Pro Ser Ser Ile Thr Leu Ala Asn Xaa Lys Arg
        115                 120                 125

Arg Lys Leu Phe Tyr Phe Tyr Leu Phe Ser Ala Lys Ile Asn Ile Val
        130                 135                 140

Phe Ser Ala Ser Val Asp Ser Phe Trp Lys Gln Ser Arg His Phe Arg
145                 150                 155                 160

Xaa Gln Leu Tyr Ser Gln Arg Phe Phe Pro Arg Arg Xaa Gln Ser Ser
                165                 170                 175

Pro Lys Cys Gly Xaa Lys Arg Thr Cys Xaa Pro Asn Gln Trp Tyr Thr
            180                 185                 190

Asp Leu Tyr Trp Ile Xaa Leu Arg Leu Leu Phe Pro Glu Cys Leu Ile
            195                 200                 205

Trp Tyr Ser Arg Cys Trp Gln Glu Thr Gln Gln Cys Lys Thr Ile Leu
        210                 215                 220

Glu Leu Asp Ile Val Trp Lys Xaa Tyr Asp Gly Xaa Pro Gln Phe Leu
225                 230                 235                 240

Xaa Ala Ser Thr Tyr Gly Arg Arg Ser Tyr Thr Asp Ser Xaa Thr Ser
                245                 250                 255

Leu Phe Xaa His Phe Thr Cys His Gly Tyr Leu Cys Gln Xaa Cys Tyr
            260                 265                 270

His Gly Ser Ile Val Tyr Xaa Gln Pro Arg Leu Arg Tyr Leu Gln His
        275                 280                 285

Val Gly Xaa Tyr His Ser Ile Leu Leu Tyr Gln Cys Xaa Ile Leu Xaa
        290                 295                 300

Trp Gln Thr Thr Cys Tyr Leu Gly Ser Ser Leu Xaa Trp Cys Leu Trp
305                 310                 315                 320

Cys Arg Leu Leu Ile Ser Ser Trp Xaa Pro Arg Trp Ile Leu Phe Leu
                325                 330                 335

Gly Cys Gln His Ser Gln Ser Xaa Cys Glu Ala Tyr Glu Ala Ser Xaa
            340                 345                 350

Ser Ser Leu Xaa Pro Gly Thr Arg Arg Pro Asn Thr Asp Asn Thr Ala
        355                 360                 365

Ile Ala Asn Phe Glu Lys Met Phe Asp Leu Asp Arg Phe Met Arg Phe
        370                 375                 380

Met Val Ile Glu Tyr Leu Thr Ala Asp Trp Asp Gly Tyr Trp Met Gly
385                 390                 395                 400

Gln Thr Asn Asp Gly Ala Tyr Arg Asp Pro Thr Asp Asn Asn Lys Trp
                405                 410                 415

Tyr Phe Leu Asp Gln Asp Phe Asp Gly Thr Phe Gly Val Asn Leu Ala
            420                 425                 430

Ala Pro Glu Gly Asn Ala Phe Leu Asp Val Ser Tyr Lys Asp Phe Pro
        435                 440                 445
```

```
Ser Arg Tyr Pro Gly Ala Val Met Ile Asn Asn Leu Leu Gln Asn Ala
    450                 455                 460

Asp Lys Lys Ala Thr Phe Glu Lys Tyr Leu Thr Glu Thr Val Arg Val
465                 470                 475                 480

Leu Phe Asn Asn Val Thr Leu Thr Asn Arg Val Leu Ala Leu His Asn
                485                 490                 495

Phe Leu Leu Pro Asp Leu Glu Trp Asp Arg Ser Ile Val Gln Gln Ser
                500                 505                 510

Pro Gly Ile Asn Phe Gly Trp Thr Phe Asp Gln Val Thr Gln Asn Leu
            515                 520                 525

Trp Gln Gly Val Thr Ala Pro Asn Asn Gly Gly Ala Ala Phe
    530                 535                 540

Gly Leu Val Glu Tyr Ile Ala Ala Lys Ala Gln Ala Val Ala Lys Glu
545                 550                 555                 560

Phe Asn Ile Ser Ile Val Ser Gln Pro Val Gly Pro Pro Ser Ala Asn
                565                 570                 575

Gly Thr Thr Ala Ala Ala Leu Leu Cys Cys Cys Asn Ser Thr Gly Lys
            580                 585                 590

Glu Lys Ser Ile Tyr Phe Leu Ala Val Leu His Gln Gln Ser Ser Ala
    595                 600                 605

Gln Gly Thr Ser Val Pro Ser Arg Ser Arg Leu Arg Pro Ser Ile Lys
    610                 615                 620

Gln Phe Ala Leu Ala Ser Leu Gly Xaa Ser Pro Lys
625                 630                 635

<210> SEQ ID NO 27
<211> LENGTH: 1909
<212> TYPE: DNA
<213> ORGANISM: Cunninghamella bertholetiae

<400> SEQUENCE: 27
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc cctatttca ctggttcagc tgaagttggt      180
gcctcaaaga catacaaagt aatcataaat ttagtttgaa ttcaatgaga ttaatcatct     240
tattctatag tatgttgcag gtggaacaga agaaagtttt gatcgttctc ttgatggaat     300
cacaaactca acacttaatg attttttataa ccgccccgtc acttatgcta accttcctca    360
attaccttgg ccaattgaaa agacgtaag ttatttatt tttatctttt ctcagctaaa       420
ataaacattg tcttctcagc ctcagtggac tcgttctgga agcaaagccg acattttcga    480
tgacaattat attcccagcg ttttttttcca cggagatgac agtcagtcc aaaatgtggt    540 taaaaacgta cctgctgacc gaatcagtgg tacactgacc tttattggat ctaattacgt   600
ctactctttc cagaatgtct catttggtat tcacggtgct ggcaagaaac acaacaatgc    660
aaaacaatct tggaactgga tattgtctgg aagtgatacg atgggtaacc gcaatttctt    720
taagcttcga catatggaag aagatcctac acagattcgt gaacgtcttt attctgacat    780
tttacatgcc atgggtactt atgccaatga tgctaccatg gttcgattgt ttattaacaa    840
ccaaggcttc ggtaccttca acatgttgga tgatatcact caattctcct atatcaatgc    900
taaattttat aatggcaaac cacctgctac cttgggtcct ctctatgatg gtgcctctgg    960
tgcagacttc ttatatcatc ctggtaacct cgatggatac tcttcttggg ttgccaacac   1020
```

```
agccaatcct aatgtgaagc ttatgaagcc tcttgatcct ctctgtagcc tggaacgaga    1080
cgacctaata ccgataatac agccattgca aactttgaaa aaatgtttga tctcgaccgt    1140
ttcatgcgtt tcatggttat tgaatacttg actgccgatt gggatggtta ctggatggga    1200
cagaccaatg atggtgccta tcgtgatcca actgataata acaagtggta cttttttagat   1260 caagactttg atggtacttt tggtgtcaac ttggctgcac ccgaaggcaa tgcttttctt    1320
gatgtttctt acaaggattt cccttctcgt taccctggcg ctgtcatgat caacaacctc    1380
ttacagaatg ctgataaaaa ggccaccttt gaaaaatatt tgactgagac tgtgcgtgtg    1440
ctgttcaata atgtcacctt gactaaccgt gtcttggccc ttcacaactt cctcttgcct    1500
gatcttgaat gggatcgttc gatcgttcaa caatctcctg gtattaactt tggttggaca    1560
tttgatcaag tcactcaaaa cttgtggcaa ggtgtcactg cacccaataa caatggaggt    1620
ggtgctgctt ttggtttagt tgaatatatt gctgcaaagg cacaagctgt agctaaggaa    1680
tttaatattt ctatcgtttc ccaacctgtt ggccctcctt ctgctaatgg tactactgct    1740
gctgctctgc tctgctgctg caattctact ggaaaagaga atcaatcta  ttttctagca    1800 gtgcttcatc aacaaagctc ggctcaaggc acatcagtgc cttctcgatc aagactgcgc    1860
ccatcgatta agcagttcgc tttagcttcc ctggggtaat ctccaaaaa              1909
```

```
<210> SEQ ID NO 28
<211> LENGTH: 636
<212> TYPE: PRT
<213> ORGANISM: Cunninghamella bertholetiae
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (173)..(173)
<223> OTHER INFORMATION: Any amino acid
```

```
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (198)..(198)
<223> OTHER INFORMATION: Any amino acid
<220> FEATURE:
<221> NAME/KEY: MOD_RES
<222> LOCATION: (232)..(232)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (259)..(259)
<223> OTHER INFORMATION: Any amino acid
<220> FEATURE:
<221> NAME/KEY: MOD_RES
<222> LOCATION: (270)..(270)
<223> OTHER INFORMATION: Any amino acid
<220> FEATURE:
<221> NAME/KEY: MOD_RES
<222> LOCATION: (279)..(279)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (304)..(304)
<223> OTHER INFORMATION: Any amino acid
<220> FEATURE:
<221> NAME/KEY: MOD_RES
<222> LOCATION: (316)..(316)
<223> OTHER INFORMATION: Any amino acid
<220> FEATURE:
<221> NAME/KEY: MOD_RES
<222> LOCATION: (329)..(329)
<223> OTHER INFORMATION: Any amino acid
<220> FEATURE:
<221> NAME/KEY: MOD_RES
<222> LOCATION: (344)..(344)
<223> OTHER INFORMATION: Any amino acid
<220> FEATURE:
<221> NAME/KEY: MOD_RES
<222> LOCATION: (352)..(352)
<223> OTHER INFORMATION: Any amino acid
<220> FEATURE:
<221> NAME/KEY: MOD_RES
<222> LOCATION: (356)..(356)
<223> OTHER INFORMATION: Any amino acid
<220> FEATURE:
<221> NAME/KEY: MOD_RES
<222> LOCATION: (633)..(633)
<223> OTHER INFORMATION: Any amino acid

<400> SEQUENCE: 28
```

-continued

```
Met Lys Leu Ser Ile Ser Ala Ala Phe Leu Val Ala Ile Thr His
1               5                   10                  15

Ala Ala Ser Ile Lys Phe Asn Val Ile Ala Pro Asn Ala Thr Asp Val
            20                  25                  30

Lys Val Ser Val Asn Gly Gln Gln Val Thr Leu Thr Ala Ser Asp Ala
            35                  40                  45

Asn Val Pro Tyr Phe Thr Gly Ser Ala Glu Val Gly Ala Ser Lys Thr
50                  55                  60

Tyr Lys Val Ile Ile Asn Leu Val Xaa Ile Gln Xaa Asp Xaa Ser Ser
65                  70                  75                  80

Tyr Ser Ile Val Cys Cys Arg Trp Asn Arg Arg Lys Phe Xaa Ser Phe
                85                  90                  95

Ser Xaa Trp Asn His Lys Leu Asn Thr Xaa Xaa Phe Leu Xaa Pro Pro
            100                 105                 110

Arg His Leu Cys Xaa Pro Ser Ser Ile Thr Leu Ala Asn Xaa Lys Arg
            115                 120                 125

Arg Lys Leu Phe Tyr Phe Tyr Leu Phe Ser Ala Lys Ile Asn Ile Val
            130                 135                 140

Phe Ser Ala Ser Val Asp Ser Phe Trp Lys Gln Ser Arg His Phe Arg
145                 150                 155                 160

Xaa Gln Leu Tyr Ser Gln Arg Phe Phe Pro Arg Arg Xaa Gln Ser Ser
                165                 170                 175

Pro Lys Cys Gly Xaa Lys Arg Thr Cys Xaa Pro Asn Gln Trp Tyr Thr
            180                 185                 190

Asp Leu Tyr Trp Ile Xaa Leu Arg Leu Leu Phe Pro Glu Cys Leu Ile
            195                 200                 205

Trp Tyr Ser Arg Cys Trp Gln Glu Thr Gln Gln Cys Lys Thr Ile Leu
210                 215                 220

Glu Leu Asp Ile Val Trp Lys Xaa Tyr Asp Gly Xaa Pro Gln Phe Leu
225                 230                 235                 240

Xaa Ala Ser Thr Tyr Gly Arg Arg Ser Tyr Thr Asp Ser Xaa Thr Ser
            245                 250                 255

Leu Phe Xaa His Phe Thr Cys His Gly Tyr Leu Cys Gln Xaa Cys Tyr
            260                 265                 270

His Gly Ser Ile Val Tyr Xaa Gln Pro Arg Leu Arg Tyr Leu Gln His
            275                 280                 285

Val Gly Xaa Tyr His Ser Ile Leu Leu Tyr Gln Cys Xaa Ile Leu Xaa
            290                 295                 300

Trp Gln Thr Thr Cys Tyr Leu Gly Ser Ser Leu Xaa Trp Cys Leu Trp
305                 310                 315                 320

Cys Arg Leu Leu Ile Ser Ser Trp Xaa Pro Arg Trp Ile Leu Phe Leu
            325                 330                 335

Gly Cys Gln His Ser Gln Ser Xaa Cys Glu Ala Tyr Glu Ala Ser Xaa
            340                 345                 350

Ser Ser Leu Xaa Pro Gly Thr Arg Arg Pro Asn Thr Asp Asn Thr Ala
            355                 360                 365

Ile Ala Asn Phe Glu Lys Met Phe Asp Leu Asp Arg Phe Met Arg Phe
370                 375                 380

Met Val Ile Glu Tyr Leu Thr Ala Asp Trp Asp Gly Tyr Trp Met Gly
385                 390                 395                 400

Gln Thr Asn Asp Gly Ala Tyr Arg Asp Pro Thr Asp Asn Asn Lys Trp
            405                 410                 415

Tyr Phe Leu Asp Gln Asp Phe Asp Gly Thr Phe Gly Val Asn Leu Ala
```

```
                420            425             430
Ala Pro Glu Gly Asn Ala Phe Leu Asp Val Ser Tyr Lys Asp Phe Pro
            435                 440                 445

Ser Arg Tyr Pro Gly Ala Val Met Ile Asn Asn Leu Leu Gln Asn Ala
    450                 455                 460

Asp Lys Lys Ala Thr Phe Glu Lys Tyr Leu Thr Glu Thr Val Arg Val
465                 470                 475                 480

Leu Phe Asn Asn Val Thr Leu Thr Asn Arg Val Leu Ala Leu His Asn
                485                 490                 495

Phe Leu Pro Asp Leu Glu Trp Asp Arg Ser Ile Val Gln Gln Ser
            500                 505                 510

Pro Gly Ile Asn Phe Gly Trp Thr Phe Asp Gln Val Thr Gln Asn Leu
        515                 520                 525

Trp Gln Gly Val Thr Ala Pro Asn Asn Asn Gly Gly Ala Ala Phe
    530                 535                 540

Gly Leu Val Glu Tyr Ile Ala Ala Lys Ala Gln Ala Val Ala Lys Glu
545                 550                 555                 560

Phe Asn Ile Ser Ile Val Ser Gln Pro Val Gly Pro Pro Ser Ala Asn
                565                 570                 575

Gly Thr Thr Ala Ala Ala Leu Leu Cys Cys Cys Asn Ser Thr Gly Lys
            580                 585                 590

Glu Lys Ser Ile Tyr Phe Leu Ala Val Leu His Gln Gln Ser Ser Ala
        595                 600                 605

Gln Gly Thr Ser Val Pro Ser Arg Ser Arg Leu Arg Pro Ser Ile Lys
    610                 615                 620

Gln Phe Ala Leu Ala Ser Leu Gly Xaa Ser Pro Lys
625                 630                 635

<210> SEQ ID NO 29
<211> LENGTH: 1807
<212> TYPE: DNA
<213> ORGANISM: Rhizopus microsporus

<400> SEQUENCE: 29
atgaaattat ctattatatc cgctgccttt ttagtggcta ttacacacgc tgcttcaata      60
aagtttaatg taattgctcc taatgcaact gatgtcaaag tatctgtaaa tggacagcaa     120
gtgacactta ctgcttcaga tgcaaatgtc cctatttca ctggttcagc tgaagttggt      180
gcctcaaaga catacaaata tgttgcaggt ggaacagaag aaagttttga tcgttctctt     240
gatggaatca caaactcaac acttaatgat ttttataacc gccccgtcac ttatgctaac     300
cttcctcaat taccttggcc aattgaaaaa gaccctcagt ggactcgttc tggaagcaaa     360
gccgacattt tcgatgacaa ttatattccc agcgtttttt tccacggaga tgacagtcaa     420
gtccaaaatg tggttaaaaa cgtacctgct gaccgaatca gtggtacact gacctttatt     480
ggatctaatt acgtctactc tttccagaat gtctcatttg gtattcacgg tgctggcaag     540
aaacacaaca atgcaaaaca atcttggaac tggatattgt ctggaagtga tacgatgggt     600
aaccgcaatt tctttaagct tcgacatatg gaagaagatc ctacacagat tcgtgaacgt     660
ctttattctg acattttaca tgccatgggt acttatgcca atgatgctac catggttcga     720
ttgtttatta caaccaagg cttcggtacc ttcaacatgt ggatgatat cactcaattc      780 tcctatatca atgctaaatt ttataatggc aaaccacctg ctaccttggg tcctctctat     840
gatggtgcct ctggtgcaga cttcttatat catcctggta acctcgatgg atactcttct     900
```

```
tgggttgcca acacagccaa tcctaatggt gaagcttatg aagctcttga tcctctctgt    960
aaggcctgga acgagacgac ctataccgat aatacagcca ttgcaaactt tgaaaaaatg   1020
tttgatctcg accgtttcat gcgtttcatg gttattgaat acttgactgc cgattgggat   1080
ggttactgga tgggacagac caatgatggt gcctatcgtg atccaactga taataacaag   1140
tggtactttt tagatcaaga cttttgatggt acttttggtg tcaacttggc tgcacccgaa   1200
ggcaatgctt tccttgatgt ttcttacaag gatttcccctt ctcgttaccc tggcgctgtc   1260
atgatcaaca acctcttaca gaatgctgat aaaaaggcca cctttgaaaa atatttgact   1320
gagactgtgc gtgtgctgtt caataatgtc accttgacta accgtgtctt ggcccttcac   1380
aacttcctct tgcctgatct tgaatgggat cgttcgatcg ttcaacaatc tcctggtatt   1440
aactttggtt ggacatttga tcaagtcact caaaacttgt ggcaaggtgt cactgcaccc   1500
aataacaatg gaggtggtgc tgcttttggt ttagttgaat atattgctgc aaaggcacaa   1560
gctgtagcta aggaatttaa tatttctatc gtttcccaac ctgttggccc tccttctgct   1620
aatggtacta ctgctgctgc tcctgctcct gctgctggca attctactgg aaaaggagga   1680
aatcaatcta tttctagcag tgcttcatcc aacaaaacct cggctcaaag cacatcaggt   1740
gcttctcgtt ccaagactgc gcccatcgtt ttagccattt ccgctttagc tctccttgta   1800
ttctaaa                                                            1807
```

<210> SEQ ID NO 30
<211> LENGTH: 602
<212> TYPE: PRT
<213> ORGANISM: Rhizopus microsporus
<220> FEATURE:
<221> NAME/KEY: MOD_RES
<222> LOCATION: (602)..(602)
<223> OTHER INFORMATION: Any amino acid

<400> SEQUENCE: 30

```
Met Lys Leu Ser Ile Ile Ser Ala Ala Phe Leu Val Ala Ile Thr His
 1               5                  10                  15

Ala Ala Ser Ile Lys Phe Asn Val Ile Ala Pro Asn Ala Thr Asp Val
                20                  25                  30

Lys Val Ser Val Asn Gly Gln Gln Val Thr Leu Thr Ala Ser Asp Ala
            35                  40                  45

Asn Val Pro Tyr Phe Thr Gly Ser Ala Glu Val Gly Ala Ser Lys Thr
        50                  55                  60

Tyr Lys Tyr Val Ala Gly Gly Thr Glu Glu Ser Phe Asp Arg Ser Leu
    65                  70                  75                  80

Asp Gly Ile Thr Asn Ser Thr Leu Asn Asp Phe Tyr Asn Arg Pro Val
                85                  90                  95

Thr Tyr Ala Asn Leu Pro Gln Leu Pro Trp Pro Ile Glu Lys Asp Pro
            100                 105                 110

Gln Trp Thr Arg Ser Gly Ser Lys Ala Asp Ile Phe Asp Asp Asn Tyr
        115                 120                 125

Ile Pro Ser Val Phe Phe His Gly Asp Asp Ser Gln Val Gln Asn Val
    130                 135                 140

Val Lys Asn Val Pro Ala Asp Arg Ile Ser Gly Thr Leu Thr Phe Ile
145                 150                 155                 160

Gly Ser Asn Tyr Val Tyr Ser Phe Gln Asn Val Ser Phe Gly Ile His
                165                 170                 175

Gly Ala Gly Lys Lys His Asn Asn Ala Lys Gln Ser Trp Asn Trp Ile
            180                 185                 190
```

```
Leu Ser Gly Ser Asp Thr Met Gly Asn Arg Asn Phe Phe Lys Leu Arg
        195                 200                 205

His Met Glu Glu Asp Pro Thr Gln Ile Arg Glu Arg Leu Tyr Ser Asp
    210                 215                 220

Ile Leu His Ala Met Gly Thr Tyr Ala Asn Asp Ala Thr Met Val Arg
225                 230                 235                 240

Leu Phe Ile Asn Asn Gln Gly Phe Gly Thr Phe Asn Met Leu Asp Asp
                245                 250                 255

Ile Thr Gln Phe Ser Tyr Ile Asn Ala Lys Phe Tyr Asn Gly Lys Pro
            260                 265                 270

Pro Ala Thr Leu Gly Pro Leu Tyr Asp Gly Ala Ser Gly Ala Asp Phe
        275                 280                 285

Leu Tyr His Pro Gly Asn Leu Asp Gly Tyr Ser Ser Trp Val Ala Asn
    290                 295                 300

Thr Ala Asn Pro Asn Gly Glu Ala Tyr Glu Ala Leu Asp Pro Leu Cys
305                 310                 315                 320

Lys Ala Trp Asn Glu Thr Thr Tyr Thr Asp Asn Thr Ala Ile Ala Asn
                325                 330                 335

Phe Glu Lys Met Phe Asp Leu Arg Phe Met Arg Phe Met Val Ile
            340                 345                 350

Glu Tyr Leu Thr Ala Asp Trp Asp Gly Tyr Trp Met Gly Gln Thr Asn
            355                 360                 365

Asp Gly Ala Tyr Arg Asp Pro Thr Asp Asn Asn Lys Trp Tyr Phe Leu
370                 375                 380

Asp Gln Asp Phe Asp Gly Thr Phe Gly Val Asn Leu Ala Ala Pro Glu
385                 390                 395                 400

Gly Asn Ala Phe Leu Asp Val Ser Tyr Lys Asp Phe Pro Ser Arg Tyr
                405                 410                 415

Pro Gly Ala Val Met Ile Asn Asn Leu Leu Gln Asn Ala Asp Lys Lys
            420                 425                 430

Ala Thr Phe Glu Lys Tyr Leu Thr Glu Thr Val Arg Val Leu Phe Asn
        435                 440                 445

Asn Val Thr Leu Thr Asn Arg Val Leu Ala Leu His Asn Phe Leu Leu
    450                 455                 460

Pro Asp Leu Glu Trp Asp Arg Ser Ile Val Gln Gln Ser Pro Gly Ile
465                 470                 475                 480

Asn Phe Gly Trp Thr Phe Asp Gln Val Thr Gln Asn Leu Trp Gln Gly
                485                 490                 495

Val Thr Ala Pro Asn Asn Gly Gly Ala Ala Phe Gly Leu Val
            500                 505                 510

Glu Tyr Ile Ala Ala Lys Ala Gln Ala Val Ala Lys Glu Phe Asn Ile
        515                 520                 525

Ser Ile Val Ser Gln Pro Val Gly Pro Pro Ser Ala Asn Gly Thr Thr
    530                 535                 540

Ala Ala Ala Pro Ala Pro Ala Ala Gly Asn Ser Thr Gly Lys Gly Gly
545                 550                 555                 560

Asn Gln Ser Ile Ser Ser Ser Ala Ser Ser Asn Lys Thr Ser Ala Gln
                565                 570                 575

Ser Thr Ser Gly Ala Ser Arg Ser Lys Thr Ala Pro Ile Val Leu Ala
            580                 585                 590

Ile Ser Ala Leu Ala Leu Leu Val Phe Xaa
        595                 600
```

<210> SEQ ID NO 31
<211> LENGTH: 1862
<212> TYPE: DNA
<213> ORGANISM: Rhizopus microsporus

<400> SEQUENCE: 31

| | | | | | |
|---|---|---|---|---|---|
| atgaaattat | ctattatatc | cgctgccttt | ttagtggcta | ttacacacgc | tgcttcaata | 60 |
| aagtttaatg | taattgctcc | taatgcaact | gatgtcaaag | tatctgtaaa | tggacagcaa | 120 |
| gtgacactta | ctgcttcaga | tgcaaatgtc | ccttatttca | ctggttcagc | tgaagttggt | 180 |
| gcctcaaaga | catacaaata | tgttgcaggt | ggaacagaag | aaagttttga | tcgttctctt | 240 |
| gatggaatca | caaactcaac | acttaatgat | ttttataacc | gccccgtcac | ttatgctaac | 300 |
| cttcctcaat | taccttggcc | aattgaaaaa | gacgtaagtt | attttatttt | tatcttttct | 360 |
| cagctaaaat | aaacattgtc | tttctcagcc | tcagtggact | cgttctggaa | gcaaagccga | 420 |
| cattttcgat | gacaattata | tcccagcgt | ttttttccac | ggagatgaca | gtcaagtcca | 480 |
| aaatgtggtt | aaaaacgtac | ctgctgaccg | aatcagtggt | acactgacct | ttattggatc | 540 |
| taattacgtc | tactctttcc | agaatgtctc | atttggtatt | cacggtgctg | caagaaaaca | 600 |
| caacaatgca | aacaatcttt | ggaactggat | attgtctgga | agtgatacga | tgggtaaccg | 660 |
| caatttcttt | aagcttcgac | atatggaaga | agatcctaca | cagattcgtg | aacgtcttta | 720 |
| ttctgacatt | ttacatgcca | tgggtactta | tgccaatgat | gctaccatgg | ttcgattgtt | 780 |
| tattaacaac | caaggcttcg | gtaccttcaa | catgttggat | gatatcactc | aattctccta | 840 |
| tatcaatgct | aaattttata | tggcaaaacc | acctgctacc | ttgggtcctc | tctatgatgg | 900 |
| tgcctctggt | gcagacttct | tatatcatcc | tggtaacctc | gatggatact | cttcttgggt | 960 |
| tgccaacaca | gccaatccta | tggtgaagc | ttatgaagct | cttgatcctc | tctgtaaggc | 1020 |
| ctggaacgag | acgacctata | ccgataatac | agccattgca | aactttgaaa | aaatgtttga | 1080 |
| tctcgaccgt | tcatgcgtt | tcatggttat | tgaatacttg | actgccgatt | gggatggtta | 1140 |
| ctggatggga | cagaccaatg | atggtgccta | tcgtgatcca | actgataata | acaagtggta | 1200 |
| cttttagat | caagactttg | atggtacttt | tggtgtcaac | ttggctgcac | ccgaaggcaa | 1260 |
| tgcttttctt | gatgtttctt | acaaggattt | cccttctcgt | taccctggcg | ctgtcatgat | 1320 |
| caacaacctc | ttacagaatg | ctgataaaaa | ggccacctt | gaaaaatatt | tgactgagac | 1380 |
| tgtgcgtgtg | ctgttcaata | atgtcacctt | gactaaccgt | gtcttggccc | ttcacaactt | 1440 |
| cctcttgcct | gatcttgaat | gggatcgttc | gatcgttcaa | caatctcctg | gtattaactt | 1500 |
| tggttggaca | tttgatcaag | tcactcaaaa | cttgtggcaa | ggtgtcactg | cacccaataa | 1560 |
| caatggaggt | ggtgctgctt | ttggtttagt | tgaatatatt | gctgcaaagg | cacaagctgt | 1620 |
| agctaaggaa | tttaatattt | ctatcgtttc | ccaacctgtt | ggccctcctt | ctgctaatgg | 1680 |
| tactactgct | gctgctcctg | ctcctgctgc | tggcaattct | actggaaaag | gaggaaatca | 1740 |
| atctattct | agcagtgctt | catccaacaa | aacctcggct | caaagcacat | caggtgcttc | 1800 |
| tcgttccaag | actgcgccca | tcgttttagc | catttccgct | ttagctctcc | ttgtattcta | 1860 |
| aa | | | | | | 1862 |

<210> SEQ ID NO 32
<211> LENGTH: 638
<212> TYPE: PRT
<213> ORGANISM: Rhizopus microsporus
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (193)..(193)
<223> OTHER INFORMATION: Any amino acid
<220> FEATURE:
<221> NAME/KEY: MOD_RES
<222> LOCATION: (391)..(391)
<223> OTHER INFORMATION: Any amino acid
<220> FEATURE:
<221> NAME/KEY: MOD_RES
<222> LOCATION: (420)..(420)
<223> OTHER INFORMATION: Any amino acid
<220> FEATURE:
<221> NAME/KEY: MOD_RES
<222> LOCATION: (457)..(457)
<223> OTHER INFORMATION: Any amino acid
<220> FEATURE:
<221> NAME/KEY: MOD_RES
<222> LOCATION: (475)..(475)
<223> OTHER INFORMATION: Any amino acid
<220> FEATURE:
<221> NAME/KEY: MOD_RES
<222> LOCATION: (488)..(488)
<223> OTHER INFORMATION: Any amino acid
<220> FEATURE:
<221> NAME/KEY: MOD_RES
<222> LOCATION: (547)..(547)
<223> OTHER INFORMATION: Any amino acid
<220> FEATURE:
<221> NAME/KEY: MOD_RES
<222> LOCATION: (558)..(558)
<223> OTHER INFORMATION: Any amino acid
<220> FEATURE:
<221> NAME/KEY: MOD_RES
<222> LOCATION: (627)..(627)
<223> OTHER INFORMATION: Any amino acid
<220> FEATURE:
<221> NAME/KEY: MOD_RES
<222> LOCATION: (632)..(632)
<223> OTHER INFORMATION: Any amino acid

<400> SEQUENCE: 32

Met Lys Leu Ser Ile Ile Ser Ala Ala Phe Leu Val Ala Ile Thr His
1               5                   10                  15

```
Ala Ala Ser Ile Lys Phe Asn Val Ile Ala Pro Asn Ala Thr Asp Val
            20                  25                  30

Lys Val Ser Val Asn Gly Gln Gln Val Thr Leu Thr Ala Ser Asp Ala
        35                  40                  45

Asn Val Pro Tyr Phe Thr Gly Ser Ala Glu Val Gly Ala Ser Lys Thr
 50                  55                  60

Tyr Lys Val Ile Ile Asn Leu Val Xaa Ile Gln Xaa Asp Xaa Ser Ser
 65                  70                  75                  80

Tyr Ser Ile Val Cys Cys Arg Trp Asn Arg Arg Lys Phe Xaa Ser Phe
                 85                  90                  95

Ser Xaa Trp Asn His Lys Leu Asn Thr Xaa Xaa Phe Leu Xaa Pro Pro
        100                 105                 110

Arg His Leu Cys Xaa Pro Ser Ser Ile Thr Leu Ala Asn Xaa Lys Arg
        115                 120                 125

Arg Lys Leu Phe Tyr Phe Tyr Leu Phe Ser Ala Lys Ile Asn Ile Val
        130                 135                 140

Phe Leu Ser Leu Ser Gly Leu Val Leu Glu Ala Lys Pro Thr Phe Ser
145                 150                 155                 160

Met Thr Ile Ile Phe Pro Ala Phe Phe Ser Thr Glu Met Thr Val Lys
                165                 170                 175

Ser Lys Met Trp Leu Lys Thr Tyr Leu Leu Thr Glu Ser Val Val His
            180                 185                 190

Xaa Pro Leu Leu Asp Leu Ile Thr Ser Thr Leu Ser Arg Met Ser His
        195                 200                 205

Leu Val Phe Thr Val Leu Ala Arg Asn Thr Thr Met Gln Asn Asn Leu
    210                 215                 220

Gly Thr Gly Tyr Cys Leu Glu Val Ile Arg Trp Val Thr Ala Ile Ser
225                 230                 235                 240

Leu Ser Phe Asp Ile Trp Lys Lys Ile Leu His Arg Phe Val Asn Val
                245                 250                 255

Phe Ile Leu Thr Phe Tyr Met Pro Trp Val Leu Met Pro Met Met Leu
            260                 265                 270

Pro Trp Phe Asp Cys Leu Leu Thr Thr Lys Ala Ser Val Pro Ser Thr
        275                 280                 285

Cys Trp Met Ile Ser Leu Asn Ser Pro Ile Ser Met Leu Asn Phe Ile
        290                 295                 300

Met Ala Asn His Leu Leu Pro Trp Val Leu Ser Met Val Pro Leu
305                 310                 315                 320

Val Gln Thr Ser Tyr Ile Ile Leu Val Thr Ser Met Asp Thr Leu Leu
                325                 330                 335

Gly Leu Pro Thr Gln Pro Ile Leu Met Val Lys Leu Met Lys Leu Leu
            340                 345                 350

Ile Leu Ser Val Arg Pro Gly Thr Arg Arg Pro Ile Pro Ile Ile Gln
        355                 360                 365

Pro Leu Gln Thr Leu Lys Lys Cys Leu Ile Ser Thr Val Ser Cys Val
        370                 375                 380

Ser Trp Leu Leu Asn Thr Xaa Leu Pro Ile Gly Met Val Thr Gly Trp
385                 390                 395                 400

Asp Arg Pro Met Met Val Pro Ile Val Ile Gln Leu Ile Ile Thr Ser
                405                 410                 415

Gly Thr Phe Xaa Ile Lys Thr Leu Met Val Leu Leu Val Ser Thr Trp
            420                 425                 430
```

Leu His Pro Lys Ala Met Leu Phe Leu Met Phe Leu Thr Arg Ile Ser
            435                 440                 445

Leu Leu Val Thr Leu Ala Leu Ser Xaa Ser Thr Thr Ser Tyr Arg Met
    450                 455                 460

Leu Ile Lys Arg Pro Pro Leu Lys Asn Ile Xaa Leu Arg Leu Cys Val
465                 470                 475                 480

Cys Cys Ser Ile Met Ser Pro Xaa Leu Thr Val Ser Trp Pro Phe Thr
                485                 490                 495

Thr Ser Ser Cys Leu Ile Leu Asn Gly Ile Val Arg Ser Phe Asn Asn
            500                 505                 510

Leu Leu Val Leu Thr Leu Val Gly His Leu Ile Lys Ser Leu Lys Thr
    515                 520                 525

Cys Gly Lys Val Ser Leu His Pro Ile Thr Met Glu Val Val Leu Leu
530                 535                 540

Leu Val Xaa Leu Asn Ile Leu Leu Gln Arg His Lys Leu Xaa Leu Arg
545                 550                 555                 560

Asn Leu Ile Phe Leu Ser Phe Pro Asn Leu Leu Ala Leu Leu Leu Leu
                565                 570                 575

Met Val Leu Leu Leu Leu Leu Leu Leu Leu Leu Ala Ile Leu Leu
            580                 585                 590

Glu Lys Glu Glu Ile Asn Leu Phe Leu Ala Val Leu His Pro Thr Lys
    595                 600                 605

Pro Arg Leu Lys Ala His Gln Val Leu Val Pro Arg Leu Arg Pro
610                 615                 620

Ser Phe Xaa Pro Phe Pro Leu Xaa Leu Ser Leu Tyr Ser Lys
625                 630                 635

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgaaattat ctattatatc cgctgcc                                      27

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctgggaata taattgtcat cga                                          23

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gatgacaatt atattcccag c                                            21

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gagtagacgt aattagatcc aa                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaacgtacct gctgaccgaa tc                                              22

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
cgcgatcaaa cgtacctgct gaccgaatcg atcgcg                               36

<210> SEQ ID NO 39
<211> LENGTH: 15
<212> TYPE: PRT
<213> ORGANISM: Unknown
<220> FEATURE:
<223> OTHER INFORMATION: Description of Unknown: Mucorales CotH
      peptide

<400> SEQUENCE: 39

Gly Ala Gly Lys Lys His Asn Asn Ala Lys Gln Ser Trp Asn Trp
1               5                   10                  15

<210> SEQ ID NO 40
<211> LENGTH: 17
<212> TYPE: PRT
<213> ORGANISM: Unknown
<220> FEATURE:
<223> OTHER INFORMATION: Description of Unknown: Mucorales CotH
      peptide

<400> SEQUENCE: 40

Met Gly Gln Thr Asn Asp Gly Ala Tyr Arg Asp Pro Thr Asp Asn Asn
1               5                   10                  15

Lys

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
```
aaaaaacccc ggatcctatg aaatccctac tttttgttgt attc    44

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tctgttccat gtcgacctag aagaaagagg caaataaagt gc    42

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aaaaaccccg gatcctatga aattatcact cactatagta tcctct    46

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctgttccat gtcgacttaa aagatagcag tggcaactaa ag    42

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aaaaaacccc ggatcctatg aaattatcta ttatatccgc tgcc    44

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctgttccat gtcgacttag aatacaagga gagctaaagc g    41

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaaaaacccc ggatcctatg attgctaccc cttttgaaa    39

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tctgttccat gtcgacttaa aagaaaataa agaatgttgc agc                        43

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atgaaattat ctattatatc cgctgcc                                          27

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttagaataca aggagagcta aagcg                                            25

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcatgctaga acagaagaaa gttttgatcg ttc                                   33

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtacgacgtt cacgaatctg tgtagg                                           26

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccgcgggacg ttcacgaatc tgtgtagg                                         28

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
gctagcagaa cagaagaaag ttttgatcgt tc                32

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
caaacaaatg atggggccta                20

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 56 cgttttgtt caagatttac acca                24

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cctaataagg acaacgcaaa cg                22

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
ttggcaatgg ctgtgttatc                20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
gccaatccta atggtgaagc                20

```
<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
catgaaacgg tcgagatcaa                                                      20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agctcctttg aaccccaagt                                                      20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acgaccagag gcatacaagg                                                      20

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcggatcgca tggcc                                                           15

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccatgatagg gcagaaaatc g                                                    21

<210> SEQ ID NO 65
<211> LENGTH: 604
<212> TYPE: PRT
<213> ORGANISM: Stigmatella aurantiaca

<400> SEQUENCE: 65

Met Pro Ser Leu Phe Leu Glu Thr Pro Glu Asp Phe Glu Phe Lys Ala
1               5                   10                  15

Ser Val Cys Leu Arg Thr Leu Arg Gly Trp Met Asn Thr Tyr Arg Pro
            20                  25                  30

Leu Val Ile Ala Ser Leu Leu Leu Ser Phe Cys Leu Leu Pro Thr Ala
```

```
                35                  40                  45
Cys Gly Asp Asp Lys Pro Gly Pro Pro Pro Asp Ala Gly Asn
 50                  55                  60
Pro Asn Asp Ala Gly Val Pro Asp Ala Gly Gly Pro Ser Glu Gly Asp
 65                  70                  75                  80
Ala Gly Asp Gly Gly Glu Ser Pro Asp Ala Gly Asp Ala Gly Glu Pro
                     85                  90                  95
Gly Asp Ala Gly Asp Gly Gly Thr Asp Gly Pro Thr Ala Asp
                100                 105                 110
Pro Ala Glu Pro Leu Phe Ser Gly His His Ile Ser Arg Phe Glu Leu
                115                 120                 125
Asn Leu Ser Gln Glu Ala Leu Ala Ser Leu Gln Ala Glu Pro Asp Glu
                130                 135                 140
Tyr Val Glu Gly Ala Leu His Leu Gln Val Gly Ala Gln Ser Ile Asp
145                 150                 155                 160
Leu Pro Lys Val Gly Val Arg Leu Lys Gly Gln Leu Gly Ser Phe Arg
                165                 170                 175
Pro Leu Asn Gln Lys Ala Ala Phe Val Leu Lys Phe Asp Lys Phe Val
                180                 185                 190
Asp Gln Asn Leu Phe Gly Leu Lys Lys Leu Thr Leu Asn Asn Met Val
                195                 200                 205
Gln Asp Pro Ser Met Ile His Glu Arg Leu Gly Tyr Ala Leu Phe Arg
                210                 215                 220
Ala Met Glu Val Pro Ala Pro Arg Ala Ala His Ala Thr Ile Arg Ile
225                 230                 235                 240
Asn Gly Ala Leu Tyr Gly Leu Tyr Thr Ala Leu Glu Ser Thr Asp Asn
                245                 250                 255
Ser Val Phe Leu Lys His Trp Phe Gly Ser Asn Asn Gly Asn Leu Tyr
                260                 265                 270
Glu Gly Gln Tyr Gly Ser Asp Leu Tyr Leu Gly Leu Glu Ala Thr Phe
                275                 280                 285
Glu Gln Asp Lys Gly Glu Asp Val Gly Phe Ala Asp Leu Thr Glu Leu
                290                 295                 300
Ala Lys Ala Leu Asp Gln Met Thr His Pro Ala Thr Phe Leu Glu Asp
305                 310                 315                 320
Val Ala Gln Val Ile Asp Leu Asp Ser Tyr Leu Arg Phe Ala Ala Thr
                325                 330                 335
Glu Leu Phe Ile Gly His Trp Asp Gly Tyr Val Ser Tyr Arg Asn Asn
                340                 345                 350
Phe Tyr Leu Tyr Arg Arg Pro Ser Asp Gly Arg Trp Val Phe Ile Pro
                355                 360                 365
Trp Gly Ile Asp Gln Thr Phe Gly Arg Tyr Val Asp Thr Trp Ser Ala
                370                 375                 380
His Gly Arg Leu Gln Arg Met Cys Ile Glu Ser Leu Pro Cys Arg Tyr
385                 390                 395                 400
Lys Leu Ala Gln Ala Tyr Glu Gln Val Leu Leu Arg Val Glu Glu Leu
                405                 410                 415
Ser Met Val Glu Gln Ala Met Ala Leu Gly Thr Phe Leu Trp Thr Asp
                420                 425                 430
Val Gln Glu Asp Pro Arg Lys Glu Val Asp Val Gly Thr Val Phe Ser
                435                 440                 445
Lys Met Thr Glu Ala Ile Asp Phe Leu Lys Asn Arg Pro Thr Asp Val
                450                 455                 460
```

```
Arg Leu Arg Leu Gly Cys Val Asp Pro Met Gly Cys Glu Arg Cys Thr
465                 470                 475                 480

Leu Ala Pro Ala Pro Gly Gly Gly Arg Leu Ala Phe Cys Thr Gly Thr
            485                 490                 495

Val Thr Trp Ala Ala Glu Ala Asp Cys Val Ala Gln Gly Gly His
        500                 505                 510

Leu Val Ser Ile His Asp Gln Pro Thr Gln Thr Ala Val Arg Ala Gly
            515                 520                 525

Ala Arg Ala Leu Ser Thr Gly Pro Trp Trp Ile Gly Leu Ser Asp Glu
530                 535                 540

Ala Glu Glu Gly Thr Phe Ala Trp Ser Asp Gln Thr Pro Ile Asn Phe
545                 550                 555                 560

Thr Leu Trp Ala Thr Ser Glu Pro Asn Asn Gln Asn Asn Glu Asp Cys
                565                 570                 575

Val Gln Leu Tyr Gly Glu Ala Gly Thr Trp Asn Asp Val Thr Cys Ser
            580                 585                 590

Gly Thr Ala Ser Tyr Val Cys Thr Leu Pro Pro Pro
            595                 600

<210> SEQ ID NO 66
<211> LENGTH: 365
<212> TYPE: PRT
<213> ORGANISM: Rhizopus oryzae

<400> SEQUENCE: 66

Met Ile Ala Thr Pro Phe Glu Met Phe Gln Cys Gln Met Tyr Ile Leu
1               5                   10                  15

Cys Leu Val Leu Ile Ala Phe Ser Phe Thr Cys Val Asn Thr Gln Gln
            20                  25                  30

Leu Cys Asn Gly Tyr Ala Glu Tyr Cys Asn Lys Pro Tyr Asn Ser Leu
        35                  40                  45

Thr Tyr Leu Leu Thr His Asn Ser Tyr Gly Tyr Val Ser Asn Pro Ala
    50                  55                  60

Ala Asn Gln Leu Cys Pro Ile Thr Thr Gln Leu Ala Asp Gly Val Arg
65                  70                  75                  80

Gly Ile Lys Leu Ser Ala Val Lys Ala Thr Asn Ala Thr Thr Asp Gly
                85                  90                  95

Thr Ile Thr Ala Asp Ser Ile Tyr Leu Cys His Thr Ser Cys Ile Ile
            100                 105                 110

Leu Asn Ala Gly Pro Ala Val Asn Thr Leu Arg Thr Ile Lys Glu Trp
        115                 120                 125

Val Glu Gln Asn Pro Asn Glu Val Val Thr Ile Met Trp Asn Asn Val
    130                 135                 140

Asp Ala Phe Asp Gly Asn Ala Phe Glu Ala Ala Tyr Asn Ala Ser Gly
145                 150                 155                 160

Ile Ile Glu Tyr Ser Tyr Gln Gln Pro Lys Lys Asn Tyr Thr Trp Pro
                165                 170                 175

Thr Leu Gly Glu Leu Ile Ala Ser Gly Lys Arg Val Ile Asn Phe Gly
            180                 185                 190

Asp Thr Tyr Tyr Gln Gln Asp Leu Pro Trp Leu Leu Thr Glu Tyr Asp
        195                 200                 205

Tyr Val Phe Glu Thr Pro Tyr Glu Asn His Asn Glu Ser Ser Phe Ser
    210                 215                 220

Cys Thr Ile Asp Arg Pro Gln Asp Pro Ala Ser Pro Thr Glu Phe Leu
```

```
                225                 230                 235                 240
Tyr Val Met Asn His Phe Leu Tyr Gly Ser Leu Gln Leu Gly Ser Leu
                    245                 250                 255

Pro Ile Glu Ile Pro Gln Lys Gly Ile Ala Asn Thr Thr Asn Ser Asp
                260                 265                 270

Asn Ser Leu Met Lys Gln Ala Lys Thr Cys Thr Glu Lys Phe Gly Arg
            275                 280                 285

Gln Pro Asn Phe Leu Glu Ile Asp Phe Tyr Asn Leu Gly Asp Ala Leu
        290                 295                 300

Lys Ile Thr Ala Glu Leu Asn Asn Val Thr Tyr Lys Gly Ser Gly Ser
305                 310                 315                 320

Leu Gln Cys Asp Thr Tyr Ala Ala Gln Gln Ala Ser Ser Ser Ser Thr
                    325                 330                 335

Asp Ser Ser Glu Ala Ile Gln Thr Ile Ser Ile Ser Ser Val Ser Leu
                340                 345                 350

Leu Leu Thr Leu Ile Ala Ala Thr Phe Phe Ile Phe Phe
            355                 360                 365

<210> SEQ ID NO 67
<211> LENGTH: 453
<212> TYPE: PRT
<213> ORGANISM: Talaromyces stipitatus

<400> SEQUENCE: 67

Met Arg Ser Leu Trp Ile Val Ala Thr Leu Leu Thr Gly Ala Leu Ala
1               5                   10                  15

Ser Thr Thr Thr Thr Ala Ser Thr Thr Thr Ser Ser Ala Thr Asp Thr
                20                  25                  30

Ala Ala Ile Val Thr Leu Ser Gly Thr Val Asp Pro Leu Ser Leu Glu
            35                  40                  45

Gly Ala Thr Gly Ser Val Thr Tyr Pro Ser Val Thr Thr Thr Ile Thr
        50                  55                  60

Leu Ser Thr Pro Lys Asp Ser Lys Thr Ser Thr Gly Thr Gly Thr Arg
65                  70                  75                  80

Ser Gly Asn Val Thr Asp Ala Tyr Thr Thr Thr Ser Gly Thr Val Thr
                85                  90                  95

Met Leu Val Gly Ser Gln Gly Thr Ser Thr Leu Ala Pro Asn Ala Thr
            100                 105                 110

Ala Leu Arg Asn Ser Thr Ala Thr Thr Ser Thr Thr Pro Leu Pro Thr
        115                 120                 125

Asn Thr Gln Pro Cys Asn Gly Tyr Val Glu Phe Cys Ala Arg Asn Tyr
130                 135                 140

Ser Asn Ile Thr Tyr Val Ala His Asn Ser Pro Phe Asp Arg Lys
145                 150                 155                 160

Gly Asn Ile Ala Ser Asn Gln Gln Tyr Ser Val Thr Thr Gln Leu Asn
                165                 170                 175

Asp Gly Ile Arg Met Leu Gln Phe Gln Ala His Leu Gln Asn Gly Thr
            180                 185                 190

Ile Arg Leu Cys His Thr Ser Cys Asp Leu Leu Asn Val Gly Pro Leu
        195                 200                 205

Glu Glu Tyr Leu Thr Thr Val Thr Arg Trp Leu Asn Asn Asn Pro Tyr
    210                 215                 220

Glu Val Ile Thr Ile Leu Met Gly Asn Tyr Asp Leu Val Gly Val Gly
225                 230                 235                 240
```

```
Asn Phe Thr Ala Pro Ile Ile Asn Ser Gly Leu Ser Arg Tyr Val Tyr
                245                 250                 255

Thr Pro Pro Lys Ile Pro Met Ser Leu Asn Asp Trp Pro Val Leu Ser
            260                 265                 270

Glu Leu Ile Leu Thr Gln Lys Arg Val Ile Phe Met Asp Tyr Asn
            275                 280                 285

Ala Asn Gln Thr Glu Val Pro Tyr Ile Leu Asp Glu Phe Thr Gln Met
            290                 295                 300

Trp Glu Thr Pro Phe Ser Pro Thr Asp Pro Ala Phe Pro Cys Thr Val
305                 310                 315                 320

Gln Arg Pro Pro Asn Leu Ser Pro Glu Ser Ala Lys Gln Ile Leu Tyr
                325                 330                 335

Met Ala Asn His Asn Leu Asn Val Glu Ile Ser Phe Ser Gly Leu Asp
                340                 345                 350

Leu Leu Ile Pro Asn Thr Ala Val Leu Asn Glu Thr Asn Gly Val Ser
                355                 360                 365

Gly Tyr Arg Ser Leu Gly Leu Met Ala Asn Ser Cys Thr Thr Thr Trp
            370                 375                 380

Gly Arg Pro Pro Asn Phe Leu Leu Val Asp Tyr Tyr Asn Glu Gly Ser
385                 390                 395                 400

Ser Pro Gly Ser Val Phe Glu Val Ala Ala Asn Met Asn Asn Val Thr
                405                 410                 415

Tyr Asn Gly His Cys Cys Gly Ser Asn Thr Ser Gly Ala Leu Arg Leu
                420                 425                 430

Gln Thr Pro Asp Ala Val Trp Met Phe Val Val Ala Ala Leu Ser Val
                435                 440                 445

Leu Leu Cys Met Asn
        450

<210> SEQ ID NO 68
<211> LENGTH: 449
<212> TYPE: PRT
<213> ORGANISM: Penicillium marneffei

<400> SEQUENCE: 68

Met Pro Ser Leu Trp Met Ala Val Ala Leu Leu Thr Gly Ala Leu Val
1               5                   10                  15

Gln Ser Thr Thr Ala Ala Ser Ser Ser Ser Thr Leu Ser Ser Ala
            20                  25                  30

Ser Asp Thr Asp Ser Ala Gly Ile Val Thr Leu Ser Gly Thr Val Asp
            35                  40                  45

Pro Leu Ser Ile Asp Gly Ala Thr Gly Ser Val Thr Tyr Pro Ser Val
    50                  55                  60

Thr Thr Thr Ile Thr Leu Ser Thr Asp Ser Thr Ile Ser Gly Thr
65                  70                  75                  80

Val Thr Arg Asn Thr Thr Asp Val Thr Thr Thr Val Leu Val Gly
                85                  90                  95

Ser Gln Ala Ala Thr Ile Leu Ala Pro Asn Ala Thr Ala Ser Ile Asn
            100                 105                 110

Ser Thr Thr Ala Thr Gly Thr Ala Thr Thr Ala Pro Leu Pro Thr Asn
            115                 120                 125

Thr Gln Pro Cys Asn Gly Tyr Val Glu Phe Cys Ala Arg Asn Tyr Ser
        130                 135                 140

Asn Ile Thr Tyr Val Ala Ala His Asn Ser Pro Phe Asn Arg Gln Gly
145                 150                 155                 160
```

```
Asn Ile Ala Ser Asn Gln Gln Tyr Pro Val Thr Thr Gln Leu Asn Asp
            165                 170                 175

Gly Ile Arg Met Leu Gln Phe Gln Val His Leu Gln Asn Gly Ser Leu
        180                 185                 190

Tyr Leu Cys His Thr Ser Cys Asp Leu Leu Asn Val Gly Thr Leu Gln
    195                 200                 205

Asp Tyr Leu Thr Thr Val Thr Lys Trp Leu Asn Asn Asn Pro Tyr Glu
    210                 215                 220

Val Ile Thr Ile Leu Met Gly Asn Tyr Asp Leu Ile Gly Val Gly Asn
225                 230                 235                 240

Phe Thr Asp Pro Ile Val Asn Ser Gly Leu Ser Lys Tyr Ala Tyr Gln
                245                 250                 255

Pro Pro Lys Ile Pro Met Gly Leu Asp Asp Trp Pro Met Leu Ser Glu
            260                 265                 270

Leu Ile Leu Thr Gln Lys Arg Ala Ile Ile Phe Met Asp Tyr Asn Ala
        275                 280                 285

Asn Gln Thr Glu Val Pro Tyr Ile Leu Asp Glu Phe Thr Gln Met Trp
    290                 295                 300

Glu Thr Pro Phe Ser Pro Thr Asp Pro Asn Phe Pro Cys Thr Val Gln
305                 310                 315                 320

Arg Pro Pro Asn Leu Ser Thr Glu Arg Ala Lys Ser Ile Met Tyr Met
                325                 330                 335

Ala Asn His Asn Leu Asn Val Glu Ile Ser Phe Ser Gly Leu Asp Ile
            340                 345                 350

Leu Ile Pro Asn Thr Ala Val Leu Asn Glu Thr Asn Gly Val Phe Gly
        355                 360                 365

Tyr Arg Ser Leu Gly Leu Met Ala Asn Asn Cys Thr Ala Thr Trp Gly
    370                 375                 380

Arg Pro Pro Asn Phe Leu Leu Val Asp Tyr Tyr Asn Asn Gly Asn Phe
385                 390                 395                 400

Pro Gly Ser Val Phe Gln Val Ala Ala Glu Met Asn Asn Val Thr Tyr
                405                 410                 415

Ser Gly His Cys Cys Arg Ser Met Ala Ser Gly Ala Leu Arg Leu Glu
            420                 425                 430

Ile Pro Gly His Trp Met Phe Ala Met Ala Val Ser Ala Phe Leu Phe
        435                 440                 445

Ile

<210> SEQ ID NO 69
<211> LENGTH: 460
<212> TYPE: PRT
<213> ORGANISM: Aspergillus niger

<400> SEQUENCE: 69

Met Arg Leu Ile Ala His Leu Leu Pro Leu Leu Ala Val Gly Val Trp
1               5                   10                  15

Pro Ser Leu Ala Lys Asp Asp Ser Thr Thr Thr Thr Thr Thr Thr Gly
            20                  25                  30

Asn Asn Gly Gly Leu Thr Leu Glu Gly Thr Val Thr Ser Ser Ile Ser
        35                  40                  45

Glu Ala Thr Leu Pro Thr Gly His Tyr Leu Ser Tyr Thr Thr Thr Met
    50                  55                  60

Thr Leu Asp Asp Gly His Thr Val Thr Ser Thr Gly Ala His Ser Ala
65                  70                  75                  80
```

```
Thr Thr Thr Ser Asn Ser Thr Thr Ser Gly Asn Phe Thr Thr Thr
                85                  90                  95

Val Thr Ser Ser Ser Gln Ser Leu Thr Leu Leu Val Gly Gly Gln Thr
            100                 105                 110

Gly Gly Val Asn Gly Thr Asn Ala Thr Thr Ala Thr Ser Thr Ala
        115                 120                 125

Ser Ser Thr Pro Val Val Asn Thr Gln Pro Cys Asn Gly His Ala Glu
130                 135                 140

Phe Cys Ala Arg Lys Tyr Ser Asn Ile Thr Met Val Ala Ala His Asn
145                 150                 155                 160

Ser Pro Phe Val Lys Pro Gly Asn Ala Ala Asn Gln Ala Leu Lys
                165                 170                 175

Val Thr Ala Gln Leu Asp Asp Gly Ile Arg Met Leu Gln Phe Gln Thr
            180                 185                 190

His Leu Val Asn Asn Thr Leu Tyr Leu Cys His Thr Ser Cys Asp Leu
        195                 200                 205

Leu Asn Met Gly Pro Leu Glu Asp Tyr Leu Thr Thr Val Thr Lys Trp
    210                 215                 220

Val Lys Thr His Pro Tyr Asp Val Val Thr Ile Leu Ile Gly Asn Tyr
225                 230                 235                 240

Asp Tyr Val Asp Pro Gly Asn Phe Thr Gly Pro Met Gln Asn Ser Gly
                245                 250                 255

Leu Met Asp Tyr Val Phe Thr Pro Ser Lys Ile Pro Met Ala Leu Asp
            260                 265                 270

Asp Trp Pro Thr Met Ser Ser Met Ile Leu Ser Gly Lys Arg Ala Val
        275                 280                 285

Val Phe Met Asp Tyr Gln Ala Asn Gln Thr Ala Tyr Pro Trp Leu Met
290                 295                 300

Asp Glu Phe Ser Gln Met Trp Glu Thr Pro Phe Ser Pro Thr Asp Ala
305                 310                 315                 320

Ala Phe Pro Cys Thr Glu Gln Arg Pro Pro Asp Leu Ser Ala Gln Asp
                325                 330                 335

Ala Lys Asp Arg Met Tyr Met Ala Asn His Asn Leu Asn Leu Asp Ile
            340                 345                 350

Asn Ile Ala Ser Ile Ser Leu Leu Ile Pro Asn Thr Ala Ser Leu Asn
355                 360                 365

Gln Thr Asn Ala Val Ser Gly Tyr Gly Ser Leu Gly Lys Met Ala Arg
    370                 375                 380

Asn Cys Thr Ala Met Trp Asp Arg Pro Pro Asn Phe Leu Leu Val Asp
385                 390                 395                 400

Tyr Tyr Asn Tyr Gly Asn Ile Asn Gly Ser Val Phe Glu Val Ala Ala
                405                 410                 415

Glu Met Asn Asn Val Thr Trp Asp Gly Lys Cys Cys Gly Ala Ala Ser
            420                 425                 430

Ala Ala Ser Ser Val Met Pro Gly Val Ser Val Met Ser Thr Leu Leu
        435                 440                 445

Leu Ile Ala Gly Val Gln Tyr Met Ala Ser Ile Phe
    450                 455                 460

<210> SEQ ID NO 70
<211> LENGTH: 470
<212> TYPE: PRT
<213> ORGANISM: Aspergillus nidulans
```

<400> SEQUENCE: 70

```
Met Arg Leu Thr Trp Leu Leu Thr Leu Leu Ala Ala Ser Arg Val Leu
1               5                   10                  15

Ser Gln Asn Thr Asp Ser Asp Ser Asp Ser Asp Ser Ser Thr
            20                  25                  30

Thr Thr Asp Ser Asn Glu Glu Ala Ile Ser Gln Ser Leu Ala Glu Ile
                35                  40                  45

Ala Ser Ala Ile Thr Thr Thr Val Asp Ala Thr Val Pro Ser Gly
        50                  55                  60

Asp Tyr Ile Thr Tyr Ser Thr Thr Val Tyr Leu Thr Gly Thr His Gly
65                  70                  75                  80

Thr Val Ile Gly Ser Thr Ala Val Gln Val Thr Gly Thr Pro Asn Ala
                85                  90                  95

Asn Ala Thr Thr Ser Ala Asn Ala Thr Ile Thr Ser Thr Ser Asp Thr
                100                 105                 110

Val Thr Val Leu Ile Gly Gly Gln Thr Thr Ile Ser Gly Asn Ser Thr
            115                 120                 125

Gly Asn Ser Thr His Ser Ala Thr Pro Ser Pro Ser Gln Thr Pro Val
    130                 135                 140

Val Asn Thr Gln Pro Cys Asn Gly Trp Pro Glu Phe Cys Asp Arg Lys
145                 150                 155                 160

Tyr Ser Asn Ile Thr Gln Val Ala Ala His Asn Ser Pro Phe Val Ala
                165                 170                 175

Gln Gly Asn Val Ala Ala Asn Gln Ala Leu Asp Val His Tyr Gln Leu
            180                 185                 190

Asp Asp Gly Val Arg Met Leu Gln Phe Gln Thr His Ile Met Asn Gly
    195                 200                 205

Thr Met Tyr Leu Cys His Thr Ser Cys Asp Leu Leu Asn Val Gly Pro
210                 215                 220

Leu Glu Asp Tyr Leu Ser Asn Ile Thr Glu Trp Leu Arg Gln His Pro
225                 230                 235                 240

Tyr Asp Val Val Thr Ile Leu Ile Gly Asn Tyr Asp Tyr Val Asp Pro
                245                 250                 255

Gly Asn Phe Thr Thr Pro Met Glu Asn Ser Gly Leu Met Asp Phe Val
            260                 265                 270

Phe Thr Pro Pro Met Ile Pro Met Gly Leu Asp Asp Trp Pro Thr Leu
        275                 280                 285

Gly Ser Ile Ile Leu Ser Gly Lys Arg Ala Ile Val Phe Met Asp Tyr
290                 295                 300

Gln Ala Asn Gln Thr Ala Tyr Pro Trp Leu Met Asp Glu Phe Ser Gln
305                 310                 315                 320

Met Trp Glu Thr Pro Phe Ser Pro Thr Asp Arg Asp Phe Pro Cys Thr
                325                 330                 335

Val Gln Arg Pro Pro Asp Leu Ala Ala Glu Asp Ala Arg Lys Arg Met
            340                 345                 350

Tyr Met Ala Asn His Asn Leu Asn Ile Asp Phe Ser Ile Ala Ser Leu
        355                 360                 365

Asn Leu Leu Ile Pro Asn Thr Ala Leu Leu Asn Glu Thr Asn Ala Asp
    370                 375                 380

His Gly Tyr Gly Ser Val Gly Arg Met Ala Glu Asn Cys Thr Thr Leu
385                 390                 395                 400

Trp Asn Arg Pro Pro Asn Phe Leu Leu Val Asp Tyr Tyr Asn Glu Gly
                405                 410                 415
```

Asn Phe Asn Gly Ser Val Phe Gln Val Ala Ala Asp Met Asn Gly Val
                420                 425                 430

Ser Tyr Asp Arg Asp Ser Cys Cys Gly Thr Leu Ser Ala Ala Ser Ser
                435                 440                 445

Leu Gly Pro Gly Ala Met Met Ser Ala Val Leu Phe Phe Val Gly Leu
        450                 455                 460

Gln Val Leu Ala Trp Leu
465             470

<210> SEQ ID NO 71
<211> LENGTH: 378
<212> TYPE: PRT
<213> ORGANISM: Ustilago maydis

<400> SEQUENCE: 71

Met Phe Gln Phe Ile Gln Leu Leu Ser Leu Val Ser Ala Leu Val Ile
1               5                   10                  15

Val Ser Ser Leu Val Gly Ala Val Pro His Pro Val Leu Asp Ala Ala
                20                  25                  30

Val Glu Thr Leu Val Lys Arg Ala Ser Val Cys Asn Gly Asp Ala Ser
            35                  40                  45

Leu Cys Ser Arg Leu Tyr Ser Asn Val Thr Tyr Ile Gly Ala His Asn
    50                  55                  60

Ser Tyr Ala Val Gly Thr Leu Ala Gly Ala Ser Val Gly Lys Asn Gln
65                  70                  75                  80

Glu Gln Ser Val Thr Gln Gln Leu Thr Asp Gly Ile Arg Leu Leu Gln
                85                  90                  95

Val Gln Ala His Lys Ser Ser Asn Ser Thr Gly Ser Gly Ile Asn
                100                 105                 110

Leu Cys His Ser Ser Cys Gln Ile Glu Asn Gly Gly Thr Leu Glu Asn
        115                 120                 125

Tyr Leu Ser Lys Val Lys Thr Trp Val Asp Ser Asn Pro Asn Asp Val
    130                 135                 140

Ile Thr Ile Leu Ile Val Asn Ser Asp Asn Gln Pro Val Ser Ser Phe
145                 150                 155                 160

Gly Thr Ala Phe Gln Ser Thr Gly Leu Ala Ser Lys Ala Tyr Ser Pro
                165                 170                 175

Gly Thr Ala Ala Leu Ala Lys Asp Ser Trp Pro Thr Leu Gly Ser Leu
            180                 185                 190

Ile Asp Ser Gly Lys Asn Leu Val Val Phe Ile Asp Asn Ser Ala Asp
        195                 200                 205

Val Ser Ser Val Pro Tyr Ile Leu Pro His Phe Gln Asn Thr Trp Glu
    210                 215                 220

Asn Pro Tyr Asn Gln Ile Ser Val Pro Phe Asn Cys Ser Val Asp Arg
225                 230                 235                 240

Ile Asn Ser Gly Ser Glu Pro Ser Asn Leu Met Tyr Leu Ile Asn His
                245                 250                 255

Tyr Leu Asp Ser Ser Phe Asn Leu Phe Gly Thr Thr Val Phe Val Pro
            260                 265                 270

Asn Thr Ala Gln Leu Asn Thr Asn Ser Leu Ser Ser Ile Met Thr
        275                 280                 285

Asp Ala Gly Asn Cys Ala Ser Leu His Gly Thr Gly Tyr Pro Thr Tyr
    290                 295                 300

Val Leu Thr Asp Phe Tyr Asp Val Gly Asp Gly Ser Val Phe Gln Ala

```
            305                 310                 315                 320
Ala Ala Gln Met Asn Gly Val Gln Tyr Thr Ala Lys Pro Ile Gly Asn
                325                 330                 335

Ala Thr Lys Ser Gly Ser Ser Gly Ser Ser Gly Ser Ser Ser Ser Gly
                340                 345                 350

Ala Ala Ser Thr His Val Asn Ala Ile Ala Ala Val Ala Thr Phe Met
                355                 360                 365

Thr Met Phe Ala Leu Ala Ser Thr Leu Ala
                370                 375

<210> SEQ ID NO 72
<211> LENGTH: 449
<212> TYPE: PRT
<213> ORGANISM: Coccidioides immitis

<400> SEQUENCE: 72

Met Leu Leu Ser Phe Arg Leu Leu Ala Val Ala Ser Leu Leu Arg Ser
1               5                   10                  15

Ile Tyr Ala Asp Asp Ile Ile Thr Leu Thr Gly Thr Asn Ile Pro Pro
                20                  25                  30

Ser Leu Ser Val Gly Asp Pro Ile Pro Ser Asp Thr Ser Gly Leu Tyr
            35                  40                  45

Lys Ser Tyr Ser Ser Val Val Thr Val Ser Ala Thr Asp Lys Gln Leu
        50                  55                  60

Glu Ser Ala Arg Thr Gly Thr Glu Thr Ala Thr Gly Ser Glu Arg Thr
65                  70                  75                  80

Ala Thr Ser Asp Gly Gly Thr Leu Leu Ile Gly Ser Lys Arg Val Ser
                85                  90                  95

Thr Thr Asn Gly Thr Thr Leu Ser Gly Asn Ala Thr Ala Thr Ser Thr
                100                 105                 110

Glu Ser Ala Ala Val Pro Thr Asn Thr Arg Pro Cys Asn Gly Tyr Pro
            115                 120                 125

Glu Phe Cys Glu Arg Lys Tyr Ser Asn Ile Thr His Ile Ala Ala His
        130                 135                 140

Asn Ser Pro Phe Val Arg Arg Gly Asn Ile Ala Gly Asn Gln Glu Leu
145                 150                 155                 160

Asp Val Thr Ile Gln Leu Asn Asp Gly Ile Arg Met Leu Gln Phe Gln
                165                 170                 175

Thr His Tyr Ile Asn Gly Thr Ile Arg Leu Cys His Ser Ser Cys Asp
                180                 185                 190

Leu Leu Asp Val Gly Pro Leu Glu Asp Tyr Leu Arg Lys Val Ala Asp
            195                 200                 205

Trp Leu Arg Ala Asn Pro Tyr Asp Val Val Ser Ile Leu Met Gly Asn
        210                 215                 220

Ser Asn Phe Ile Leu Pro Thr Asn Tyr Thr Lys Pro Ile Glu Asn Ser
225                 230                 235                 240

Gly Leu Ile Asp Tyr Val Tyr Thr Pro Pro Lys Ile Pro Met Ala Leu
                245                 250                 255

Asp Asp Trp Pro Leu Leu Ser His Phe Ile Leu Thr Gly Gln Arg Ala
                260                 265                 270

Ile Val Tyr Leu Asp Tyr Lys Ala Asn Gln Thr Glu Val Pro Tyr Leu
            275                 280                 285

Leu Asp Glu Phe Ser Gln Met Trp Glu Thr Pro Phe Ser Pro Thr Asn
        290                 295                 300
```

```
Arg Asp Phe Pro Cys Val Val His Arg Pro Gly Leu Ser Ala Glu
305                 310                 315                 320

Asp Ala Lys Lys Arg Leu Tyr Met Ala Asn His Asn Leu Asn Thr Glu
            325                 330                 335

Val Ser Leu Ala Gly Ala Ser Leu Leu Val Pro Asn Thr Val Leu Leu
            340                 345                 350

Asn Glu Thr Asn Ala Val Ser Gly Tyr Gly Ser Ala Gly Ala Met Ala
            355                 360                 365

Gly Asn Cys Thr Glu Gln Trp Thr Arg Pro Pro Asn Phe Ile Leu Val
    370                 375                 380

Asp Tyr Tyr Asn Ile Gly Asn Phe Asn Gly Ser Val Phe Glu Val Ala
385                 390                 395                 400

Ala Asn Cys Asn Asn Val Thr Tyr Asn Arg Lys Cys Cys Gly Arg Gln
            405                 410                 415

Thr Ser Ala Ala Ser Lys Gly Leu Ser Ser Gly Ala Lys Gln Ser Phe
            420                 425                 430

Phe Val Gly Leu Leu Ala Thr Ile Thr Thr Ser Leu Leu Phe Thr Leu
            435                 440                 445

Pro

<210> SEQ ID NO 73
<211> LENGTH: 396
<212> TYPE: PRT
<213> ORGANISM: Neurospora crassa

<400> SEQUENCE: 73

Met Pro Ser Leu Ile Ser Ser Leu Ala Thr Ala Leu Leu Leu Val Ser
1               5                   10                  15

Gly Ile Cys Ala Ile Pro Gln Gly Pro Ser Gly Ala Glu Ser Gly Ile
                20                  25                  30

Val Ser Ala Val Ser Ala Ala Ser Val Ser Thr Ala Gly Val Ala Val
            35                  40                  45

Ser Gln Ala Thr Thr Ala Ser Pro Ser Thr Ser Asn Ala Ala Ser Gly
    50                  55                  60

Ile Ser Ala Cys Asn Asn Ser Pro Leu Leu Cys Asp Arg Ala Tyr Asn
65                  70                  75                  80

Asn Val Thr His Met Gly Ala His Asp Ser Ser Phe Leu Arg Asp Ala
                85                  90                  95

Ser Thr Ser Asp Ser Leu Ala Gly Asn Gln Tyr Phe Asn Ala Thr Val
            100                 105                 110

Ala Leu Asp Ala Gly Ile Arg Leu Gln Ala Gln Val His Asp Val
            115                 120                 125

Asn Gly Thr Leu Gln Leu Cys His Thr Ser Cys Ser Leu Leu Asp Ala
    130                 135                 140

Gly Pro Leu Gln Asp Trp Leu Ala Lys Ile Lys Phe Trp Met Asp Asn
145                 150                 155                 160

Asn Pro Asn Glu Val Val Thr Ile Leu Leu Val Asn Ser Asp Asn Lys
                165                 170                 175

Leu Val Ser Asp Tyr Ala Ala Val Phe Glu Gly Ser Gly Ile Ser Thr
            180                 185                 190

Tyr Gly Tyr Gln Leu Ser Asn Gly Ser Ser Ala Ser Asn Thr Trp Pro
    195                 200                 205

Thr Leu Gly Asp Met Ile Thr Ser Asn Lys Arg Leu Val Thr Phe Ile
    210                 215                 220
```

```
Ala Ser Ile Asp Tyr Ser Pro Thr Tyr Pro Tyr Leu Leu Ser Glu Phe
225                 230                 235                 240

Asp His Val Phe Glu Thr Ala Tyr Asn Val Leu Ser Leu Ser Gly Phe
                245                 250                 255

Asn Cys Thr Leu Asp Arg Pro Lys Gly Gln Gly Ser Ala Gly Asp Ala
            260                 265                 270

Ile Ser Ala Gly Leu Met Pro Leu Met Asn His Phe Ala Asp Ser Leu
        275                 280                 285

Leu Leu Gln Gly Val Gln Ile Pro Asp Glu Thr Asp Ile Asp Ile Thr
    290                 295                 300

Asn Ser Pro Asp Thr Ser Thr Thr Gly Asn Leu Gly Leu His Ala Asp
305                 310                 315                 320

Thr Cys Val Lys Gln Trp Gly Val Lys Pro Thr Phe Ile Leu Val Asp
                325                 330                 335

Phe Phe Asp His Gly Pro Ala Ile Asp Thr Ala Asp Arg Leu Asn Gly
            340                 345                 350

Ile Thr Ala Thr Gly Arg Lys Ser Val Ser Gly Glu Ser Lys Gly Asn
        355                 360                 365

Thr Ser Gly Ala Gly Glu Asn His Ser Pro Met Gly Met Asn Val Ala
    370                 375                 380

Leu Ile Ala Phe Val Val Phe Ala Leu Ala Met Val
385                 390                 395

<210> SEQ ID NO 74
<211> LENGTH: 360
<212> TYPE: PRT
<213> ORGANISM: Cryptococcus neoformans

<400> SEQUENCE: 74

Met Leu Pro His Leu Ile Leu Ser Leu Ala Ser Ile Phe Ala Leu Pro
1               5                   10                  15

Ala Val Phe Ala Ala Thr Thr Cys Asn Gly His Ser Glu Leu Cys Ser
                20                  25                  30

Arg Leu Tyr Ser Asn Val Thr Phe Ile Gly Ala His Asp Ser Tyr Ala
            35                  40                  45

Val Gly Ser Ser Val Ala Asp Asp Gln Asp Lys Asp Val Thr Ser Gln
        50                  55                  60

Leu Asn Asp Gly Ile Arg Thr Leu Gln Ile Gln Ala His Asn Ala Ser
65                  70                  75                  80

Asp Gly Ile His Leu Cys His Ser Ser Cys Ser Leu Leu Asp Gly Gly
                85                  90                  95

Leu Met Ser Asp Tyr Leu Ser Thr Val Ala Ser Trp Val Asn Asp Asn
            100                 105                 110

Pro Asn Asp Val Ile Thr Ile Val Ile Val Asn Ser Asp Asn Leu Pro
        115                 120                 125

Pro Thr Ser Phe Ser Pro Val Phe Glu Ser Ala Gly Leu Ser Ser Lys
    130                 135                 140

Val Tyr Thr Pro Ala Ser Gln Pro Thr Gln Leu Ser Asp Trp Pro Ser
145                 150                 155                 160

Leu Ser Asp Met Ile Asp Ala Gly Thr Thr Val Val Ala Phe Met Asp
                165                 170                 175

Tyr Glu Ala Asp Thr Ser Ser Val Pro Tyr Leu Leu Asp Glu Phe Ala
            180                 185                 190

Ala Met Trp Glu Asp Ala Tyr Gly Val Thr Thr Gln Glu Phe Gly Cys
        195                 200                 205
```

```
Ala Val Asn Arg Ser Ser Gly Asp Thr Ser Ser Gln Pro Phe Leu Ile
    210                 215                 220

Asn His Phe Leu Asp Ser Thr Tyr Ser Phe Ser Ser Ile Gln Val Phe
225                 230                 235                 240

Val Pro Asn Lys Asp Lys Leu Asn Glu Thr Asn Ala Glu Thr Gly Thr
                245                 250                 255

Gly Ser Ile Gly Tyr His Val Asn Asn Cys Arg Gln Leu Trp Gly Arg
            260                 265                 270

Asn Pro Asn His Ile Leu Leu Asp Phe Tyr Asp Ser Asn Gly Asn Ser
                275                 280                 285

Pro Phe Asn Val Ala Ala Ser Leu Asn Gly Val Ser Ala Pro Thr Asn
            290                 295                 300

Thr Val Thr Ala Gly Thr Ala Ser Ala Thr Ser Ser Gly Thr Ala Ala
305                 310                 315                 320

Val Val Ser Thr Gln Ser Leu Ser Gly Ser Val Thr Ser Ile Glu Gly
                325                 330                 335

Ile Ala Lys Gly Ile Thr Leu Gly Phe Gly Val Met Leu Gly Val Gly
                340                 345                 350

Met Gly Val Gly Arg Val Phe Leu
            355                 360

<210> SEQ ID NO 75
<211> LENGTH: 740
<212> TYPE: PRT
<213> ORGANISM: Streptomyces lividans

<400> SEQUENCE: 75

Met Ser Leu Thr Val Leu Ala Ala Ala Val Val Arg Ser Thr Val
1               5                   10                  15

Leu Asp Pro Gly Phe Tyr Gly Gln Val Leu Glu Asp Glu His Ala Tyr
                20                  25                  30

Gln Arg Phe Tyr Asp Glu Val Leu Val Asp Pro Arg Ser Thr Pro Phe
            35                  40                  45

Thr Ser Asp Leu Leu Glu Arg Leu Pro Val Pro Gln Ser Thr Ile Thr
    50                  55                  60

Ser Asn Leu Lys Val Val Pro Pro Glu Thr Leu Arg Thr Met Gly
65                  70                  75                  80

Gln Gly Gln Ile Ala Glu Met Val His Tyr Leu Glu Gly Asp Arg Glu
                85                  90                  95

Arg Leu Arg Ile Thr Val Asp Leu Glu Pro Val Val Ala Asn Val Glu
            100                 105                 110

Arg Leu Ser Gln Ala Tyr Phe Gly Asp Ala Val Ala Ala Leu Gln Lys
        115                 120                 125

Arg Ser Glu Pro Asp Phe Gln Ala Phe Val Gln His Leu Ser Glu Leu
    130                 135                 140

Val Ala Arg Val Val Ala Gly Glu Ala Pro Leu Asp Glu Leu Pro Thr
145                 150                 155                 160

Leu Pro Leu Ser His Ser Gln Ala Asp Ala Ala Thr Asp Ala Leu Met
                165                 170                 175

Arg Leu Val Pro Asp Gly Ala Ala Arg Asp Gly Val Arg Ser Thr Val
            180                 185                 190

Leu Thr Ala Leu Asp Arg Gly Asp Val Ala Ser Ala Leu Ala Ala Ile
        195                 200                 205

Ala Pro Val Ala Leu Thr Asp Gln Val Arg Asp Ala Ala Glu Glu Met
```

```
              210                 215                 220
Leu Arg Glu Ala Lys Gln Gly Thr Trp Val Val Ser Val Asp Val Glu
225                 230                 235                 240

Pro Gly Thr Glu Ala Leu Ala Pro Leu Asp Arg Ala Arg Lys Val Thr
                245                 250                 255

Arg Leu Phe Gln Glu Val Val Glu Pro Ala Ala Ala Val Leu Cys Ala
                260                 265                 270

Ala Ala Leu Thr Leu Leu Trp Phe Leu Arg Pro Ser Pro Ala Lys Arg
                275                 280                 285

Arg Leu Ile Pro Leu Gly Trp Val Pro Ala Ala Ala Ser Leu Met
290                 295                 300

Ala Leu Thr Val Leu Val Leu Arg Leu Thr Leu Gly Asp Thr Leu Phe
305                 310                 315                 320

Gly Thr Pro Pro Ser Trp Pro Pro Ala Ala Thr Gly Leu Leu Ala Asp
                325                 330                 335

Val Gln Ala Ala Ala Leu Asp Arg Leu Leu Thr Thr Ala Val Val Val
                340                 345                 350

Ala Val Ile Leu Leu Ala Ala Gly Ala Leu Leu Ile Thr Val Gly Trp
                355                 360                 365

Val Trp Gln Thr Arg Pro Ser Val Pro Val Leu Thr Asp Pro Arg His
370                 375                 380

Val Pro Ala Leu Thr Phe Thr Val Thr Ala Val Ala Leu Val Gly Thr
385                 390                 395                 400

Met Leu Ala Pro Val Ala Ile Ser Gly Ser Ser Pro Arg Ile Cys Gln
                405                 410                 415

Gly Ser Ala Glu Leu Cys Asp Ala Arg Tyr Asp Glu Ile Ala Gln Leu
                420                 425                 430

Ala Ser His Asn Ala Met Ala Thr Thr Ala Asp Arg Phe Ile Gly Pro
                435                 440                 445

Leu Gln Asp Pro Asp Ile Val Gly Gln Leu Gly Ala Gly Ser Arg Val
                450                 455                 460

Leu Leu Leu Asp Thr His Arg Trp Glu Arg Pro Glu Glu Val Ala Glu
465                 470                 475                 480

Arg Leu Ser Thr Ser Asp Phe Ser Pro Ala Glu Arg Arg Leu Thr
                485                 490                 495

Ala Ile Leu Gln Arg Val Asn Pro Pro His Pro Gly Leu Trp Leu Cys
                500                 505                 510

His Ser Val Cys Gly Ala Gly Ala Ile Glu Leu Glu Pro Thr Leu Arg
                515                 520                 525

Gln Ile Gly Glu Trp Leu Arg Asp Asn Pro Thr Glu Ile Val Thr Leu
530                 535                 540

Ile Leu Gln Asp Gly Val Asp Ala Val Thr Thr Gln Asp Ala Phe Glu
545                 550                 555                 560

Arg Ala Gly Leu Ser Asp Leu Leu Tyr Glu Pro Asp Arg Asp Pro Asp
                565                 570                 575

Arg Pro Trp Pro Lys Leu Gly Asp Met Ile Asp Ser Gly Arg Arg Leu
                580                 585                 590

Val Val Phe Ala Glu Lys Ala Asp Gly Pro Ala Pro Trp Tyr Arg Asn
                595                 600                 605

Leu Tyr Arg Tyr Gly Met Glu Thr Pro Phe Ala Phe Arg Ser Pro Asp
                610                 615                 620

Glu Met Ser Cys Leu Pro Asn Arg Gly Gly Ser Asp Lys Arg Leu Phe
625                 630                 635                 640
```

```
Leu Leu Asn His Phe Val Thr Ala Gly Gly Gly Leu Arg Leu Asp Ala
            645             650             655

Gly Val Val Asn Ser Arg Gln Arg Val Leu Glu Arg Ala His Asn Cys
            660             665             670

Glu Arg Gln Arg Gly Arg Pro Val Asn Phe Ile Ala Val Asp Tyr Ala
            675             680             685

Thr Ile Gly Asp Ala Leu Gly Ala Val Asn Glu Leu Asn Ala Glu Arg
            690             695             700

Val Glu Asp Gly Pro Arg Val Pro Val Glu Arg Thr Pro Gly Arg Ile
705             710             715             720

Pro Gly Ala Ala Glu Ala Arg Arg Gly Gly Ala Pro Arg Arg Arg
            725             730             735

Ala Val Ser Arg
            740
```